United States Patent
Campbell et al.

(10) Patent No.: US 7,365,178 B2
(45) Date of Patent: Apr. 29, 2008

(54) ACYL-NUCLEOTIDE PROBES AND METHODS OF THEIR SYNTHESIS AND USE IN PROTEOMIC ANALYSIS

(75) Inventors: David Alan Campbell, San Diego, CA (US); Marek Liyanage, Carlsbad, CA (US); Anna Katrin Szardenings, San Diego, CA (US); Min Wu, San Diego, CA (US)

(73) Assignee: Activx Biosciences, Inc., La Jolla, CA (US)

( * ) Notice: Subject to any disclaimer, the term of this patent is extended or adjusted under 35 U.S.C. 154(b) by 463 days.

(21) Appl. No.: 10/817,454

(22) Filed: Apr. 1, 2004

(65) Prior Publication Data
US 2005/0043507 A1    Feb. 24, 2005

Related U.S. Application Data

(60) Provisional application No. 60/459,797, filed on Apr. 1, 2003.

(51) Int. Cl.
*C07H 21/02* (2006.01)
*C07H 21/00* (2006.01)
*C12Q 1/68* (2006.01)
*G01N 33/53* (2006.01)
*A61K 38/00* (2006.01)
*C07K 1/00* (2006.01)

(52) U.S. Cl. .................. 536/23.1; 536/25.3; 435/6; 435/7.1; 530/300; 530/350

(58) Field of Classification Search .............. 435/6, 435/7.1; 536/23.1, 25.3; 530/300, 350
See application file for complete search history.

(56) References Cited

U.S. PATENT DOCUMENTS

| | | | |
|---|---|---|---|
| 4,415,655 A | 11/1983 | De Castro et al. | |
| 4,481,094 A | 11/1984 | Fernandez de Castro et al. | |
| 4,865,707 A | 9/1989 | Karger et al. | |
| 4,946,794 A | 8/1990 | Berube | |
| 5,215,970 A | 6/1993 | Datema et al. | |

(Continued)

FOREIGN PATENT DOCUMENTS

WO    WO 00/11208    3/2000

(Continued)

OTHER PUBLICATIONS

Smith et al. "The quantitation of biotinylated compounds by a solid-phase assay using a 125I-labelled biotin derivative" FEB Letters, vol. 215, No. 2, pp. 305-310, 1987.*

(Continued)

*Primary Examiner*—Jezia Riley
(74) *Attorney, Agent, or Firm*—Foley & Lardner LLP; Stephen E. Reiter

(57) ABSTRACT

The present invention provides tagged acyl phosphate probes ("TAPPs"), and methods of their preparation and use. The subject methods and compositions can provide enhanced simplicity and accuracy in identifying changes in the presence, amount, or activity of target proteins in a complex protein mixture, preferably nucleotide binding proteins using nucleotide binding protein-directed TAPPs. The profiling methods described herein can have a number of steps leading to the identification of target nucleotide binding protein(s) in a complex protein mixture.

28 Claims, 5 Drawing Sheets

U.S. PATENT DOCUMENTS

| | | | |
|---|---|---|---|
| 6,008,373 | A | 12/1999 | Waggoner et al. |
| 6,043,060 | A | 3/2000 | Imanishi |
| 6,255,292 | B1 | 7/2001 | Liang |

FOREIGN PATENT DOCUMENTS

| | | |
|---|---|---|
| WO | WO 01/77668 | 10/2001 |
| WO | WO 01/77684 | 10/2001 |
| WO | WO 03/079014 | 1/2003 |

OTHER PUBLICATIONS

Clontech Catalog: Innovative Tools to Accelerate Discovery. 6-Carboxyfluorescein-ON™ phosphoramidite user manual. PT-3354-1 (PR95959), Published May 3, 1999.

Madoyan et al., "Affinity labeling of tryptophanyl-tRNA synthetase with mesitoyl-amp." FEBS Letters, 123: 156-160, Jan. 1981.

Manabe et al., Preparation of glycosylated amino acid derivatives for glycoprotein synthesis by in vitro translation system. Bioorganic & Medicinal Chemistry, 10:573-581, 2002.

International Search Report for PCT Application No. PCT/US2004/10075, 2005.

Bergseid et al., Small molecule-based chemical affinity system for the purification of proteins, Biotechniques (2000) 29(5):1126-1133.

Bishop et al., Magic bullets for protein kinases. Trends Cell Biol (2001) 11(4):167-172.

Clauser, et al., Rapid mass spectrometric peptide sequencing and mass matching for characterization of human melanoma proteins isolated by two-dimensional PAGE. Proc. Natl. Acad. Sci. USA (1995) 92:5072-76.

Daniel, SM et al., FastTag™ Nucleic Acid Labeling System: A Versatile Method for Incorporating Haplens, Fluorochromes and Affinity Ligands into DNA, RNA and Oligonucleotides. Biotechniques (1998) 24(3), 484-489.

De Leenheer, et al., Applications of isotope dilution-mass spectrometry in clinical chemistry, pharmacokinetics, and toxicology. Mass Spectrom. Rev. (1992) 11:249-307.

Deutscher (ed.), Methods in Enzymology, (1990) vol. 182, pp. 147-238, chapter 12 by Cull and McHenry entitled "Preparation of extracts from Prokaryotes".

Eisen et al., Cluster analysis and display of genome-wide expression patterns. *Proc. Natl. Acad. Sci. USA* (1998) 95:14863-14868.

Eng. et al. An Approach to Correlate Tandem Mass Spectral Data of Peptides with Amino Acid Sequences in a Protein Database. J. Am. Soc. Mass Spectrom. (1994) 5:976-989.

Gibson et al., Nonpeptidic $\alpha_\nu\beta_3$ Integrin Antagonist Libraries: On-Bead Screening and Mass Spectrometric Identification without Tagging. Agnew. Chem. Int. Ed. (2001) 40: 165-169.

Gottschling et al., Cellular Solid-Phase Binding Assay and Mass Spectrometry for Screening of $\alpha 4\beta 7$ Integrin Antagonists. Bioorg. And Medicinal Chem. Lett. (2001) 11: 2997.

Gygi et al., Protein analysis by mass spectrometry and sequence database searching: Tools for cancer research in the post-genomic era. Mol. Cell. Biol. (1999) 19:1720-1730.

Gygi, et al., Correlation between Protein and mRNA Abundance in Yeast. Mol. And Cell. Biol. (1999) 20:310-319.

Hanks and Hunter, "The eukaryotic protein kinase superfamily: kinase (catalytic) domain structure and classification." FASEB J. (1995) 9(8):576-596.

Kidd et al., Profiling Serine Hydrolast Activities in Complex Proteomes. *Biochemistry* (2001) 40: 4005-15.

Kolb et al., Click Chemistry: Diverse Chemical Function from a Few Good Reactions. *Agnew Chem. Int. Ed. Engl.* (2001) 40:2004-21.

Laemmli, Cleavage of Structural Proteins during the Assembly of the Head of Bacteriophage T4. *Nature* (1970) 227:680-685.

Lemieux et al. A Fluorogenic Dye Activated by the Staudinger Ligation. J. Am. Chem. Soc. (2003) 125: 4708-4709.

Leon et al., Evaluation of Resins for On-Bead Screening: A Study of Papain and Chymotrypsin Specificity Using Pega-Bound Combinatorial Peptide Libraries. Bioorg. Med. Chem. Lett. (1998) 8: 2997.

Link, et al., Identifying the major proteome components of *Haemophilus influenzae* type-strain NCTC 8143. Electrophoresis (1997) 18:1314-34.

Mann and Wilm, Error-Tolerant Identification of Peptides in Sequence Databases by Peptide Sequence Tags. Anal. Chem. (1994) 66:4390-99.

Orain and Bradley, Solid phase synthesis of trypanothione reductase inhibitors-towards single bead screening. Tetrahedron Lett. (2001) 42: 515-518.

Papanikos et al., $\alpha$-Ketocarbonyl Peptides: A General Approach to Reactive Resin-Bound Intermediates in the Synthesis of Peptide Isosteres for Protease Inhibitor Screening on Solid Support. J. Am. Chem. Soc. (2001) 123: 2176 2181.

Porco, Organic Synthesis Using Chemical Tags: The "Third Leg" of Parallel Synthesis. JA Comb. Chem. High Throughput Screening (2000) 3(2) 93-102.

Ross et al., Systematic variation in gene expression patters in human cancer cell lines. *Nat. Genet.* (2000)24:227-235.

Seo et al., Click Chemistry to Construct Fluorescent Oligonucleotides for DNA Sequencing. *J. Org. Chem.* (2003) 68: 609-612.

Smith and Bradley, Comparison of Resin and Solution Screening of Methodologies in Combinatorial Chemistry and the Identification of a 100nM Inhibitor of Trypanothione Reductase. J. Comb. Med. (1999) 1: 326-332.

* cited by examiner

Diisopropylcarbodiimide

L =

![L structure: HN-(CH2)n-(X-CH2)m]  or no linker n = 0-4
m = 0-4
x = O or CH$_2$ n = 0-4
m = 0-4
x = O or CH$_2$ pyrrolopyrimidine pyrrazolopyrimidine

ACYL-NUCLEOTIDE PROBES AND METHODS OF THEIR SYNTHESIS AND USE IN PROTEOMIC ANALYSIS

RELATED APPLICATION

This application claims the benefit of U.S. Provisional application 60/459,797, filed Apr. 1, 2003, which is incorporated herein by reference in its entirety, including drawings.

FIELD OF THE INVENTION

The invention relates generally to compositions and methods for labeling proteins, especially nucleotide binding proteins, preferably kinases, and most preferably protein kinases, using tagged acyl phosphate derivatives.

BACKGROUND

Nucleotide-binding proteins play an extremely important role as regulators of genomic and proteomic function. Examples of nucleotide binding proteins include G proteins, which act as coupling factors in association with certain receptors; protein kinases, which transfer a phosphate group to target proteins; non-protein kinases, such as hexokinase, which are involved in the metabolic pathways within cells; proteins utilizing the energy stored within nucleotide-based molecules such as ATP; etc.

Protein kinases are the enzymes responsible for catalyzing the transfer of a γ-phosphoryl group from ATP to the hydroxyl group of serine, threonine or tyrosine residues in peptides, polypeptides, and proteins in a process known as "phosphorylation." Protein phosphorylation is a ubiquitous regulatory mechanism in eukaryotic cells, where it is of central importance in controlling cell function, growth and differentiation. A protein kinase that phosphorylates, for example, tyrosine residues in its substrates is termed a protein-tyrosine:ATP phosphotransferase, or, more commonly, a tyrosine (or Tyr) kinase. The eukaryotic protein kinases make up a large superfamily of related proteins. They are related by virtue of their kinase domains (also known as catalytic domains), which consist of approximately 250-300 amino acid residues. The kinase domains that define this group of enzymes contain 12 conserved subdomains that fold into a common catalytic core structure. See, e.g., Hanks and Hunter, FASEB J. (1995) 9(8):576-96.

Eukaryotic protein kinases can be classified on the basis of their sequence, substrate specificity and regulation. One major subdivision is between Ser/Thr kinases and the Tyr kinases. Yeast have numerous Ser/Thr kinases, many of which have readily recognizable counterparts in all higher organisms, but very few dedicated Tyr kinases (an example of a yeast Tyr kinase is Swe1 from *Saccharomyces cerevisiae* and its homolog in *S. pombe* Wee1). By contrast, many signaling pathways of multicellular organisms depend on two large and important Tyr kinase families, the receptor-Tyr kinases which have intracellular Tyr kinase domains, and the Src family of cytoplasmic Tyr kinases. There are also dual-specificity enzymes, present in both unicellular and multicellular eukaryotes, such as the mitogen-activated protein kinase kinases (MAPKKs).

Overexpression and/or mutation of certain kinases in tumor cell is believed to upregulate a number of cell cycle and anti-apoptosis pathways leading to subversion of cell cycle checkpoints and enhanced cancer cell survival and metastatic potential. Conversely, inhibition of these kinases may reverse the aberrant signaling in receptor-overexpressing cells and may result in growth arrest and/or tumor cell death. Thus, it is no surprise that kinases have been considered important targets for the identification of therapeutics. See, e.g., Bishop et al., Trends Cell Biol (2001) 11(4):167-72.

SUMMARY OF THE INVENTION

The present invention provides compositions and methods for assessing protein profiles in biological samples. In various embodiments, one or more samples, most preferably one or more complex protein mixtures as defined below, are contacted with one or more probes, referred to herein as "tagged acyl phosphate probes" or "TAPPs." These probes, have the following general structure:

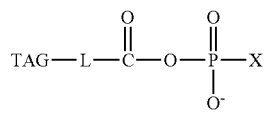

wherein TAG is a detectable label, L is a linker moiety covalently bound to the carbonyl through a carbon atom, and X is an affinity moiety for directing the binding of a TAPP to a set of target proteins. In preferred embodiments, X is linked through a carbon to form an acyl phosphonate, but is most preferably linked through an oxygen to form an acyl phosphate. The skilled artisan will understand that the activated acyl group of such a structure readily forms protein-bound adducts by reaction with nucleophilic groups such as an amino group on target protein molecules.

TAPPs are described herein in terms of nucleotide binding protein-directed affinity probes" or "NBAPs," comprising: a nucleotide or nucleotide analogue covalently bound through the terminal phosphate of a 5' mono- di- or tri-phosphate to an acyl group, which is itself further covalently bound to a detectable tag via a linker moiety. As described hereinafter, the nucleotide portion directs the binding of an NBAP to nucleotide binding proteins, or proteins intimately associated with nucleotide binding proteins. But the skilled artisan will understand that the affinity moiety X of a TAPP may be varied widely to provide probes directed to a number of proteins or protein families.

The binding selectivity of the probe(s) may be selected to allow the skilled artisan to analyze the presence, amount, and/or activity of a selected portion of the nucleotide binding proteins present in a sample, thereby simplifying the analysis of complex protein mixtures.

One or more TAPPs are combined with a protein-containing sample under conditions for binding and reaction of the TAPP(s) with target proteins that are present in the sample. The resulting products are then used to assess the target protein profile of the sample, and can be correlated to the presence, amount, or activity of one or more target proteins present in the original complex protein mixture.

In a first aspect, the present invention relates to methods and compositions for determining an enzyme profile in a complex protein mixture. These methods comprise contacting the complex protein mixture with one or more distinct TAPPs, each of which specifically reacts with one or more target proteins, preferably target nucleotide binding proteins, and most preferably target kinases. The labeled protein profile can then be analyzed by the screening and/or identification methods described hereinafter.

In preferred embodiments, the TAPP-protein conjugates can be separated from other components of the complex protein mixture, for example by sequestering one or more conjugates (e.g., by binding to a receptor that binds the TAG portion of the TAPP or by using a "tethered" TAPP), by chromatographic methods, by mass spectrographic methods, and/or by other means such as electrophoresis. Thus, in related aspects, the present invention also relates to purified polypeptides (e.g., proteins or protein fragments) bound to TAPP(s). In these aspects, the labeled polypeptides have the following structure:

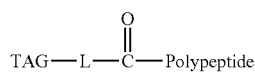

wherein the polypeptide is covalently bound to the carbonyl through an amide, ester, or thioester linkage.

In various embodiments, following reaction of the complex protein mixture with one or more TAPPs, the resulting TAPP-protein conjugates may be proteolytically digested to provide TAPP-labeled peptides. This digestion may occur while the protein conjugates are sequestered to a solid phase, or while free in solution. In preferred embodiments, TAPPs are selected such that each target protein forms a conjugate with a single TAPP, most preferably at a single discrete location in the target nucleotide binding protein; thus, each conjugate gives rise to a single TAPP-labeled peptide. Enrichment separation, or identification of one or more TAPP-labeled peptides may be achieved using liquid chromatography and/or electrophoresis. Additionally, mass spectrometry may be employed to identify one or more TAPP-labeled peptides by molecular weight and/or amino acid sequence. In particularly preferred embodiments, the sequence information derived from the TAPP-labeled peptide(s) is used to identify the protein from which the peptide originally derived. Variations of these aspects can involve the comparison of two or more proteomes, e.g., with TAPPs having different TAGs, or, when analysis comprises mass spectrometry, having different isotopic compositions.

In yet another aspect, the instant invention relates to methods for comparing the presence, amount, or activity of one or more target proteins in two or more complex protein mixtures using the methods and compositions described herein. In various embodiments, these methods comprise one or more of the following steps: contacting one or more complex protein mixture(s) with one or more TAPPs, where the TAPP(s) specifically bind to one or more target proteins present in each complex protein mixture; combining the complex protein mixtures following this contacting step to form a combined complex protein mixture; prior to and/or following this combination, removing one or more non-sequestered components of the complex protein mixture(s). The labeled protein profile can then be analyzed by the screening and/or identification methods described hereinafter.

In preferred embodiments, the methods and compositions described herein are applied to determining the nucleotide binding protein profiles of cancerous and other diseased tissue by obtaining one or more samples of diseased tissue, and determining the nucleotide binding protein profile of the tissue sample(s). In particularly preferred embodiments, the nucleotide binding protein profile of diseased tissues can be compared to that of normal tissue sample(s) to determine differences in the enzyme activity profiles of the two tissue samples.

In still another aspect, the present invention relates to methods and compositions for detecting disease in a test sample. In preferred embodiments the test sample will be a cell or tissue sample. In particularly preferred embodiments, the tissue sample will be a neoplasmic sample and the disease is a cancer. The methods involve determining the target protein profile of the test sample using one or more TAPPs; comparing the labeled protein profiles of the test sample with the labeled protein profile(s) of one or more known non-diseased sample and/or with the labeled protein profile(s) of one or more known diseased samples; and determining whether the test sample is in a state of disease. A "non-diseased" sample is a sample of cells or tissues that is known to not have the disease being tested for. It is preferably a normal, healthy sample of the cells or tissue.

In another aspect the present invention provides methods of determining the inhibitory potency of a test compound against one or more target proteins. The methods involve contacting one or more TAPPs with a test sample containing the test compound and the target protein(s); allowing the TAPPs to react with proteins contained in the test sample; and detecting a signal that indicates the level of TAPP binding to the target protein(s) in the test sample.

In preferred embodiments, this level of TAPP binding is compared to the level of TAPP binding to the target protein(s) in the absence of the test compound. By such methods, the inhibitory and/or stimulatory potency of the test compound against the target protein(s) can be determined. The "inhibitory potency" is the extent to which the presence of the compound causes the inhibition of TAPP binding, while "stimulatory potency" is the extent to which the presence of the compound causes an increase in TAPP binding.

In yet another aspect, the present invention provides kits for performing the methods described. The kits contain one or more of the materials described for conducting the methods. The kits can include TAPPs in the solid phase or in a liquid phase (such as buffers provided) in a package. The kits also can include buffers for preparing solutions for conducting the methods, and pipettes for transferring liquids from one container to another. By "package" is meant material enveloping a vessel containing the TAPPs. In preferred embodiments, the package can be a box or wrapping. The kit can also contain items that are not contained within the package but are attached to the outside of the package, for example, pipettes.

The summary of the invention described above is not limiting and other features and advantages of the invention will be apparent from the following detailed description of the preferred embodiments, as well as from the claims.

DETAILED DESCRIPTION OF THE INVENTION

Figure 1:
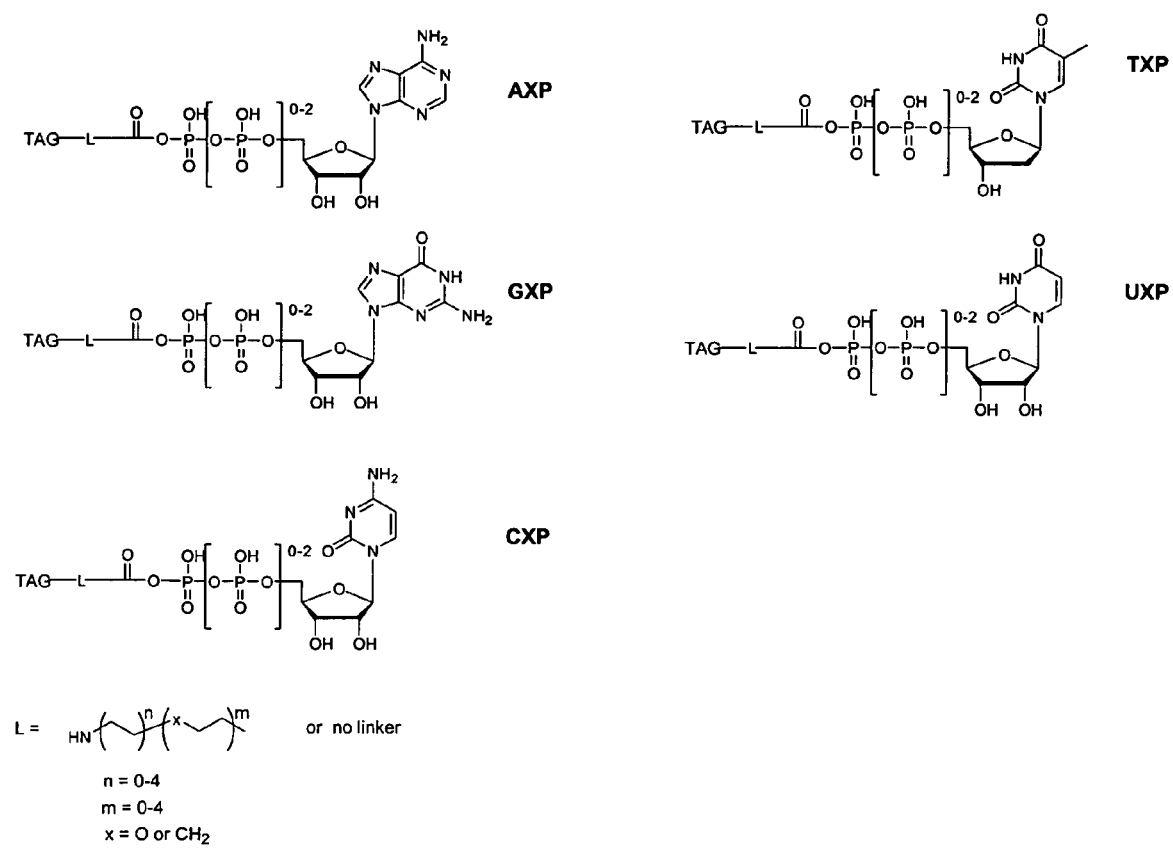
FIG. 1 shows exemplary acyl phosphate probes of the invention.

The subject methods and compositions provide enhanced simplicity and accuracy in identifying changes in the presence, amount, or activity of proteins in a complex protein mixture using TAPPs. As described hereinafter, preferred TAPPs are NBAPs that bind to target nucleotide binding protein(s) and proteins that interact with nucleotide binding protein(s). The profiling methods described herein can have a number of steps leading to the identification of, or determining the presence or amount of, target protein(s) in a complex protein mixture. A complex protein mixture, and preferably two or more complex protein mixtures, e.g., a sample and a control, can be used as obtained from a natural source or as processed, e.g., to remove interfering components and/or enrich the target protein components. Each complex protein mixture to be analyzed is combined under reaction conditions with at least one TAPP to produce conjugates with target nucleotide binding protein(s). The TAPPs used in two or more complex protein mixtures can differ as to the choice of TAG moiety, linker moieties, affinity moieties, and/or isotopic composition. In preferred embodiments, the labeled complex protein mixtures may be directly compared (e.g., in the same capillary of a capillary electrophoresis apparatus or lane in an electrophoresis gel, or in a mass spectrometer).

The analysis platforms described herein can differ as to the methods of enrichment and analysis using liquid chromatography and/or electrophoresis, and/or mass spectrometry for identification and quantitation. The choice of the platform is affected by the size of the sample, the rate of throughput of the samples, the mode of identification, and the need for and level of quantitation.

Of particular interest as target proteins in the present invention are nucleotide binding proteins, and most preferably protein kinases. The term "nucleotide binding protein" refers to proteins that bind nucleotide mono-, di- and/or tri-phosphates. Exemplary nucleotide binding protein families include kinase families described below; guanine nucleotide binding proteins (e.g. in G protein-coupled receptors); motor-related proteins (e.g., myosin, actin, tubulin, dynein, kinesin, etc.); nucleic acid polymerases; UspA and related proteins; P2 receptors; etc. This list is not meant to be limiting.

Protein kinases are the enzymes responsible for catalyzing the transfer of a γ-phosphoryl group from ATP to the hydroxyl group of serine, threonine or tyrosine residues in peptides, polypeptides, and proteins in a process known as "phosphorylation." Protein kinases have been identified in both prokaryotes and eukaryotes, and in both plants and animals. The list of identified kinases is extensive, including the following families of proteins: cyclic nucleotide regulated protein kinase (PKA & PKG) family; diacylglycerol-activated/phospholipid-dependent protein kinase C (PKC) family; kinases that phoshorylate G protein-coupled receptors family; budding yeast AGC-related protein kinase family; kinases that phosphorylate ribosomal protein S6 family; budding yeast DBF2/20 family; flowering plant PVPK1 protein kinase homolog family; kinases regulated by $Ca^{2+}$/CaM and close relatives family; KIN1/SNF1/Nim1 family; cyclin-dependent kinases (CDKs) and close relatives family; ERK (MAP) kinase family; glycogen synthase kinase 3 (GSK3) family; casein kinase II family; Clk family; Src family; Tec/Atk family; Csk family; Fes (Fps) family; Abl family; Syk/ZAP70 family; Tyk2/Jak1 family; Ack family; focal adhesion kinase (Fak) family; epidermal growth factor receptor family; Eph/Elk/Eck receptor family; Axl family; Tie/Tek family; platelet-derived growth factor receptor family; fibroblast growth factor receptor family; insulin receptor family; LTK/ALK family; Ros/Sevenless family; Trk/Ror family; DDR/TKT family; hepatocyte growth factor receptor family, nematode Kin15/16 family; Polo family; MEK/STE7 family; PAK/STE20 family; MEKK/STE11 family; NimA family; wee1/mik1 family; kinases involved in transcriptional control family; Raf family; activin/TGFb receptor family; flowering plant putative receptor kinases and close relatives family; PSK/PTK "mixed lineage" leucine zipper domain family; casein kinase I family; and PKN prokaryotic protein kinase family.

The compositions and methods described herein find use for the most part with biological samples, which may have been subject to processing before reaction with the TAPPs. "Biological sample" intends a sample obtained from a cell, tissue, or organism. Examples of biological samples include proteins obtained from cells (e.g., mammalian cells, bacterial cells, cultured cells, human cells, plant cells, etc.), particularly as a lysate, a biological fluid, such as blood, plasma, serum, urine, bile, saliva, tears, cerebrospinal fluid, aqueous or vitreous humor, or any bodily secretion), a transudate or exudate (e.g. fluid obtained from an abscess or other site of infection or inflammation), a fluid obtained from a joint (e.g. synovial fluid obtained from a normal joint or a joint affected by disease such as rheumatoid arthritis, osteoarthritis, gout or septic arthritis), or the like.

Biological samples may be obtained from any organ or tissue (including a biopsy or autopsy specimen) or may comprise cells (including primary cells, passaged or cultured primary cells, cell lines, cells conditioned by a specific medium) or medium conditioned by cells. In preferred embodiments, a biological sample is free of intact cells. If desired, the biological sample may be subjected to prior processing, such as lysis, extraction, subcellular fractionation, and the like. See, Deutscher (ed.), 1990, Methods in Enzymology, vol. 182, pp. 147-238.

Of particular interest are samples that are "complex protein mixtures." As used herein, this phrase refers to protein mixtures having at least about 20, more usually at least about 50, even 100 or more different proteins, where the particular distribution of proteins is of interest. An example of such a complex protein mixture is a proteome, as defined hereinafter. Complex protein mixtures may be obtained from cells that are normal or abnormal in some particular, where the abnormality is informative as to treatment, status, disease, or the like, can be analyzed using the methods of the subject invention.

The term "proteome" as used herein refers to a complex protein mixture obtained from a biological sample. Preferred proteomes comprise at least about 5% of the total repertoire of proteins present in a biological sample (e.g., the cells, tissue, organ, or organism from which a lysate is obtained; the serum or plasma, etc.), preferably at least about 10%, more preferably at least about 25%, even more preferably about 75%, and generally 90% or more, up to and including the entire repertoire of proteins obtainable from the biological sample. Thus the proteome may be obtained from an intact cell, a tissue, an organ, and the like. The proteome will be a mixture of proteins, generally having at least about 20 different proteins, usually at least about 50 different proteins and in most cases 100 different proteins or more.

Generally, the sample will have at least about $1 \times 10^{-11}$ g of protein, and may have 1 g of protein or more, preferably at a concentration in the range of about 0.1-50 mg/ml. For screening applications, the sample will typically be between about 1×10⁻¹¹ g of protein and about 1×10⁻³ g of protein, preferably between about 1×10⁻⁶ g of protein and 1×10⁻⁴ g of protein. For identification of labeled active target kinases, the sample will typically be between about 1×10⁻⁹ g of protein and about 1 g of protein, preferably between about 1×10⁻⁴ g of protein and 1×10⁻¹ g of protein. The term "about" in this context refers to +/−10% of the amount listed.

The sample may be adjusted to the appropriate buffer concentration and pH, if desired. One or more TAPPs may then be added, each at a concentration in the range of about 1 nM to 20 mM, preferably 10 nM to 1 mM, most preferably 10 nm to 100 μM. After incubating the reaction mixture, generally for a time for the reaction to go substantially to completion, generally for about 0.11-60 minutes, at a temperature in the range of about 5-40° C., preferably about 10° C. to about 30° C., most preferably about 20° C., the reaction may be quenched.

In one aspect of the invention, the methods and compositions provide for qualitative (e.g., relative comparison between two samples) and/or quantitative measurement of target nucleotide binding protein(s) in biological fluids, cells or tissues. Moreover, the same general strategy can be broadened to achieve the proteome-wide, qualitative and quantitative analysis of target protein(s), by employing TAPPs with differing target specificities. The methods and compositions of this invention can be used to identify labeled target protein(s) of low abundance that are present in complex protein mixtures and can be used to selectively analyze specific-groups or classes of proteins, such as membrane or cell surface kinases, or kinases contained within organelles, sub-cellular fractions, or biochemical fractions such as immunoprecipitates. Further, these methods can be applied to analyze differences in expressed target proteins in different cell states. For example, the methods and reagents herein can be employed in diagnostic assays for the detection of the presence or the absence of one or more target proteins indicative of a disease state, such as cancer.

The subject methods and compositions can be used for a variety of purposes, such as the diagnosis of disease, the response of cells to an external agent, e.g. a drug, staging diseases, such as neoplasia, identifying cell differentiation and maturation, identifying new proteins, screening for active drugs, determining side effects of drugs, determining selectivity of drugs, identifying responses to drugs specific to certain genotypes (e.g., allelic differences in individuals), identifying useful probes from combinatorial libraries, etc.

The system uses TAPPs that are typically directed to an active site on target protein(s). However, many proteins may be labeled, not as a result of their own interaction with a TAPP, but by their proximity to a second protein that does interact with a TAPP. For example, numerous nucleotide binding proteins (e.g., kinases, G-protein coupled receptors, etc.) are members of multisubunit complexes. An NBAP may be selected for its ability to interact with the nucleotide binding site of a particular kinase; but may bind to one or more member(s) of the complex that lie sufficiently close to that nucleotide binding site, even though the other member(s) do not themselves bind to the NBAP.

This ability to bind members of the complex may also be related to various physiological states, as it may be that the other member(s) of the complex are only sufficiently close to that nucleotide binding site under certain circumstances (e.g., when the kinase is phosphorylated, or when a cofactor is present). Similarly, different sites on a target protein may be differentially labeled in different physiological states, as when the target protein changes three-dimensional conformation under similar circumstances.

In certain embodiments, a plurality of TAPPs may be combined for use in a labeling method, depending on the specificity of the TAPPs and the variety in the group or groups of proteins to be assayed. In the present invention, it is not necessary that there be no reaction of a TAPP with non-target protein(s). Rather, a TAPP is defined as being "specific for," as "specifically reacting with," or as "specifically binding to," target protein(s) if the TAPP provides at least about twice the amount of signal from TAPP labeling of target protein(s) when compared to an equivalent amount of non-target protein. Preferably the signal obtained from target protein(s) will be at least about five fold, preferably 10 fold, more preferably 25-fold, even more preferably 50-fold, and most preferably 100-fold or more, greater than that obtained from an equivalent amount of non-target protein.

The term "target protein" as used herein refers to one or more protein(s), a residue of which specifically reacts with, and becomes covalently labeled by, one or more TAPPs. Preferred targets are kinases generally classified under the Enzyme Commission number 2.7.1.X. Particularly preferred kinases are protein kinases, classified under the Enzyme Commission number 2.7.1.37. The reaction mixture can provide conditions under which the TAPP(s) react substantially preferentially with functional target proteins, preferably functional target kinases. Particularly preferred target kinases include phosphorylase b kinase; glycogen synthase a kinase; hydroxyalkyl-protein kinase; serine(threonine) protein kinase; A-kinase; AP50 kinase; ATP-protein transphosphorylase; βIIPKC; β-andrenergic receptor kinase; calcium/phospholipid-dependent protein kinase; calcium-dependent protein kinase C; cAMP-dependent protein kinase A; cAMP-dependent protein kinase; casein kinase; casein kinase I; casein kinase II; casein kinase 2; cGMP-dependent protein kinase; CK-2; CKI; CKII; cyclic monophosphate-dependent protein kinase; cyclic AMP-dependent protein kinase; cyclic AMP-dependent protein kinase A; cyclic nucleotide-dependent protein kinase; cyclin-dependent kinase; cytidine 3',5'-cyclic monophosphate-responsive protein kinase; ε PKC; glycogen synthase kinase; Hpr kinase; hydroxyalkyl-protein kinase; protein kinase (phosphorylating); casein kinase (phosphorylating); MAPK; mitogen-activated protein kinase; mitogen-activated S6 kinase; M phase-specific cdc2 kinase; p82 kinase; phosphorylase b kinase; PKA; PKC; protein serine kinase; protein kinase A; protein kinase p58; protein phosphokinase; protein glutamyl kinase; protein serine-threonine kinase; protein kinase CK2; protein-aspartyl kinase; protein-cysteine kinase; protein-serine kinase; Raf kinase; Raf-1; ribosomal S6 protein kinase; ribosomal protein S6 kinase II; serine kinase; serine-specific protein kinase; serine protein kinase; serine/threonine protein kinase; T-antigen kinase; threonine-specific protein kinase; twitchin kinase; and type-2 casein kinase.

The term "functional target protein" refers to a target protein that is in its native conformation and is able to interact with an entity with which it normally interacts, e.g. enzyme with substrate and/or cofactor, receptor with ligand, etc., e.g. phosphorylated active form as compared to unphosphorylated inactive form and vice versa. Preferably, the functional target protein is in the form in which it can carry out its biological function.

The term "inactivated" as used herein refers to a sample that has been treated so that at least a portion of target protein(s) that were functional in the original sample are rendered unable to interact with those entities with which it normally interacts. For example, an "inactive nucleotide binding protein" can result from various mechanisms such as denaturation, inhibitor binding, either covalently or non-covalently, mutation, secondary processing, e.g. phosphorylation or dephosphorylation, etc.

The term "untreated" as used herein refers to a sample that has not been exposed to one or more conditions as compared to a second sample not exposed to such conditions. An untreated sample may be a sample that has not been inactivated; alternatively, an untreated sample may be one not exposed to one or more molecules (e.g., drug lead compounds) in a screening assay. Thus the compositions and methods described herein may comprise comparing a complex protein mixture obtained from cell(s), tissue(s), or organism(s) treated with one or more compounds (e.g., lead compounds in drug discovery) to a complex protein mixture obtained from cell(s), tissue(s), or organism(s) not so treated. TAPP-labeled proteins and/or peptides from the two samples may be compared for relative signal intensity. Such methods may indicate alterations in active protein content due to the treatment regimen. Additionally, such methods can also differentiate between treatments that act by direct inhibition of specific proteins ("primary effects") versus treatments that affect active protein content upstream, e.g., by altering expression of protein(s) ("secondary effects").

As used herein, the term "purified" in reference to labeled target proteins or polypeptides does not require absolute purity. Instead, it represents an indication that the labeled target proteins or polypeptides are relatively more pure than in the environment in which the proteins or polypeptides were labeled. A "purified" labeled target protein or polypeptide is preferably at least 10% pure. A "substantially purified" labeled target protein or polypeptide is preferably at least 50% pure, more preferably at least 75% pure, and most preferably at least 95% pure.

An "active site" of a protein refers to an area on the surface of a protein, e.g., an enzyme molecule or surface membrane receptor, to which a binding molecule, e.g. substrate, reciprocal ligand, allosteric modulator, etc., is bound and results in a change in the protein and/or ligand. For a receptor, the conformation may change, the protein may become susceptible to phosphorylation or dephosphorylation or other processing. For the most part, the active site will be the site(s) of an enzyme where the substrate and/or a cofactor bind, where the substrate and cofactor undergo a catalytic reaction; where two proteins form a complex, e.g. the site at which a G protein binds to a surface membrane receptor, two kringle structures bind, sites at which transcription factors bind to other proteins; or sites at which proteins bind to specific nucleic acid sequences, etc. The skilled artisan will understand that an active site need not be presently performing a catalytic function, but may still bind a TAPP. For example, numerous kinases may bind to adenine nucleotides, but the catalytic function of the kinase may be inhibited due to phosphorylation state, etc.

Structure of TAPPs

The term "tagged acyl phosphate probes" or "TAPPs" refers to molecules having the following general structure:

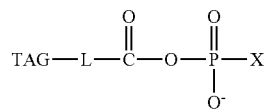

wherein TAG is a detectable label, L is a linker moiety covalently bound to the carbonyl through a carbon atom, and X is an affinity moiety for directing the binding of a TAPP to a set of target proteins. A detailed description of a design strategy that can be adapted to the preparation of TAPPs in which a fluorescent moiety can act as a TAG is provided in PCT Application No. PCT/US02/03808, entitled "Activity Based Probe Analysis", filed Feb. 5, 2002, PCT Application No. PCT/US00/34187, WO 01/77684, entitled "Proteomic Analysis," and PCT Application No. PCT/US00/34167, WO 01/77668, entitled "Proteomic Analysis," each of which is hereby incorporated by reference in its entirety, including all tables, figures, and claims. Goals of a design strategy are to provide NBAPs that are able to react covalently with a targeted group of nucleotide binding protein(s), while minimizing non-specific labeling.

The term acyl refers to the structure:

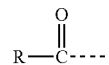

where the carbonyl carbon is bound to a carbon in R.

The term "linker moiety" refers to a bond or chain of atoms used to link one moiety to another, serving as a covalent linkage between two or more moieties. Since in many cases, the synthetic strategy will be able to include a functionalized site for linking, the functionality can be taken advantage of in choosing the linking moiety. The choice of linker moiety may alter the specificity of a TAPP. See, e.g., Kidd et al., *Biochemistry* (2001) 40: 4005-15. For example, an alkylene linker moiety and a linker moiety comprising a repeating alkyleneoxy structure (polyethylene glycols, or "PEG"), have distinct specificities and provide distinct protein profiles. Thus, one of skill in the art can select the linker moiety of the TAPP in order to provide additional specificity of the TAPP for a particular protein or protein class.

Linker moieties include among others, ethers, polyethers, diamines, ether diamines, polyether diamines, amides, polyamides, polythioethers, disulfides, silyl ethers, alkyl or alkenyl chains (straight chain or branched and portions of which may be cyclic) aryl, diaryl or alkyl-aryl groups, having from 0 to 3 sites of aliphatic unsaturation. While normally amino acids and oligopeptides are not preferred, when used they will normally employ amino acids of from 2-3 carbon atoms, i.e. glycine and alanine. Aryl groups in linker moieties can contain one or more heteroatoms (e.g., N, O or S atoms). The linker moieties, when other than a bond, will have from about 1 to 60 atoms, usually 1 to 30 atoms, where the atoms include C, N, O, S, P, etc., particularly C, N and O, and will generally have from about 1 to 12 carbon atoms and from about 0 to 8, usually 0 to 6 heteroatoms. The number of atoms referred to above are exclusive of hydrogen in referring to the number of atoms in a group, unless indicated otherwise.

Linker moieties may be varied widely depending on their function, including alkyleneoxy and polyalkyleneoxy groups, where alkylene is of from 2-3 carbon atoms, methylene and polymethylene, polyamide, polyester, and the like, where individual monomers will generally be of from 1 to 6, more usually 1 to 4 carbon atoms. The oligomers will generally have from about 1 to 10, more usually 1 to 8 monomeric units. The monomeric units may be amino acids, both naturally occurring and synthetic, oligonucleotides, both naturally occurring and synthetic, condensation polymer monomeric units and combinations thereof.

Linker moieties provide a covalent linkage between a TAG and the carbonyl of the acyl group; thus, the final atom of the linker moiety that is covalently linked to the carbonyl must be carbon. A linker moiety may form a branching structure, whereby additional groups, such as a second TAG, may be included in the TAPP structure.

The term "TAG" as used herein refers to a molecule that can be used to detect and/or capture the TAPP in combination with any other moieties that are bound strongly to the TAG, so as to be retained in the process of the reaction of the reactive group with the target active protein. The TAG may be added to the linker moiety combination after reaction of the acyl-nucleotide with the target protein, to form the complete TAPP. For this purpose, the linker moiety will include a chemically reactive group, normally not found in proteins, that will react with a reciprocal functionality on the TAG, e.g. viccinal-diols with boronic acid, photoactivated groups, such as diazo, azide with an alkene or alkyne, o-alkyl hydroxylamine with a ketone or aldehyde, etc. The TAG portion permits capture of the conjugate of the target protein and the TAPP. The TAG may be displaced from the capture reagent by addition of a displacing-TAG, which may be free TAG or a derivative of the TAG, or by changing solvent (e.g., solvent type or pH) or temperature or the linker may be cleaved chemically, enzymatically, thermally or photochemically to release the isolated materials (see discussion of the linker moiety, below).

Examples of TAGs include, but are not limited to, detectable labels such as fluorescent moieties and electrochemical labels, biotin, digoxigenin, maltose, oligohistidine, 2,4-dinitrobenzene, phenylarsenate, ssDNA, dsDNA, a polypeptide, a metal chelate, a saccharide, and/or a solid phase. Examples of TAGs and their capture reagents also include but are not limited to: dethiobiotin or structurally modified biotin-based reagents, including deiminobiotin, which bind to proteins of the avidin/streptavidin family, which may, for example, be used in the forms of strepavidin-Agarose, oligomeric-avidin-Agarose, or monomeric-avidin-Agarose; any vicinal diols, such as 1,2-dihydroxyethane ($HO-CH_2-CH_2-OH$), and other 1,2-dihyroxyalkanes including those of cyclic alkanes, e.g., 1,2-dihydroxycyclohexane which bind to an alkyl or aryl boronic acid or boronic acid esters, such as phenyl-$B(OH)_2$ or hexyl-$B(OEthyl)_2$ which may be attached via the alkyl or aryl group to a solid support material, such as Agarose; maltose which binds to maltose binding protein (as well as any other sugar/sugar binding protein pair or more generally to any TAG/TAG binding protein pairs that has properties discussed above); a hapten, such as the dinitrophenyl group, to which an antibody can be generated; a TAG which binds to a transition metal, for example, an oligomeric histidine will bind to Ni(II), the transition metal capture reagent may be used in the form of a resin bound chelated transition metal, such as nitrilotriacetic acid-chelated Ni(II) or iminodiacetic acid-chelated Ni(II); glutathione which binds to glutathione-S-transferase. In preferred embodiment, the TAGs will be haptens that bind to a naturally occurring receptor, e.g. biotin and avidin, or an antibody or will be a detectable label, that is also a hapten.

One may use chemical affinity resins, e.g. metal chelates, to allow for digestion of proteins on the solid phase resin and facilitate automation. One example of this is the use of immobilized nickel (II) chelates to purify peptides that have six consecutive histidine residues (His-6 tag) (as described in the Invitrogen product brochureProBond™ Resin (Purification) Catalog nos. R801-01, R801-15 Version D 000913 28-0076), which could be adapted to include non-peptidic chemical linkage coupling a series of imidazole-containing moieties. Alternative chemical attachments include phenyldiboronic acids (described in Bergseid, M. et al. Biotechniques (2000) 29(5), 1126-1133), and disulfide reagents (described in Daniel, S M et al., Biotechniques (1998) 24(3), 484-489). Additionally, chemical affinity tags that are useful in combinatorial synthesis could be adapted for modified peptide purification (reviewed in Porco, J A (2000) Comb. Chem. High Throughput Screening 3(2) 93-102

The term "fluorescent moiety" ("Fl") refers to a TAG that can be excited by electromagnetic radiation, and that emits electromagnetic radiation in response in an amount sufficient to be detected in an assay. The skilled artisan will understand that a fluorescent moiety absorbs and emits over a number of wavelengths, referred to as an "absorbance spectrum" and an "emission spectrum." A fluorescent moiety will exhibit a peak emission wavelength that is a longer wavelength than its peak absorbance wavelength. The term "peak" refers to the highest point in the absorbance or emission spectrum.

The fluorescent moiety Fl may be varied widely depending upon the protocol to be used, the number of different TAPPs employed in the same assay, whether a single or plurality of lanes are used in the electrophoresis, the availability of excitation and detection devices, and the like. For the most part, the fluorescent moieties that are employed as TAG will absorb in the ultraviolet, infrared, and/or most preferably in the visible range and emit in the ultraviolet, infrared, and/or most preferably in the visible range. Absorption will generally be in the range of about 250 to 750 nm and emission will generally be in the range of about 350 to 800 nm. Illustrative fluorescent moieties include xanthene dyes, naphthylamine dyes, coumarins, cyanine dyes and metal chelate dyes, such as fluorescein, rhodamine, rosamine, the BODIPY dyes (FL, TMR, and TR), dansyl, lanthanide cryptates, erbium. terbium and ruthenium chelates, e.g. squarates, and the like. Additionally, in certain embodiments, one or more fluorescent moieties can be energy transfer dyes such as those described in Waggoner et al., U.S. Pat. No. 6,008,373. The literature amply describes methods for linking fluorescent moieties through a wide variety of linker moieties to other groups. The fluorescent moieties that find use will normally be under 2 kDal, usually under 1 kDal.

Preferred fluorescent moieties Fl can include elaborated conjugated pyran molecules, including xanthenes. Such molecules include eosin, erythrosin, fluorescein, Oregon green, and various commercially available Alexa Fluor® dyes (Molecular Probes, Inc.). Structural examples of such dyes include:

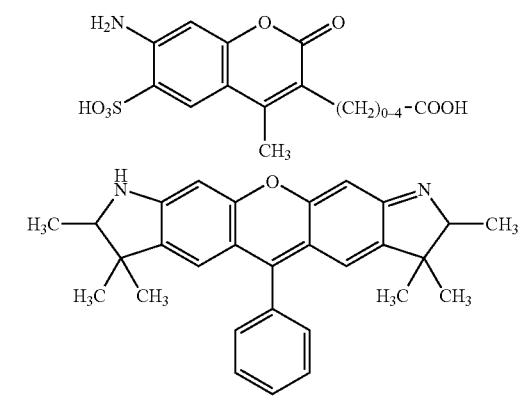

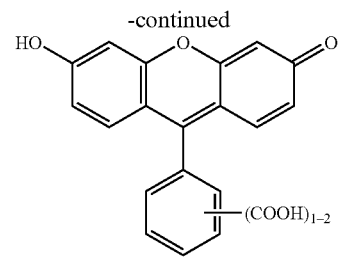

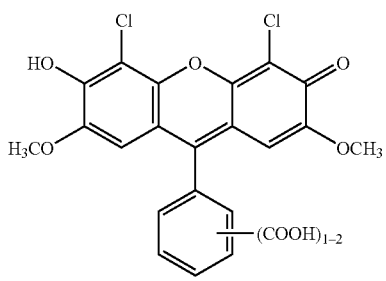

Particularly preferred fluorescent moieties are the rhodamine dyes. These molecules typically have the general structure:

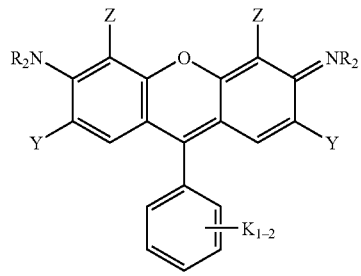

Where K is —CO$_2$H, or —SO$_3$H; Y is —H, —CH$_3$, or together with R forms a six-membered ring; Z is —H or together with R forms a six-membered ring; and R is —H, —CH$_3$, —CH$_2$CH$_3$, or together with Y or Z forms a six-membered ring. Rhodamine molecules such as tetramethylrhodamine, 5-carboxytetramethylrhodamine, 6-carboxytetramethylrhodamine, carboxyrhodamine-6G, rhodamine-B sulfonyl chloride, rhodamine-red-X, and carboxy-X-rhodamine are well known to those of skill in the art. See, e.g., Handbook of Fluorescent Probes and Research Products, Molecular Probes, Inc., 2001, which is hereby incorporated by reference in its entirety. Advantageous properties of rhodamines include high quantum yields, low sensitivity of fluorescence over a pH range of from about pH 3 to about pH 8, advantageous water solubility, good photostability, and absorption of light in the visible spectrum. Particularly preferred fluorescers are 5-carboxytetramethylrhodamine and 6-carboxytetramethylrhodamine.

Other preferred fluorescent moieties Fl include the BODIPY dyes, which are elaborations of a 4-bora-3a,4a-diaza-s-indacene structure. Exemplary structures are provided below:

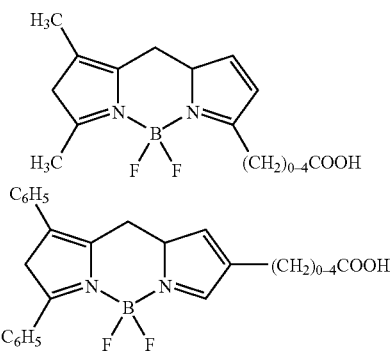

Yet other preferred fluorescent moieties include the cyanine dyes, conjugated structures comprising a polymethine chain terminating in nitrogen atoms. Typically, the nitrogens are themselves part of a conjugated heterocycle. An exemplary structures is provided below:

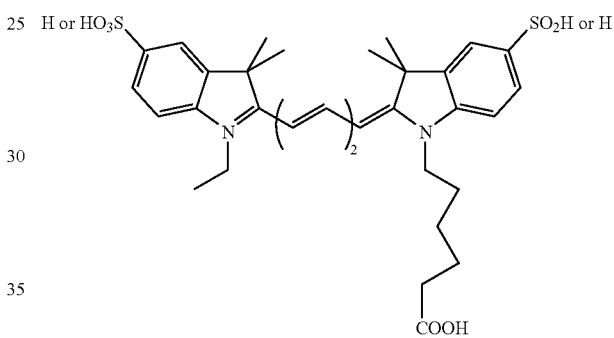

Also of interest for use as TAGs are matched dyes as described in U.S. Pat. No. 6,127,134, which is hereby incorporated by reference in its entirety, including all tables, figures, and claims, which is concerned with labeling proteins with dyes that have different emissions, but have little or no effect on relative migration of labeled proteins in an electrophoretic separation. Of particular interest are the cyanine dyes disclosed therein, being selected in '134 because of their positive charge, which matches the lysine to which the cyanine dyes bind. In addition there is the opportunity to vary the polyene spacer between cyclic ends, while keeping the molecular weight about the same with the introduction of an alkyl group in the shorter polyene chain dye to offset the longer polyene. Also described are the BODIPY dyes, which lack a charge. The advantage of having two dyes that similarly affect the migration of the protein would be present when comparing the native and inactivated samples, although this would require that in the inactivated sample at least a portion of the protein is monosubstituted.

In each of the foregoing examples of preferred fluorescent moieties, carboxyl groups can provide convenient attachment sites for linker moieties. In the particularly preferred 5- and 6-carboxyrhodamine molecules, the 5- or 6-carboxyl is particularly preferred as an attachment site:

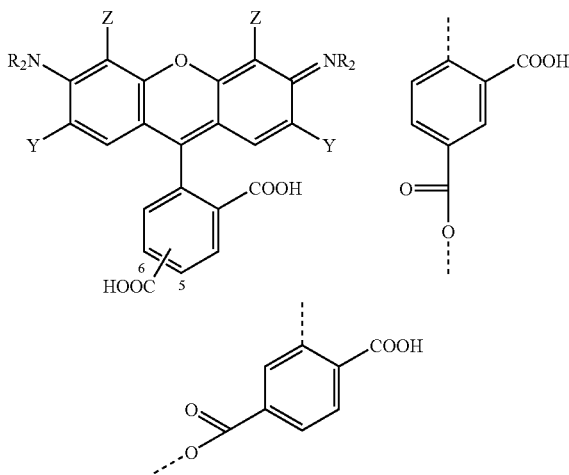

While the following preferred embodiments and exemplified compounds are generally described using only the 5-carboxyrhodamine molecules for the sake of brevity, in each case the 6-carboxyrhodamine version of the indicated molecule, or a mixture of the 5- and 6-carboxyrhodamine molecules should also be considered as an exemplified preferred embodiment.

In general, any affinity label-capture reagent commonly used for affinity enrichment, which meets the suitability criteria discussed above, can be used in the method of the invention. Biotin and biotin-based affinity TAGs are particularly illustrated herein. Of particular interest are structurally modified biotins, such as deiminobiotin or dethiobiotin, which will elute from avidin or streptavidin (strept/avidin) columns with biotin or under solvent conditions compatible with ESI-MS analysis, such as dilute acids containing 10-20% organic solvent. For example, deiminobiotin tagged compounds will elute in solvents below about pH 4.

In certain embodiments, TAPPs can be immobilized on a solid phase to form a "tethered" TAPP in which the TAG is represented by the solid phase. In preferred embodiments, a plurality of different TAPPs may be tethered to different regions of one or more solid phases to form a patterned array. Such a patterned array having two or more regions comprising TAPPs that differ in structure and/or reactivities from each other could be used to simultaneously measure the presence, amount, or activity of a plurality of target nucleotide binding proteins. The term "solid phase" as used herein refers to a wide variety of materials including solids, semi-solids, gels, films, membranes, meshes, felts, composites, particles, and the like typically used by those of skill in the art to sequester molecules. The solid phase can be non-porous or porous. Suitable solid phases include those developed and/or used as solid phases in solid phase binding assays. See, e.g., chapter 9 of Immunoassay, E. P. Diamandis and T. K. Christopoulos eds., Academic Press: New York, 1996, hereby incorporated by reference. Examples of suitable solid phases include membrane filters, cellulose-based papers, beads (including polymeric, latex, glass, and paramagnetic particles), glass, silicon wafers, microparticles, nanoparticles, TentaGels, AgroGels, PEGA gels, SPOCC gels, and multiple-well plates. See, e.g., Leon et al., Bioorg. Med. Chem. Lett. 8: 2997 (1998); Kessler et al., Agnew. Chem. Int. Ed. 40: 165 (2001); Smith et al., J. Comb. Med. 1: 326 (1999); Orain et al., Tetrahedron Lett. 42: 515 (2001); Papanikos et al., J. Am. Chem. Soc. 123: 2176 (2001); Gottschling et al., Bioorg. And Medicinal Chem. Lett. 11: 2997 (2001).

The specificity and affinity of a TAPP may be affected by the choice of the affinity moiety, the linker moiety, the TAG, or a combination thereof. In certain embodiments, the affinity moiety X may be deleted; in these embodiments, L can provide an affinity moiety either inherently in its own structure, or by means of a branched L linking both a TAG and a separate affinity moiety. One or more TAPPs may be designed that exhibit specificity for a single target protein, or that exhibit specificity for a plurality of targets that may be structurally or functionally related.

Figure 5:
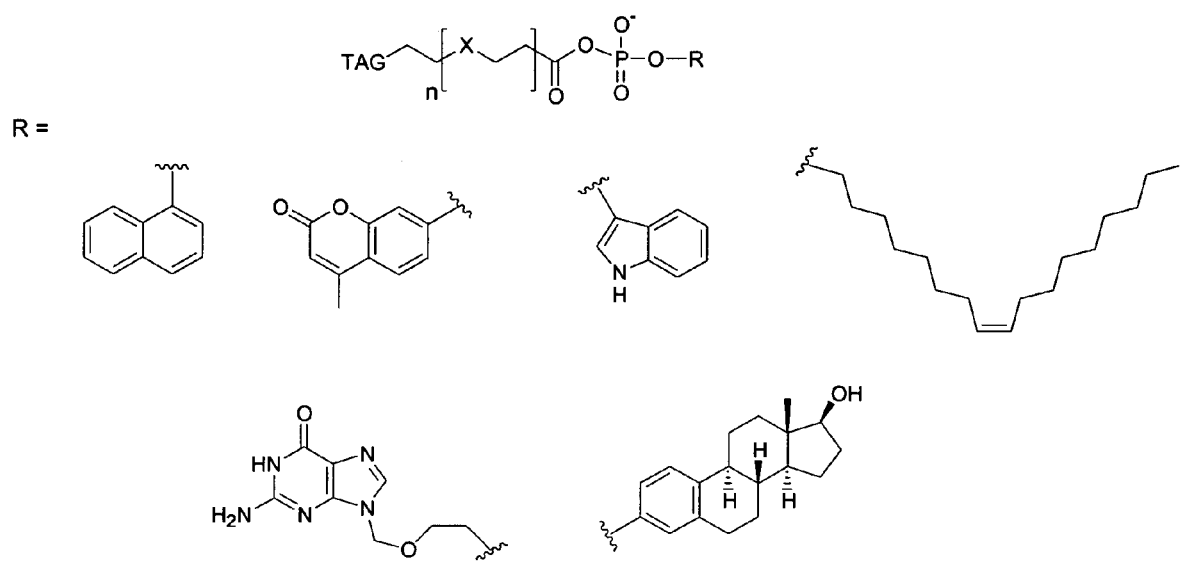
FIG. 5 shows exemplary affinity moieties for use in preparing acyl phosphate probes of the invention.

TAPPs of the present invention may comprise any affinity moiety that directs a TAPP to target proteins of interest. Suitable affinity moieties include small molecules, such as combinatorial libraries or therapeutic lead compounds; hormones, such as steroids, peptide hormones, etc.; cofactors; vitamins; enzyme substrates; lipids; prostaglandins; receptor ligands; nucleotides and nucleotide analogues, optionally substituted naphthyl groups, etc. As used herein, the term "small molecule" refers to compounds having molecular mass of less than 3000 Daltons, preferably less than 2000 or 1500, still more preferably less than 1000, and most preferably less than 600 Daltons. Exemplary alternative affinity moieties are shown in FIG. 5. All that is required of an affinity moiety is that it comprises an available alcohol for attachment of the acyl phosphate; or an available carbon atom for attachment of the acyl phosphonate.

Exemplary Acyl Nucleotide NBAPs

Exemplary TAPPs described in detail below are those in which the affinity moiety X is selected to provide an acyl-nucleotide structure. Referred to herein by the term "nucleotide binding protein-directed affinity probes" ("NBAPs"), these preferred TAPPs comprise a nucleotide or nucleotide anlogue covalently bound through the terminal phosphate of a 5' mono- di- or tri-phosphate (or 2' or 3' mono-, di-, or tri-phosphate) to an acyl group, which is itself further covalently bound to a TAG via a linker moiety.

The term "nucleotide" as used herein refers to a purine or pyrimidine base linked glycosidically to ribose, 2' or 3' deoxyribose, or 2',3' dideoxyribose; and which comprise a 5' mono- di- or tri-phosphate. Preferred bases include adenine, thymine, uracil, guanine, cytosine, and inosine. Normaturally occurring bases such as 5-bromouracil, 5-fluorouracil, 2-aminopurine, $N^6$-cyclohexyl adenine, $1,N^6$-ethenoadenosine; 8-azaguanine, and 5-fluorocytosine are also well known in the art. This list is not meant to be limiting, and any purine or pyrimidine base is within the scope of the present invention. The general structure of nucleotides is as follows:

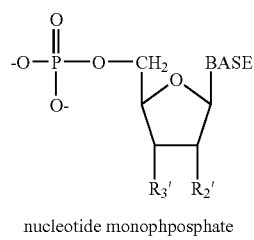

nucleotide monophposphate

-continued

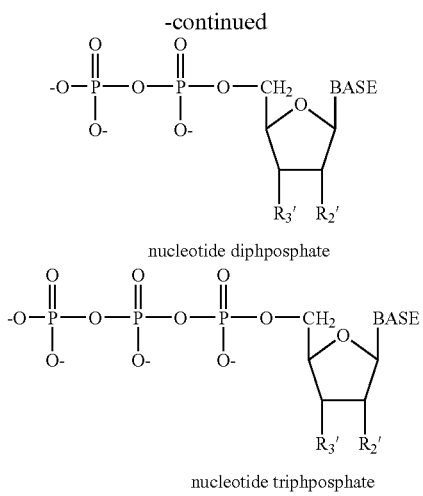

nucleotide diphposphate nucleotide triphposphate where $R_{2'}$ and $R_{3'}$ are independently H or OH, and where BASE is a purine or pyrimidine.

The term "nucleotide analogue" as used herein refers to a nucleotide-like structure in which the purine or pyrimidine BASE is replaced with a non-purine or non-pyrimidine structure (e.g., substituted or unsubstituted triazine, pyridazine, pyrazine, pyrrolopyrimidine, or pyrrazolopyrimidine); in which the ribose is replaced with a non-ribose structure; in which the oxygen lying between adjacent phosphates is replaced (e.g., with NH, S, or methylene); in which $R_{2'}$ and $R_{3'}$ are other than H or OH or in which the phosphate moiety or moieties is at the $R_{2'}$ or $R_{3'}$ position; and which binds to a nucleotide binding site of at least one nucleotide binding protein. See, e.g., U.S. Pat. Nos. 6,255, 292; 6,043,060; and 5,215,970.

Figure 4:
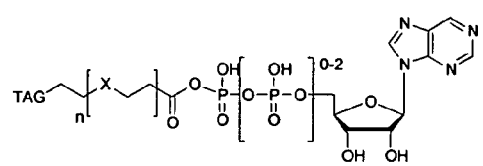
FIG. 4 shows exemplary BASEs for use in preparing acyl phosphate probes of the invention.
Figure 4:
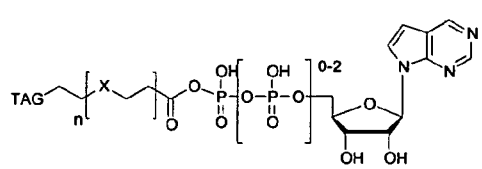
Figure 4:
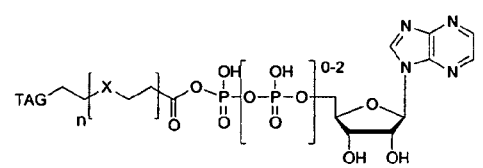
Figure 4:
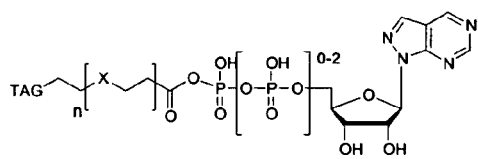
Figure 4:
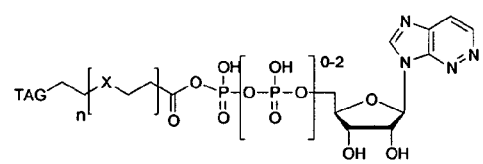
Figure 4:
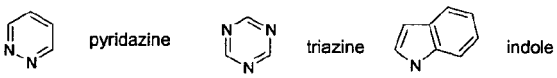
Figure 4:
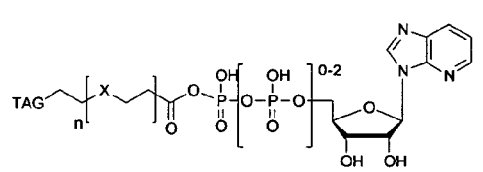
Figure 4:
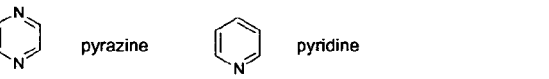
Figure 4:

The term "BASE" as used herein refers to a 5- or 6-membered unsaturated heterocyclic ring comprising from 1 to 3 nitrogen heteroatoms; attached through a ring heteroatom to the 1' position of a ribose, wherein the 5- or 6-membered heterocyclic ring may comprise a 6-membered unsaturated carbocyclic or heterocyclic ring comprising from 1 to 2 nitrogen heteroatoms. Each carbon position in the BASE may be optionally substituted by a substituent independently selected from the group consisting of —H, —F, —Br, —Cl, —SCH$_3$, —C(O)N(R)(R), —CN, —NO$_2$, —N(R)(R), ═O, acetoxy, —C(R)(R)(R), —OCH$_3$, —OCH$_2$CH$_3$, methylene dioxy, trihalomethyl, trihalomethoxy, or —(CH$_2$)$_n$OH, where each R is independently H or —C$_{1-6}$ alkyl straight or branched chain, and n is 0-6. Exemplary BASE structures are shown in FIG. 4.

In preferred embodiments, a nucleotide or nucleotide analogue of the present invention comprises a base (preferably a substituted or unsubstituted purine or pyrimidine) linked glycosidically to ribose, and $R_{2'}$ and $R_{3'}$ are independently selected from the group consisting of —H, —OH, —F, —Br, —Cl, —SCH$_3$, —C(O)N(R)(R), —CN, —NO$_2$, —N(R)(R), benzoyl, benzoylbenzoyl, azido, acetoxy, —C(R)(R)(R), —OCH$_3$, —OCH$_2$CH$_3$, methylene dioxy, trihalomethyl, trihalomethoxy, —(CH$_2$)$_n$OH, or —(CH$_2$)$_n$-phenyl where phenyl is optionally substituted with —F, —Br, —Cl, —SCH$_3$, —C(O)N(R)(R), —CN, —NO$_2$, —N(R)(R), acetoxy, —C(R)(R)(R), —OCH$_3$, —OCH$_2$CH$_3$, methylene dioxy, trihalomethyl, trihalomethoxy, —(CH$_2$)$_n$OH; where each R is independently H or —C$_{1-6}$ alkyl straight or branched chain, or optionally form an optionally substituted fused carbocyclic or heterocyclic ring structure, and n is 0-6, or where one of $R_{2'}$ and $R_{3'}$ comprises a phosphate moiety or moieties, e.g., a mono-, di-, or triphosphate moiety as is linked at the ribose 5'-position in conventional nucleotide mono-, di-, and tri-phosphates respectively as illustrated above.

In preferred embodiments, the NBAP(s) of the present invention have one of the following general formulae:

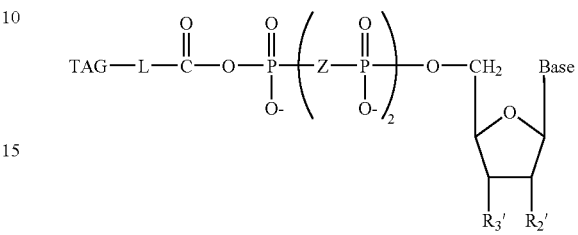

Preferably, each $R_{2'}$ and $R_{3'}$ is independently selected from the group consisting of —H, —OH, —F, —Br, —Cl, —SCH$_3$, —C(O)N(R)(R), —CN, —NO$_2$, —N(R)(R), acetoxy, —C(R)(R)(R), —OCH$_3$, —OCH$_2$CH$_3$, methylene dioxy, trihalomethyl, trihalomethoxy, —(CH$_2$)$_n$OH, or —(CH$_2$)$_n$-phenyl where phenyl is optionally substituted with —F, —Br, —Cl, —SCH$_3$, —C(O)N(R)(R), —CN, —NO$_2$, —N(R)(R), acetoxy, —C(R)(R)(R), —OCH$_3$, —OCH$_2$CH$_3$, methylene dioxy, trihalomethyl, trihalomethoxy, —(CH$_2$)$_n$OH; and each $R_{2'}$ and $R_{3'}$ are most preferably independently H or OH;

each Z is independently O, S, NH, or methylene;

n is between 0 and 6 inclusive;

BASE is a substituted or unsubstituted purine, pyrmidine, triazine, pyridazine, pyrazine, pyrrolopyrimidine, orpyrrazolopyrimidine, and is most preferably selected from the group consisting of include adenine, thymine, uracil, guanine, cytosine, and inosine;

TAG is a detectable label or solid phase;

L is an optionally present alkyl or heteroalkyl groups of 1-40, 1-30, or 1-20 backbone atoms selected from the group consisting of —N(R)—, —O—, —S— or —C(R)(R)—, which may include a carbocyclic or heterocyclic moiety, e.g., a triazole ring; and each R is independently H or —C$_{1-6}$ alkyl straight or branched chain, or optionally form an optionally substituted fused carbocyclic or heterocyclic ring structure.

In certain embodiments, the NBAP(s) are as described for the immediately preceding structure, except that the moiety shown above attached at the ribose 5' carbon is instead attached at $R_{2'}$ or $R_{3'}$, and is replaced at the ribose 5' carbon with a group $R_{5'}$. $R_{5'}$ is selected from the group consisting of —H, —OH, —F, —Br, —Cl, —SCH$_3$, —C(O)N(R)(R), —CN, —NO$_2$, —N(R)(R), acetoxy, —C(R)(R)(R), —OCH$_3$, —OCH$_2$CH$_3$, methylene dioxy, trihalomethyl, trihalomethoxy, —(CH$_2$)$_n$OH, or —(CH$_2$)$_n$-phenyl where phenyl is optionally substituted with —F, —Br, —Cl, —SCH$_3$, —C(O)N(R)(R), —CN, —NO$_2$, —N(R)(R), acetoxy, —C(R)(R)(R), —OCH$_3$, —OCH$_2$CH$_3$, methylene dioxy, trihalomethyl, trihalomethoxy, —(CH$_2$)$_n$OH; and is most preferably H or OH.

The person of ordinary skill will realize that pharmaceutically acceptable salt or complexes of these compounds are also useful and are also contemplated within the scope of the invention. Exemplary purine and pyrimidine-based NBAPs are shown in FIG. 1.

A preferred group of linking moieties L fall within the following formulae:

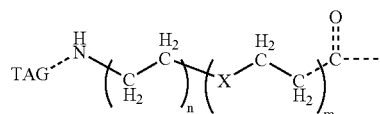

where n and m are independently in the range of 0 to 4, and X is O or $CH_2$;

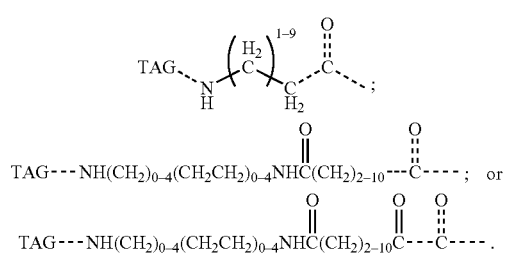

TAG---$NH(CH_2)_{0-4}(CH_2CH_2)_{0-4}NHC(CH_2)_{2-10}$---C----; or

TAG---$NH(CH_2)_{0-4}(CH_2CH_2)_{0-4}NHC(CH_2)_{2-10}$C---C----.

In particularly preferred embodiments, L is —$NH(CH_2)_2$ $(OCH_2CH_2)_{1-4}$—.

Another preferred group of linkers are those that can be formed using "click" chemistry", such as triazole linkers. The use of such click chemistry in the preparation of certain activity-based probes is described in Shreder et al., International Application PCT/US03/07898, WO 03/079014, which is incorporated herein by reference in its entirety, including drawings. Additional useful descriptions of "click chemistry" are available, for example, in Kolb et al., *Agnew Chem. Int. Ed. Engl.* 40: 2004-21 (2001); Seo et al., *J. Org. Chem.* 68: 609-12 (2003), both of which are incorporated herein in their entireties.

An exemplary triazole linker moiety formed using "click chemistry" is shown below. The first structure shows the linker extending to the nitrogens that further link the dye and the acyl phosphate/affinity moieties. The second structure is focused on the formation of the triazole ring, for example, using an azide/alkyne reaction.

Another example of ligation chemistry that has been applied to proteomic samples and is useful in forming the present probes is the Staudinger reaction between a phosphine and an azide (Bertozzi et al. J. Am. Chem. Soc. 125: 4708-4709 (2003)) which is incorporated herein by reference in its entirety. In this reaction a stable amide bond is formed between the two components. The reaction is illustrated below, where Ph stands for phenyl.

Click Chemistry

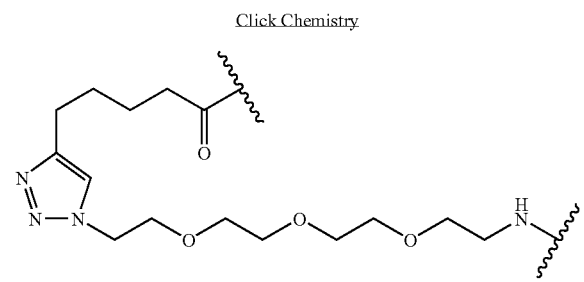

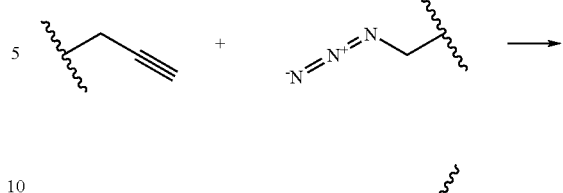

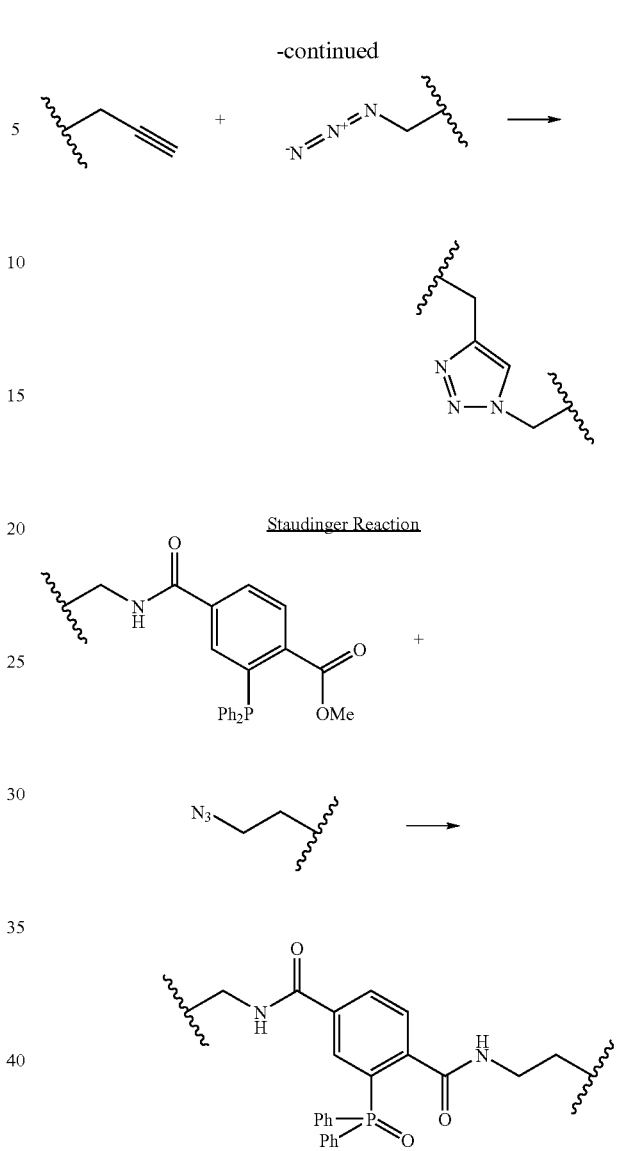

Thus, typically a linker resulting from such a Staudinger reaction will contain the following structure:

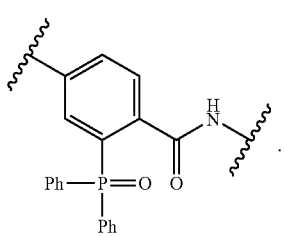

The "click chemistry" and Staudinger reaction allow convenient ligation in aqueous solutions.

TAGs of particular interest come within the following formulae:

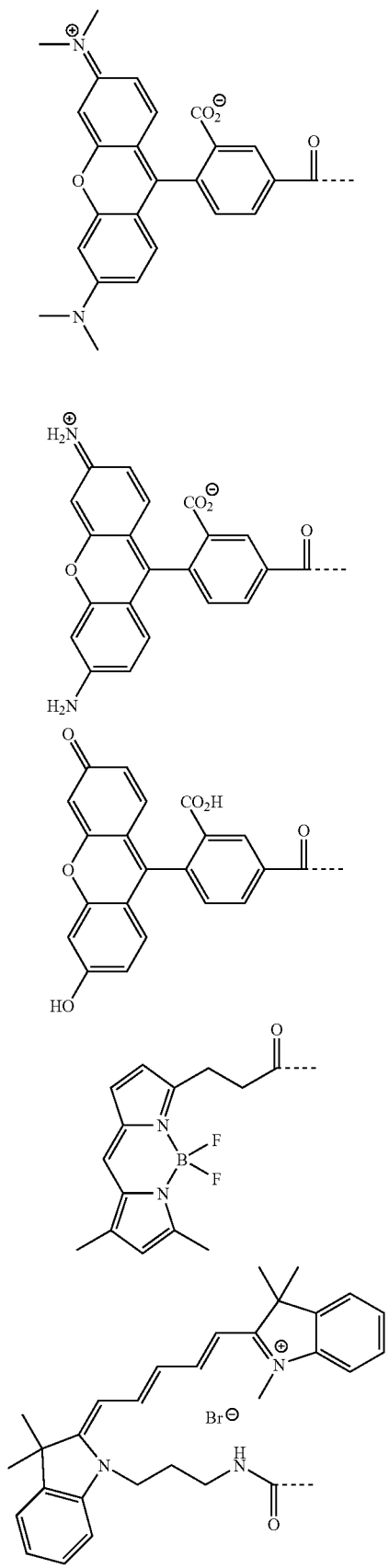

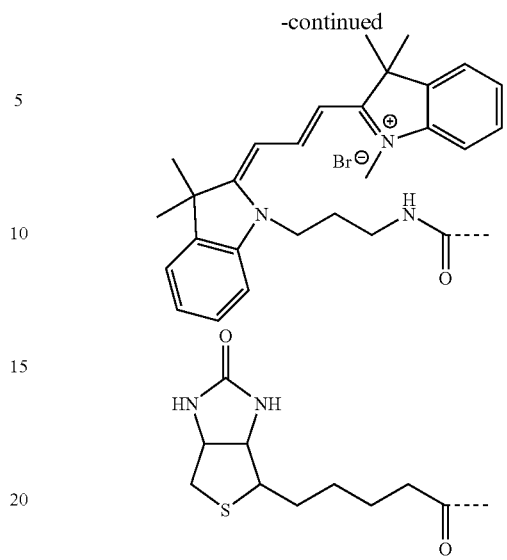

-continued where the exemplified 5-carboxyrhodamine or 5-carboxyfluorescein may also be the equivalent 6-substituted molecule or a mixture of 5- and 6-substituted molecules.

Analysis of Samples with TAPPs

After the reaction between the complex protein mixture and the TAPP(s) is completed, the conjugates of the TAPP(s) and protein targets will be analyzed. Preferably, the TAPPs of the present invention comprise a TAG that allows for manipulation of the conjugates, either for sequestering the conjugates or detecting the conjugates or both. The TAPPs may be analyzed by separating into components, e.g., by electrophoresis, for example gel electrophoresis, capillary electrophoresis or microfluidic electrophoresis; mass spectrometry, e.g., MALDI-TOF, microcapillary liquid chromatography-electrospray tandem MS, or other technique. To enhance the analysis, the conjugates may be deglycosylated using an appropriate glycosidase, such as PGNaseF, under conventional deglycosylation conditions indicated by the enzyme supplier. Labeled target proteins can be identified based on a variety of physical criteria, such as apparent molecular weight, peptide sequence composition, enzymatic activity (e.g., kinase activity), or a combination of such criteria.

The term "separating" as used herein refers to methods that enrich the concentration of a molecule of interest in a particular location or container relative to other molecules originally present. For example, gel electrophoresis enriches the concentration of molecules that migrate at a particular rate relative to other molecules originally present that migrate at different rates; sequestration methods enrich the concentration of molecules capable of being sequestered (e.g., by binding to a receptor) relative to other molecules not so capable (e.g., removed by washing out molecules that do not bind to a receptor). Numerous additional analytical procedures are known to the artisan for separating and analyzing complex protein mixtures (e.g., chromatographic methods such as HPLC, FPLC, ion exchange, size exclusion; mass spectrometry; differential centrifugation).

In preferred embodiments, the TAPP-labeled products are analyzed by electrophoresis, e.g., slab gel, capillary or microfluidic, optionally using a gel for separation of the different components. In particularly preferred embodiments, SDS-PAGE is used, including 2D PAGE. The sample composition may be preliminarily separated using isoelectric focusing, followed by using bands or regions for further electrophoretic separation. Conventional conditions can be employed for the electrophoresis, using a denaturing medium, so that the active sample and the inactivated sample are both denatured in the gel. Numerous patents have issued for performing electrophoresis for the separation of proteins. See, e.g., U.S. Pat. Nos. 4,415,655; 4,481,094; 4,865,707; and 4,946,794. Texts describing procedures include Laemmli, *Nature* 227:680-685 (1970); Sambrook et al., "Molecular Cloning: A Laboratory Manual." $3^{rd}$ Edition, Cold Spring Harbor Press, Cold Spring Harbor, N.Y. (2001).

Using the TAPPs of the present invention, labeled target protein(s) may be identified by excitation and detection of light emitted upon excitation of the fluorescent moiety, e.g., in electrophoresis gels. In certain embodiments, such as when the TAPP labels a plurality of target proteins or when the identity of a labeled target protein is unknown, the labeled target protein(s) present in various electophoretic bands may be further assayed to identify the specific proteins to which the TAPP(s) bound, e.g., by fragmentation and mass spectrometric analysis. In particular, the sequence of proteins can be determined using tandem MS ($MS^n$) techniques. By application of sequence database searching techniques, the protein from which a sequenced peptide originated can be identified. Exemplary methods for performing such analyses are described in U.S. Patent Application No. 60/446,960, entitled "Macromolecule Identification Made by Mass Spectroscopy and Database Searching," filed Feb. 11, 2003, which is hereby incorporated by reference in its entirety, including all tables, figures, and claims.

In designing a gel-based analysis system, the artisan may balance various considerations, such as speed, resolution, sample volume, choice of fluorophore, detection methods, etc., in order to arrive at an optimal solution. For example, for simple screening analysis (i.e., when gel bands are not to be identified by means of eluting proteins from the gel matrix for further analysis), very thin gels may be run quickly. Additionally, such thin gels are amenable to the use of laser-induced fluorescence scanning systems and narrow gel lanes, as laser focusing and confocal detection optics permit the detection of very small amounts of TAPP-labeled protein in a sample. Conversely, thicker gels may be advantageous in protein identification analysis, as a sufficient amount of material must be obtained from a gel band to permit further manipulations.

For rapid screening analysis, a suitable gel electrophoresis platform would consist of a glass sandwich gel format of from 15-40 cm in width, 20-40 cm in length, and from 0.6 to 0.2 cm in thickness. A partciularly preferred format is from about 30-35 cm in width, about 25-30 cm in length, and about 0.4 mm in thickness. The term "about" in this context refers to +/−10% of a given dimension. The gel format is preferably combined with a laser-induced fluorescence detector apparatus comprising detection optics that permit sampling of the gel without removal from the gel plates, as such thin gels may be extremely fragile. Typically, such an instrument uses confocal optics for detection. By matching the thickness of the gel to the thickness of the confocal "slice," signal detection can be matched to a minimal amount of sample.

The spacing between sample wells is limited only by the amount of sample necessary to obtain a sufficient signal for measurement. Appropriate spacings are between 1 and 4 mm, most preferably about 2.25-3 mm. The term "about" in this context refers to +/−10% of the spacing between wells. Selecting a spacing between wells of about 2.25 mm as an example, a gel platform 25 cm in width could accommodate as many as 96 individual samples.

After completing the electropherogram, the bands may then be read using any convenient detection means (e.g., a fluorescent reader, e.g., Hitachi FMbio Flatbed Fluorescence Scanner, when the TAPP comprises a fluorescent moiety), where the intensity of each band may be transferred to a data processor for processing. Depending on whether one or more lanes are involved with the analysis, the data may be compiled from a single or multiple lanes to establish the bands associated with active target proteins that are absent with the inactive sample, the different target proteins that reacted with different TAPPs as evidenced by the different fluorescence emission for each of the TAPPs, and any cross-reactivity between the TAPPs. The bands that are obtained in the gel are sharp and provide for excellent resolution. Particularly, much better resolution and sensitivity may be obtained than when biotin-labeled TAPPs are used, followed by complex formation with labeled avidin, and Western blotting.

The results obtained from analyzing the nucleotide binding protein profiles may then be organized in a manner that allows for ready comparisons and differentiation between samples. One technique that finds utility is cluster analysis. One applies a hierarchical clustering algorithm to the samples using the Pearson correlation coefficient as the measure of similarity and average linking clustering (Cluster program: Ross et al., *Nat. Genet.* 24:227-35 (2000); Eisen et al., *Proc. Natl. Acad. Sci. USA* 95:14863-68 (1998)). For each enzyme activity, averaged cell sample values are compared to identify the cell sample that expressed the highest level of a particular enzyme activity. The activity levels may then be expressed as a percentage of this highest activity to normalize the data sets. As data sets are built up from cell samples, the cluster analysis can be modified in light of new data that provides a new maximum for a particular enzyme, so that one may have cluster analysis within a given group of samples as well as cluster analysis extending over many samples and groups of samples. Cluster analysis can also be applied as to the individual fractions and pair-wise combinations, so as to maximize information from the cell samples in relating the samples to each other and standards. For large numbers of samples, clustergrams can be used to rapidly identify the similarities between samples, for example, in terms of origin of the cells, aggressiveness and invasiveness, diagnosis, prognosis, preferential therapies and how the tumor has responded to a course of treatment.

Following TAPP labeling of target nucleotide binding protein(s), protein digestion may be employed to produce both unlabeled and TAPP-labeled peptides. The digestion may be performed while the proteins are in solution or when the conjugates are sequestered, e.g., by receptors bound to a solid support. Digestion preferably employs only one protease; however, two or more, usually not more than three, proteases may be used. The proteases may be in solution or bound to a surface. The proteases may be combined in the same reaction mixture, or the sample may be divided into aliquots and each of the aliquots treated with a different protease. Digestion may also occur before binding to the conjugate to a support and/or a after the conjugates are bound to a solid support. Enzymes that find use include, but are not limited to, trypsin, chymotrypsin, bromelain, papain, carboxypeptidase A, B and Y, proteinase A and K, chymopapain, plasmin, subtilisin, clostripain etc.

In particularly preferred embodiments, additional steps can be used to reduce the complexity of the analysis to be performed. For example, the complex protein mixture can be denatured following labeling, e.g., by the addition of urea, guanidinium salts, detergents, organic solvents, etc., in order to reduce or eliminate unwanted proteolysis from endogenous proteases present in the mixture. Additionally, cysteine residues can be reduced and alkylated to maintain the homogeneity of cysteine-containing peptides and to prevent refolding of endogenous proteases following removal of the denaturant. Moreover, proteases can be combined with additional enzymes, such as glycosidases, phosphatases, sulfatases, etc., that can act to remove post-translational modifications from proteins. Examples of such post-translational modifications include, but are not limited to, glycosylations, phosphorylations, sulfations, prenylations, methylations, amidations, and myristolations. Such steps can be mixed and matched by the skilled artisan, depending on the requirements of a particular analysis.

Prior to digestion, a buffer exchange step may be employed, e.g., by gel filtration, dialysis, etc. This step may be used to remove excess TAPPs, to remove denaturant, and/or to provide suitable buffer conditions for digestion. In particularly preferred embodiments, buffer exchange is performed by gravity flow gel filtration.

Digestion will be carried out in an aqueous buffered medium, generally at a pH in the range of about 4 to 10, depending on the requirements of the protease. The concentration of the protease will generally be in the range of about $6 \times 10^{-8}$ M to about $6 \times 10^{-6}$ M, more preferably in the range of about $1.8 \times 10^{-8}$ M to about $2 \times 10^{-7}$ M, and most preferably about $6 \times 10^{-7}$ M (e.g., 150 ng/10 µL). The term "about" in this context means +/−10% of a givem measurement. The time for the digestion will be sufficient to go to at least substantial completion, so that at least substantially all of the protein will have been digested. Digests may be performed at a temperature that is compatible with the protease(s) employed, preferably from 20° C. to 40° C., most preferably about 37° C. Where the digestion takes place in solution, the protease may be quenched by any convenient means, including heating or acidification of the sample. Alternatively, quenching can be achieved by sequestering the fragment conjugates with a receptor for the TAG bound to a surface, or by addition of a protease inhibitor (e.g., E64, DIFP, PMSF, etc.). Where the proteins are bound to a surface, the proteases may be washed away before the bound digested protein is released.

Following protein digestion, peptides can be sequestered, e.g., by binding to receptors for the TAG of one or more TAPP-labeled peptides. Preferably, sequestration relies on receptors bound to a solid support that can be easily manipulated during wash steps. The support may be beads, including paramagnetic beads, prepared from various materials, such as Bioglas, polystyrene, polyacrylate, polymethylmethacrylate, polyethylene, polysaccharides, such as Agarose, cellulose, amylose, etc., polyurethane, and the like. Desirably, the support surface will not interfere with the binding of TAG to its cognate receptor, and the receptor may be linked to the support by a hydrophilic bridge that allows for the receptor to be removed from the surface. When beads are employed, the beads will generally have a cross-dimension in the range of about 5 to 100 µm. Instead of beads, one may use solid supports, such as slides, the walls of vessels, e.g. microtiter well walls, capillaries, etc. There is an extensive literature of receptor bound supports that is readily applicable to this invention, since the sequestering step is conventional. The sample is contacted with the support for sufficient time, usually about 5 to 60 min, to allow all of the conjugate to become bound to the surface. At this time, all of the non-specifically bound components from the sample may be washed away, greatly enriching the target proteins as compared to the rest of the sample.

Following separation by sequestration, TAPP-labeled peptides may then be released from the receptor. The particular method of release will depend upon the TAG-receptor pair. In some instances, one may use an analog of the TAG as a "releasing agent" to release the conjugate. This is illustrated by the use of deimino- or dethiobiotin as the TAG and biotin as the releasing agent. Where this is not convenient, as in the case of many fluorescent moieties as TAGs where there may not be a convenient analog, conditions such as high salt concentrations, chaeotropic agents (e.g., isothiocyanate or urea) low pH, detergents, organic solvents, etc., may be used to effect release. Once the conjugate has been released, dialysis, ion exchange resins, precipitation, or the like may be used to prepare the conjugate solution for the next stage.

Where the migration rates in various separation procedures provide the necessary identification of the peptide(s) generated and, therefore, the protein from which they are obtained, no further analysis may be required. However, where further identification is desired or the earlier results do not provide certainty as to the identification and amount of a particular component, an identification method using mass spectrometry (MS) can be employed. See, for example, WO 00/11208. The use of mass spectrometry will be described below. Such identification methods potentially provide greater information, but requires greater sample size in comparison to, for example, capillary electrohoresis, and has a lower throughput.

Chromatographic and/or electrophoretic separation methods as described herein may be used to simplify the mixtures introduced into the mass spectrometer, allowing for a more accurate analysis. For TAPP-labeled peptides, the use of fluorescent moieties as TAPP TAGs can permit the use of an online fluorescence detector to trigger ESI-MS data collection or fraction collection for subsequent analysis, e.g., providing sample on a MALDI plate. In this way, only fractions and bands that contain TAPP-labeled peptides will be selected for further processing, thereby avoiding using the MS with certain fractions.

In particularly preferred embodiments, the identification methods described herein can be combined with one or more separation methods to develop a "separation profile" that can be used to identify peptides without the need for MS analysis. In these methods, a sample (e.g., material from a chromatography column) is divided into at least two portions; one portion is used for MS analysis, and the other portion(s) are used for one or more separation methods (e.g., a single CE run, or two or more CE runs using different separation conditions). The peptide identification obtained from the MS analysis can be assigned to the observed separation profile (e.g., the elution time of the peptide observed in the CE run(s)). Observation of this separation profile in subsequent samples can then be correlated to the peptide known to exhibit that separation profile.

The identification methods described herein may also utilize TAPPs that differ isotopically in order to enhance the information obtained from MS procedures. For example, using automated multistage MS, the mass spectrometer may be operated in a dual mode in which it alternates in successive scans between measuring the relative quantities of peptides obtained from the prior fractionation and recording the sequence information of the peptides. Peptides may be quantified by measuring in the MS mode the relative signal intensities for pairs of peptide ions of identical sequence that are tagged with the isotopically light or heavy forms of the reagent, respectively, and which therefore differ in mass by the mass differential encoded with the TAPP. Peptide sequence information may be automatically generated by selecting peptide ions of a particular mass-to-charge (m/z) ratio for collision-induced dissociation (CID) in the mass spectrometer operating in the $MS^n$ mode. (Link, et al., (1997) Electrophoresis 18:1314-34; Gygi, et al., (1999) idid 20:310-9; and Gygi et al., (1999) Mol. Cell. Biol. 19:1720-30). The resulting CID spectra may be then automatically correlated with sequence databases to identify the protein from which the sequenced peptide originated. Combination of the results generated by MS and $MS^n$ analyses of affinity tagged and differentially labeled peptide samples allows the determination of the relative quantities as well as the sequence identities of the components of protein mixtures.

Protein identification by $MS^n$ may be accomplished by correlating the sequence contained in the CID mass spectrum with one or more sequence databases, e.g., using computer searching algorithms (Eng. et al. (1994) J. Am. Soc. Mass Spectrom. 5:976-89; Mann, et al., (1994) Anal. Chem. 66:4390-99; Qin, et al., (1997) ibid 69:3995-4001; Clauser, et al., (1995) Proc. Natl. Acad. Sci. USA 92:5072-76); see also, U.S. Patent Application No. 60/446,960, entitled "Macromolecule Identification Made by Mass Spectroscopy and Database Searching," filed Feb. 11, 2003. Pairs of identical peptides tagged with the light and heavy affinity tagged reagents, respectively (or in analysis of more than two samples, sets of identical tagged peptides in which each set member is differentially isotopically labeled) are chemically identical and therefore serve as mutual internal standards for accurate quantitation. The MS measurement readily differentiates between peptides originating from different samples, representing different cell states or other parameter, because of the difference between isotopically distinct reagents attached to the peptides. The ratios between the intensities of the differing weight components of these pairs or sets of peaks provide an accurate measure of the relative abundance of the peptides and the correlative proteins because the MS intensity response to a given peptide is independent of the isotopic composition of the reagents. The use of isotopically labeled internal standards is standard practice in quantitative mass spectrometry (De Leenheer, et al., (1992) Mass Spectrom. Rev. 11:249-307).

The following examples are offered by way of illustration and not by way of limitation.

In the following examples, $^1$H-NMR spectra were recorded using deuterated DMSO as the solvent unless otherwise indicated. Preparative HPLC was carried out on a reverse phase Polaris $C_{18}$ column (5µ column; 150 mm×21 mm; Metachem/Ansys; Torrance, Calif.) using a binary system of water and acetonitrile with TFA as a modifier (water 0.1%, acetonitrile 0.1%). Analytical LC-MS was carried out on a Polaris C18 column (5µ column; 50 mm×4.6 mm; Metachem/Ansys; Torrance, Calif.) using a binary system of water and acetonitrile with TFA as a modifier (water 0.1%, acetonitrile 0.1%). All compounds were obtained from the Aldrich Chemical Company (Milwaukee, Wis.) unless indicated otherwise. Fmoc-4-(aminomethyl) benzoic acid was obtained from Advanced ChemTech (Louisville, Ky.); the mixed 5- and 6-succinimidyl ester of tetramethylrhodamine was obtained from Molecular Probes (TAMRA-SE; Eugene, Oreg.); and fluoroacetyl fluoride was obtained from ProChem, Inc (Rockford, Ill.).

EXAMPLE 1

Preparation of Acyl-Nucleotide NBAPs

Figure 2:
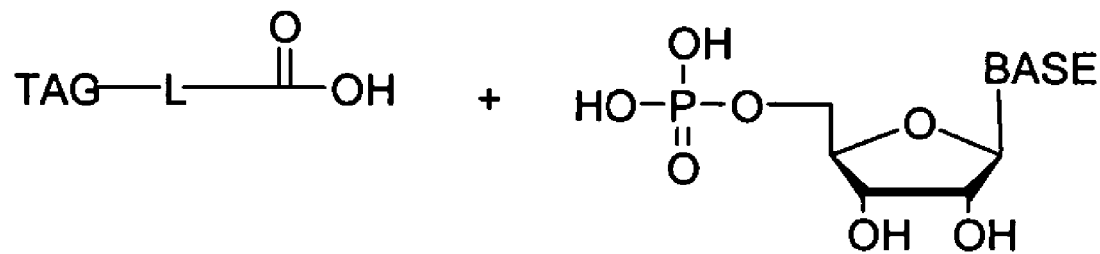
FIG. 2 shows an exemplary synthesis scheme for preparing acyl phosphate probes of the invention.
Figure 2:
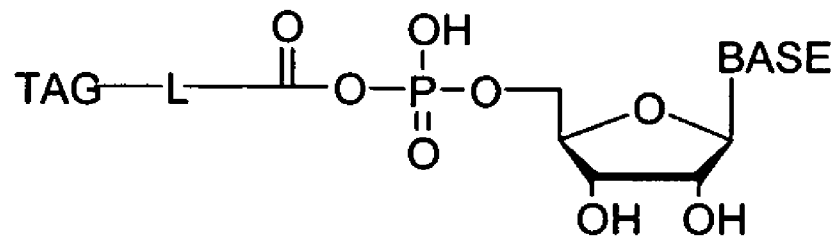
Figure 3:
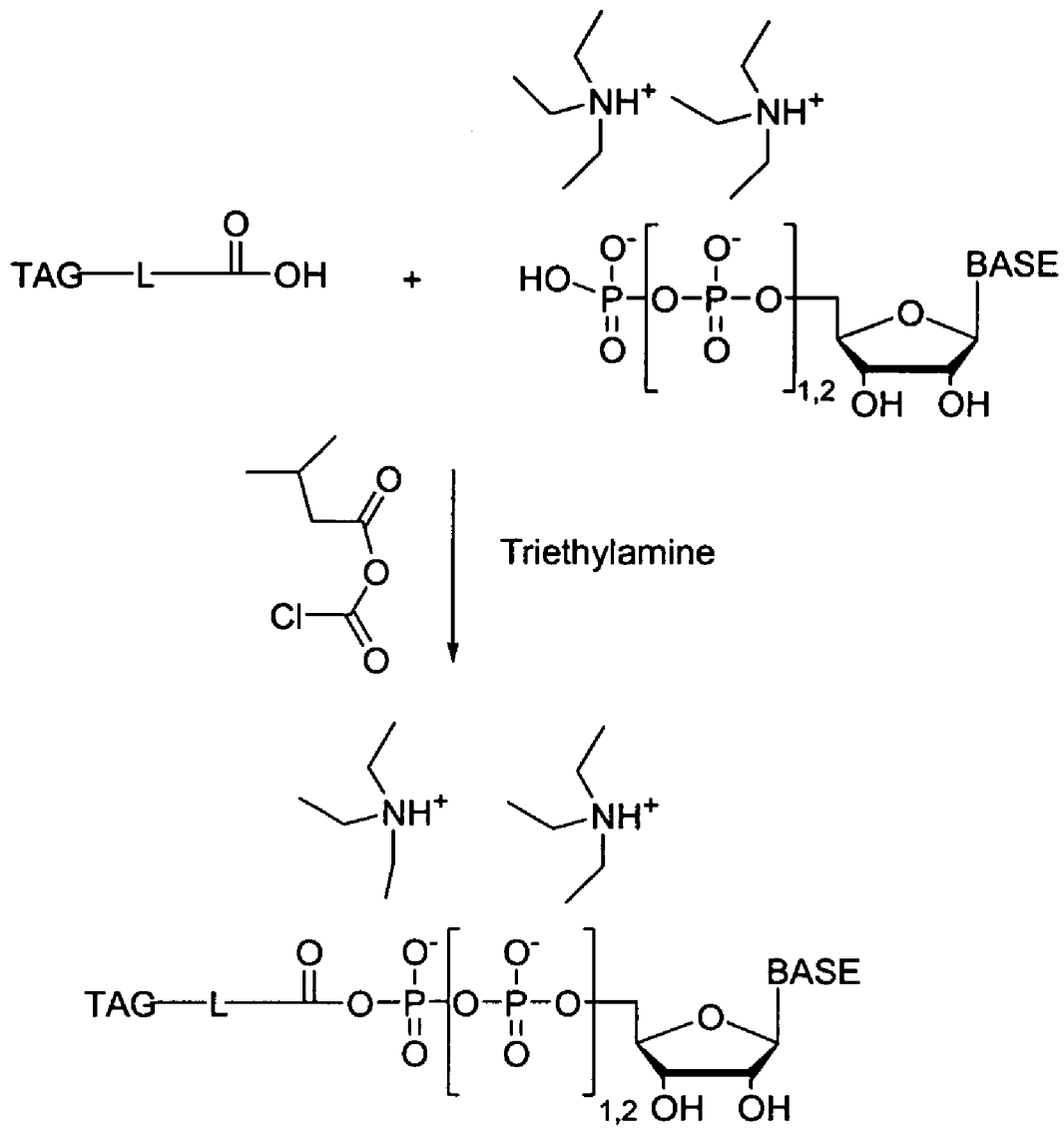
FIG. 3 shows an alternative exemplary synthesis scheme for preparing acyl phosphate probes of the invention.
Figure 3:
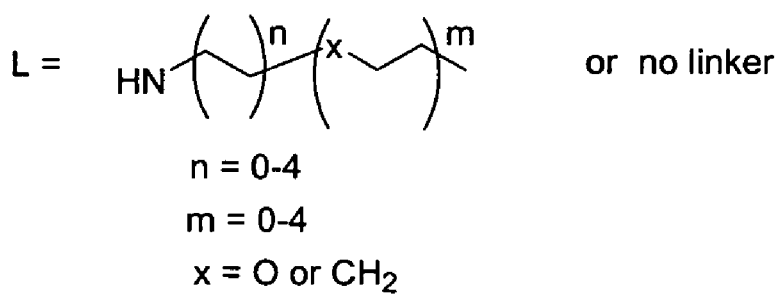

Exemplary general reaction schemes for the formation of acyl-nucleotide monophosphate NBAPs; and for the formation of acyl-nucleotide diphosphate and triphosphate NBAPs; are shown in FIGS. 2 and 3, respectively. Specific exemplary reaction schemes follow in the following examples.

EXAMPLE 2

TAMRA-6'-NH—$(CH_2)_{10}$—COOH (1)

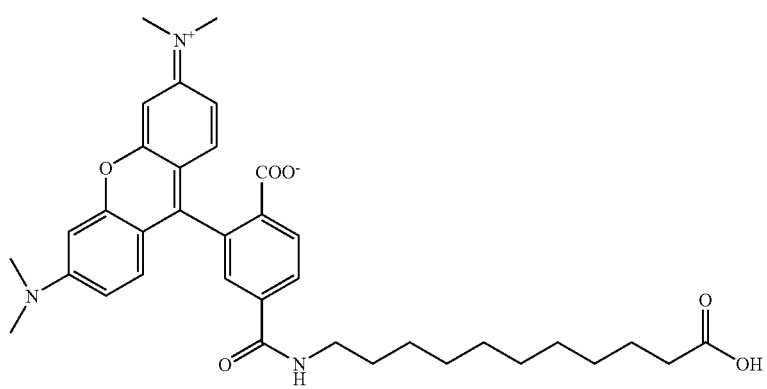

(1)

To a stirred solution of TAMRA acid (2.5 g, 5.8 mmole), DMAP (781 mg, 6.4 mmole) in dry DMF (22 ml) was added disuccinimidyl carbonate (1.64 g, 6.4 mmole) at room temperature. The resulting red solution was stirred at that temperature for four hours. HPLC analysis showed that TAMRA-SE was formed in over 90% yield. In another flask was added 11-aminoundecanoic acid (1.17 g, 5.8 mmole), bis(trimethylsilyl)acetamide and DMF (6 ml), the suspension was heated with a heat-gun until a clear solution appeared. The flask was allowed to cool to room temperature and stirred for one hour before transferring the solution into the flask containing the TAMRA-SE. The resulting mixture was stirred overnight before it was quenched with a few drops of acetic acid and water. The mixture was concentrated and purified by flash column chromatography (SiO$_2$, 45×260 mm, gradient 10% MeOH/CH$_2$Cl$_2$/1% AcOH to 20% MeOH/CH$_2$Cl$_2$/1% AcOH) to give compound 1 as a red solid (608 mg, 17% yield, 5'-isomer of compound 1 was also obtained along with fractions containing both 5'- and 6'-isomers), compound 1 can be further purified by HPLC. $^1$H-NMR (400 MHz, DMSO-d$_6$) δ 8.72 (t, 1H, CONH), 8.28 (d, J=8.0 Hz, 1H, aromatic proton), 8.24 (d, J=8.0 Hz, 1H, aromatic proton), 7.87 (s, 1H, aromatic proton), 7.04 (m, 4H, aromatic protons), 6.93 (m, 2H, aromatic protons), 3.24 (m, 2H, CONHCH$_2$), 3.24 (s, 6H, NCH$_3$), 2.10 (t, J=7.4 Hz, 2H, CH$_2$COOH), 1.42 (m, 4H, NHCH$_2$CH$_2$, CH$_2$CH$_2$COOH), 1.18 (m, 12H, CH$_2$); LRMS (ESI, [M+H$^+$]) calculated for C$_{36}$H$_{43}$N$_3$O$_6$: 614; found: 614.

EXAMPLE 3

TAMRA-dAMP Acylphosphates (2) and (3)

0.016 mmole) in D$_2$O/Pyridine (10:1, 110 μl) was added. The reaction was monitored by $^{31}$P-NMR and quenched by water (2 ml) after 25 minutes. The mixture was extracted with EtOAc (2×2 ml). The aqueous layer was lyophilized. The resulting red solid was dissolved in a mixture of DMSO/H$_2$O (1:1, 2 ml), filtered and purified by a 150×21.2 mm Polaris 5μ C18-A column (MetaChem) at a flow rate of 20 ml/min with a gradient of 0.1% TFA/2% CH$_3$CN/H$_2$O to 0.1% TFA/100% CH$_3$CN over 30 min. The fractions were collected at 550 nm. The compounds 2 (RT=21.4 min) and 3 (RT=22.1 min) were obtained along with a side product and the hydrolyzed starting material. 2: $^1$H-NMR (400 MHz, DMSO-d$_6$) δ 8.75 (t, 1H, CONH), 8.50 (s, 1H), 8.25 (m, 2H), 8.22 (s, 1H), 7.87 (s, 1H), 7.03 (m, 4H), 6.95 (m, 2H), 6.35 (t, 1H, H-1'), 4.40 (m, 1H), 3.97 (m, 2H), 3.26 (s, 6H, NCH$_3$), 3.00 (m, 2H, CONHCH$_2$), 2.70 (m, 2H), 2.29 (m, 2H, CH$_2$COOH), 1.49 (m, 4H, NHCH$_2$CH$_2$, CH$_2$CH$_2$COOH), 1.19 (m, 12H, CH$_2$); $^{31}$P-NMR (162 MHz,

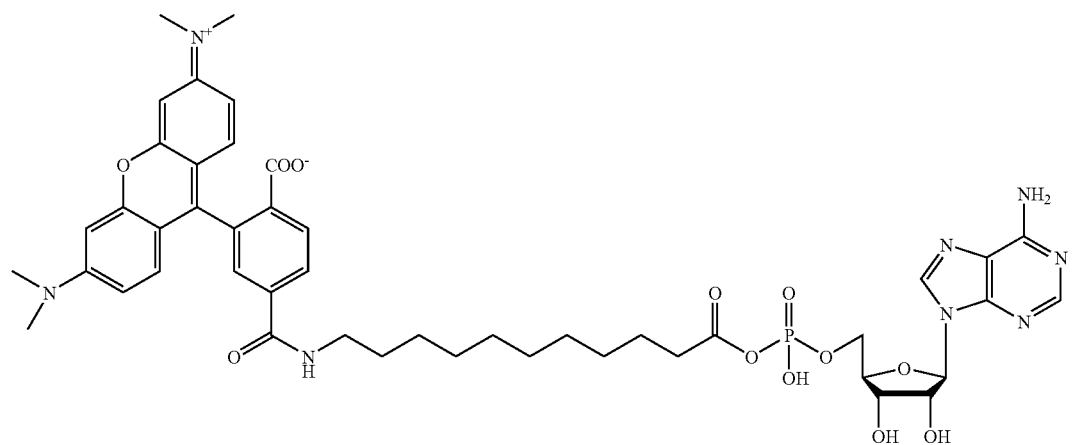

(2)

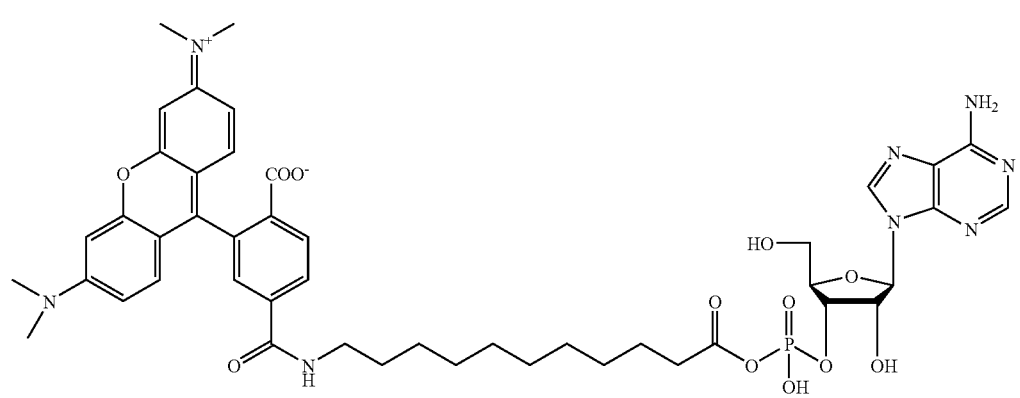

(3)

In a NMR tube fitted with a cap was added 1,3-diisopropylcarbodiimide (12.4 μl, 0.08 mmole) to a solution of 1 (9.7 mg, 0.016 mmole) in pyridine (400 μl). The resulting red mixture was kept at room temperature for ten minutes before a solution of 2'-deoxyadenosine 5'-monophosphate (5.2 mg, DMSO-d$_6$) δ −7.92 (s, 1P). 3: $^1$H-NMR (400 MHz, DMSO-d$_6$) δ 8.73 (t, 1H, CONH), 8.47 (s, 1H), 8.28 (m, 3H), 7.86 (s, 1H), 7.05 (m, 4H), 6.91 (m, 2H), 6.34 (t, 1H, H-1'), 4.25 (m, 1H), 3.86 (m, 2H), 3.24 (m, 6H, NCH$_3$), 2.98 (m, 2H, CONHCH$_2$), 2.29 (m, 2H), 2.16 (t, J=7.2 Hz, 2H, CH$_2$COOH), 1.48 (m, 4H, NHCH$_2$CH$_2$, CH$_2$CH$_2$COOH), 1.22 (m, 12H, CH$_2$); $^{31}$P-NMR (162 MHz, DMSO-d$_6$) δ-7.62 (s, 1P).

EXAMPLE 4

Synthesis of TAMRA-AMP Acylphosphate (4)

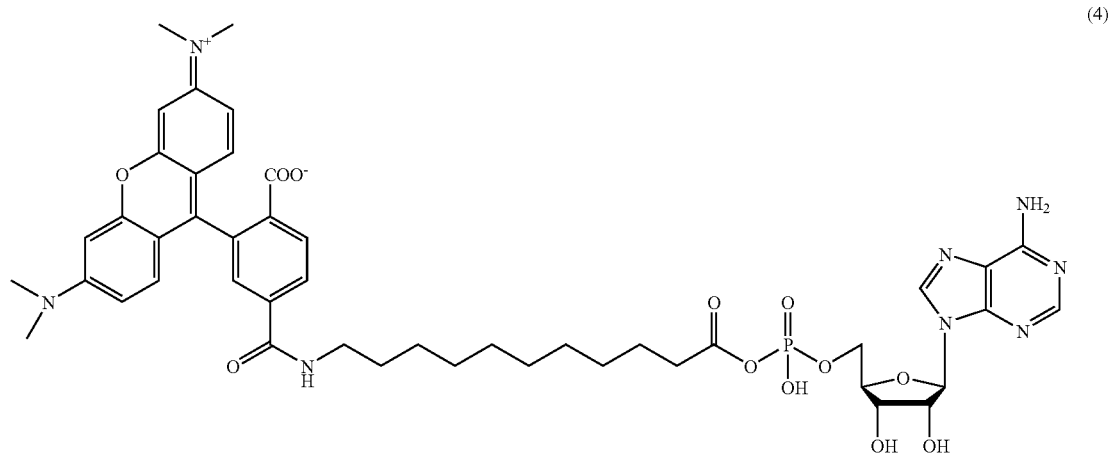

This compound was prepared using the procedure described for 2 and 3. $^1$H-NMR (400 MHz, DMSO-d$_6$) δ 9.45-7.80 (m, 4H), 7.55-7.00 (m, 6H), 7.10-6.10 (m, 2H), 6.00-4.55 (m, 2H), 4.80-3.30 (m, 18H), 3.05-2.80 (m, 6H), 2.55-2.45 (m, 1H), 2.00-1.55 (m, 7H), 2.70 (m, 2H), 0.60-0.50 (m, 2H); $^{31}$P-NMR (162 MHz, DMSO-d$_6$) δ −7.97 (s, 1P).

EXAMPLE 5

TAMRA-6'-NH—(CH$_2$)$_{10}$-1-Nap-Acylphosphate (5)

This compound was prepared using the same procedure as for 2 and 3 with one exception, HPLC purification was run with a gradient of 2% CH$_3$CN/H$_{20}$ to 100% CH$_3$CN: $^1$H-NMR (400 MHz, DMSO-d$_6$) δ 8.75 (t, 1H, CONH), 8.18 (m, 2H), 7.95 (d, J=8.8 Hz, 1H), 7.85 (d, J=8.4 Hz, 1H), 7.82 (s, 1H), 7.49 (m, 2H), 7.42 (m, 1H), 7.23 (m, 1H), 7.12 (m, 1H), 6.96 (m, 4H), 6.79 (m, 2H), 3.24 (m, 2H, CONHCH$_2$), 3.22 (s, 6H, NCH$_3$), 2.16 (t, J=7.4 Hz, 2H, CH$_2$COOH), 1.47 (m, 4H, NHCH$_2$CH$_2$, CH$_2$CH$_2$COOH), 1.23 (m, 12H, CH$_2$); $^{31}$P-NMR (162 MHz, DMSO-d$_6$) δ −13.62 (s, 1P).

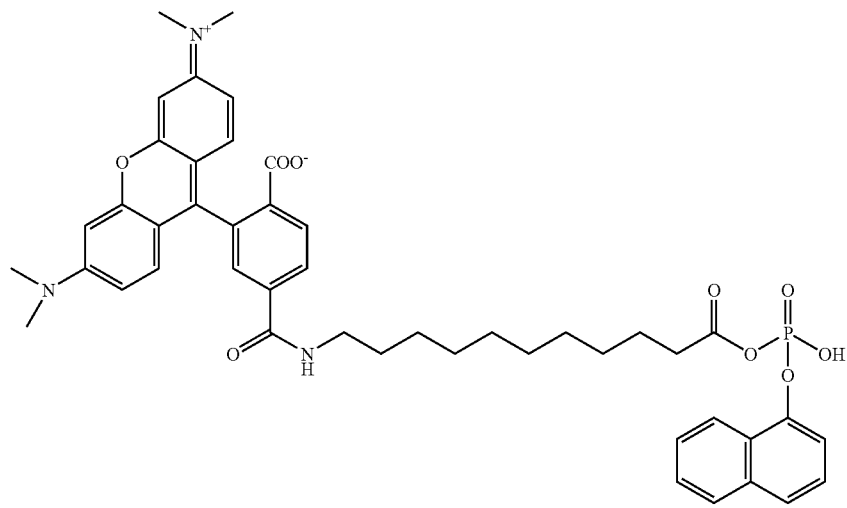

EXAMPLE 6

(+)-Biotin-Acyl-AMP (6)

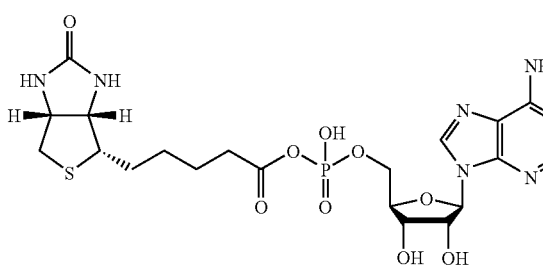

In a NMR tube fitted with a cap was added (+)-biotin (6.9 mg, 0.03 mmole), pyridine/DMF (8:1, 440 µl) and 1,3-diisopropylcarbodiimide (22.0 µl, 0.14 mmole). The resulting mixture was kept at room temperature for ten minutes before a solution of adenosine 5'-monophosphate (10.3 mg, 0.03 mmole) in D$_2$O/pyridine (10:1, 110 µl) was added. The reaction was monitored by $^{31}$P-NMR and quenched with water (2 ml) after 3 hours. The mixture was extracted with EtOAc (2×3 ml). The aqueous layer was lyophilized. The resulting red solid was dissolved in a mixture of DMSO/H$_2$O (1:1, 2 ml), filtered and purified on a 150×21.2 mm Polaris 5µ C18-A column (MetaChem) at a flow rate of 20 ml/min with a gradient of 0.1% TFA/2% CH$_3$CN/H$_2$O to 0.1% TFA/100% CH$_3$CN/H$_2$O over 30 min. The fractions were monitored at 550 nm. The fractions containing the product (RT=15.5 min) were pooled and lyophilized to give the title compound 6 as a white solid (7.3 mg, 45%): $^1$H-NMR (400 MHz, D$_2$O) δ 8.63 (s, 1H), 8.46 (s, 1H), 6.19 (d, J=5.6 Hz, 1H, H-1'), 4.75 (m, 1H), 4.52 (m, 2H), 4.39 (m, 1H), 4.34 (m, 1H), 4.24 (m, 1H), 3.20 (m, 1H), 2.90 (dd, 1H), 2.68 (d, 1H), 2.36 (t, J=7.0 Hz, 2H), 1.55 (m, 3H), 1.40 (m, 1H), 1.30 (m, 2H); $^{31}$P-NMR (162 MHz, D$_2$O) δ −6.37 (s, 1P); LRMS (ESI, [M+H]$^+$) calculated for C$_{20}$H$_{29}$N$_7$O$_9$PS: 574; found: 574.

EXAMPLE 7

Azide-PEG-Acyl-AMP (7)

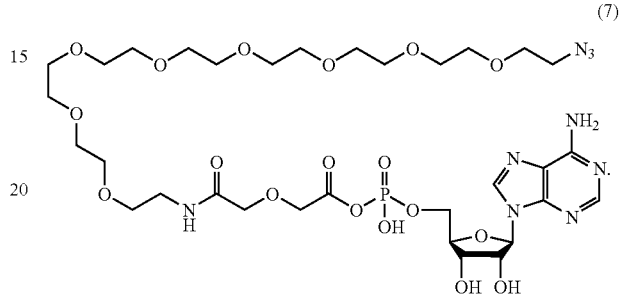

This compound was prepared using the procedure described for compound 6. $^1$H-NMR (400 MHz, D$_2$O) δ 8.56 (s, 1H), 8.40 (s, 1H), 6.16 (d, J=5.2 Hz, 1H, H-1'), 4.75 (m, 1H), 4.50 (m, 1H), 4.38 (m, 1H), 4.28 (s, 2H), 4.25 (m, 2H), 4.08 (s, 2H), 3.68 (m, 30H), 3.61 (m, 2H), 3.48 (m, 2H), 3.42 (m, 2H); $^{31}$P-NMR (162 MHz, D$_2$O) δ −6.69 (s, 1P); LRMS (ESI, [M+H]$^+$) calculated for C$_{32}$H$_{55}$N$_9$O$_{18}$P: 884; found: 884.

EXAMPLE 8

(+)-Biotin-Hex-Acyl-AMP (8)

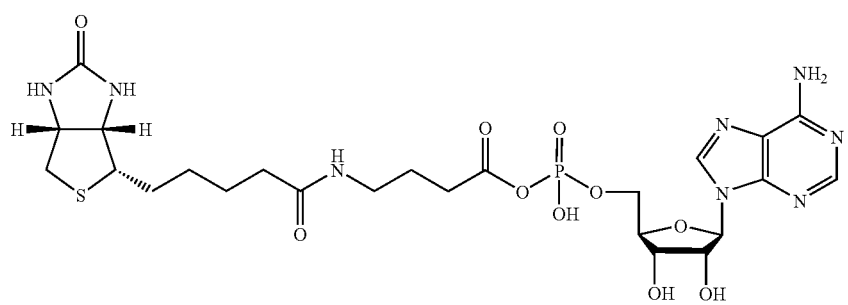

This compound was prepared using the procedure described for compound 6.

$^1$H-NMR (400 MHz, D$_2$O) δ 8.49 (s, 1H), 8.33 (s, 1H), 6.06 (d, J=5.6 Hz, 1H, H-1'), 4.63 (m, 1H), 4.42 (m, 1H), 4.39 (m, 1H), 4.27 (m, 2H), 4.11 (m, 2H), 3.15 (m, 1H), 3.00

(m, 2H), 2.95 (dd, 1H), 2.63 (d, 1H), 2.27 (t, J=7.0 Hz, 2H), 2.09 (t, J=7.0 Hz, 2H), 1.43 (m, 8H), 1.20 (m, 4H); $^{31}$P-NMR (162 MHz, D$_2$O) δ −6.42 (s, 1P); LRMS (ESI, [M+H]$^+$) calculated for C$_{26}$H$_{40}$N$_8$O$_{10}$PS: 687; found: 687.

EXAMPLE 9

Fmoc-L-Lys(ε-(+)-Biotin)-Acyl-AMP (9)

This compound was prepared using the procedure described for compound 6.

$^1$H-NMR (400 MHz, D$_2$O) δ 8.60 (s, 1H), 8.44 (s, 1H), 6.19 (d, J=4.8 Hz, 1H, H-1'), 4.75 (m, 1H), 4.50 (m, 1H), 4.39 (m, 1H), 4.23 (m, 2H), 3.70 (m, 10H), 3.59 (m, 2H), 3.47 (m, 2H), 3.36 (m, 2H), 2.44 (t, J=7.4 Hz, 2H), 2.25 (t, J=7.6 Hz, 2H), 1.82 (m, 2H); $^{31}$P-NMR (162 MHz, D$_2$O) δ −6.47 (s, 1P); LRMS (ESI, [M+H]$^+$) calculated for C$_{23}$H$_{37}$N$_9$O$_{12}$P: 662; found: 662.

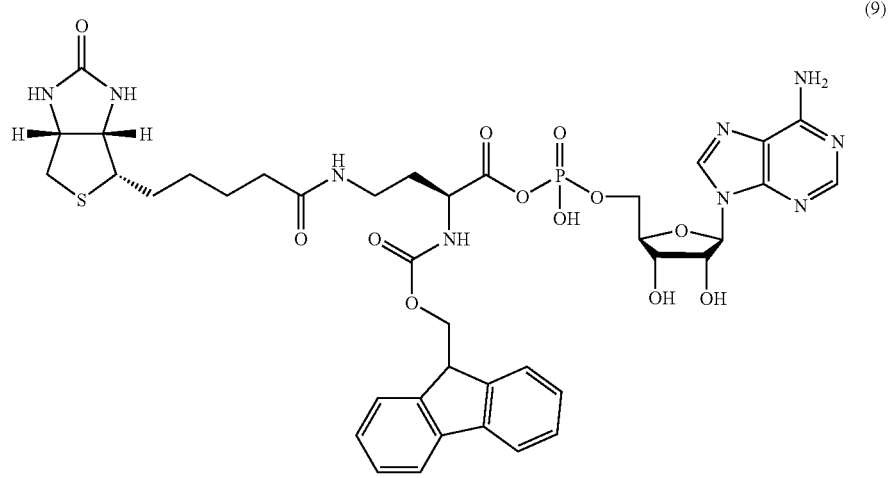

(9)

This compound was prepared using the procedure described for compound 6. $^1$H-NMR (400 MHz, DMSO-d$_6$) δ 8.34 (s, 0.7H), 8.22 (s, 0.3H), 8.07 (s, 0.7H), 7.95 (s, 0.3H), 7.63 (d, 1.4H), 7.55 (t, 0.6H), 7.41-7.14 (m, 6H), 5.80 (d, J=5.2 Hz, 1H), 4.50-3.60 (m, 11H), 2.98 (m, 3H), 2.67 (dd, 1H), 2.50 (m, 1H), 2.01 (m, 1H), 1.44-1.13 (m, 12H); $^{31}$P-NMR (162 MHz, DMSO-d$_6$) δ −6.90 (s, 0.8P), −7.37 (s, 0.2P); LRMS (ESI, [M+H]$^+$) calculated for C$_{41}$H$_{51}$N$_9$O$_{22}$PS: 924; found: 924.

EXAMPLE 10

Azide-PEG-C3-Acyl-AMP (10)

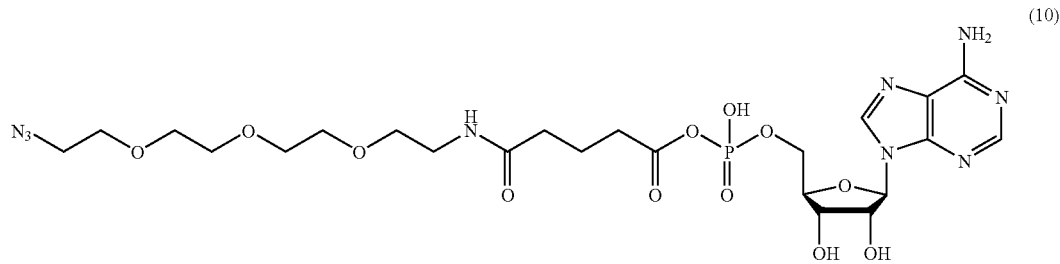

(10)

EXAMPLE 11

(+)-Biotin-Hex-PEG4-Acyl-AMP (11)

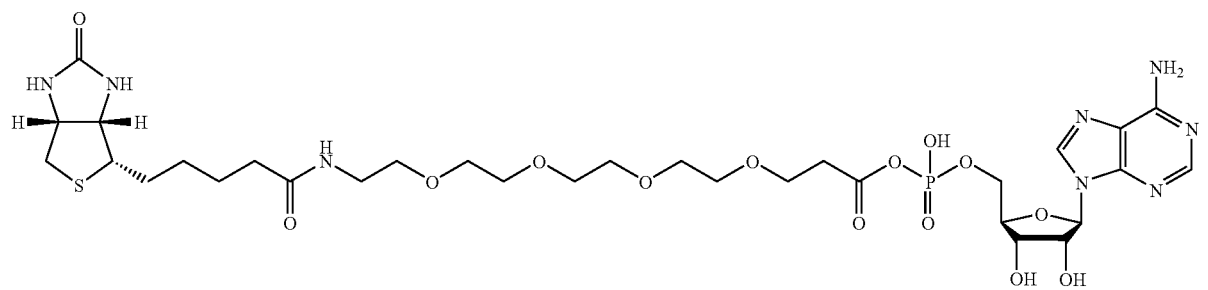

This compound was prepared using the procedure described for compound 6. $^1$H NMR (400 MHz, D$_2$O) δ 8.48 (s, 1H), 8.30 (s, 1H), 6.06 (d, J=5.2 Hz, 1H, H–1'), 4.64 (m, 1H), 4.42 (m, 1H), 4.39 (m, 1H), 4.27 (m, 2H), 4.11 (m, 2H), 3.56 (m, 16H), 3.25 (m, 2H), 3.20 (m, 1H), 2.55 (dd, 1H), 2.63 (m, 3H), 2.12 (t, J=7.4 Hz, 2H), 1.50 (m, 4H), 1.25 (m, 2H); $^{31}$P NMR (162 MHz, D$_2$O) δ –6.59 (s, 1P); LRMS (ESI, [M+H]$^+$) calculated for C$_{31}$H$_{50}$N$_8$O$_{14}$PS: 821; found: 821.

EXAMPLE 12

(+)-Biotin-Acyl-ATP (12)

To a stirred suspension of (+)-biotin (23.2 mg, 0.10 mmole) in a mixture of solvents (dioxane/DMF/DMSO, 1:1:1, 3 ml) was added triethylamine (19.9 μl, 0.14 mmole) and isobutyl chloroformate (12.3 μl, 0.10 mmole) at 0° C. The mixture was kept at that temperature for 5 minutes and was allowed to warm up to room temperature and stirred for 1.5 hours. A solution of ATP bistriethylammonium salt (32.8 mg, 0.05 mmole) in DMSO (1 ml) was added to the above mixture to give a clear solution. The reaction was monitored by $^{31}$P-NMR by preparing a sample of 500 μl of the reaction mixture and 100 μl of D$_2$O (or DMSO-d$_6$). After 20 hours 1 ml of the solution was drawn from the reaction mixture and water (2 ml) was added. The solution was extracted with ethyl acetate (2×3 ml). The aqueous layer was lyophilized. The resulting solid was suspended in water (1 ml) and purified by a short C18 column (14×45 mm) using a gradient of water to 40% acetonitrile/water to give the title compound 12 as a white powder: $^1$H-NMR (400 MHz, D$_2$O) δ 8.57 (s, 1H), 8.22 (s, 1H), 6.13 (d, J=6 Hz, 1H, H–1'), 4.75 (m, 1H),

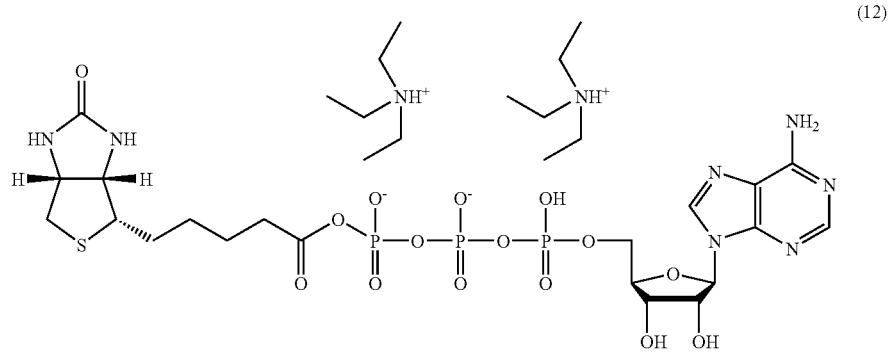

4.55 (m, 2H), 4.39 (m, 1H), 4.30 (m, 1H), 4.24 (m, 2H), 3.19 (q, J=7.2 Hz, 12H), 3.15 (m, 1H), 2.90 (dd, 1H), 2.70 (m, 1H), 2.36 (t, J=7.4 Hz, 2H), 1.47 (m, 4H), 1.26 (t, J=7.2 Hz, 18H), 1.21 (m, 2H); $^{31}$P-NMR (162 MHz, D$_2$O) δ –10.41 (d, J=19.6 Hz, 1P), –18.70 (d, J=19.9 Hz, 1P), –22.64 (t, J=19.8 Hz, 1P); LRMS (ESI, [M–H]$^-$) calculated for C$_{20}$H$_{29}$N$_7$O$_{15}$P$_3$S: 732; found: 732.

EXAMPLE 13

(+)-Biotin-Hex-Acyl-ATP (13)

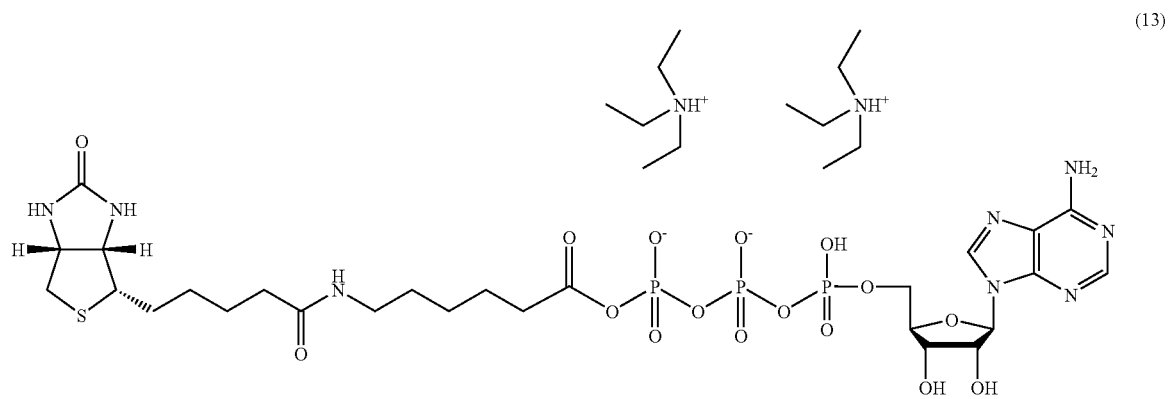

This compound was prepared using the procedure described for compound 12. $^1$H-NMR (400 MHz, D$_2$O) δ 8.57 (s, 1H), 8.28 (s, 1H), 6.12 (d, J=6.0 Hz, 1H, H–1'), 4.75 (m, 1H), 4.56 (m, 2H), 4.36 (m, 2H), 4.22 (m, 2H), 3.24 (m, 1H), 3.19 (q, J=7.2 Hz, 12H), 3.09 (m, 2H), 2.95 (dd, 1H), 2.74 (d, 1H), 2.37 (m, 2H), 2.20 (t, J=7.0 Hz, 2H), 1.50 (m, 6H), 1.38 (m, 6H), 1.26 (t, J=7.2H, 18H); $^{31}$P-NMR (162 MHz, D$_2$O) δ –10.44 (d, J=19.8 Hz, 1P), –18.71 (d, J=19.6 Hz, 1P), –22.66 (t, J=19.4 Hz, 1P).

EXAMPLE 14

Azide-PEG-C3-Acyl-ATP (14)

This compound was prepared using the procedure described for compound 12. $^1$H-NMR (400 MHz, D$_2$O) δ 8.51 (s, 1H), 8.27 (s, 1H), 6.02 (d, J=5.6 Hz, 1H, H–1'), 4.63 (m, 1H), 4.44 (m, 1H), 4.29 (m, 1H), 4.14 (m, 2H), 3.59 (m, 10H), 3.48 (t, J=5.4 Hz, 2H), 3.36 (m, 2H), 3.23 (t, J=5.4 Hz, 2H), 3.06 (q, J=7.3 Hz, 12H), 2.35 (t, J=7.2 Hz, 2H), 2.15 (t, J=7.8 Hz, 2H), 1.73 (m, 2H), 1.14 (t, J=7.4 Hz, 18H); $^{31}$P-NMR (162 MHz, D$_2$O) δ –10.45 (d, J=19.1 Hz, 1P), –18.81 (d, J=19.8 Hz, 1P), –22.66 (t, J=19.6 Hz, 1P); LRMS (ESI, [M–H]$^-$) calculated for C$_{23}$H$_{37}$N$_9$O$_{18}$P$_3$: 820; found: 820.

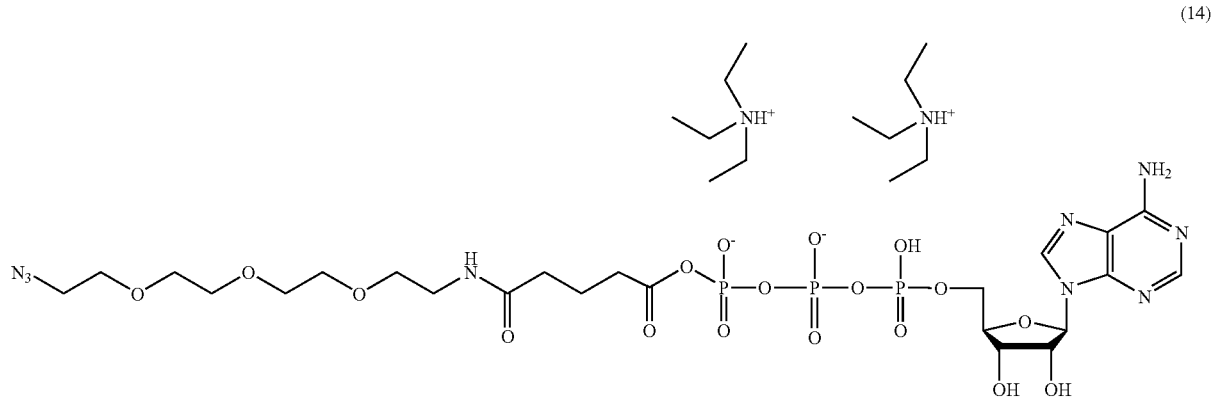

EXAMPLE 15
(+)-Biotin-Hex-PEG4-Acyl-ATP (15)
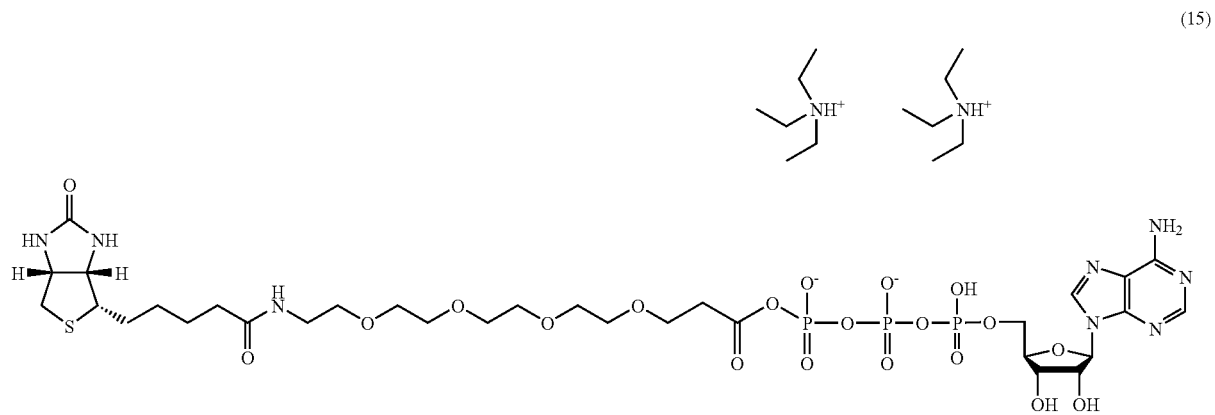
This compound was prepared using the procedure described for compound 12. $^1$H-NMR (400 MHz, D$_2$O) δ 8.56 (s, 1H), 8.28 (s, 1H), 6.13 (d, J=6.4 Hz, 1H, H-1'), 4.75 (m, 1H), 4.56 (m, 2H), 4.39 (m, 2H), 4.24 (m, 2H), 3.66 (m, 16H), 3.37 (m, 2H), 3.30 (m, 1H), 3.20 (t, J=7.3 Hz, 12H), 2.95 (dd, 1H), 2.73 (m, 3H), 2.24 (t, J=7.4 Hz, 2H), 1.65 (m, 4H), 1.34 (m, 2H), 1.26 (t, J=7.4 Hz, 18H); $^{31}$P-NMR (162 MHz, D$_2$O) δ −10.45 (d, J=19.1 Hz, 1P), −18.81 (d, J=19.6 Hz, 1P), −22.67 (t, J=19.6 Hz, 1P); LRMS (ESI, [M−H]$^−$) calculated for C$_{31}$H$_{50}$N$_8$O$_{20}$P$_3$S: 979; found: 979.
EXAMPLE 16
(+)-Biotin-Acyl-ADP (16):
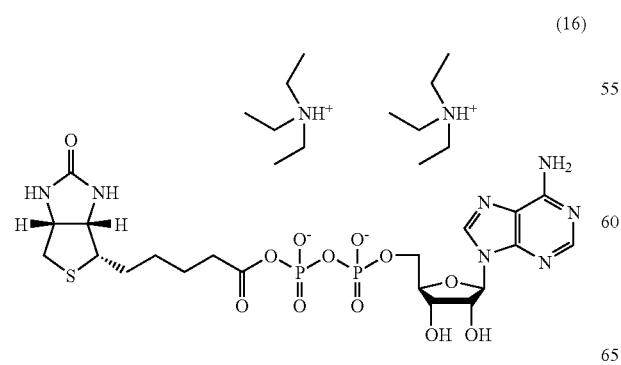

This compound was prepared using the procedure described for compound 12. $^1$H-NMR (400 MHz, D$_2$O) δ 8.55 (s, 1H), 8.28 (s, 1H), 6.14 (d, J=6 Hz, 1H, H–1'), 4.74 (m, 1H), 4.51 (m, 2H), 4.39 (m, 1H), 4.27 (m, 1H), 4.24 (m, 2H), 3.19 (q, J=7.2 Hz, 12H), 3.15 (m, 1H), 2.90 (dd, 1H), 2.70 (m, 1H), 2.31 (t, J=7.4 Hz), 1.47 (m, 4H), 1.27 (t, J=7.2H, 18H), 1.16 (m, 2H); $^{31}$P-NMR (162 MHz, D$_2$O) δ −10.72 (d, J=22.5 Hz, 1P), −18.75 (d, J=21.5 Hz, 1P); LRMS (ESI, [M−H]$^-$) calculated for C$_{20}$H$_{29}$N$_7$O$_{12}$P$_2$S: 652; found: 652.

EXAMPLE 17

Azide-PEG-C3-Acyl-ADP (17)

This compound was prepared using the procedure described for compound 12. $^1$H-NMR (400 MHz, D$_2$O) δ 8.51 (s, 1H), 8.26 (s, 1H), 6.13 (d, J=6.0 Hz, 1H, H–1'), 4.75 (m, 1H), 4.52 (m, 1H), 4.38 (m, 1H), 4.21 (m, 2H), 3.67 (m, 10H), 3.56 (t, J=5.4 Hz, 2H), 3.47 (m, 2H), 3.31 (t, J=5.4 Hz, 2H), 3.19 (q, J=7.3 Hz, 12H), 2.40 (t, J=7.2 Hz, 2H), 2.20 (t, J=7.8 Hz, 2H), 1.80 (m, 2H), 1.27 (t, J=7.4 Hz, 18H); $^{31}$P-NMR (162 MHz, D$_2$O) δ −10.70 (d, J=21.7 Hz, 1P), −18.73 (d, J=21.7 Hz, 1P).

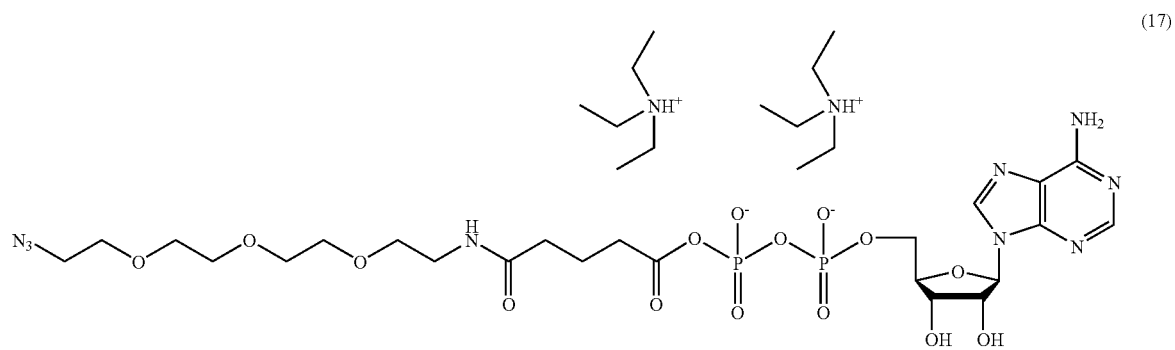

(17)

EXAMPLE 18

(+)-Biotin-Hex-Acyl-ADP (18)

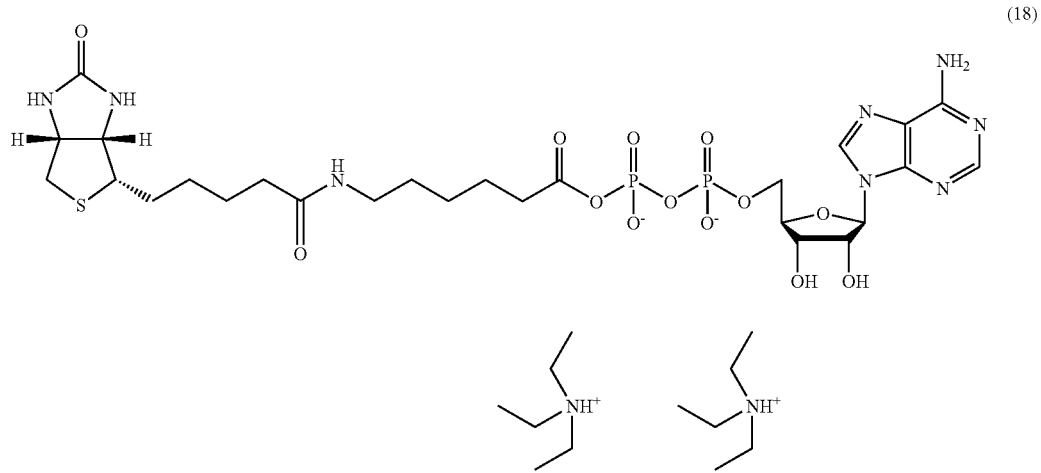

(18)

This compound was prepared using the procedure described for compound 12. $^1$H-NMR (400 MHz, D$_2$O) δ 8.54 (s, 1H), 8.28 (s, 1H), 6.14 (d, J=6.0 Hz, 1H, H-1'), 4.75 (m, 1H), 4.52 (m, 2H), 4.37 (m, 2H), 4.22 (m, 2H), 3.22 (m, 1H), 3.17 (q, J=7.2 Hz, 8H), 3.05 (m, 2H), 2.95 (dd, 1H), 2.74 (d, 1H), 2.37 (t, J=7.2 Hz, 2H), 2.20 (t, J=7.0 Hz, 2H), 1.50 (m, 4H), 1.45 (m, 2H), 1.32 (m, 2H), 1.26 (t, J=7.2H, 12H), 1.17(m, 2H); $^{31}$P-NMR (162 MHz, D$_2$O) δ −10.73 (d, J=22.0 Hz, 1P), −18.73 (d, J=21.9 Hz, 1P); LRMS (MALDI, [M+H]$^+$) calculated for C$_{26}$H$_{41}$N$_8$O$_{13}$P$_2$S: 767; found: 767.

EXAMPLE 19

(+)-Biotin-Hex-PEG4-Acyl-ADP (19)

This compound was prepared using the procedure described for compound 12. $^1$H-NMR (400 MHz, D$_2$O) δ 8.69 (s, 1H), 8.40 (s, 1H), 6.14 (d, J=5.2 Hz, 1H, H-1'), 4.75 (m, 1H), 4.58 (m, 1H), 4.54 (m, 1H), 4.40 (m, 2H), 4.22 (m, 2H), 3.28 (m, 1H), 3.17 (q, J=7.2 Hz, 6H), 3.11 (m, 2H), 2.95 (dd, 1H), 2.74 (d, 1H), 2.43 (t, J=20.0 Hz), 2.37 (t, J=7.2 Hz, 2H), 2.20 (t, J=7.0 Hz, 2H), 1.55 (m, 6H), 1.43 (m, 2H), 1.32 (m, 2H), 1.26 (t, J=7.2H, 12H); $^{31}$P-NMR (162 MHz, D$_2$O) δ 17.22 (d, J=11.2 Hz, 1P), 14.71 (d, J=11.2 Hz, 1P); LRMS (ESI, [M−H]$^−$) calculated for C$_{27}$H$_{41}$N$_8$O$_{12}$P$_2$S: 763; found: 763.

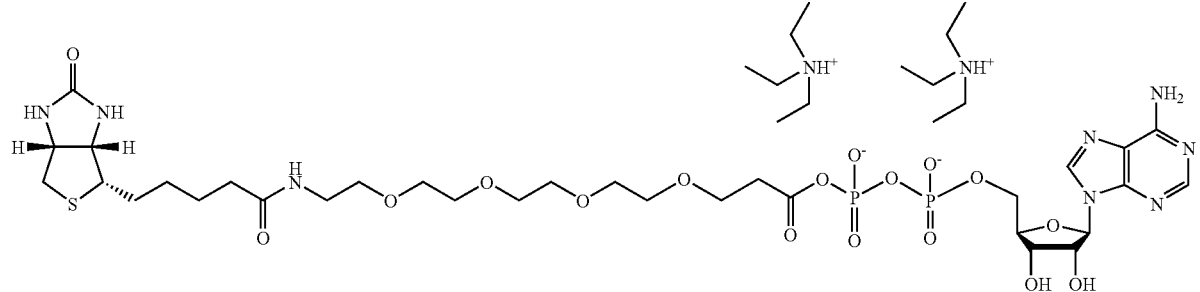

(19)

This compound was prepared using the procedure described for compound 12. $^1$H NMR (400 MHz, D$_2$O) δ 8.54 (s, 1H), 8.29 (s, 1H), 6.14 (d, J=6.0 Hz, 1H, H-1'), 4.75 (m, 1H), 4.56 (m, 2H), 4.39 (m, 2H), 4.22 (m, 2H), 3.66 (m, 16H), 3.37 (m, 2H), 3.30 (m, 1H), 3.20 (t, J=7.3 Hz, 12H), 2.95 (dd, 1H), 2.75 (m, 1H), 2.73 (t, 3H), 2.23 (t, J=7.4 Hz, 2H), 1.65 (m, 4H), 1.36 (m, 2H), 1.27 (t, J=7.4 Hz, 18H); $^{31}$P NMR (162 MHz, D$_2$O) δ −10.67 (d, J=21.5 Hz, 1P), −18.87 (d, J=21.7 Hz, 1P).

EXAMPLE 20

(+)-Biotin-Hex-Acyl-AMPCP (20)

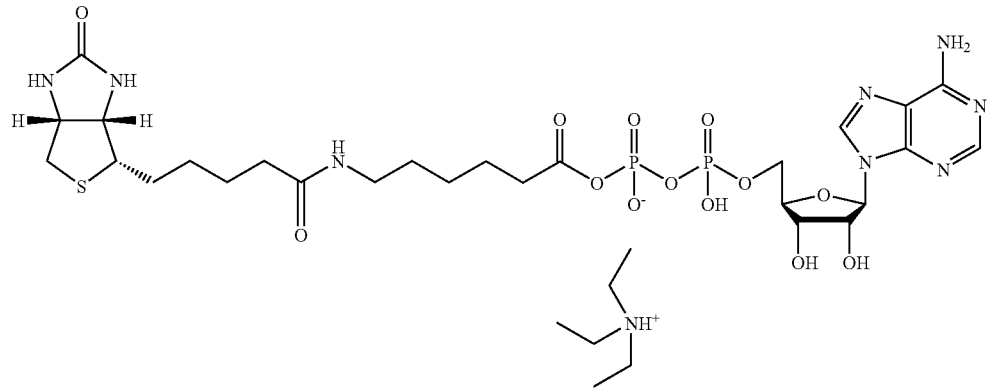

(20)

EXAMPLE 21

(+)-Biotin-Pent-Acyl-ADP (21)

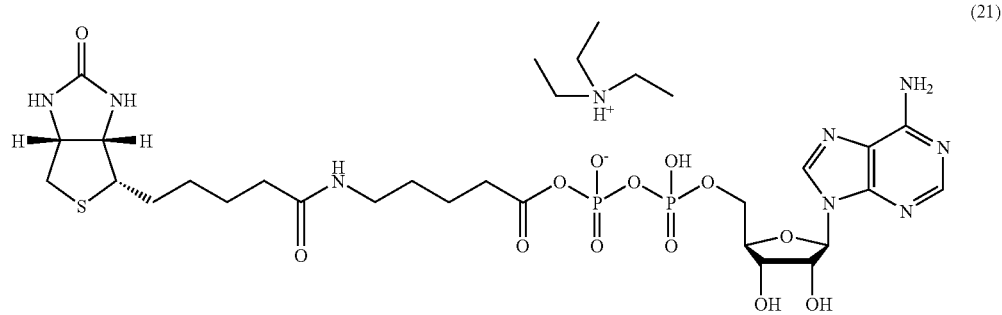

This compound was prepared using the procedure described for compound 12. $^1$H-NMR (400 MHz, D$_2$O) δ 8.65 (s, 1H), 8.43 (s, 1H), 6.18 (d, J=5.6 Hz, 1H, H-1'), 4.75 (m, 1H), 4.56 (m, 1H), 4.54 (m, 1H), 4.39 (m, 2H), 4.23 (m, 2H), 3.22 (m, 1H), 3.17 (q, J=7.2 Hz, 4H), 3.12 (m, 2H), 2.95 (dd, 1H), 2.74 (d, 1H), 2.37 (t, J=7.2 Hz, 2H), 2.21 (t, J=7.0 Hz, 2H), 1.59 (m, 8H), 1.35 (m, 2H), 1.27 (t, J=7.2H, 4H); $^{31}$P-NMR (162 MHz, D$_2$O) δ −10.70 (d, J=21.7 Hz, 1P), −18.64 (d, J=21.5 Hz, 1P); LRMS (ESI, [M−H]$^-$) calculated for C$_{25}$H$_{37}$N$_8$O$_{13}$P$_2$S: 751; found: 751.

EXAMPLE 22

(+)-Biotin-Pen-Acyl-ATP (22)

This compound was prepared using the procedure described for compound 12. $^1$H-NMR (400 MHz, D$_2$O) δ 8.59 (s, 1H), 8.32 (s, 1H), 6.12 (d, J=6.0 Hz, 1H, H-1'), 4.75 (m, 1H), 4.55 (m, 2H), 4.38 (m, 2H), 4.25 (m, 2H), 3.20 (m, 1H), 3.17 (q, J=7.2 Hz, 12H), 3.09 (m, 2H), 2.95 (dd, 1H), 2.73 (d, 1H), 2.43 (m, 2H), 2.20 (t, J=7.0 Hz, 2H), 1.55 (m, 10H), 1.26 (t, J=7.2H, 18H); $^{31}$P-NMR (162 MHz, D$_2$O) δ −10.68 (d, J=19.2 Hz, 1P), −18.75 (d, J=19.4 Hz, 1P), −22.62 (t, J=19.6 Hz, 1P); LRMS (MALDI, [M+H]$^+$) calculated for C$_{25}$H$_{40}$N$_8$O$_{16}$P$_3$S: 833; found: 833.

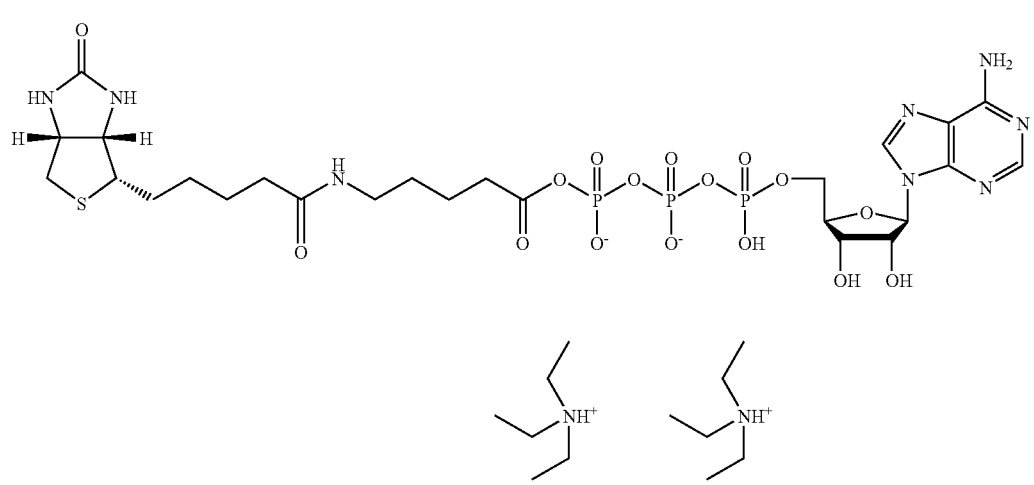

EXAMPLE 23

Alkyne-Acyl-ADP (23)

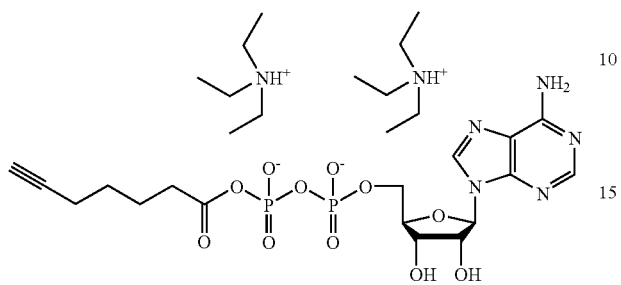

This compound was prepared according to the procedure for compound 12. $^{1}$H-NMR (400 MHz, D$_2$O) δ 8.53 (s, 1H), 8.27 (s, 1H), 6.13 (d, J=6.0 Hz, 1H, H-1'), 4.75 (m, 1H), 4.51 (m, 1H), 4.38 (m, 1H), 4.22 (m, 2H), 3.19 (q, J=7.2 Hz, 12H), 2.32 (t, J=7.4 Hz, 2H), 2.24 (s, 1H), 2.05 (t, J=7.0 Hz, 2H), 1.49 (m, 2H), 1.32 (m, 2H), 1.26 (t, J=7.2H, 18H); $^{31}$P-NMR (162 MHz, D$_2$O) δ −10.73 (d, J=22.1 Hz, 1P), −18.74 (d, J=22.1 Hz, 1P).

EXAMPLE 24

TAMRA-5'-Triazole-Acyl-ADP (24)

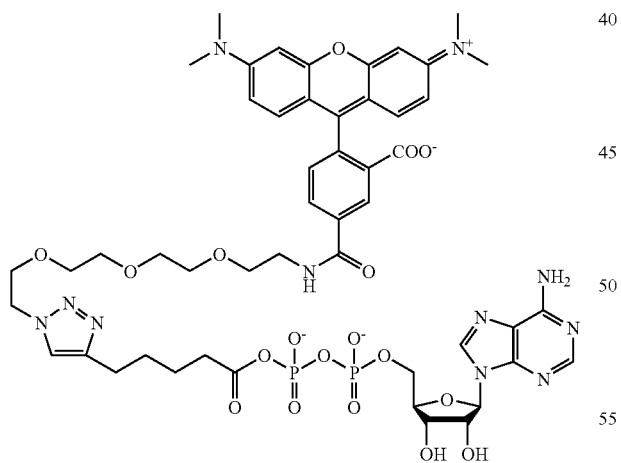

A solution of TAMRA-5'-CONH—(CH$_2$O)$_3$—CH2CH2-N3 (4.0 mg, 6.3 μmole), compound 23 (4.7 mg, 6.3 μmole), sodium ascorbate (0.6 mg, 3.2 μmole) and copper sulfate pentahydrate (0.4 mg, 1.6 μmole) in 2 mL of water was kept at 37° C. for two hours and was then lyophilized. The residue was dissolved in water and purified by a short C18 column (14×45 mm) using a gradient of water to 80% acetonitrile/water to give the title compound 24 as a red powder: $^{31}$P-NMR (162 MHz, D$_2$O) δ −10.78 (m, 1P), −18.70 (m, 1P); LRMS (MALDI, [M−H]$^-$) calculated for C$_{50}$H$_{61}$N$_{11}$O$_{18}$P$_2$: 1165; found: 1165.

EXAMPLE 25

TAMRA-6'-Carbamate-Triazole-Acyl-ADP (25)

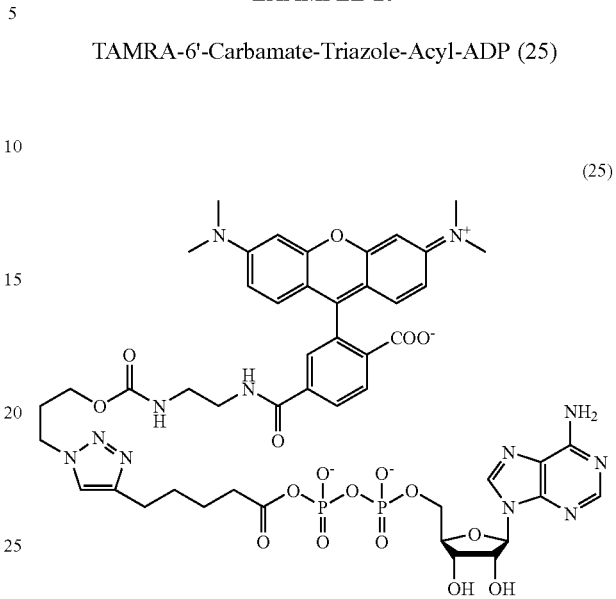

This compound was prepared according to the procedure for compound 24: LRMS (MALDI, [M−H]$^-$) calculated for C$_{48}$H$_{55}$N$_{12}$O$_{17}$P$_2$: 1133; found: 1133.

EXAMPLE 26

TAMRA-6'-Reversed Carbamate-Triazole-Acyl-ADP (26)

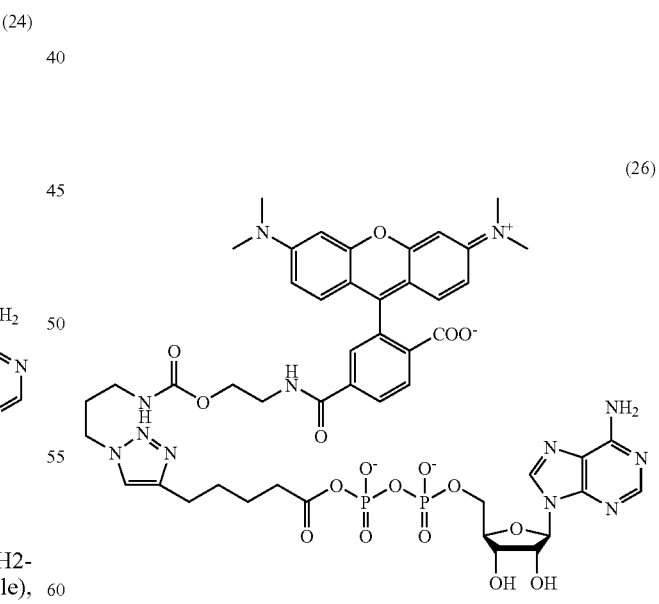

This compound was prepared according to the procedure for compound 24: LRMS (MALDI, [M−H]$^-$) calculated for C$_{48}$H$_{55}$N$_{12}$O$_{17}$P$_2$: 1133; found: 1133.

EXAMPLE 27

Alkyne-Acyl-ATP (27)

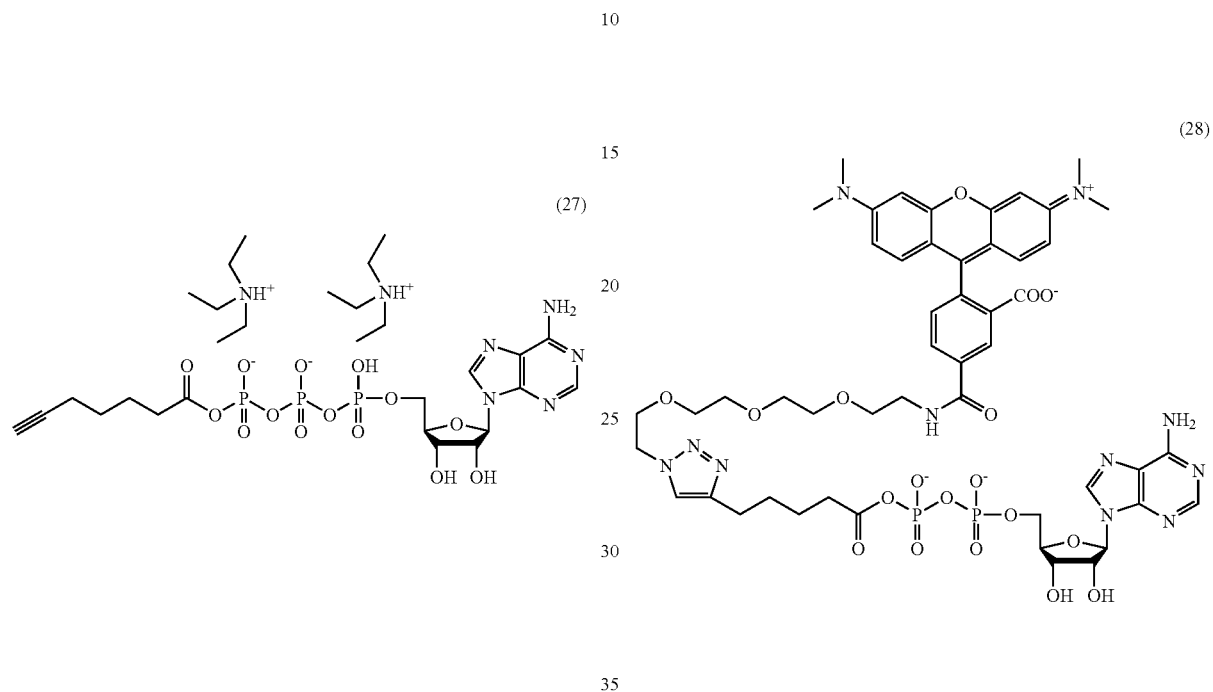

This compound was prepared according to the procedure described for compound 12. $^1$H-NMR (400 MHz, D$_2$O) δ 8.53 (s, 1H), 8.29 (s, 1H), 6.02 (d, J=5.6 Hz, 1H, H-1'), 4.63 (m, 1H), 4.44 (m, 1H), 4.29 (m, 1H), 4.16 (m, 2H), 3.08 (q, J=7.2 Hz, 12H), 2.34 (t, J=7.2 Hz, 2H), 2.16 (s, 1H), 2.03 (t, J=7.2 Hz, 2H), 1.51 (m, 2H), 1.34 (m, 2H), 1.15 (t, J=7.2H, 18H); $^{31}$P-NMR (162 MHz, D$_2$O) δ −10.45 (d, J=19.6 Hz, 1P), −18.69 (d, J=19.8 Hz, 1P), −22.56 (d, J=19.4 Hz, 1P).

EXAMPLE 28

TAMRA-5'-PEG-Triazole-Acyl-ATP (28)

This compound was prepared according to the procedure described for compound 24: LRMS (MALDI, [M−H]$^−$) calculated for C$_{50}$H$_{62}$N$_{11}$O$_{21}$P$_3$: 1244; found: 1244.

EXAMPLE 29

Biotin-Acyl-CTP (29)

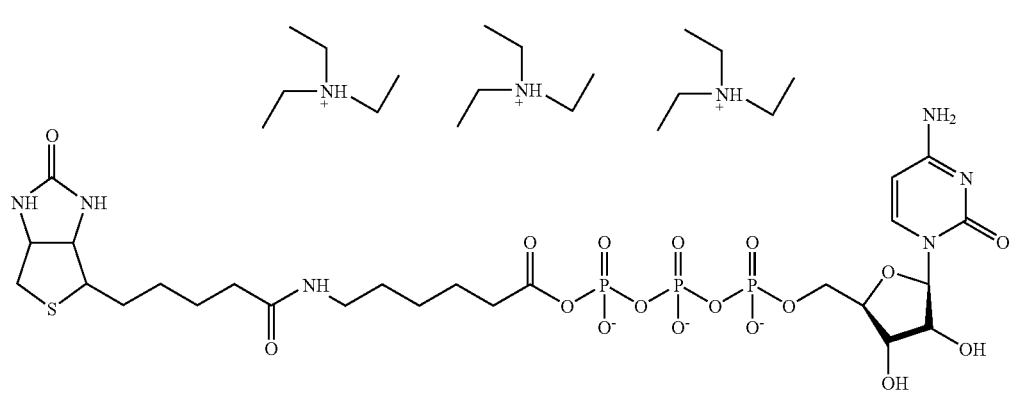

This compound was prepared according to the procedure described for compound 12. $^1$H NMR (400 MHz, D$_2$O) δ 8.1 (d, 2H), 6.2 (d, 1H), 5.8 (d, 1H), 4.1-4.3 (m, 6H), 3.9 (d, 2H), 3.1 (q, 15H), 1.2 (t, 27H), 0.8 (d, 7H). $^{31}$P-NMR (162 MHz, D$_2$O) 6-10.38 (d, J=19.4 Hz, 1P), -19.17 (d, J=18.0, 1P), -22.8 (t, J=17.8 Hz, 1P).

EXAMPLE 30

Biotin-Acyl-GTP (30)

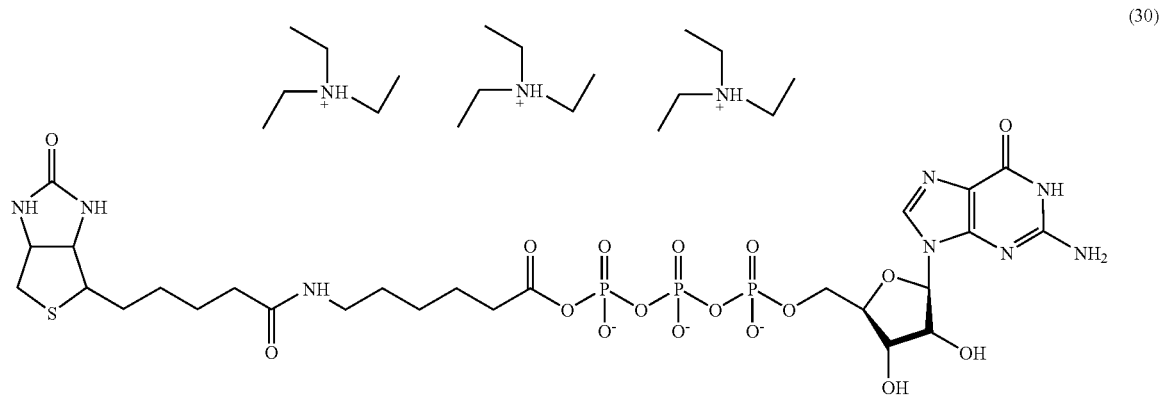

(30)

This compound was prepared according to the procedure described for compound 12. $^1$H NMR (400 MHz, D$_2$O) δ 8.0 (s, 1H), 5.9 (d, 1H), 4.5 (m, 2H), 4.2 (m, 2H), 4.1 (m, 2H), 3.1 (q, 20H), 2.9 (d, 1H), 2.6 (d, 1H). 1.1 (t, 34H), 1.0 (d, 3H). $^{31}$P-NMR (162 MHz, D$_2$O) δ -10.5 (d, J=26.2, 1P), -19.0 (d, J=19.76, 1P), -22.7 (t, J=19.1, 1P). MALDI, [M–H]$^-$ calculated for C$_{26}$H$_{41}$N$_8$O$_{17}$P$_3$S: 862.63; found: 861.3 (M–H)

EXAMPLE 31

Biotin-Acyl-GDP (31)

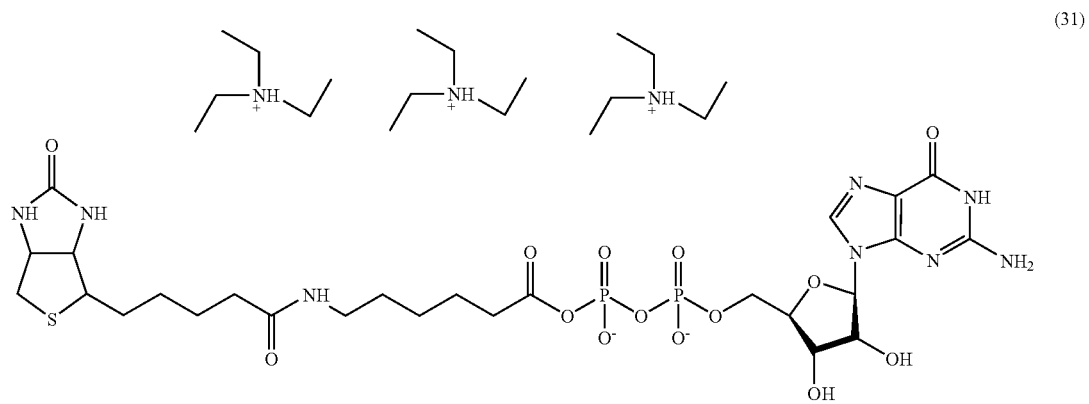

(31)

This compound was prepared according to the procedure described for compound 12. $^1$H NMR (400 MHz, D$_2$O) δ 7.9 (s, 1H), 5.8(d, 1H), 4.5(t, 1H), 4.4 (t, 1H), 4.3 (m, 2H), 4.1 (m, 2H), 3.1 (q, 14H), 2.9 (q, 1H), 2.8 (m, 1H), 2.6 (m, 1H), 2.2 (t, 2H), 2.1 (t, 2H), 1.3-1.5 (m, 7H), 1.1 (t, 27H), 1.0 (d, 1H). $^{31}$P-NMR (162 MHz, D$_2$O) δ −10.7 (d, J=21.2, 1P), −18.7 (d, J=22.0, 1P).

EXAMPLE 32

Biotin-Acyl-UTP (32)

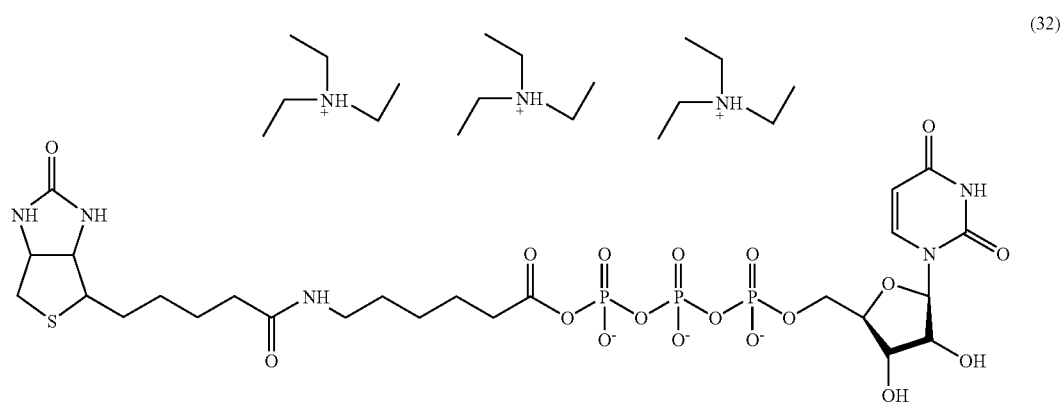

(32)

This compound was prepared according to the procedure described for compound 12. $^1$H NMR (400 MHz, D$_2$O) δ 7.9 (d, 1H), 5.8(d, 1H), 4.6 (m, 4H), 4.3 (m, 4H), 4.1-4.2 (d, 4H), 3.1 (m, 27H), 2.8 (m, 2H), 2.68 (d, 1H), 2.4 (t, 2H), 2.1 (t, 2H), 2.4-2.6 (m, 10H), 1.2 (t, 39H), 1.0 (d, 2H). $^{31}$P-NMR (162 MHz, D$_2$O) δ −10.6 (d, J=18.1, 1P), −18.7 (d, J=19.4, 1P), −22.7 (t, J=19.6, 1P).

EXAMPLE 33

Biotin-Acyl-UDP (33)

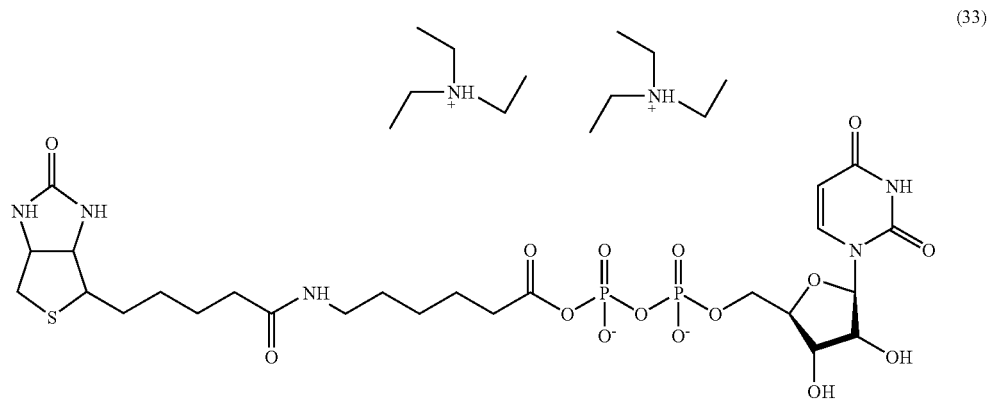

(33)

This compound was prepared according to the procedure described for compound 12. $^1$H NMR (400 MHz, D$_2$O) δ 7.9 (d, 1H), 5.9(m, 1H), 4.6 (m, 4H), 4.1-4.3 (m, 9H), 3.2 (m, 3H), 3.0 (m, 17H), 2.7-2.8 (m, 2H), 2.6-2.7 (m, 2H), 2.3 (t, 3H), 2.11 (t, 3H), 1.3-1.5 (m, 14H), 1.16 (t, 29H). $^{31}$P-NMR (162 MHz, D$_2$O) δ −10.7 (d, J=21.2, 1P), −18.7 (d, J=21.4, 1P).

EXAMPLE 34

Biotin-Acyl-CDP (34)

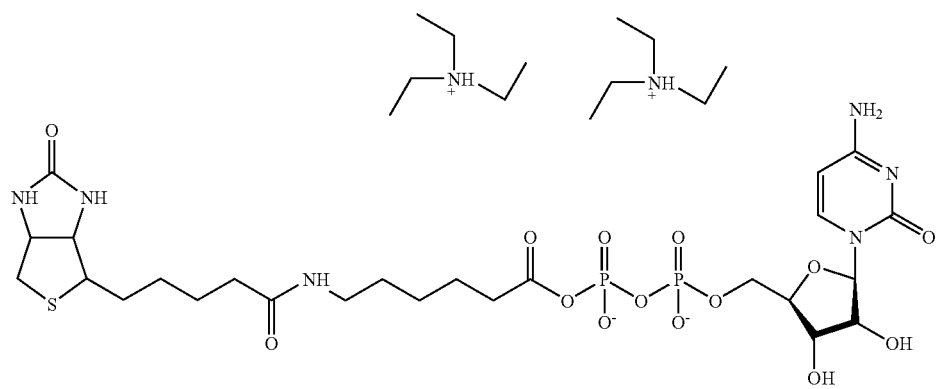

34

This compound was prepared according to the procedure described for compound 12. $^1$H NMR (400 MHz, D$_2$O) δ 7.9 (d, 1H), 6.1 (d, 1H), 5.8(d, 1H), 4.5 (m, 3H), 4.1-4.3 (m, 8H), 3.1 (q, 18H), 2.9 (m, 1H), 2.7 (m, 1H), 2.3-2.4 (m, 3H), 2.2 (t, 3H), 1.3-1.5 (m, 10H), 1.2 (25H), 0.9 (2H). $^{31}$P-NMR (162 MHz, D$_2$O) δ −10.7 (d, J=21.87 Hz, 1P), −18.6 (d, J=21.7 Hz, 1P).

EXAMPLE 35

Labeling of Polypeptides

The following is a procedure for preparing and analyzing samples from primary tissue according to methods of the present invention. Exemplary components needed are a mortar and pestle, cryule vials, labels, Eppendorf 1.5 ml tubes, Beckman tubes for TL100.3 rotor, TL100 ultracentrifige, spatulas, liquid nitrogen in dewar, dry ice, Omni 5 mm probe and homogenizer, sonicator, beakers for waste and washes, pipettors, 50 mM tris buffer pH 7.4+/−0.1% Triton X100, BioRad Dc protein assay, microtiter plate and reader, 2×SDS-PAGE loading buffer, FP probe.

Flash-frozen tissue is crushed into ~1 mm pieces or smaller in pool of liquid nitrogen using a ceramic pestle and mortar. With the help of a spatula, frozen pieces are transferred into a cruyule vial on dry ice. The liquid nitrogen is allowed to vaporize before capping. About 0.1 g of tissue is then transferred into an Eppendorf tube for processing, keeping all samples on dry ice. The 0.1 g of frozen tissue is transferred from the Eppendorf tube to a 12×75 mm polypropylene round bottom tube. Approximately 400 µl of cold 50 mM Tris, pH 7.4, is added to each sample. Each sample is then homogenized with a 5 mm stainless steel Omni probe using 2×4 sec bursts at highest speed, making sure to keep the tube on ice the entire time.

In between samples, the homogenizer probe tip is washed by running it in a large beaker of water, replacing this water often and bleaching the waste. Any fibers are removed out of the probe tip with tweezers, and the end of the probe is blotted with a Kimwipe to remove trapped liquid.

The homogenized sample is sonicated using a microtip at setting 2.5, 4×3 second pulses, keeping the sample on ice the entire time. The sonicated sample is then transferred a microcentrifuge tube and spun at 2000×g for 10 min at 4° C. in a microcentrifuge to pellet unlysed material. The supernatant from this tube is then transferred to Beckman tubes (# 357448) and spun in a prechilled ultracentifuge at 64K rpm (170,000×g) at 4° C. for 1 hour. The supernatant (soluble protein fraction) is then transferred to a fresh tube, leaving behind the membrane pellet (membrane bound protein fraction). The membrane pellet is rinsed with about 100 µl cold 50 mM Tris, pH 7.4, and solubilized with 400 µl cold 50 mM Tris pH 7.4+0.1% Triton X-100 buffer on ice using a sonicator.

The protein concentration of both soluble and membrane fractions is determined using the BioRad Dc protein assay (#500-0116) as follows. Serial dilutions of samples (neat, ½, ¼, ⅛) are tested using BSA standard concentrations of 1.4, 1.05, 0.787, 0.54, 0.44, 0.33, 0.249 and 0 mg/ml (¾ dilutions). Tris+0.1% Triton buffer are used as the diluent and as the blank. In a 96 well microtiter plate, 5 µl of sample or standard is used per well, adding 25 µl Reagent A, then 200 µl Reagent B. The reaction color is developed for 15 minutes at room temperature and the plates read to determine the OD at 750 nm. Sample protein concentrations are then adjusted to 1 to 1.5 mg/ml with Tris or Tris/Triton buffer for soluble or membrane fractions, respectively.

A heated control sample is prepared by heating ~60 µL of sample in a microcentrifuge tube in a block heater at 95° C. for 6 minutes prior to labeling. After heating, the sample is chilled down on ice, then spun in a microcentrifuge. Samples containing precipitate that does not disperse by vortexing may be sonicated prior to labeling.

Samples are labeled by adding probe to a lysate sample to a final concentration of 2 µM and mixed quickly by flicking the tube. A minimum volume of probe is used such that the amount of added probe did not exceed 5% of the final sample volume. Samples are typically labeled using 50 µl with 1 µl of 100 µM probe for 1 hour at room temperature. At the end of the labeling period, an equal volume (50 µl) of 2×SDS-PAGE loading buffer is added and the mixture heated at 95° C. for 6 minutes, cooled to room temperature, spun, and loaded on 12.5% SDS-PAGE gels. Long gels are loaded with 20 μg of samples and electrophoresed for 4 hours at 300 volts, and maximum current. The gels are then rinsed with water and wiped dry, keeping the gel in the glass plates for scanning.

EXAMPLE 36

Protein Identification

For identification of proteins by mass spectrometry, samples are prepared as described in the previous example through the probe labeling step. At the end of the labeling period, 80 mg urea is added per 100 uL of sample, and DTT is added to a final concentration of 10 mM from a fresh 1M stock. The resulting mixture is heated to 65° C. for 20 minutes, then cooled to room temperature. Iodoacetamide is then added to a final concentration of 40 mM from a fresh 1M stock. The resulting mixture is incubated at 37° C. for 45 minutes in the dark.

The sample as prepared above is then added to a desalting (Pharmacia PD10 or Bio-Rad 10DG) preequilabrated with 2M urea, 20 mM Ammonium Bicarbonate. The protein peak is identified by absorbance at 280 nm and collected.

$\frac{1}{10}$ volume of 10% SDS is then added to the pooled protein fractions, and the mixture heated to 65° C. for 5 minutes. This is then diluted with 1 volume of 2× Binding Buffer (2% Triton X-100, 1% Tergitol NP40 type, 300 mM NaCl, 2 mM EDTA, 20 mM Tris pH 7.4). Antibody affinity beads (either monoclonal or goat polyclonal antibody directed to TAG are added using a cut off pipette tip (anywhere from 30-200 uL of 50% bead slurry to yield 15-100 uL of beads). The mixture is mixed by rocking at room temperature for from 2 hours to 15 hours.

The antibody beads are then pelleted by centrifugation, and the supernatant carefully removed and discarded. The beads are washed at least three times with 1 mL of binding buffer+0.2% SDS. The beads are then washed twice with 0.5 mL of 50 mM tris, 100 mM NaCl to remove excess detergents.

Captured proteins are eluted with 1 bed volume of 1× non-reducing loading/elution buffer (50 mM Tris pH 7.5, 10% glycerol, 5% SDS, 150 mM NaCl, bromophenol blue (5 mg/50 mL)). The beads are allowed to sit in this buffer at 65° C. for 10 minutes when monoclonal antibodies are employed for capture. For goat polyclonal antibody beads, captured proteins are eluted at room temperature for 10 minutes. The sample (beads and buffer liquid) are then loaded onto a micro spin column and spun at 5000 rpm for 3 minutes in a microcentrifuge for collection of eluted proteins.

If goat polyclonal antibodies are used for capture, the eluted proteins are loaded directly onto an SDS-PAGE gel. If monoclonal antibodies are used, DTT is added to 10 mM, and the resulting solution is boiled briefly before loading onto the gel. Following electrophoresis and staining, sections of the gel containing the protein bands of interest are excised, the gel pieces cut into several small pieces and destained with methanol, washed with 100 mM ammonium bicarbonate in 30% acetonitrile a few times, and the proteins digested with trypsin (100 ng) in 3 mM Tris-HCl at pH 8, at 37° C. overnight. The tryptic peptides are extracted out of the gel using 50% acetonitrile/0.1% TFA, concentrated to 10 μl, and subjected to nano-capillpary HPLC-tandem mass spectrometry (MS/MS) for analysis. This analysis is performed on a combination system of Agilent 1100 capillary HPLC/Micro Auto-sampler (Agilent Technologies, Palo Alto, Calif.) and Finnigan LCQ DecaXP ion trap mass spectrometer (Finnigan, San Jose, Calif.).

Liquid chromatographic separation is performed on 3 μl of digested sample mixed with 3 μl of 5% acetic acid, loaded onto a 100 μm fused silica capillary $C_{18}$ column. A sixty minute gradient of 5-95% solvent B (A: $H_2O$/0.1% formic acid, B: MeCN/0.08% formic acid) and a 500 nl/minute column flow rate is used to separate the tryptic peptides in the digested sample. Peptides eluted off the column are directly injected into LCQ DecaXP mass spectrometer.

The heated desolvation capillary in mass spectrometer is held at 200° C., the spray voltage is set at 2.0 kV, and the capillary voltage is set at 30 V. During the experiment, the mass spectrometer is set to alternate between MS and MS/MS mode. The scan range for MS was set at m/z 400-1600. The MS/MS spectra are acquired in dependent scan mode with an initiating minimum MS signal at $2 \times 10^5$ counts, and a 35% normalized collision energy. The scan range for MS/MS is varied from 80-2000 depending on the precursor ion.

The ion masses and the fragmentation information generated by nano-LCMS/MS experiment are analyzed and converted into peptide masses and sequence information with TurboSEQUEST, which is protein identification software. Using this program, peptide sequence information may be compared against the protein database to identify proteins.

EXAMPLE 37

Labeling of Polypeptides

For tissue culture cells, media is aspirated and cells rinsed twice with 10 ml PBS, adding the PBS onto the side of the dish. Cells are harvested by scraping into in extraction buffer (50 mM Tris, pH 7.5, 1 mM EDTA, 0.5 mM EGTA, 5 ug/ml each of protease inhibitors Aprotinin, Pepstatin, Leupeptin, 100 mM PMSF) and then transferred to a 1 ml glass douncer. Cells are dounced up and down 20 times on ice. Then cell lysates are sonicated using a microtip at setting 2.5, using 4 sec pulses, 3 times. Samples are kept on ice during the procedure. After the sample is spun in microcentrifuge tube at 1.0 K rpm for 10 min at 4 C in the microcentrifuge to pellet unlysed material it is spun at 100-110,000×g for 1 h at 4 C. The supernatent (cytosol) is collected and the membrane pellet washed by brief sonication in tris buffer followed by centrifugation. The washed membrane pellet is then solubilized in extraction buffer containing 0.1% Triton X-100 detergent and sonicated again. The protein concentration of both cytosol and membrane fractions is determined using the BioRad Dc protein assay. Serial dilutions of samples (neat, ½, ¼, ⅛) and BSA standard concentrations of 1.4, 1.05, 0.787, 0.54, 0.44, 0.33, 0.249 and 0 mg/ml (¾ dilutions) are tested using Tris buffer as the diluent and as the blank. Sample protein concentrations are adjusted to 5 mg/ml with extraction buffer. The acylphosphate probe is then added to 5 mg of extract in a volume of 1 ml at a final concentration of 10 μM and mixed by flicking the tube. Labeling occurs for 1 h at RT. After labeling is completed 800 mg of urea and DTT to 10 mM final concentration from a fresh 1M stock is added. The sample is heated to 65° C. for 15 min.

After cooling to room temperature Iodoacetamide is added to 40 mM from a fresh 1M stock and the sample incubated at 37° C. for 30 minutes in the dark. After equilibration of a Bio-Rad 10 DG gel filtration column with 2M urea, 10 mM Ammonium Bicarbonate, 5 mM methionine the labeled protein sample is applied to column and fractions collected. The absorbance at $A_{280}$ is followed to find and collect the protein peak. 10 μL of 20% triton X-100 and 30 μL sequencing grade modified trypsin (Promega) is added to the purified sample and the digest incubated at 37° C. for 1 h. Following the digest of the sample 100 μL of 10% SDS is added to the digested sample and heated to 65° C. for 5 minutes. The protein sample is then diluted with 1 volume of 2× Binding Buffer (2% Triton X-100, 1% Tergitol NP40 type, 300 mM NaCl, 2 mM EDTA, 20 mM Tris pH 7.4). 100 μL of a 50% slurry of avidin-beads (Upstate Biotechnology) are added and the sample rocked at room temperature for 1 h. The beads are then spun down and the supernatant removed by aspiration. The beads are then transferred to a microspin column that is set on a 2 mL eppendorf tube. The column is spun briefly in a nanofuge for 3-5 seconds to drain the liquid. The beads are then washed 2× more with 1 mL of 1× binding buffer+1% SDS.

Beads are then washed 3× with 1 mL of 1×PBS and then 3× with 1 mL of ddH2O. Captured peptides are then eluted with 2 separate 50 μL volumes of freshly prepared 50% Acetonitrile with 0.1% TFA and the eluates analyzed by mass spectrometry.

EXAMPLE 38

Identification of Labeled Proteins

Using the methods of the present invention, the following table lists proteins that have been identified by labeling with nucleotide-based TAPPs:

Protein kinases

| | |
|---|---|
| AAK1_HUMAN | 5'-AMP-activated protein kinase, catalytic alpha-1 chain (EC 2.7.1.-) (AMPK alpha-1 chain). [*Homo sapiens*] |
| AAK1_RAT | 5'-AMP-activated protein kinase, catalytic alpha-1 chain (EC 2.7.1.-) (AMPK alpha-1 chain). [*Rattus norvegicus*] |
| AAK2_HUMAN | 5'-AMP-activated protein kinase, catalytic alpha-2 chain (EC 2.7.1.-) (AMPK alpha-2 chain). [*Homo sapiens*] |
| AAKG_HUMAN | 5'-AMP-activated protein kinase, gamma-1 subunit (AMPK gamma-1 chain) (AMPKg). [*Homo sapiens*] |
| ABL1_HUMAN | Proto-oncogene tyrosine-protein kinase ABL1 (EC 2.7.1.112) (p150) (c-ABL). [*Homo sapiens*] |
| ABL2_HUMAN | Tyrosine-protein kinase ABL2 (EC 2.7.1.112) (Tyrosine kinase ARG). [*Homo sapiens*] |
| AKT2_HUMAN | RAC-beta serine/threonine protein kinase (EC 2.7.1.-) (RAC-PK-beta) (Protein kinase Akt-2) (Protein kinase B, beta) (PKB beta). [*Homo sapiens*] |
| ANR3_HUMAN | Serine/threonine-protein kinase ANKRD3 (EC 2.7.1.-) (Ankyrin repeat domain protein 3) (PKC-delta-interacting protein kinase). [*Homo sapiens*] |
| ARK1_HUMAN | Beta-adrenergic receptor kinase 1 (EC 2.7.1.126) (Beta-ARK-1) (G- protein coupled receptor kinase 2). [*Homo sapiens*] |
| ARK1_RAT | Beta-adrenergic receptor kinase 1 (EC 2.7.1.126) (Beta-ARK-1) (G- protein coupled receptor kinase 2). [*Rattus norvegicus*] |
| ARK2_HUMAN | Beta-adrenergic receptor kinase 2 (EC 2.7.1.126) (Beta-ARK-2) (G-protein coupled receptor kinase 3). [*Homo sapiens*] |
| BCKD_HUMAN | [3-methyl-2-oxobutanoate dehydrogenase [lipoamide]] kinase, mitochondrial precursor (EC 2.7.1.115) (Branched-chain alpha-ketoacid dehydrogenase kinase) (BCKDHKIN) (BCKD-kinase). [*Homo sapiens*] |
| BCR_HUMAN | Breakpoint cluster region protein (EC 2.7.1.-). [*Homo sapiens*] |
| BTK_HUMAN | Tyrosine-protein kinase BTK (EC 2.7.1.112) (Bruton's tyrosine ki |
| CDC2_HUMAN | Cell division control protein 2 homolog (EC 2.7.1.-) (p34 protein kinase) (Cyclin-dependent kinase 1) (CDK1). [*Homo sapiens*] |
| CDC2_MOUSE | Cell division control protein 2 homolog (EC 2.7.1.-) (p34 protein kinase) (Cyclin-dependent kinase 1) (CDK1). [*Mus musculus*] |
| CDC2_RAT | Cell division control protein 2 homolog (EC 2.7.1.-) (p34 protein kinase) (Cyclin-dependent kinase 1) (CDK1). [*Rattus norvegicus*] |
| CDK2_HUMAN | Cell division protein kinase 2 (EC 2.7.1.-) (p33 protein kinase). [*Homo sapiens*] |
| CDK2_MOUSE | Cell division protein kinase 2 (EC 2.7.1.-). [*Mus musculus*] |
| CDK2_RAT | Cell division protein kinase 2 (EC 2.7.1.-). [*Rattus norvegicus*] |
| CDK5_HUMAN | Cell division protein kinase 5 (EC 2.7.1.-) (Tau protein kinase II catalytic subunit) (TPKII catalytic subunit) (Serine/threonine protein kinase PSSALRE). [*Homo sapiens*] |
| CDK5_MOUSE | Cell division protein kinase 5 (EC 2.7.1.-) (Tau protein kinase II catalytic subunit) (TPKII catalytic subunit) (Serine/threonine protein kinase PSSALRE) (CRK6). [*Mus musculus*] |
| CDK5_RAT | Cell division protein kinase 5 (EC 2.7.1.-) (Tau protein kinase II catalytic subunit) (TPKII catalytic subunit) (Serine/threonine protein kinase PSSALRE). [*Rattus norvegicus*] |
| CDK6_HUMAN | Cell division protein kinase 6 (EC 2.7.1.37) (Serine/threonine protein kinase PLSTIRE). [*Homo sapiens*] |
| CDK9_HUMAN | Cell division protein kinase 9 (EC 2.7.1.-) (Serine/threonine-protein kinase PITALRE) (C-2K). [*Homo sapiens*] |
| CHK1_HUMAN | Serine/threonine-protein kinase Chk1 (EC 2.7.1.-). [*Homo sapiens*] |
| CHK2_HUMAN | Serine/threonine-protein kinase Chk2 (EC 2.7.1.37) (Cds1). [*Homo sapiens*] |
| CNE3_HUMAN | Copine III. [*Homo sapiens*] |
| CSKP_HUMAN | Peripheral plasma membrane protein CASK (EC 2.7.1.-) (hCASK) (Calcium/calmodulin-dependent serine protein kinase) (Lin-2 homolog). [*Homo sapiens*] |
| CSK_HUMAN | Tyrosine-protein kinase CSK (EC 2.7.1.112) (C-SRC kinase) (Protein- tyrosine kinase CYL). [*Homo sapiens*] |
| CSK_MOUSE | Tyrosine-protein kinase CSK (EC 2.7.1.112) (C-SRC kinase) (Protein- tyrosine kinase MPK-2). [*Mus musculus*] |
| CSK_RAT | Tyrosine-protein kinase CSK (EC 2.7.1.112) (C-SRC kinase). [*Rattus norvegicus*] |
| DAPK_HUMAN | Death-associated protein kinase 1 (EC 2.7.1.-) (DAP kinase 1). [*Homo sapiens*] |
| DCK1_MOUSE | Serine/threonine-protein kinase DCAMKL1 (EC 2.7.1.-) (Doublecortin- like and CAM kinase-like 1). [*Mus musculus*] |
| DYRA_HUMAN | Dual-specificity tyrosine-phosphorylation regulated kinase 1A (EC 2.7.1.-) (Protein kinase minibrain homolog) (MNBH) (HP86) (Dual specificity YAK1-related kinase). [*Homo sapiens*] |

-continued

| | |
|---|---|
| E2K2__HUMAN | Interferon-induced, double-stranded RNA-activated protein kinase (EC 2.7.1.-) (Interferon-inducible RNA-dependent protein kinase) (p68 kinase) (P1/eIF-2A protein kinase). [*Homo sapiens*] |
| E2K2__MOUSE | Interferon-induced, double-stranded RNA-activated protein kinase (EC 2.7.1.-) (Interferon-inducible RNA-dependent protein kinase) (p68 kinase) (P1/eIF-2A protein kinase) (Serine/threonine-protein kinase TIK). [*Mus musculus*] |
| EF2K__HUMAN | Elongation factor 2 kinase (EC 2.7.1.-) (eEF-2 kinase) (eEF-2K) (Calcium/calmodulin-dependent eukaryotic elongation factor-2 kinase). [*Homo sapiens*] |
| EF2K__RAT | Elongation factor 2 kinase (EC 2.7.1.-) (eEF-2 kinase) (eEF-2K) (Calcium/calmodulin-dependent eukaryotic elongation factor-2 kinase). [*Rattus norvegicus*] |
| EGFR__HUMAN | Epidermal growth factor receptor precursor (EC 2.7.1.112) (Receptor protein-tyrosine kinase ErbB-1). [*Homo sapiens*] |
| EPA1__HUMAN | Ephrin type-A receptor 1 precursor (EC 2.7.1.112) (Tyrosine-protein kinase receptor EPH). [*Homo sapiens*] |
| EPA2__HUMAN | Ephrin type-A receptor 2 precursor (EC 2.7.1.112) (Tyrosine-protein kinase receptor ECK) (Epithelial cell kinase). [*Homo sapiens*] |
| EPA7__HUMAN | Ephrin type-A receptor 7 precursor (EC 2.7.1.112) (Tyrosine-protein kinase receptor EHK-3) (Eph homology kinase-3) (Receptor protein- tyrosine kinase HEK11). [*Homo sapiens*] |
| FAK1__HUMAN | Focal adhesion kinase 1 (EC 2.7.1.112) (FADK 1) (pp125FAK) (Protein- tyrosine kinase 2). [*Homo sapiens*] |
| FAK2__HUMAN | Protein tyrosine kinase 2 beta (EC 2.7.1.112) (Focal adhesion kinase 2) (FADK 2) (Proline-rich tyrosine kinase 2) (Cell adhesion kinase beta) (CAK beta) (Calcium-dependent tyrosine kinase) (CADTK) (Related adhesion focal tyrosine kinase). [*Homo sapiens*] |
| FER__HUMAN | Proto-oncogene tyrosine-protein kinase FER (EC 2.7.1.112) (p94-FER) (c-FER). [*Homo sapiens*] |
| FES__HUMAN | Proto-oncogene tyrosine-protein kinase FES/FPS (EC 2.7.1.112) (C-FES). [*Homo sapiens*] |
| FGR1__MOUSE | Basic fibroblast growth factor receptor 1 precursor (EC 2.7.1.112) (FGFR-1) (bFGF-R) (MFR). [*Mus musculus*] |
| FGR__HUMAN | Proto-oncogene tyrosine-protein kinase FGR (EC 2.7.1.112) (P55-FGR) (C-FGR). [*Homo sapiens*] |
| FLK__RAT | Tyrosine-protein kinase FLK (EC 2.7.1.112) (Fragment). [*Rattus norvegicus*] |
| GRK5__RAT | G protein-coupled receptor kinase GRK5 (EC 2.7.1.-) (G-protein-coupled receptor kinase 5). [*Rattus norvegicus*] |
| HCK__HUMAN | Tyrosine-protein kinase HCK (EC 2.7.1.112) (P59-HCK and P60-HCK) |
| IKKA__HUMAN | Inhibitor of nuclear factor kappa-B kinase alpha subunit (EC 2.7.1.-) (I kappa-B kinase alpha) (IkBKA) (IKK-alpha) (IKK-A) (IkappaB kinase) (I-kappa-B kinase 1) (IKK1) (Conserved helix-loop-helix ubiquitous kinase) (Nuclear factor NFkappaB inhibitor kinas |
| IKKA__MOUSE | Inhibitor of nuclear factor kappa-B kinase alpha subunit (EC 2.7.1.-) (I kappa-B kinase alpha) (IkBKA) (IKK-alpha) (IKK-A) (IkappaB kinase) (I-kappa-B kinase 1) (IKK1) (Conserved helix-loop-helix ubiquitous kinase) (Nuclear factor NFkappaB inhibitor kinas |
| IKKB__HUMAN | Inhibitor of nuclear factor kappa B kinase beta subunit (EC 2.7.1.-) (I-kappa-B-kinase beta) (IkBKB) (IKK-beta) (IKK-B) (I-kappa-B kinase 2) (IKK2) (Nuclear factor NF-kappa-B inhibitor kinase beta) (NFKBIKB). [*Homo sapiens*] |
| IKKB__MOUSE | Inhibitor of nuclear factor kappa B kinase beta subunit (EC 2.7.1.-) (I-kappa-B-kinase beta) (IkBKB) (IKK-beta) (IKK-B) (I-kappa-B kinase 2) (IKK2) (Nuclear factor NF-kappa-B inhibitor kinase beta) (NFKBIKB). [*Mus musculus*] |
| IKKB__RAT | Inhibitor of nuclear factor kappa B kinase beta subunit (EC 2.7.1.-) (I-kappa-B-kinase beta) (IkBKB) (IKK-beta) (IKK-B) (I-kappa-B kinase 2) (IKK2) (Nuclear factor NF-kappa-B inhibitor kinase beta) (NFKBIKB). [*Rattus norvegicus*] |
| ILK1__HUMAN | Integrin-linked protein kinase 1 (EC 2.7.1.-) (ILK-1) (59 kDa serine/threonine protein kinase) (p59ILK). [*Homo sapiens*] |
| ILK__MOUSE | Integrin-linked protein kinase (EC 2.7.1.-). [*Mus musculus*] |
| INSR__HUMAN | Insulin receptor precursor (EC 2.7.1.112) (IR) (CD220 antigen). [*Homo sapiens*] |
| IRA1__HUMAN | Interleukin-1 receptor-associated kinase 1 (EC 2.7.1.-) (IRAK-1). [*Homo sapiens*] |
| JAK1__HUMAN | Tyrosine-protein kinase JAK1 (EC 2.7.1.112) (Janus kinase 1) (JAK-1). [*Homo sapiens*] |
| JAK2__MOUSE | Tyrosine-protein kinase JAK2 (EC 2.7.1.112) (Janus kinase 2) (JAK-2). [*Mus musculus*] |
| JAK3__HUMAN | Tyrosine-protein kinase JAK3 (EC 2.7.1.112) (Janus kinase 3) (JAK-3) (Leukocyte janus kinase) (L-JAK). [*Homo sapiens*] |
| JAK3__RAT | Tyrosine-protein kinase JAK3 (EC 2.7.1.112) (Janus kinase 3) (JAK-3). [*Rattus norvegicus*] |
| K6A1__HUMAN | Ribosomal protein S6 kinase alpha 1 (EC 2.7.1.37) (S6K-alpha 1) (90 kDa ribosomal protein S6 kinase 1) (p90-RSK 1) (Ribosomal S6 kinase 1) (RSK-1) (pp90-RSK). [*Homo sapiens*] |
| K6A1__RAT | Ribosomal protein S6 kinase alpha 1 (EC 2.7.1.37) (S6K-alpha 1) (90 kDa ribosomal protein S6 kinase 1) (p90-RSK 1) (Ribosomal S6 kinase 1) (RSK-1) (pp90RSK1). [*Rattus norvegicus*] |
| K6A2__HUMAN | Ribosomal protein S6 kinase alpha 2 (EC 2.7.1.37) (S6K-alpha 2) (90 kDa ribosomal protein S6 kinase 2) (p90-RSK 2) (Ribosomal S6 kinase 3) (RSK-3) (pp90RSK3). [*Homo sapiens*] |
| K6A2__MOUSE | Ribosomal protein S6 kinase alpha 2 (EC 2.7.1.37) (S6K-alpha 2) (90 kDa ribosomal protein S6 kinase 2) (p90-RSK 2) (Ribosomal S6 kinase 3) (RSK-3) (pp90RSK3) (Protein-tyrosine kinase Mpk-9). [*Mus musculus*] |
| K6A3__HUMAN | Ribosomal protein S6 kinase alpha 3 (EC 2.7.1.-) (S6K-alpha 3) |
| K6A3__MOUSE | Ribosomal protein S6 kinase alpha 3 (EC 2.7.1.37) (S6K-alpha 3) (90 kDa ribosomal protein S6 kinase 3) (p90-RSK 3) (Ribosomal S6 kinase 2) (RSK-2) (pp90RSK2). [*Mus musculus*] |
| K6A6__HUMAN | Ribosomal protein S6 kinase alpha 6 (EC 2.7.1.37) (S6K-alpha 6) (90 kDa ribosomal protein S6 kinase 6) (p90-RSK 6) (Ribosomal S6 kinase 4) (RSK-4) (pp90RSK4). [*Homo sapiens*] |
| K6B1__HUMAN | Ribosomal protein S6 kinase (EC 2.7.1.-) (S6K) (p70-S6K). [*Homo sapiens*] |
| K6B1__RAT | Ribosomal protein S6 kinase I (EC 2.7.1.-) (S6K) (p70-S6K). [*Rattus norvegicus*] |
| K6B2__MOUSE | Ribosomal protein S6 kinase beta 2 (EC 2.7.1.-) (S6K-beta 2) (70 kDa ribosomal protein S6 kinase 2) (p70-S6KB) (p70 ribosomal S6 kinase beta) (p70 S6Kbeta) (S6K2). [*Mus musculus*] |
| KC1A__RAT | Casein kinase I, alpha isoform (EC 2.7.1.-) (CKI-alpha) (CK1). [*Rattus norvegicus*] |
| KC21__HUMAN | Casein kinase II, alpha chain (CK II) (EC 2.7.1.37). [*Homo sapiens*] |
| KC22__HUMAN | Casein kinase II, alpha' chain (CK II) (EC 2.7.1.37). [*Homo sapiens*] |
| KC2B__HUMAN | Casein kinase II beta chain (CK II) (Phosvitin) (G5a). [*Homo sapiens*] |
| KCC1__HUMAN | Calcium/calmodulin-dependent protein kinase type I (EC 2.7.1.123) (CAM kinase I). [*Homo sapiens*] |

-continued

| | |
|---|---|
| KCC4_HUMAN | Calcium/calmodulin-dependent protein kinase type IV catalytic chain (EC 2.7.1.123) (CAM kinase-GR) (CaMK IV). [*Homo sapiens*] |
| KCC4_MOUSE | Calcium/calmodulin-dependent protein kinase type IV catalytic chain (EC 2.7.1.123) (CAM kinase-GR) (CaMK IV). [*Mus musculus*] |
| KCC4_RAT | Calcium/calmodulin-dependent protein kinase type IV catalytic chain (EC 2.7.1.123) (CAM kinase-GR) (CaMK IV) (Calspermin). [*Rattus norvegicus*] |
| KCCB_MOUSE | Calcium/calmodulin-dependent protein kinase type II beta chain (EC 2.7.1.123) (CaM-kinase II beta chain) (CaM kinase II beta subunit) (CaMK-II beta subunit). [*Mus musculus*] |
| KCCG_HUMAN | Calcium/calmodulin-dependent protein kinase type II gamma chain (EC 2.7.1.123) (CaM-kinase II gamma chain) (CaM kinase II gamma subunit) (CaMK-II gamma subunit) (Fragment). [*Homo sapiens*] |
| KCCG_RAT | Calcium/calmodulin-dependent protein kinase type II gamma chain (EC 2.7.1.123) (CaM-kinase II gamma chain) (CaM kinase II gamma subunit) (CaMK-II gamma subunit). [*Rattus norvegicus*] |
| KCH1_HUMAN | Potassium voltage-gated channel subfamily H member 1 (Ether-a-go-go potassium channel 1) (hEAG1) (h-eag). [*Homo sapiens*] |
| KG3A_HUMAN | Glycogen synthase kinase-3 alpha (EC 2.7.1.37) (GSK-3 alpha). [*Homo sapiens*] |
| KG3A_RAT | Glycogen synthase kinase-3 alpha (EC 2.7.1.37) (GSK-3 alpha) (Factor A) (FA). [*Rattus norvegicus*] |
| KG3B_HUMAN | Glycogen synthase kinase-3 beta (EC 2.7.1.37) (GSK-3 beta). [*Homo sapiens*] |
| KG3B_MOUSE | Glycogen synthase kinase-3 beta (EC 2.7.1.37) (GSK-3 beta). [*Mus musculus*] |
| KIST_HUMAN | Serine/threonine-protein kinase Kist (EC 2.7.1.37) (Kinase interacting with stathmin). [*Homo sapiens*] |
| KMLS_HUMAN | Myosin light chain kinase, smooth muscle and non-muscle isozymes (EC 2.7.1.117) (MLCK) [Contains: Telokin (Kinase related protein) (KRP)]. [*Homo sapiens*] |
| KPBH_HUMAN | Phosphorylase B kinase gamma catalytic chain, testis/liver isoform (EC 2.7.1.38) (PHK-gamma-T) (Phosphorylase kinase gamma subunit 2) (PSK-C3). [*Homo sapiens*] |
| KPCA_HUMAN | Protein kinase C, alpha type (EC 2.7.1.37) (PKC-alpha) (PKC-A). [*Homo sapiens*] |
| KPCA_RAT | Protein kinase C, alpha type (EC 2.7.1.37) (PKC-alpha) (PKC-A). [*Rattus norvegicus*] |
| KPCB_HUMAN | Protein kinase C, beta type (EC 2.7.1.37) (PKC-beta) (PKC-B). [*Homo sapiens*] |
| KPCD_HUMAN | Protein kinase C, delta type (EC 2.7.1.-) (nPKC-delta). [*Homo sapiens*] |
| KPCG_MOUSE | Protein kinase C, gamma type (EC 2.7.1.37) (PKC-gamma). [*Mus musculus*] |
| KPCI_HUMAN | Protein kinase C, iota type (EC 2.7.1.37) (nPKC-iota) (Atypical protein kinase C-lamda/iota) (aPKC-lambda/iota). [*Homo sapiens*] |
| KPCI_MOUSE | Protein kinase C, iota type (EC 2.7.1.-) (nPKC-iota) (Protein k |
| KPCM_HUMAN | Protein kinase C, mu type (EC 2.7.1.-) (nPKC-mu) (Protein kinase D). [*Homo sapiens*] |
| KPCT_HUMAN | Protein kinase C, theta type (EC 2.7.1.-) (nPKC-theta). [*Homo sapiens*] |
| KPCZ_RAT | Protein kinase C, zeta type (EC 2.7.1.37) (nPKC-zeta). [*Rattus norvegicus*] |
| KPSH_HUMAN | Serine/threonine-protein kinase H1 (EC 2.7.1.37) (PSK-H1). [*Homo sapiens*] |
| KROS_HUMAN | Proto-oncogene tyrosine-protein kinase ROS precursor (EC 2.7.1.112) (c-ros-1). [*Homo sapiens*] |
| KSYK_MOUSE | Tyrosine-protein kinase SYK (EC 2.7.1.112) (Spleen tyrosine kinase). [*Mus musculus*] |
| LCK_HUMAN | Proto-oncogene tyrosine-protein kinase LCK (EC 2.7.1.112) (P56-LCK) (LSK) (T cell-specific protein-tyrosine kinase). [*Homo sapiens*] |
| LTBL_HUMAN | Latent transforming growth factor beta binding protein, isoform 1L precursor (LTBP-1) (Transforming growth factor beta-1 binding protein 1) (TGF-beta1-BP-1). [*Homo sapiens*] |
| M3K1_HUMAN | Mitogen-activated protein kinase kinase kinase 1 (EC 2.7.1.-) ( |
| M3K2_HUMAN | Mitogen-activated protein kinase kinase kinase 2 (EC 2.7.1.-) (MAPK/ERK kinase kinase 2) (MEK kinase 2) (MEKK 2). [*Homo sapiens*] |
| M3K3_HUMAN | Mitogen-activated protein kinase kinase kinase 3 (EC 2.7.1.-) (MAPK/ERK kinase kinase 3) (MEK kinase 3) (MEKK 3). [*Homo sapiens*] |
| M3K4_HUMAN | Mitogen-activated protein kinase kinase kinase 4 (EC 2.7.1.-) (MAPK/ERK kinase kinase 4) (MEK kinase 4) (MEKK 4) (MAP three kinase 1). [*Homo sapiens*] |
| M3K5_HUMAN | Mitogen-activated protein kinase kinase kinase 5 (EC 2.7.1.-) (MAPK/ERK kinase kinase 5) (MEK kinase 5) (MEKK 5) (Apoptosis signal- regulating kinase 1) (ASK-1). [*Homo sapiens*] |
| M4K2_HUMAN | Mitogen-activated protein kinase kinase kinase kinase 2 (EC 2.7 |
| M4K2_MOUSE | Mitogen-activated protein kinase kinase kinase kinase 2 (EC 2.7.1.37) (MAPK/ERK kinase kinase 2) (MEK kinase kinase 2) (MEKKK 2) (Germinal center kinase) (GCK) (Rab8 interacting protein). [*Mus musculus*] |
| MAK_HUMAN | Serine/threonine-protein kinase MAK (EC 2.7.1.-) (Male germ cell- associated kinase). [*Homo sapiens*] |
| MET_HUMAN | Hepatocyte growth factor receptor precursor (EC 2.7.1.112) (Met proto- oncogene tyrosine kinase) (c-met) (HGF receptor) (HGF-SF receptor). [*Homo sapiens*] |
| MK01_BOVIN | Mitogen-activated protein kinase 1 (EC 2.7.1.37) (Extracellular signal-regulated kinase 2) (ERK-2) (Mitogen-activated protein kinase 2) (MAP kinase 2) (MAPK 2) (p42-MAPK) (ERT1). [*Bos taurus*] |
| MK01_HUMAN | Mitogen-activated protein kinase 1 (EC 2.7.1.37) (Extracellular signal-regulated kinase 2) (ERK-2) (Mitogen-activated protein kinase 2) (MAP kinase 2) (MAPK 2) (p42-MAPK) (ERT1). [*Homo sapiens*] |
| MK01_MOUSE | Mitogen-activated protein kinase 1 (EC 2.7.1.37) (Extracellular signal-regulated kinase 2) (ERK-2) (Mitogen-activated protein kinase 2) (MAP kinase 2) (MAPK 2) (p42-MAPK) (ERT1). [*Mus musculus*] |
| MK03_HUMAN | Mitogen-activated protein kinase 3 (EC 2.7.1.37) (Extracellular signal-regulated kinase 1) (ERK-l) (Insulin-stimulated MAP2 kinase) (MAP kinase 1) (MAPK 1) (p44-ERK1) (ERT2) (p44-MAPK) (Microtubule-associated protein-2 kinase). [*Homo sapiens*] |
| MK03_MOUSE | Mitogen-activated protein kinase 3 (EC 2.7.1.37) (Extracellular signal-regulated kinase 1) (ERK-1) (Insulin-stimulated MAP2 kinase) (MAP kinase 1) (MAPK 1) (p44-ERK1) (ERT2) (p44-MAPK) (Microtubule-associated protein-2 kinase) (MNK1) (Fragments). [*Mus mu* |
| MK03_RAT | Mitogen-activated protein kinase 3 (EC 2.7.1.37) (Extracellular signal-regulated kinase 1) (ERK-1) (Insulin-stimulated MAP2 kinase) (MAP kinase 1) (MAPK 1) (p44-ERK1) (ERT2) (p44-MAPK) (Microtubule-associated protein-2 kinase) (MNK1). [*Rattus norvegicus*] |
| MK08_HUMAN | Mitogen-activated protein kinase 8 (EC 2.7.1.37) (Stress-activated protein kinase JNK1) (c-Jun N-terminal kinase 1) (JNK-46). [*Homo sapiens*] |
| MK08_MOUSE | Mitogen-activated protein kinase 8 (EC 2.7.1.37) (Stress-activated protein kinase JNK1) (c-Jun N-terminal kinase 1). [*Mus musculus*] |
| MK12_HUMAN | Mitogen-activated protein kinase 12 (EC 2.7.1.37) (Extracellular signal-regulated kinase 6) (ERK-6) (ERK5) (Stress-activated protein kinase-3) (Mitogen-activated protein kinase p38 gamma) (MAP kinase p38 gamma). [*Homo sapiens*] |

-continued

| | |
|---|---|
| MK14_HUMAN | Mitogen-activated protein kinase 14 (EC 2.7.1.37) (Mitogen-activated protein kinase p38alpha) (MAP kinase p38alpha) (Cytokine suppressive anti-inflammatory drug binding protein) (CSAID binding protein) (CSBP) (MAX-interacting protein 2) (MAP kinase MXI2) |
| MKK2_HUMAN | MAP kinase-activated protein kinase 2 (EC 2.7.1.-) (MAPK-activated protein kinase 2) (MAPKAP kinase 2) (MAPKAPK-2). [*Homo sapiens*] |
| MPK1_RABIT | Dual specificity mitogen-activated protein kinase kinase 1 (EC 2.7.1.-) (MAP kinase kinase 1) (MAPKK 1) (ERK activator kinase 1) (MAPK/ERK kinase 1) (MEK1). [*Oryctolagus cuniculus*] |
| MPK2_HUMAN | Dual specificity mitogen-activated protein kinase kinase 2 (EC 2.7.1.-) (MAP kinase kinase 2) (MAPKK 2) (ERK activator kinase 2) (MAPK/ERK kinase 2) (MEK2). [*Homo sapiens*] |
| MPK2_MOUSE | Dual specificity mitogen-activated protein kinase kinase 2 (EC 2.7.1.-) (MAP kinase kinase 2) (MAPKK 2) (ERK activator kinase 2) (MAPK/ERK kinase 2) (MEK2). [*Mus musculus*] |
| MPK2_RAT | Dual specificity mitogen-activated protein kinase kinase 2 (EC 2.7.1.-) (MAP kinase kinase 2) (MAPKK 2) (ERK activator kinase 2) (MAPK/ERK kinase 2) (MEK2). [*Rattus norvegicus*] |
| MPK3_HUMAN | Dual specificity mitogen-activated protein kinase kinase 3 (EC 2.7.1.-) (MAP kinase kinase 3) (MAPKK 3) (MAPK/ERK kinase 3). [*Homo sapiens*] |
| MPK4_HUMAN | Dual specificity mitogen-activated protein kinase kinase 4 (EC 2.7.1.-) (MAP kinase kinase 4) (JNK activating kinase 1) (c-Jun N- terminal kinase kinase 1) (JNKK) (SAPK/ERK kinase 1) (SEK1). [*Homo sapiens*] |
| MPK4_MOUSE | Dual specificity mitogen-activated protein kinase kinase 4 (EC 2.7.1.-) (MAP kinase kinase 4) (MAPKK 4) (MAPK/ERK kinase 4) (JNK activating kinase 1) (C-JUN N-terminal kinase kinase 1) (JNK kinase 1) (JNKK 1) (SAPK/ERK kinase 1) (SEK1). [*Mus musculus*] |
| MPK5_ARATH | Mitogen-activated protein kinase homolog |
| MPK6_HUMAN | Dual specificity mitogen-activated protein kinase kinase 6 (EC 2.7.1.-) (MAP kinase kinase 6) (MAPKK 6) (MAPK/ERK kinase 6) (SAPKK3). [*Homo sapiens*] |
| MPK6_MOUSE | Dual specificity mitogen-activated protein kinase kinase 6 (EC 2.7.1.-) (MAP kinase kinase 6) (MAPKK 6) (MAPK/ERK kinase 6) (SAPKK3). [*Mus musculus*] |
| MRK4_HUMAN | MAP/microtubule affinity-regulating kinase 4 (EC 2.7.1.27) (MAP/microtubule affinity-regulating kinase like 1). [*Homo sapiens*] |
| NRP1_HUMAN | Neuropilin-1 precursor (Vascular endothelial cell growth factor |
| O88664 | Serine/threonine protein kinase TAO1. [*Rattus norvegicus*] |
| PAK2_HUMAN | Serine/threonine-protein kinase PAK 2 (EC 2.7.1.-) (p21-activated kinase 2) (PAK-2) (PAK65) (Gamma-PAK) (S6/H4 kinase). [*Homo sapiens*] |
| PDK1_HUMAN | [Pyruvate dehydrogenase [lipoamide]] kinase isozyme 1, mitochondrial precursor (EC 2.7.1.99) (Pyruvate dehydrogenase kinase isoform 1). [*Homo sapiens*] |
| PDK3_HUMAN | [Pyruvate dehydrogenase [lipoamide]] kinase isozyme 3, mitochondrial precursor (EC 2.7.1.99) (Pyruvate dehydrogenase kinase isoform 3). [*Homo sapiens*] |
| PDK4_MOUSE | [Pyruvate dehydrogenase [lipoamide]] kinase isozyme 4, mitochondrial precursor (EC 2.7.1.99) (Pyruvate dehydrogenase kinase isoform 4). [*Mus musculus*] |
| PDPK_HUMAN | 3-phosphoinositide dependent protein kinase-1 (EC 2.7.1.37) (hPDK1). [*Homo sapiens*] |
| PGDR_HUMAN | Beta platelet-derived growth factor receptor precursor (EC 2.7.1.112) (PDGF-R-beta) (CD140b antigen). [*Homo sapiens*] |
| PGDS_RAT | Alpha platelet-derived growth factor receptor precursor (EC 2.7.1.112) (PDGF-R-alpha). [*Rattus norvegicus*] |
| PKL1_HUMAN | Protein kinase C-like 1 (EC 2.7.1.-) (Protein-kinase C-related |
| PKL2_HUMAN | Protein kinase C-like 2 (EC 2.7.1.-) (Protein-kinase C-related kinase 2). [*Homo sapiens*] |
| PKX1_HUMAN | Protein kinase PKX1 (EC 2.7.1.-). [*Homo sapiens*] |
| PLK1_HUMAN | Serine/threonine-protein kinase PLK (EC 2.7.1.-) (PLK-1) (Serine- threonine protein kinase 13) (STPK13). [*Homo sapiens*] |
| PLK1_MOUSE | Serine/threonine-protein kinase PLK (EC 2.7.1.-) (PLK-1) (Serine- threonine protein kinase 13) (STPK13). [*Mus musculus*] |
| PRKD_HUMAN | DNA-dependent protein kinase catalytic subunit (EC 2.7.1.37) (DNA- PKcs) (DNPK1). [*Homo sapiens*] |
| PRPK_HUMAN | p53-related protein kinase (EC 2.7.1.-) (Nori-2). [*Homo sapiens*] |
| PTK7_HUMAN | Tyrosine-protein kinase-like 7 precursor (Colon carcinoma kinase-4) (CCK-4). [*Homo sapiens*] |
| Q63709 | Fibroblast growth factor receptor subtype 4. [*Rattus rattus*] |
| Q8IWY7 | Tau-tubulin kinase. [*Homo sapiens*] |
| RET_HUMAN | Proto-oncogene tyrosine-protein kinase receptor ret precursor (EC 2.7.1.112) (C-ret). [*Homo sapiens*] |
| RIK1_HUMAN | Receptor-interacting serine/threonine protein kinase 2 (EC 2.7.1.37) (Serine/threonine protein kinase RIP) (Cell death protein RIP) (Receptor interacting protein). [*Homo sapiens*] |
| RIK2_HUMAN | Receptor-interacting serine/threonine protein kinase 2 (EC 2.7.1.37) (RIP-like interacting CLARP kinase) (Receptor-interacting protein 2) (RIP-2) (CARD-containing interleukin-1 beta converting enzyme associated kinase) (CARD-containing IL-1 beta ICE-kinas |
| RIK3_MOUSE | Receptor-interacting serine/threonine protein kinase 3 (EC 2.7.1.37) (RIP-like protein kinase 3) (Receptor-interacting protein 3) (RIP-3) (mRIP3). [*Mus musculus*] |
| RN5A_HUMAN | 2-5A-dependent ribonuclease (EC 3.1.26.-) (2-5A-dependent RNase) (Ribonuclease L) (RNase L) (Ribonuclease 4). [*Homo sapiens*] |
| SGK1_HUMAN | Serine/threonine-protein kinase Sgk1 (EC 2.7.1.37) (Serum/glucocorticoid-regulated kinase 1). [*Homo sapiens*] |
| SGK3_HUMAN | Serine/threonine-protein kinase Sgk3 (EC 2.7.1.37) (Serum/glucocorticoid regulated kinase 3) (Serum/glucocorticoid regulated kinase-like). [*Homo sapiens*] |
| SNK_HUMAN | Serine/threonine-protein kinase SNK (EC 2.7.1.-) (Serum inducible kinase). [*Homo sapiens*] |
| SPAK_RAT | STE20/SPS1-related proline-alanine rich protein kinase (EC 2.7.1.-) (Ste-20 related kinase) (Serine/threonine-protein kinase 39) (Pancreatic serine/threonine kinase) (PS/TK) (PSTK1). [*Rattus norvegicus*] |
| ST24_HUMAN | Serine/threonine protein kinase 24 (EC 2.7.1.37) (STE20-like kinase MST3) (MST-3) (Mammalian STE20-like protein kinase 3). [*Homo sapiens*] |
| ST25_HUMAN | Serine/threonine protein kinase 25 (EC 2.7.1.37) (Sterile 20/oxidant stress-response kinase 1) (Ste20/oxidant stress response kinase-1) (SOK-1) (Ste20-like kinase). [*Homo sapiens*] |
| STK3_HUMAN | Serine/threonine protein kinase 3 (EC 2.7.1.37) (STE20-like kinase MST2) (MST-2) (Mammalian STE20-like protein kinase 2) (Serine/threonine protein kinase Krs-1). [*Homo sapiens*] |

-continued

| | |
|---|---|
| STK4_HUMAN | Serine/threonine protein kinase 4 (EC 2.7.1.37) (STE20-like kinase MST1) (MST-1) (Mammalian STE20-like protein kinase 1) (Serine/threonine protein kinase Krs-2). [*Homo sapiens*] |
| STK6_HUMAN | Serine/threonine kinase 6 (EC 2.7.1.37) (Serine/threonine kinase 15) (Aurora/IPL1-related kinase 1) (Aurora-related kinase 1) (hARK1) (Aurora-A) (Breast-tumor-amplified kinase). [*Homo sapiens*] |
| STKA_HUMAN | Serine/threonine protein kinase 10 (EC 2.7.1.37) (Lymphocyte-oriented kinase). [*Homo sapiens*] |
| STKA_MOUSE | Serine/threonine protein kinase 10 (EC 2.7.1.37) (Lymphocyte-oriented kinase). [*Mus musculus*] |
| T2D1_HUMAN | Transcription initiation factor TFIID 250 kDa subunit (TAFII-250) (TAFII250) (TBP-associated factor 250 kDa) (P250) (Cell cycle gene 1 protein). [*Homo sapiens*] |
| TNIK_HUMAN | TRAF2 and NCK interacting kinase (EC 2.7.1.37). [*Homo sapiens*] |
| VGR2_HUMAN | Vascular endothelial growth factor receptor 2 precursor (EC 2.7.1.112) (VEGFR-2) (Kinase insert domain receptor) (Protein-tyrosine kinase receptor Flk-1). [*Homo sapiens*] |
| WEE1_HUMAN | Wee1-like protein kinase (EC 2.7.1.112) (WEE1hu). [*Homo sapiens*] |
| YES_HUMAN | Proto-oncogene tyrosine-protein kinase YES (EC 2.7.1.112) (p61-YES) (C-YES). [*Homo sapiens*] |
| ZA70_HUMAN | Tyrosine-protein kinase ZAP-70 (EC 2.7.1.112) (70 kDa zeta-associated protein) (Syk-related tyrosine kinase). [*Homo sapiens*] |
| Other kinases | |
| ADK_HUMAN | Adenosine kinase (EC 2.7.1.20) (AK) (Adenosine 5'-phosphotransferase). [*Homo sapiens*] |
| ADK_MOUSE | Adenosine kinase (EC 2.7.1.20) (AK) (Adenosine 5'-phosphotransferase) (Fragment). [*Mus musculus*] |
| DCK_HUMAN | Deoxycytidine kinase (EC 2.7.1.74) (dCK). [*Homo sapiens*] |
| DCK_RAT | Deoxycytidine kinase (EC 2.7.1.74) (dCK). [*Rattus norvegicus*] |
| DGK_HUMAN | Deoxyguanosine kinase, mitochondrial precursor (EC 2.7.1.113) (dGK). [*Homo sapiens*] |
| EKI1_HUMAN | Ethanolamine kinase (EC 2.7.1.82) (EKI). [*Homo sapiens*] |
| ER19_HUMAN | Diphosphomevalonate decarboxylase (EC 4.1.1.33) (Mevalonate pyrophosphate decarboxylase) (Mevalonate (diphospho)decarboxylase). [*Homo sapiens*] |
| F263_HUMAN | 6-phosphofructo-2-kinase/fructose-2,6-biphosphatase 3 (6PF-2-K/Fru- 2,6-P2ASE brain/placenta-type isozyme) (iPFK-2) [Includes: 6- phosphofructo-2-kinase (EC 2.7.1.105); Fructose-2, 6-bisphosphatase (EC 3.1.3.46)]. [*Homo sapiens*] |
| FRAP_HUMAN | FKBP-rapamycin associated protein (FRAP) (Rapamycin target protein). [*Homo sapiens*] |
| FYV1_HUMAN | FYVE finger-containing phosphoinositide kinase (EC 2.7.1.68) (1- phosphatidylinositol-4-phosphate 5-kinase) (PIP5K) (PtdIns(4)P-5- kinase) (p235) (Fragment). [*Homo sapiens*] |
| HXK1_HUMAN | Hexokinase, type I (EC 2.7.1.1) (HK I) (Brain form hexokinase). [*Homo sapiens*] |
| K6PL_HUMAN | 6-phosphofructokinase, liver type (EC 2.7.1.11) (Phosphofructokinase 1) (Phosphohexokinase) (Phosphofructo-1-kinase isozyme B) (PFK-B). [*Homo sapiens*] |
| K6PL_MOUSE | 6-phosphofructokinase, liver type (EC 2.7.1.11) (Phosphofructokinase 1) (Phosphohexokinase) (Phosphofructo-1-kinase isozyme B) (PFK-B). [*Mus musculus*] |
| K6PL_RAT | 6-phosphofructokinase, liver type (EC 2.7.1.11) (Phosphofructokinase 1) (Phosphohexokinase) (Phosphofructo-1-kinase isozyme B) (PFK-B). [*Rattus norvegicus*] |
| K6PP_HUMAN | 6-phosphofructokinase, type C (EC 2.7.1.11) (Phosphofructokinase 1) (Phosphohexokinase) (Phosphofructo-1-kinase isozyme C) (PFK-C) (6-phosphofructokinase, platelet type). [*Homo sapiens*] |
| K6PP_MOUSE | 6-phosphofructokinase, type C (EC 2.7.1.11) (Phosphofructokinase 1) (Phosphohexokinase) (Phosphofructo-1-kinase isozyme C) (PFK-C). [*Mus musculus*] |
| KAD1_BOVIN | Adenylate kinase isoenzyme 1 (EC 2.7.4.3) (ATP-AMP transphosphorylase) (AK1) (Myokinase). [*Bos taurus*] |
| KAD1_HUMAN | Adenylate kinase isoenzyme 1 (EC 2.7.4.3) (ATP-AMP transphosphorylase) (AK1) (Myokinase). [*Homo sapiens*] |
| KAD1_MOUSE | Adenylate kinase isoenzyme 1 (EC 2.7.4.3) (ATP-AMP transphosphorylase) (AK1) (Myokinase). [*Mus musculus*] |
| KAD1_RAT | Adenylate kinase isoenzyme 1 (EC 2.7.4.3) (ATP-AMP transphosphorylase) (AK1) (Myokinase). [*Rattus norvegicus*] |
| KAD2_BOVIN | Adenylate kinase isoenzyme 2, mitochondrial (EC 2.7.4.3) (ATP-AMP transphosphorylase). [*Bos taurus*] |
| KAD2_MOUSE | Adenylate kinase isoenzyme 2, mitochondrial (EC 2.7.4.3) (ATP-AMP transphosphorylase). [*Mus musculus*] |
| KAD4_HUMAN | Adenylate kinase isoenzyme 4 (EC 2.7.4.3) (ATP-AMP transphosphorylase). [*Homo sapiens*] |
| KAD4_MOUSE | Adenylate kinase isoenzyme 4 (EC 2.7.4.3) (ATP-AMP transphosphorylase). [*Mus musculus*] |
| KAD4_RAT | Adenylate kinase isoenzyme 4 (EC 2.7.4.3) (ATP-AMP transphosphorylase). [*Rattus norvegicus*] |
| KAD5_MOUSE | Adenylate kinase isoenzyme 5 (EC 2.7.4.3) (ATP-AMP transphosphorylase). [*Mus musculus*] |
| KCRB_MOUSE | Creatine kinase, B chain (EC 2.7.3.2) (B-CK). [*Mus musculus*] |
| KCRM_MOUSE | Creatine kinase, M chain (EC 2.7.3.2) (M-CK). [*Mus musculus*] |
| KCRS_RAT | Creatine kinase, sarcomeric mitochondrial precursor (EC 2.7.3.2) (S- MtCK) (Mib-CK) (Basic-type mitochondrial creatine kinase). [*Rattus norvegicus*] |
| KCY_HUMAN | UMP-CMP kinase (EC 2.7.4.14) (Cytidylate kinase) (Deoxycytidylate kinase) (Cytidine monophosphate kinase). [*Homo sapiens*] |
| KCY_MOUSE | UMP-CMP kinase (EC 2.7.4.14) (Cytidylate kinase) (Deoxycytidylate kinase) (Cytidine monophosphate kinase). [*Mus musculus*] |
| KDGA_HUMAN | Diacylglycerol kinase, alpha (EC 2.7.1.107) (Diglyceride kinase) (DGK- alpha) (DAG kinase alpha) (80 kDa diacylglycerol kinase). [*Homo sapiens*] |
| KDGG_HUMAN | Diacylglycerol kinase, gamma (EC 2.7.1.107) (Diglyceride kinase) (DGK- gamma) (DAG kinase gamma). [*Homo sapiens*] |
| KICH_HUMAN | Choline kinase (EC 2.7.1.32) (CK) (CHETK-alpha). [*Homo sapiens*] |
| KIME_MOUSE | Mevalonate kinase (EC 2.7.1.36) (MK). [*Mus musculus*] |
| KIME_RAT | Mevalonate kinase (EC 2.7.1.36) (MK). [*Rattus norvegicus*] |
| KPY1_FELCA | Pyruvate kinase, M1 isozyme (EC 2.7.1.40) (Pyruvate kinase muscle isozyme). [*Felis silvestris*] |
| KPY1_HUMAN | Pyruvate kinase, M1 isozyme (EC 2.7.1.40) (Pyruvate kinase muscle isozyme) (Cytosolic thyroid hormone-binding protein) (CTHBP) (THBP1). [*Homo sapiens*] |
| KPY2_MOUSE | Pyruvate kinase, M2 isozyme (EC 2.7.1.40). [*Mus musculus*] |

-continued

| | |
|---|---|
| KPY2_RAT | Pyruvate kinase, M2 isozyme (EC 2.7.1.40). [*Rattus norvegicus*] |
| KTHY_HUMAN | Thymidylate kinase (EC 2.7.4.9) (dTMP kinase). [*Homo sapiens*] |
| MPP2_HUMAN | MAGUK p55 subfamily member 2 (MPP2 protein) (Discs, large homolog 2). [*Homo sapiens*] |
| NDK3_HUMAN | Nucleoside diphosphate kinase 3 (EC 2.7.4.6) (NDK 3) (NDP kinase 3) (nm23-H3) (DR-nm23). [*Homo sapiens*] |
| NDK8_HUMAN | Putative nucleoside diphosphate kinase (EC 2.7.4.6) (NDK) (NDP kinase). [*Homo sapiens*] |
| NDKA_HUMAN | Nucleoside diphosphate kinase A (EC 2.7.4.6) (NDK A) (NDP kinase A) (Tumor metastatic process-associated protein) (Metastasis inhibition factor nm23) (nm23-H1). [*Homo sapiens*] |
| NDKA_RAT | Nucleoside diphosphate kinase A (EC 2.7.4.6) (NDK A) (NDP kinase A) (Tumor metastatic process-associated protein) (Metastasis inhibition factor NM23). [*Rattus norvegicus*] |
| NDKB_HUMAN | Nucleoside diphosphate kinase B (EC 2.7.4.6) (NDK B) (NDP kinase B) (nm23-H2) (C-myc purine-binding transcription factor PUF). [*Homo sapiens*] |
| NDKB_MOUSE | Nucleoside diphosphate kinase B (EC 2.7.4.6) (NDK B) (NDP kinase B) (nm23-M2) (P18). [*Mus musculus*] |
| NDKB_RAT | Nucleoside diphosphate kinase B (EC 2.7.4.6) (NDK B) (NDP kinase B) (P18). [*Rattus norvegicus*] |
| O00334 | Phosphatidylinositol 3-kinase delta catalytic subunit. [*Homo sapiens*] |
| P11B_HUMAN | Phosphatidylinositol-4,5-bisphosphate 3-kinase catalytic subunit, beta isoform (EC 2.7.1.153) (PI3-kinase p110 subunit beta) (PtdIns-3-kinase p110) (PI3K) (PI3Kbeta). [*Homo sapiens*] |
| P11G_HUMAN | Phosphatidylinositol-4,5-bisphosphate 3-kinase catalytic subunit, gamma isoform (EC 2.7.1.153) (PI3-kinase p110 subunit gamma) (PtdIns- 3-kinase p110) (PI3K) (PI3Kgamma). [*Homo sapiens*] |
| P11G_MOUSE | Phosphatidylinositol-4,5-bisphosphate 3-kinase catalytic subunit, gamma isoform (EC 2.7.1.153) (PI3-kinase p110 subunit gamma) (PtdIns- 3-kinase p110) (PI3K) (PI3Kgamma). [*Mus musculus*] |
| P5CS_HUMAN | Delta 1-pyrroline-5-carboxylate synthetase (P5CS) [Includes: Glutamate 5-kinase (EC 2.7.2.11) (Gamma-glutamyl kinase) (GK); Gamma-glutamyl phosphate reductase (GPR) (EC 1.2.1.41) (Glutamate-5-semialdehyde dehydrogenase) (Glutamyl-gamma-semialdehyde dehydr |
| P85B_HUMAN | Phosphatidylinositol 3-kinase regulatory beta subunit (PI3-kinase p85-beta subunit) (PtdIns-3-kinase p85-beta). [*Homo sapiens*] |
| PDK1_RAT | [Pyruvate dehydrogenase [lipoamide]] kinase isozyme 1, mitochondrial precursor (EC 2.7.1.99) (Pyruvate dehydrogenase kinase isoform 1) (PDK P48). [*Rattus norvegicus*] |
| PGK1_HUMAN | Phosphoglycerate kinase 1 (EC 2.7.2.3) (Primer recognition protein 2) (PRP 2). [*Homo sapiens*] |
| PGK2_MOUSE | Phosphoglycerate kinase, testis specific (EC 2.7.2.3). [*Mus musculus*] |
| PGK_SCHMA | Phosphoglycerate kinase |
| PI52_HUMAN | Phosphatidylinositol-4-phosphate 5-kinase type II alpha (EC 2.7.1.149) (PIP5KII-alpha) (1-phosphatidylinositol-4-phosphate 5-kinase) (PtdIns(4)P-5-kinase B isoform) (Diphosphoinositide kinase). [*Homo sapiens*] |
| PI52_MOUSE | Phosphatidylinositol-4-phosphate 5-kinase type II alpha (EC 2.7.1.149) (PIP5KII-alpha) (1-phosphatidylinositol-4-phosphate 5-kinase) (PtdIns(4)P-5-kinase B isoform) (Diphosphoinositide kinase). [*Mus musculus*] |
| PK3G_MOUSE | Phosphatidylinositol-4-phosphate 3-kinase C2 domain-containing gamma polypeptide (EC 2.7.1.154) (Phosphoinositide 3-Kinase-C2-gamma) (PtdIns-3-kinase C2 gamma) (PI3K-C2gamma). [*Mus musculus*] |
| PPCC_RAT | Phosphoenolpyruvate carboxykinase, cytosolic [GTP] (EC 4.1.1.32) (Phosphoenolpyruvate carboxylase) (PEPCK-C). [*Rattus norvegicus*] |
| PPNK_HUMAN | Putative inorganic polyphosphate/ATP-NAD kinase (EC 2.7.1.23) (Poly(P)/ATP NAD kinase). [*Homo sapiens*] |
| RBSK_HUMAN | Ribokinase (EC 2.7.1.15). [*Homo sapiens*] |
| UDP1_HUMAN | UTP--glucose-1-phosphate uridylyltransferase 1 (EC 2.7.7.9) (UDP- glucose pyrophosphorylase 1) (UDPGP 1) (UGPase 1). [*Homo sapiens*] |
| UDP2_BOVIN | UTP--glucose-1-phosphate uridylyltransferase 2 (EC 2.7.7.9) (UDP- glucose pyrophosphorylase 2) (UDPGP 2) (UGPase 2). [*Bos taurus*] |
| URL1_HUMAN | Uridine kinase-like 1. [*Homo sapiens*] |
| ATPases | |
| A10B_HUMAN | Potential phospholipid-transporting ATPase VB (EC 3.6.3.1). [*Homo sapiens*] |
| A11A_HUMAN | Potential phospholipid-transporting ATPase IH (EC 3.6.3.1) (ATPase class I type 11A) (ATPase IS). [*Homo sapiens*] |
| A1A1_HUMAN | Sodium/potassium-transporting ATPase alpha-1 chain precursor (EC 3.6.3.9) (Sodium pump 1) (Na+/K+ ATPase 1). [*Homo sapiens*] |
| A1A1_RAT | Sodium/potassium-transporting ATPase alpha-1 chain precursor (EC 3.6.3.9) (Sodium pump 1) (Na+/K+ ATPase 1). [*Rattus norvegicus*] |
| A1A4_HUMAN | Sodium/potassium-transporting ATPase alpha-4 chain (EC 3.6.3.9) (Sodium pump 4) (Na+/K+ ATPase 4). [*Homo sapiens*] |
| A8A1_HUMAN | Potential phospholipid-transporting ATPase IA (EC 3.6.3.1) (Chromaffin granule ATPase II) (ATPase class I type 8A member 1). [*Homo sapiens*] |
| AB10_HUMAN | ATP-binding cassette, sub-family B, member 10, mitochondrial precursor (ATP-binding cassette transporter 10) (ABC transporter 10 protein) (Mitochondrial ATP-binding cassette 2) (M-ABC2). [*Homo sapiens*] |
| AB11_HUMAN | Bile salt export pump (ATP-binding cassette, sub-family B, member 11). [*Homo sapiens*] |
| AB11_RAT | Bile salt export pump (ATP-binding cassette, sub-family B, member 11) (Sister of P-glycoprotein). [*Rattus norvegicus*] |
| ABC1_MOUSE | ATP-binding cassette, sub-family A, member 1 (ATP-binding cassette transporter 1) (ATP-binding cassette 1) (ABC-1). [*Mus musculus*] |
| ABC7_HUMAN | ATP-binding cassette, sub-family B, member 7, mitochondrial precursor (ATP-binding cassette transporter 7) (ABC transporter 7 protein). [*Homo sapiens*] |
| ABCR_HUMAN | Retinal-specific ATP-binding cassette transporter (RIM ABC transporter) (RIM protein) (RMP) (Stargardt disease protein). [*Homo sapiens*] |
| ABD3_HUMAN | ATP-binding cassette, sub-family D, member 3 (70 kDa peroxisomal membrane protein) (PMP70). [*Homo sapiens*] |
| ABG5_HUMAN | ATP-binding cassette, sub-family G, member 5 (Sterolin-1). [*Homo sapiens*] |
| ACA1_ARATH | Calcium-transporting ATPase 1, plasma mem |
| ACIN_HUMAN | Apoptotic chromatin condensation inducer in the nucleus (Acinus). [*Homo sapiens*] |

-continued

| | |
|---|---|
| ALA8_ARATH | Potential phospholipld-transporting ATPas |
| ARS1_HUMAN | Arsenical pump-driving ATPase (EC 3.6.3.16) (Arsenite-translocating ATPase) (Arsenical resistance ATPase) (Arsenite-transporting ATPase) (ARSA) (ASNA-I). [*Homo sapiens*] |
| ARS1_MOUSE | Arsenical pump-driving ATPase (EC 3.6.3.16) (Arsenite-translocating ATPase) (Arsenical resistance ATPase) (Arsenite-transporting ATPase) (ARSA). [*Mus musculus*] |
| AT7A_HUMAN | Copper-transporting ATPase 1 (EC 3.6.3.4) (Copper pump 1) (Menkes disease-associated protein). [*Homo sapiens*] |
| AT7B_HUMAN | Copper-transporting ATPase 2 (EC 3.6.3.4) (Copper pump 2) (Wilson disease-associated protein). [*Homo sapiens*] |
| ATA1_HUMAN | Sarcoplasmic/endoplasmic reticulum calcium ATPase 1 (EC 3.6.3.8) (Calcium pump 1) (SERCA1) (SR Ca(2+)-ATPase 1) (Calcium-transporting ATPase sarcoplasmic reticulum type, fast twitch skeletal muscle isoform) (Endoplasmic reticulum class ½ Ca(2+) ATPase). |
| ATA1_RABIT | Sarcoplasmic/endoplasmic reticulum calcium ATPase 1 (EC 3.6.3.8) (Calcium pump 1) (SERCA1) (SR Ca(2+)-ATPase 1) (Calcium-transporting ATPase sarcoplasmic reticulum type, fast twitch skeletal muscle isoform) (Endoplasmic reticulum class ½ Ca(2+) ATPase). |
| ATA1_RAT | Sarcoplasmic/endoplasmic reticulum calcium ATPase 1 (EC 3.6.3.8) (Calcium pump 1) (SERCA1) (SR Ca(2+)-ATPase 1) (Calcium-transporting ATPase sarcoplasmic reticulum type, fast twitch skeletal muscle isoform) (Endoplasmic reticulum class ½ Ca(2+) ATPase). |
| ATA2_HUMAN | Sarcoplasmic/endoplasmic reticulum calcium ATPase 2 (EC 3.6.3.8) (Calcium pump 2) (SERCA2) (SR Ca(2+)-ATPase 2) (Calcium-transporting ATPase sarcoplasmic reticulum type, slow twitch skeletal muscle isoform) (Endoplasmic reticulum class ½ Ca(2+) ATPase). |
| ATA2_MOUSE | Sarcoplasmic/endoplasmic reticulum calcium ATPase 2 (EC 3.6.3.8) (Calcium pump 2) (SERCA2) (SR Ca(2+)-ATPase 2) (Calcium-transporting ATPase sarcoplasmic reticulum type, slow twitch skeletal muscle isoform) (Endoplasmic reticulum class ½ Ca(2+) ATPase). |
| ATA2_RAT | Sarcoplasmic/endoplasmic reticulum calcium ATPase 2 (EC 3.6.3.8) (Calcium pump 2) (SERCA2) (SR Ca(2+)-ATPase 2) (Calcium-transporting ATPase sarcoplasmic reticulum type, slow twitch skeletal muscle isoform) (Endoplasmic reticulum class ½ Ca(2+) ATPase). |
| ATA3_HUMAN | Sarcoplasmic/endoplasmic reticulum calcium ATPase 3 (EC 3.6.3.8) (Calcium pump 3) (SERCA3) (SR Ca(2+)-ATPase 3). [*Homo sapiens*] |
| ATA3_MOUSE | Sarcoplasmic/endoplasmic reticulum calcium ATPase 3 (EC 3.6.3.8) (Calcium pump 3) (SERCA3) (SR Ca(2+)-ATPase 3). [*Mus musculus*] |
| ATA3_RAT | Sarcoplasmic/endoplasmic reticulum calcium ATPase 3 (EC 3.6.3.8) (Calcium pump 3) (SERCA3) (SR Ca(2+)-ATPase 3). [*Rattus norvegicus*] |
| ATB1_HUMAN | Plasma membrane calcium-transporting ATPase 1 (EC 3.6.3.8) (PMCA1) (Plasma membrane calcium pump isoform 1) (Plasma membrane calcium ATPase isoform 1). [*Homo sapiens*] |
| ATB2_HUMAN | Plasma membrane calcium-transporting ATPase 2 (EC 3.6.3.8) (PMCA2) (Plasma membrane calcium pump isoform 2) (Plasma membrane calcium ATPase isoform 2). [*Homo sapiens*] |
| ATB4_HUMAN | Plasma membrane calcium-transporting ATPase 4 (EC 3.6.3.8) (PMCA4) (Plasma membrane calcium pump isoform 4) (Plasma membrane calcium ATPase isoform 4). [*Homo sapiens*] |
| ATC1_HUMAN | Calcium-transporting ATPase type 2C, member 1 (EC 3.6.3.8) (ATPase 2C1) (ATP-dependent Ca2+ pump PMR1) (HUSSY-28). [*Homo sapiens*] |
| ATHL_HUMAN | Potassium-transporting ATPase alpha chain 2 (EC 3.6.3.10) (Proton pump) (Non-gastric H+/K+ ATPase alpha subunit). [*Homo sapiens*] |
| ATPB_BOVIN | ATP synthase beta chain, mitochondrial precursor (EC 3.6.3.14). [*Bos taurus*] |
| ATPB_HUMAN | ATP synthase beta chain, mitochondrial precursor (EC 3.6.3.14). [*Homo sapiens*] |
| ATPB_RAT | ATP synthase beta chain, mitochondrial precursor (EC 3.6.3.14). [*Rattus norvegicus*] |
| CFTR_HUMAN | Cystic fibrosis transmembrane conductance regulator (CFTR) (cAMP- dependent chloride channel). [*Homo sapiens*] |
| CHD5_HUMAN | Chromodomain-helicase-DNA-binding protein 5 (CHD-5). [*Homo sapiens*] |
| DD15_HUMAN | Putative pre-mRNA splicing factor RNA helicase (DEAH box protei |
| DD18_HUMAN | ATP-dependent RNA helicase DDX18 (DEAD-box protein 18) (Myc-regulated DEAD-box protein) (MrDb). [*Homo sapiens*] |
| DD21_HUMAN | Nucleolar RNA helicase II (Nucleolar RNA helicase Gu) (RH II/Gu) (DEAD-box protein 21). [*Homo sapiens*] |
| DD24_HUMAN | ATP-dependent RNA helicase DDX24 (DEAD-box protein 24). [*Homo sapiens*] |
| DD35_HUMAN | Probable ATP-dependent helicase DHX35 (DEAH-box protein 35). [*Homo sapiens*] |
| DDX1_HUMAN | ATP-dependent helicase DDX1 (DEAD-box protein 1) (DEAD-box protein- retinoblastoma) (DBP-RB). [*Homo sapiens*] |
| DDX4_MOUSE | DEAD-box protein 4 (VASA homolog) (Mvh). [*Mus musculus*] |
| DDX5_HUMAN | Probable RNA-dependent helicase p68 (DEAD-box protein p68) (DEAD-box protein 5). [*Homo sapiens*] |
| DDX7_HUMAN | ATP-dependent helicase DDX7 (DEAD-box protein 7) (NP-52). [*Homo sapiens*] |
| G3BP_HUMAN | Ras-GTPase-activating protein binding protein 1 (GAP SH3-domain binding protein 1) (G3BP-1). [*Homo sapiens*] |
| HE47_HUMAN | Probable ATP-dependent RNA helicase p47 (HLA-B associated transcript- 1). [*Homo sapiens*] |
| IF41_HUMAN | Eukaryotic initiation factor 4A-I (eIF4A-I) (eIF-4A-I). [*Homo sapiens*] |
| K052_HUMAN | Protein KIAA0052 (Fragment). [*Homo sapiens*] |
| KF1B_HUMAN | Kinesin-like protein KIF1B (Kip). [*Homo sapiens*] |
| M10L_HUMAN | Moloney leukemia virus 10-like protein 1 (MOV10-like 1). [*Homo sapiens*] |
| MCM5_HUMAN | DNA replication licensing factor MCM5 (CDC46 homolog) (P1-CDC46). |
| MCM6_HUMAN | DNA replication licensing factor MCM6 (P105MCM). [*Homo sapiens*] |
| MCM6_RAT | DNA replication licensing factor MCM6 (Intestinal DNA replication protein) (Fragment). [*Rattus norvegicus*] |
| MCM7_HUMAN | DNA replication licensing factor MCM7 (CDC47 homolog) (P1.1-MCM3). [*Homo sapiens*] |
| MCM8_HUMAN | DNA replication licensing factor MCM8 (Minichromosome maintenance 8). [*Homo sapiens*] |
| MDR1_HUMAN | Multidrug resistance protein 1 (P-glycoprotein 1) (CD243 antigen). [*Homo sapiens*] |
| MRP2_RAT | Canalicular multispecific organic anion transporter 1 (Multidrug resistance-associated protein 2) (Canalicular multidrug resistance protein). [*Rattus norvegicus*] |
| MRP3_HUMAN | Canalicular multispecific organic anion transporter 2 (Multidrug resistance-associated protein 3) (Multi-specific organic anion tranporter-D) (MOAT-D). [*Homo sapiens*] |

-continued

| | |
|---|---|
| MRP4_HUMAN | Multidrug resistance-associated protein 4 (MRP/cMOAT-related ABC transporter) (Multi-specific organic anion tranporter-B) (MOAT-B). [Homo sapiens] |
| PIA1_HUMAN | Protein inhibitor of activated STAT protein 1 (Gu binding protein) (GBP) (RNA helicase II binding protein) (DEAD/H box-binding protein 1). [Homo sapiens] |
| PR16_HUMAN | Pre-mRNA splicing factor ATP-dependent RNA helicase PRP16 (ATP- dependent RNA helicase DHX38) (DEAH-box protein 38). [Homo sapiens] |
| PRS4_HUMAN | 26S protease regulatory subunit 4 (P26s4). [Homo sapiens] |
| PRS6_HUMAN | 26S protease regulatory subunit 6B (MIP224) (MB67 interacting protein) (TAT-binding protein-7) (TBP-7). [Homo sapiens] |
| PRSX_HUMAN | 26S protease regulatory subunit S10B (Proteasome subunit p42) (p44) (Conserved ATPase domain protein 44) (CADp44). [Homo sapiens] |
| R51C_HUMAN | DNA repair protein RAD51 homolog 3. [Homo sapiens] |
| SKIW_HUMAN | Helicase SKI2W (Helicase-like protein) (HLP). [Homo sapiens] |
| U520_HUMAN | U5 small nuclear ribonucleoprotein 200 kDa helicase (EC 3.6.1.-) (U5 snRNP-specific 200 kDa protein) (U5-200KD) (Fragment). [Homo sapiens] |
| VAA1_HUMAN | Vacuolar ATP synthase catalytic subunit A, ubiquitous isoform (EC 3.6.3.14) (V-ATPase A subunit 1) (Vacuolar proton pump alpha subunit 1) (V-ATPase 69 kDa subunit 1) (Isoform VA68). [Homo sapiens] |
| VAB1_HUMAN | Vacuolar ATP synthase subunit B, kidney isoform (EC 3.6.3.14) (V- ATPase B1 subunit) (Vacuolar proton pump B isoform 1) (Endomembrane proton pump 58 kDa subunit). [Homo sapiens] |
| VATH_HUMAN | Vacuolar ATP synthase subunit H (EC 3.6.3.14) (V-ATPase H subunit) (Vacuolar proton pump H subunit) (V-ATPase 50/57 kDa subunits) (Vacuolar proton pump subunit SFD) (CGI-11). [Homo sapiens] |
| GTPases | |
| 8ODP_HUMAN | 7,8-dihydro-8-oxoguanine triphosphatase (EC 3.1.6.-) (8-oxo-dGTPase). [Homo sapiens] |
| DYN2_HUMAN | Dynamin 2 (EC 3.6.1.50). [Homo sapiens] |
| EF11_HUMAN | Elongation factor 1-alpha 1 (EF-1-alpha-1) (Elongation factor 1 A-1) (eEF1A-1) (Elongation factor Tu) (EF-Tu). [Homo sapiens] |
| EF11_MOUSE | Elongation factor 1-alpha 1 (EF-1-alpha-1) (Elongation factor 1 A-1) (eEF1A-1) (Elongation factor Tu) (EF-Tu). [Mus musculus] |
| EF12_HUMAN | Elongation factor 1-alpha 2 (EF-1-alpha-2) (Elongation factor 1 A-2) (eEF1A-2) (Statin S1). [Homo sapiens] |
| EFTU_HUMAN | Elongation factor Tu, mitochondrial precursor (EF-Tu) (P43). [Homo sapiens] |
| GB02_HUMAN | Guanine nucleotide-binding protein G(O), alpha subunit 2. [Homo sapiens] |
| GBB1_HUMAN | Guanine nucleotide-binding protein G(I)/G(S)/G(T) beta subunit 1 (Transducin beta chain 1). [Homo sapiens] |
| GBGB_HUMAN | Guanine nucleotide-binding protein G(I)/G(S)/G(O) gamma-11 subunit. [Homo sapiens] |
| GSP1_HUMAN | G1 to S phase transition protein 1 homolog (GTP-binding protein GST1-HS). [Homo sapiens] |
| GTB1_HUMAN | GTP-binding protein 1 (G-protein 1) (GP-1) (GP1). [Homo sapiens] |
| IF2P_HUMAN | Translation initiation factor IF-2. [Homo sapiens] |
| IF5_HUMAN | Eukaryotic translation initiation factor 5 (eIF-5). [Homo sapiens] |
| NCF1_HUMAN | Neutrophil cytosol factor 1 (NCF-1) (Neutrophil NADPH oxidase factor 1) (47 kDa neutrophil oxidase factor) (p47-phox) (NCF-47K) (47 kDa autosomal chronic granulomatous disease protein). [Homo sapiens] |
| NGP1_HUMAN | Autoantigen NGP-1. [Homo sapiens] |
| OPA1_HUMAN | Dynamin-like 120 kDa protein, mitochondrial precursor (Optic atrophy 1 gene protein). [Homo sapiens] |
| R11A_HUMAN | Ras-related protein Rab-11A (Rab-11) (24KG) (YL8). [Homo sapiens] |
| R27B_HUMAN | Ras-related protein Rab-27B (C25KG). [Homo sapiens] |
| R33B_HUMAN | Ras-related protein Rab-33B. [Homo sapiens] |
| R39A_HUMAN | Ras-related protein Rab-39A (Rab-39). [Homo sapiens] |
| R39B_HUMAN | Ras-related protein Rab-39B. [Homo sapiens] |
| RAB7_HUMAN | Ras-related protein Rab-7. [Homo sapiens] |
| RAB7_MOUSE | Ras-related protein Rab-7. [Mus musculus] |
| RAC1_HUMAN | Ras-related C3 botulinum toxin substrate 1 (p21-Rac1) (Ras-like protein TC25). [Homo sapiens] |
| RAC2_HUMAN | Ras-related C3 botulinum toxin substrate 2 (p21-Rac2) (Small G protein) (GX). [Homo sapiens] |
| RALA_HUMAN | Ras-related protein Ral-A. [Homo sapiens] |
| RAN_HUMAN | GTP-binding nuclear protein RAN (TC4) (Ran GTPase) (Androgen receptor- associated protein 24). [Homo sapiens] |
| RAPA_HUMAN | Ras-related protein Rap-1A (C21KG) (KREV-1 protein) (GTP-binding protein SMG-P21A) (G-22K). [Homo sapiens] |
| RASH_HUMAN | Transforming protein p21/H-Ras-1 (c-H-ras). [Homo sapiens] |
| RB14_HUMAN | Ras-related protein Rab-14. [Homo sapiens] |
| RB1A_HUMAN | Ras-related protein Rab-1A (YPT1-related protein). [Homo sapiens] |
| RB20_HUMAN | Ras-related protein Rab-20. [Homo sapiens] |
| RB4B_HUMAN | Ras-related protein Rab-4B. [Homo sapiens] |
| RB5A_HUMAN | Ras-related protein Rab-5A. [Homo sapiens] |
| RB6A_HUMAN | Ras-related protein Rab-6A (Rab-6). [Homo sapiens] |
| RGSB_HUMAN | Regulator of G-protein signaling 11 (RGS11). [Homo sapiens] |
| RHOG_HUMAN | Rho-related GTP-binding protein RhoG (Sid10750). [Homo sapiens] |
| RHON_HUMAN | Rho-related GTP-binding protein RhoN (Rho7) (Rnd2). [Homo sapiens] |
| SAD1_HUMAN | SAM domain and HD domain-containing protein 1 (Dendritic cell-derived IFNG-induced protein) (DCIP) (Monocyte protein 5) (MOP-5). [Homo sapiens] |
| Other ATP binding proteins | |
| ACLY_HUMAN | ATP-citrate synthase (EC 2.3.3.8) (ATP-citrate (pro-S-)-lyase) (Citrate cleavage enzyme). [Homo sapiens] |
| ACLY_RAT | ATP-citrate synthase (EC 2.3.3.8) (ATP-citrate (pro-S-)-lyase) (Citrate cleavage enzyme). [Rattus norvegicus] |
| ASSY_HUMAN | Argininosuccinate synthase (EC 6.3.4.5) (Citrulline--aspartate |
| ASSY_MOUSE | Argininosuccinate synthase (EC 6.3.4.5) (Citrulline--aspartate ligase). [Mus musculus] |

-continued

| | |
|---|---|
| ASSY_RAT | Argininosuccinate synthase (EC 6.3.4.5) (Citrulline--aspartate ligase). [*Rattus norvegicus*] |
| ATPA_HUMAN | ATP synthase alpha chain, mitochondrial precursor (EC 3.6.3.14). [*Homo sapiens*] |
| C1TC_HUMAN | C-1-tetrahydrofolate synthase, cytoplasmic (C1-THF synthase) [Includes: Methylenetetrahydrofolate dehydrogenase (EC 1.5.1.5); Methenyltetrahydrofolate cyclohydrolase (EC 3.5.4.9); Formyltetrahydrofolate synthetase (EC 6.3.4.3)]. [*Homo sapiens*] |
| C2TA_HUMAN | MHC class II transactivator (CIITA). [*Homo sapiens*] |
| CCAB_HUMAN | Voltage-dependent N-type calcium channel alpha-1B subunit (Calcium channel, L type, alpha-1 polypeptide isoform 5) (Brain calcium channel III) (BIII). [*Homo sapiens*] |
| CH60_CRIGR | 60 kDa heat shock protein, mitochondrial precursor (Hsp60) (60 |
| CH60_HUMAN | 60 kDa heat shock protein, mitochondrial precursor (Hsp60) (60 |
| CH60_MOUSE | 60 kDa heat shock protein, mitochondrial precursor (Hsp60) (60 kDa chaperonin) (CPN60) (Heat shock protein 60) (HSP-60) (Mitochondrial matrix protein P1) (HSP-65). [*Mus musculus*] |
| COA1_HUMAN | Acetyl-CoA carboxylase 1 (EC 6.4.1.2) (ACC-alpha) [Includes: Biotin carboxylase (EC 6.3.4.14)]. [*Homo sapiens*] |
| CPSM_HUMAN | Carbamoyl-phosphate synthase [ammonia], mitochondrial precursor (EC 6.3.4.16) (Carbamoyl-phosphate synthetase I) (CPSase I). [*Homo sapiens*] |
| CPSM_RAT | Carbamoyl-phosphate synthase [ammonia], mitochondrial precursor (EC 6.3.4.16) (Carbamoyl-phosphate synthetase I) (CPSASE I). [*Rattus norvegicus*] |
| DN2L_HUMAN | DNA2-like homolog (DNA replication helicase-like homolog) (Fragment). [*Homo sapiens*] |
| DNL1_HUMAN | DNA ligase I (EC 6.5.1.1) (Polydeoxyribonucleotide synthase [ATP]). [*Homo sapiens*] |
| DYH9_HUMAN | Ciliary dynein heavy chain 9 (Axonemal beta dynein heavy chain 9). [*Homo sapiens*] |
| DYHB_HUMAN | Ciliary dynein heavy chain 11 (Axonemal beta dynein heavy chain 11). [*Homo sapiens*] |
| DYHC_HUMAN | Dynein heavy chain, cytosolic (DYHC) (Cytoplasmic dynein heavy chain 1) (DHC1) (Fragment). [*Homo sapiens*] |
| EHD3_HUMAN | EH-domain containing protein 3. [*Homo sapiens*] |
| EHD3_MOUSE | EH-domain containing protein 3. [*Mus musculus*] |
| EHD4_HUMAN | EH-domain containing protein 4 (EH domain-containing protein FKSG7) (Hepatocellular carcinoma-associated protein 10/11). [*Homo sapiens*] |
| ENPL_CANFA | Endoplasmin precursor (94 kDa glucose-regulated protein) (GRP94). [*Canis familiaris*] |
| ENPL_HUMAN | Endoplasmin precursor (94 kDa glucose-regulated protein) (GRP94) (gp96 homolog) (Tumor rejection antigen 1). [*Homo sapiens*] |
| ENPL_MOUSE | Endoplasmin precursor (Endoplasmic reticulum protein 99) (94 kDa glucose-regulated protein) (GRP94) (ERP99) (Polymorphic tumor rejection antigen 1) (Tumor rejection antigen gp96). [*Mus musculus*] |
| FOLC_HUMAN | Folylpolyglutamate synthase, mitochondrial precursor (EC 6.3.2.17) (Folylpoly-gamma-glutamate synthetase) (FPGS). [*Homo sapiens*] |
| GEF2_HUMAN | Ganglioside expression factor 2 (GEF-2) (General protein transport factor p16) (GATE-16) (GABA(A) receptor-associated protein-like 2) (MAP1 light chain 3 related protein). [*Homo sapiens*] |
| GR75_MOUSE | Stress-70 protein, mitochondrial precursor (75 kDa glucose regulated protein) (GRP 75) (Peptide-binding protein 74) (PBP74) (P66 MOT) (Mortalin). [*Mus musculus*] |
| GR78_HUMAN | 78 kDa glucose-regulated protein precursor (GRP 78) (Immunoglobulin heavy chain binding protein) (BiP) (Endoplasmic reticulum lumenal Ca(2+) binding protein grp78). [*Homo sapiens*] |
| GR78_RAT | 78 kDa glucose-regulated protein precursor (GRP 78) (Immunoglobulin heavy chain binding protein) (BiP) (Steroidogenesis-activator polypeptide). [*Rattus norvegicus*] |
| GUAA_HUMAN | GMP synthase [glutamine-hydrolyzing] (EC 6.3.5.2) (Glutamine amidotransferase) (GMP synthetase). [*Homo sapiens*] |
| HELZ_HUMAN | Potential helicase with zinc-finger domain. [*Homo sapiens*] |
| HS71_HUMAN | Heat shock 70 kDa protein 1 (HSP70.1) (HSP70-1/HSP70-2). [*Homo sapiens*] |
| HS72_HUMAN | Heat shock-related 70 kDa protein 2 (Heat shock 70 kDa protein 2). [*Homo sapiens*] |
| HS72_MOUSE | Heat shock-related 70 kDa protein 2 (Heat shock protein 70.2). [*Mus musculus*] |
| HS72_RAT | Heat shock-related 70 kDa protein 2 (Heat shock protein 70.2) (Te |
| HS7C_BOVIN | Heat shock cognate 71 kDa protein. [*Bos taurus*] |
| HS7C_MOUSE | Heat shock cognate 71 kDa protein. [*Mus musculus*] |
| HS7H_HUMAN | Heat shock 70 kDa protein 1-HOM (HSP70-HOM). [*Homo sapiens*] |
| HS9A_HUMAN | Heat shock protein HSP 90-alpha (HSP 86). [*Homo sapiens*] |
| HS9A_PIG | Heat shock protein HSP 90-alpha (HSP 86). [*Sus scrofa*] |
| HS9B_MOUSE | Heat shock protein HSP 90-beta (HSP 84) (Tumor specific transplantation 84 kDa antigen) (TSTA). [*Mus musculus*] |
| KF11_HUMAN | Kinesin-like protein KIF11 (Kinesin-related motor protein Eg5) (Kinesin-like spindle protein HKSP) (Thyroid receptor interacting protein 5) (TRIP5) (Kinesin-like protein 1). [*Homo sapiens*] |
| KF14_HUMAN | Kinesin-like protein KIF14. [*Homo sapiens*] |
| KF1A_HUMAN | Kinesin-like protein KIF1A (Axonal transporter of synaptic vesicles). [*Homo sapiens*] |
| KF23_HUMAN | Kinesin-like protein KIF23 (Mitotic kinesin-like protein-1) (Kinesin- like protein 5). [*Homo sapiens*] |
| KF2C_HUMAN | Kinesin-like protein KIF2C (Mitotic centromere-associated kinesin) (MCAK) (Kinesin-like protein 6). [*Homo sapiens*] |
| KF4A_HUMAN | Chromosome-associated kinesin KIF4A (Chromokinesin). [*Homo sapiens*] |
| KF5C_HUMAN | Kinesin heavy chain isoform 5C (Kinesin heavy chain neuron-specific 2). [*Homo sapiens*] |
| KG88_HUMAN | Protein KIAA1688. [*Homo sapiens*] |
| KI67_HUMAN | Antigen KI-67. [*Homo sapiens*] |
| KIF9_HUMAN | Kinesin-like protein KIF9. [*Homo sapiens*] |
| KINH_HUMAN | Kinesin heavy chain (Ubiquitous kinesin heavy chain) (UKHC). [*Homo sapiens*] |
| MCCA_HUMAN | Methylcrotonyl-CoA carboxylase alpha chain, mitochondrial precursor (EC 6.4.1.4) (3-Methylcrotonyl-CoA carboxylase 1) (MCCase alpha subunit) (3-methylcrotonyl-CoA:carbon dioxide ligase alpha subunit). [*Homo sapiens*] |
| METK_HUMAN | S-adenosylmethionine synthetase gamma form (EC 2.5.1.6) (Methionine adenosyltransferase) (AdoMet synthetase) (MAT-II). [*Homo sapiens*] |
| METK_RAT | S-adenosylmethionine synthetase gamma form (EC 2.5.1.6) (Methionine adenosyltransferase) (AdoMet synthetase) (MAT-II). [*Rattus norvegicus*] |
| METL_HUMAN | S-adenosylmethionine synthetase alpha and beta forms (EC 2.5.1.6) (Methionine adenosyltransferase) (AdoMet synthetase) (MAT-I/III). [*Homo sapiens*] |

-continued

| | |
|---|---|
| MSH4_HUMAN | MutS protein homolog 4. [*Homo sapiens*] |
| MY15_HUMAN | Myosin XV (Unconventional myosin-15). [*Homo sapiens*] |
| MY1B_MOUSE | Myosin Ib (Myosin I alpha) (MMI-alpha) (MMIa) (MIH-L). [*Mus musculus*] |
| MY1C_HUMAN | Myosin Ic (Myosin I beta) (MMI-beta) (MMIb). [*Homo sapiens*] |
| MY5C_HUMAN | Myosin Vc (Myosin 5C). [*Homo sapiens*] |
| MY7A_HUMAN | Myosin VIIa. [*Homo sapiens*] |
| MY9B_HUMAN | Myosin IXb (Unconventional myosin-9b). [*Homo sapiens*] |
| MYH1_HUMAN | Myosin heavy chain, skeletal muscle, adult 1 (Myosin heavy chain IIx/d) (MyHC-IIx/d). [*Homo sapiens*] |
| MYH3_HUMAN | Myosin heavy chain, fast skeletal muscle, embryonic (Muscle embryonic myosin heavy chain) (SMHCE). [*Homo sapiens*] |
| MYH6_HUMAN | Myosin heavy chain, cardiac muscle alpha isoform (MyHC-alpha). [*Homo sapiens*] |
| MYH6_MOUSE | Myosin heavy chain, cardiac muscle alpha isoform (MyHC-alpha). [*Mus musculus*] |
| MYH7_HUMAN | Myosin heavy chain, cardiac muscle beta isoform (MyHC-beta). [*Homo sapiens*] |
| MYH7_RAT | Myosin heavy chain, cardiac muscle beta isoform (MyHC-beta). [*Rattus norvegicus*] |
| MYH9_HUMAN | Myosin heavy chain, nonmuscle type A (Cellular myosin heavy chain, type A) (Nonmuscle myosin heavy chain-A) (NMMHC-A). [*Homo sapiens*] |
| MYH9_RAT | Myosin heavy chain, nonmuscle type A (Cellular myosin heavy chain, type A) (Nonmuscle myosin heavy chain-A) (NMMHC-A). [*Rattus norvegicus*] |
| MYHA_HUMAN | Myosin heavy chain, nonmuscle type B (Cellular myosin heavy chain, type B) (Nonmuscle myosin heavy chain-B) (NMMHC-B). [*Homo sapiens*] |
| NAL1_HUMAN | NACHT-, LRR- and PYD-containing protein 2 (Death effector filament- forming ced-4-like apoptosis protein) (Nucleotide-binding domain and caspase recruitment domain) (Caspase recruitment domain protein 7). [*Homo sapiens*] |
| NP14_HUMAN | Nucleolar phosphoprotein p130 (Nucleolar 130 kDa protein) (140 kDa nucleolar phosphoprotein) (Nopp140) (Nucleolar and coiled-body phosphoprotein 1). [*Homo sapiens*] |
| NSF_HUMAN | Vesicle-fusing ATPase (EC 3.6.4.6) (Vesicular-fusion protein NSF) (N- ethylmaleimide sensitive fusion protein) (NEM-sensitive fusion protein). [*Homo sapiens*] |
| NUDM_HUMAN | NADH-ubiquinone oxidoreductase 42 kDa subunit, mitochondrial precursor (EC 1.6.5.3) (EC 1.6.99.3) (Complex I-42KD) (CI-42KD). [*Homo sapiens*] |
| OASL_HUMAN | 59 kDa 2'-5'-oligoadenylate synthetase like protein (p59 OASL) (p59OASL) (Thyroid receptor interacting protein 14) (TRIP14). [*Homo sapiens*] |
| OXRP_HUMAN | 150 kDa oxygen-regulated protein precursor (Orp150) (Hypoxia up- regulated 1). [*Homo sapiens*] |
| P2X1_RAT | P2X purinoceptor 1 (ATP receptor) (P2X1) (Purinergic receptor) (RP-2 protein). [*Rattus norvegicus*] |
| PCCA_HUMAN | Propionyl-CoA carboxylase alpha chain, mitochondrial precursor |
| PEBP_BOVIN | Phosphatidylethanolamine-binding protein (PEBP) (HCNPpp) (Basic cytosolic 21 kDa protein) [Contains: Hippocampal cholinergic neurostimulating peptide (HCNP)]. [*Bos taurus*] |
| PEBP_MACFA | Phosphatidylethanolamine-binding protein (PEBP) (HCNPpp) [Contains: Hippocampal cholinergic neurostimulating peptide (HCNP)]. [*Macaca fascicularis*] |
| PEBP_MOUSE | Phosphatidylethanolamine-binding protein (PEBP). [*Mus musculus*] |
| PEBP_RAT | Phosphatidylethanolamine-binding protein (PEBP) (Hippocampal chol |
| PMS2_HUMAN | PMS1 protein homolog 2 (DNA mismatch repair protein PMS2). [*Homo sapiens*] |
| PRS7_HUMAN | 26S protease regulatory subunit 7 (MSS1 protein). [*Homo sapiens*] |
| PRS7_MOUSE | 26S protease regulatory subunit 7 (MSS1 protein). [*Mus musculus*] |
| PRS7_RAT | 26S protease regulatory subunit 7 (MSS1 protein). [*Rattus norvegi* |
| PRSA_MOUSE | 26S protease regulatory subunit 6A (TAT-binding protein 1) (TBP-1). [*Mus musculus*] |
| PRSA_RAT | 26S protease regulatory subunit 6A (TAT-binding protein 1) (TBP-1) (Spermatogenic cell/sperm-associated TAT-binding protein homolog SATA). [*Rattus norvegicus*] |
| PUR4_HUMAN | Phosphoribosylformylglycinamidine synthase (EC 6.3.5.3) (FGAM synthase) (FGAMS) (Formylglycinamide ribotide amidotransferase) (FGARAT) (Formylglycinamide ribotide synthetase). [*Homo sapiens*] |
| PYC_HUMAN | Pyruvate carboxylase, mitochondrial precursor (EC 6.4.1.1) (Pyruvic carboxylase) (PCB). [*Homo sapiens*] |
| PYC_MOUSE | Pyruvate carboxylase, mitochondrial precursor (EC 6.4.1.1) (Pyruvic carboxylase) (PCB). [*Mus musculus*] |
| PYC_RAT | Pyruvate carboxylase, mitochondrial precursor (EC 6.4.1.1) (Pyruvic carboxylase) (PCB). [*Rattus norvegicus*] |
| PYR1_HUMAN | CAD protein [Includes: Glutamine-dependent carbamoyl-phosphate synthase (EC 6.3.5.5); Aspartate carbamoyltransferase (EC 2.1.3.2); Dihydroorotase (EC 3.5.2.3)]. [*Homo sapiens*] |
| Q63861 | Smooth muscle myosin heavy chain isoform SM1A (Fragment). [*Rattus norvegicus*] |
| Q8IUN3 | Similar to kinesin-like protein at 64D (Fragment). [*Homo sapiens*] |
| RNT1_HUMAN | Regulator of nonsense transcripts 1 (Nonsense mRNA reducing factor 1) (NORF1) (Up-frameshift suppressor 1 homolog). [*Homo sapiens*] |
| RNT1_MOUSE | Regulator of nonsense transcripts 1 (Nonsense mRNA reducing factor 1) (NORF1) (Up-frameshift suppressor 1 homolog). [*Mus musculus*] |
| ROU_HUMAN | Heterogenous nuclear ribonucleoprotein U (hnRNP U) (Scaffold attachment factor A) (SAF-A). [*Homo sapiens*] |
| RUV1_HUMAN | RuvB-like 1 (EC 3.6.1.-) (49-kDa TATA box-binding protein-interacting protein) (49 kDa TBP-interacting protein) (TIP49a) (Pontin 52) (Nuclear matrix protein 238) (NMP 238) (54 kDa erythrocyte cytosolic protein) (ECP-54) (TIP60-associated protein 54-alpha) |
| STCH_HUMAN | Microsomal stress 70 protein ATPase core precursor. [*Homo sapiens*] |
| SYA_HUMAN | Alanyl-tRNA synthetase (EC 6.1.1.7) (Alanine--tRNA ligase) (AlaRS). [*Homo sapiens*] |
| SYD_HUMAN | Aspartyl-tRNA synthetase (EC 6.1.1.12) (Aspartate-tRNA ligase) (AspRS). [*Homo sapiens*] |
| SYEP_HUMAN | Bifunctional aminoacyl-tRNA synthetase [Includes: Glutamyl-tRNA synthetase (EC 6.1.1.17) (Glutamate--tRNA ligase); Prolyl-tRNA synthetase (EC 6.1.1.15) (Proline--tRNA ligase)]. [*Homo sapiens*] |
| SYFA_HUMAN | Phenylalanyl-tRNA synthetase alpha chain (EC 6.1.1.20) (Phenylalanine- -tRNA ligase alpha chain) (PheRS) (CML33). [*Homo sapiens*] |
| SYFB_HUMAN | Phenylalanyl-tRNA synthetase beta chain (EC 6.1.1.20) (Phenylalanine-- tRNA ligase beta chain) (PheRS) (HSPC173). [*Homo sapiens*] |
| SYG_HUMAN | Glycyl-tRNA synthetase (EC 6.1.1.14) (Glycine-tRNA ligase) (GlyRS). [*Homo sapiens*] |
| SYG_MOUSE | Glycyl-tRNA synthetase (EC 6.1.1.14) (Glycine-tRNA ligase) (GlyRS). [*Mus musculus*] |
| SYH_HUMAN | Histidyl-tRNA synthetase (EC 6.1.1.21) (Histidine--tRNA ligase) (HisRS). [*Homo sapiens*] |

-continued

| | |
|---|---|
| SYI_HUMAN | Isoleucyl-tRNA synthetase, cytoplasmic (EC 6.1.1.5) (Isoleucine--tRNA ligase) (IleRS) (IRS). [*Homo sapiens*] |
| SYK_HUMAN | Lysyl-tRNA synthetase (EC 6.1.1.6) (Lysine-tRNA ligase) (LysRS). [*Homo sapiens*] |
| SYLM_HUMAN | Probable leucyl-tRNA synthetase, mitochondrial precursor (EC 6.1.1.4) (Leucine--tRNA ligase) (LeuRS). [*Homo sapiens*] |
| SYN_HUMAN | Asparaginyl-tRNA synthetase, cytoplasmic (EC 6.1.1.22) (Asparagi |
| SYQ_HUMAN | Glutaminyl-tRNA synthetase (EC 6.1.1.18) (Glutamine--tRNA ligase) (GlnRS). [*Homo sapiens*] |
| SYR_HUMAN | Arginyl-tRNA synthetase (EC 6.1.1.19) (Arginine--tRNA ligase) (ArgRS). [*Homo sapiens*] |
| SYR_MOUSE | Arginyl-tRNA synthetase (EC 6.1.1.19) (Arginine--tRNA ligase) (ArgRS). [*Mus musculus*] |
| SYV2_HUMAN | Valyl-tRNA synthetase 2 (EC 6.1.1.9) (Valine--tRNA ligase 2) (ValRS 2) (G7a). [*Homo sapiens*] |
| SYV_RAT | Valyl-tRNA synthetase (EC 6.1.1.9) (Valine--tRNA ligase) (ValRS) (Fragment). [*Rattus norvegicus*] |
| SYWM_HUMAN | Tryptophanyl-tRNA synthetase, mitochondrial precursor (EC 6.1.1.2) (Tryptophan--tRNA ligase) (TrpRS) ((Mt)TrpRS). [*Homo sapiens*] |
| SYWM_MOUSE | Tryptophanyl-tRNA synthetase, mitochondrial precursor (EC 6.1.1.2) (Tryptophan--tRNA ligase) (TrpRS) ((Mt)TrpRS). [*Mus musculus*] |
| SYW_HUMAN | Tryptophanyl-tRNA synthetase (EC 6.1.1.2) (Tryptophan--tRNA liga |
| SYW_MOUSE | Tryptophanyl-tRNA synthetase (EC 6.1.1.2) (Tryptophan--tRNA ligase) (TrpRS). [*Mus musculus*] |
| SYY_HUMAN | Tyrosyl-tRNA synthetase (EC 6.1.1.1) (Tyrosyl--tRNA ligase) (TyrRS). [*Homo sapiens*] |
| TCPA_HUMAN | T-complex protein 1, alpha subunit (TCP-1-alpha) (CCT-alpha). [*Homo sapiens*] |
| TCPD_HUMAN | T-complex protein 1, delta subunit (TCP-1-delta) (CCT-delta) (Stimulator of TAR RNA binding). [*Homo sapiens*] |
| TCPD_MOUSE | T-complex protein 1, delta subunit (TCP-1-delta) (CCT-delta) (A45). [*Mus musculus*] |
| TCPE_MOUSE | T-complex protein 1, epsilon subunit (TCP-1-epsilon) (CCT-epsilon). [*Mus musculus*] |
| TCPG_HUMAN | T-complex protein 1, gamma subunit (TCP-1-gamma) (CCT-gamma). |
| TCPH_HUMAN | T-complex protein 1, eta subunit (TCP-1-eta) (CCT-eta) (HIV-1 Nef interacting protein). [*Homo sapiens*] |
| TCPQ_HUMAN | T-complex protein 1, theta subunit (TCP-1-theta) (CCT-theta). [*Homo sapiens*] |
| TCPW_HUMAN | T-complex protein 1, zeta-2 subunit (TCP-l-zeta-2) (CCT-zeta-2) (TCP- 1-zeta-like) (CCT-zeta-like) (Testis-specific Tcp20) (Testis-specific protein TSA303). [*Homo sapiens*] |
| TCPZ_HUMAN | T-complex protein 1, zeta subunit (TCP-1-zeta) (CCT-zeta) (CCT-zeta-1) (Tcp20) (HTR3). [*Homo sapiens*] |
| TERA_HUMAN | Transitional endoplasmic reticulum ATPase (TER ATPase) (15S Mg(2+)- ATPase p97 subunit) (Valosin containing protein) (VCP) [Contains: Valosin]. [*Homo sapiens*] |
| TERA_MOUSE | Transitional endoplasmic reticulum ATPase (TER ATPase) (15S Mg(2+)- ATPase p97 subunit) (Valosin containing protein) (VCP) [Contains: Valosin]. [*Mus musculus*] |
| TERA_PIG | Transitional endoplasmic reticulum ATPase (TER ATPase) (15S Mg(2+)- ATPase p97 subunit) (Valosin containing protein) (VCP) [Contains: Valosin (Peptide VQY)]. [*Sus scrofa*] |
| TERA_RAT | Transitional endoplasmic reticulum ATPase (TER ATPase) (15S Mg(2+)- ATPase p97 subunit) (Valosin containing protein) (VCP) [Contains: Valosin]. [*Rattus norvegicus*] |
| TP2A_HUMAN | DNA topoisomerase II, alpha isozyme (EC 5.99.1.3). [*Homo sapiens*] |
| TP2B_HUMAN | DNA topoisomerase II, beta isozyme (EC 5.99.1.3). [*Homo sapiens*] |
| TRAL_HUMAN | Heat shock protein 75 kDa, mitochondrial precursor (HSP 75) (Tumor necrosis factor type 1 receptor associated protein) (TRAP-1) (TNFR- associated protein 1). [*Homo sapiens*] |
| TRAL_MOUSE | Heat shock protein 75 kDa, mitochondrial precursor (HSP 75) (Tumor necrosis factor type 1 receptor associated protein) (TRAP-1) (TNFR- associated protein 1). [*Mus musculus*] |
| Transmembrane receptors | |
| 5H1F_RAT | 5-hydroxytryptamine 1F receptor (5-HT-1F) (Serotonin receptor). [*Rattus norvegicus*] |
| ACHE_HUMAN | Acetylcholine receptor protein, epsilon chain precursor. [*Homo sapiens*] |
| AG2S_HUMAN | Type-1B angiotensin II receptor (AT1B) (AT1BR). [*Homo sapiens*] |
| AMRP_HUMAN | Alpha-2-macroglobulin receptor-associated protein precursor (Alpha-2-MRAP) (Low density lipoprotein receptor-related protein- associated protein 1) (RAP). [*Homo sapiens*] |
| B2MG_HUMAN | Beta-2-microglobulin precursor (HDCMA22P). [*Homo sapiens*] |
| CD45_HUMAN | Leukocyte common antigen precursor (EC 3.1.3.48) (L-CA) (CD45 antigen) (T200). [*Homo sapiens*] |
| CD4_HUMAN | T-cell surface glycoprotein CD4 precursor (T-cell surface antigen T4/Leu-3). [*Homo sapiens*] |
| CKR4_HUMAN | C-C chemokine receptor type 4 (C-C CKR-4) (CC-CKR-4) (CCR-4) (CCR4) (K5-5). [*Homo sapiens*] |
| CRCP_HUMAN | Calcitonin gene-related peptide-receptor component protein (CGRP- receptor component protein) (CGRP-RCP) (CGRPRCP). [*Homo sapiens*] |
| DAG1_HUMAN | Dystroglycan precursor (Dystrophin-associated glycoprotein 1) [Contains: Alpha-dystroglycan (Alpha-DG); Beta-dystroglycan (Beta- DG)]. [*Homo sapiens*] |
| DBDR_HUMAN | D(1B) dopamine receptor (D(5) dopamine receptor) (D1beta dopamine receptor). [*Homo sapiens*] |
| ENTK_HUMAN | Enteropeptidase precursor (EC 3.4.21.9) (Enterokinase). [*Homo sapiens*] |
| FZD6_HUMAN | Frizzled 6 precursor (Frizzled-6) (Fz-6) (hFz6). [*Homo sapiens*] |
| GAA6_HUMAN | Gamma-aminobutyric-acid receptor alpha-6 subunit precursor (GABA(A) receptor). [*Homo sapiens*] |
| GAD_HUMAN | Gamma-aminobutyric-acid receptor delta subunit precursor (GABA(A) receptor). [*Homo sapiens*] |
| GAE_HUMAN | Gamma-aminobutyric-acid receptor epsilon subunit precursor (GABA(A) receptor). [*Homo sapiens*] |
| GLK1_HUMAN | Glutamate receptor, ionotropic kalnate 1 precursor (Glutamate receptor 5) (GluR-5) (GluR5) (Excitatory amino acid receptor 3) (EAA3). [*Homo sapiens*] |
| GLK2_HUMAN | Glutamate receptor, ionotropic kalnate 2 precursor (Glutamate receptor 6) (GluR-6) (GluR6) (Excitatory amino acid receptor 4) (EAA4). [*Homo sapiens*] |
| GLK3_HUMAN | Glutamate receptor, ionotropic kalnate 3 precursor (Glutamate receptor 7) (GluR-7) (GluR7) (Excitatory amino acid receptor 5) (EAA5). [*Homo sapiens*] |
| GP35_HUMAN | Probable G protein-coupled receptor GPR35. [*Homo sapiens*] |
| GP61_HUMAN | Probable G protein-coupled receptor GPR61 (Biogenic amine receptor- like G-protein-coupled receptor). [*Homo sapiens*] |
| GPBA_HUMAN | Platelet glycoprotein Ib alpha chain precursor (GP-Ib alpha) (G |
| HB2B_HUMAN | HLA class II histocompatibility antigen, DR-1 beta chain precursor (Clone P2-beta-3). [*Homo sapiens*] |
| I12S_HUMAN | Interleukin-12 receptor beta-2 chain precursor (IL-12 receptor beta- 2) (IL-12R-beta2). [*Homo sapiens*] |
| INGR_HUMAN | Interferon-gamma receptor alpha chain precursor (CDw119). [*Homo sapiens*] |
| INGR_MOUSE | Interferon-gamma receptor alpha chain precursor. [*Mus musculus*] |

| | |
|---|---|
| K2S1_HUMAN | Killer cell immunoglobulin-like receptor 2DS1 precursor (MHC class I NK cell receptor Eb6 ActI). [*Homo sapiens*] |
| LDVR_HUMAN | Very low-density lipoprotein receptor precursor (VLDL receptor). |
| LEPR_RAT | Leptin receptor precursor (LEP-R) (OB receptor) (OB-R). [*Rattus norvegicus*] |
| LGR5_HUMAN | Leucine-rich repeat-containing G protein-coupled receptor 5 precursor (Orphan G protein-coupled receptor HG38) (G protein-coupled receptor 49). [*Homo sapiens*] |
| LGR8_HUMAN | Relaxin receptor 2 (Leucine-rich repeat-containing G protein-coupled receptor 8) (G protein-coupled receptor affecting testicular descent). [*Homo sapiens*] |
| MGR1_HUMAN | Metabotropic glutamate receptor 1 precursor (mGluR1). [*Homo sapiens*] |
| MGR5_HUMAN | Metabotropic glutamate receptor 5 precursor (mGluR5). [*Homo sapiens*] |
| MGR7_HUMAN | Metabotropic glutamate receptor 7 precursor (mGluR7). [*Homo sapiens*] |
| NTR1_RAT | Neurotensin receptor type 1 (NT-R-1) (High-affinity levocabastine- insensitive neurotensin receptor) (NTRH). [*Rattus norvegicus*] |
| OPCM_HUMAN | Opioid binding protein/cell adhesion molecule precursor (OBCAM) (Opioid-binding cell adhesion molecule) (OPCML). [*Homo sapiens*] |
| OPSG_HUMAN | Green-sensitive opsin (Green cone photoreceptor pigment). [*Homo sapiens*] |
| OX2R_HUMAN | Orexin receptor type 2 (Ox2r) (Hypocretin receptor type 2). [*Homo sapiens*] |
| PLX4_HUMAN | Plexin A3 precursor (Plexin 4) (Transmembrane protein sex). [*Homo sapiens*] |
| PTPK_HUMAN | Receptor-type protein-tyrosine phosphatase kappa precursor (EC 3.1.3.48) (R-PTP-kappa). [*Homo sapiens*] |
| PTPU_HUMAN | Receptor-type protein-tyrosine phosphatase U precursor (EC 3.1.3.48) (R-PTP-U) (Protein-tyrosine phosphatase J) (PTP-J) (Pancreatic carcinoma phosphatase 2) (PCP-2). [*Homo sapiens*] |
| PTPX_HUMAN | Receptor-type protein-tyrosine phosphatase N2 precursor (EC 3.1.3.48) (R-PTP-N2) (Islet cell autoantigen related protein) (ICAAR) (IAR) (Phogrin). [*Homo sapiens*] |
| PTPZ_HUMAN | Receptor-type protein-tyrosine phosphatase zeta precursor (EC 3.1.3.48) (R-PTP-zeta). [*Homo sapiens*] |
| Q30120 | MHC class II HLA-DR-beta precursor. [*Homo sapiens*] |
| RGR_HUMAN | RPE-retinal G protein-coupled receptor. [*Homo sapiens*] |
| ROM_HUMAN | Heterogeneous nuclear ribonucleoprotein M (hnRNP M). [*Homo sapiens*] |
| RRB1_MOUSE | Ribosome-binding protein 1 (Ribosome receptor protein) (mRRp). [*Mus musculus*] |
| RSP4_HUMAN | 40S ribosomal protein SA (P40) (34/67 kDa laminin receptor) (Colon carcinoma laminin-binding protein) (NEM/1CHD4) (Multidrug resistance- associated protein MGr1-Ag). [*Homo sapiens*] |
| TFR1_HUMAN | Transferrin receptor protein 1 (TfR1) (TR) (TfR) (Trfr) (CD71 antigen) (T9) (p90). [*Homo sapiens*] |
| TLR2_MOUSE | Toll-like receptor 2 precursor. [*Mus musculus*] |
| TLR9_HUMAN | Toll-like receptor 9 precursor. [*Homo sapiens*] |
| TMS2_HUMAN | Transmembrane protease, serine 2 precursor (EC 3.4.21.-). [*Homo sapiens*] |
| Other nucleotide binding proteins | |
| AFP2_HUMAN | Arfaptin 2 (ADP-ribosylation factor interacting protein 2) (Partner of RAC1) (POR1 protein). [*Homo sapiens*] |
| CNG1_HUMAN | cGMP-gated cation channel alpha 1 (CNG channel alpha 1) (CNG-1) |
| DEK_HUMAN | DEK protein. [*Homo sapiens*] |
| DPOZ_HUMAN | DNA polymerase zeta catalytic subunit (EC 2.7.7.7) (hREV3). [*Homo sapiens*] |
| DPOZ_MOUSE | DNA polymerase zeta catalytic subunit (EC 2.7.7.7) (Seizure-related protein 4). [*Mus musculus*] |
| GBAS_MOUSE | Guanine nucleotide-binding protein G(S), alpha subunit (Adenylate cyclase-stimulating G alpha protein). [*Mus musculus*] |
| HCN1_RAT | Potassium/sodium hyperpolarization-activated cyclic nucleotide-gated channel 1. [*Rattus norvegicus*] |
| PTD4_HUMAN | Putative GTP-binding protein PTD004 (PRO2455). [*Homo sapiens*] |
| PTD4_MOUSE | Putative GTP-binding protein PTD004 homolog. [*Mus musculus*] |
| Q9GKK5 | Gamma tubulin. [*Canis familiaris*] |
| SEP6_HUMAN | Septin 6. [*Homo sapiens*] |
| SRPR_HUMAN | Signal recognition particle receptor alpha subunit (SR-alpha) (Docking protein alpha) (DP-alpha). [*Homo sapiens*] |
| SUCA_HUMAN | Succinyl-CoA ligase [GDP-forming] alpha-chain, mitochondrial precursor (EC 6.2.1.4) (Succinyl-CoA synthetase, alpha chain) (SCS-alpha). [*Homo sapiens*] |
| SUCA_MOUSE | Succinyl-CoA ligase [GDP-forming] alpha-chain, mitochondrial precursor (EC 6.2.1.4) (Succinyl-CoA synthetase, alpha chain) (SCS-alpha). [*Mus musculus*] |
| SUCA_RAT | Succinyl-CoA ligase [GDP-forming] alpha-chain, mitochondrial precursor (EC 6.2.1.4) (Succinyl-CoA synthetase, alpha chain) (SCS-alpha). [*Rattus norvegicus*] |
| TBA1_HUMAN | Tubulin alpha-1 chain (Alpha-tubulin 1). [*Homo sapiens*] |
| TBA1_MOUSE | Tubulin alpha-1 chain. [*Mus musculus*] |
| TBA4_HUMAN | Tubulin alpha-4 chain (Alpha-tubulin 4). [*Homo sapiens*] |
| TBA6_HUMAN | Tubulin alpha-6 chain (Alpha-tubulin 6). [*Homo sapiens*] |
| TBA8_HUMAN | Tubulin alpha-8 chain (Alpha-tubulin 8). [*Homo sapiens*] |
| TBA_PIG | Tubulin alpha chain. [*Sus scrofa*] |
| TBB1_HUMAN | Tubulin beta-1 chain. [*Homo sapiens*] |
| TBB1_RAT | Tubulin beta chain (T beta-15). [*Rattus norvegicus*] |
| TBB2_HUMAN | Tubulin beta-2 chain. [*Homo sapiens*] |
| TBB3_MOUSE | Tubulin beta-3. [*Mus musculus*] |
| TBB4_MOUSE | Tubulin beta-4 chain. [*Mus musculus*] |
| TBB5_HUMAN | Tubulin beta-5 chain. [*Homo sapiens*] |
| TBBQ_HUMAN | Tubulin beta-4q chain. [*Homo sapiens*] |
| TBB_PIG | Tubulin beta chain. [*Sus scrofa*] |
| TBD_HUMAN | Tubulin delta chain (Delta tubulin). [*Homo sapiens*] |
| Oxidoreductases, acting on NADH or NADPH | |
| GSHR_HUMAN | Glutathione reductase, mitochondrial precursor (EC 1.8.1.7) (GR) (GRase). [*Homo sapiens*] |
| GSHR_MOUSE | Glutathione reductase, mitochondrial precursor (EC 1.8.1.7) (GR) (GRase). [*Mus musculus*] |
| GTO1_HUMAN | Glutathione transferase omega 1 (EC 2.5.1.18) (GSTO 1-1). [*Homo sapiens*] |
| NCPR_HUMAN | NADPH-cytochrome P450 reductase (EC 1.6.2.4) (CPR) (P450R). [*Homo sapiens*] |

-continued

| | |
|---|---|
| NIA1_HORVU | Nitrate reductase [NADH] (NR) |
| NU5M_HUMAN | NADH-ubiquinone oxidoreductase chain 5 (EC 1.6.5.3). [Homo sapiens] |
| NUAM_HUMAN | NADH-ubiquinone oxidoreductase 75 kDa subunit, mitochondrial precursor (EC 1.6.5.3) (EC 1.6.99.3) (Complex I-75Kd) (CI-75Kd). [Homo sapiens] |
| PDX3_HUMAN | Thioredoxin-dependent peroxide reductase, mitochondrial precursor (EC 1.11.1.-) (Peroxiredoxin 3) (Antioxidant protein 1) (AOP-1) (MER5 protein homolog) (HBC189) (PRX III). [Homo sapiens] |
| QOR_HUMAN | Quinone oxidoreductase (EC 1.6.5.5) (NADPH:quinone reductase) (Zeta- crystallin). [Homo sapiens] |
| QOR_MOUSE | Quinone oxidoreductase (EC 1.6.5.5) (NADPH:quinone reductase) (Zeta- crystallin). [Mus musculus] |
| VAT1_HUMAN | Synaptic vesicle membrane protein VAT-1 homolog. [Homo sapiens] |
| Other oxidoreductases | |
| 3BH2_RAT | 3 beta-hydroxysteroid dehydrogenase/delta 5-->4-isomerase type II (3Beta-HSD II) [Includes: 3-beta-hydroxy-delta(5)-steroid dehydrogenase (EC 1.1.1.145) (3-beta-hydroxy-5-ene steroid dehydrogenase) (Progesterone reductase); Steroid delta-isomerase (EC 5.3 |
| 6PGD_SHEEP | 6-phosphogluconate dehydrogenase, decarboxylating (EC 1.1.1.44). [Ovis aries] |
| ACD8_HUMAN | Acyl-CoA dehydrogenase family member 8, mitochondrial precursor (EC 1.3.99.-) (ACAD-8) (Isobutyryl-CoA dehydrogenase) (Activator- recruited cofactor 42 kDa component) (ARC42). [Homo sapiens] |
| ACDB_HUMAN | Acyl-CoA dehydrogenase, short/branched chain specific, mitochondrial precursor (EC 1.3.99.-) (SBCAD) (2-methyl branched chain acyl-CoA dehydrogenase) (2-MEBCAD) (2-methylbutyryl-coenzyme A dehydrogenase) (2-methylbutyryl-CoA dehydrogenase). [Homo sapiens] |
| ACDB_MOUSE | Acyl-CoA dehydrogenase, short/branched chain specific, mitochondrial precursor (EC 1.3.99.-) (SBCAD) (2-methyl branched chain acyl-CoA dehydrogenase) (2-MEBCAD) (2-methylbutyryl-coenzyme A dehydrogenase) (2-methylbutyryl-CoA dehydrogenase). [Mus musculus] |
| ACDM_MOUSE | Acyl-CoA dehydrogenase, medium-chain specific, mitochondrial precursor (EC 1.3.99.3) (MCAD). [Mus musculus] |
| ACDS_MOUSE | Acyl-CoA dehydrogenase, short-chain specific, mitochondrial precursor (EC 1.3.99.2) (SCAD) (Butyryl-CoA dehydrogenase). [Mus musculus] |
| ACDS_RAT | Acyl-CoA dehydrogenase, short-chain specific |
| ACDV_HUMAN | Acyl-CoA dehydrogenase, very-long-chain specific, mitochondrial precursor (EC 1.3.99.-) (VLCAD). [Homo sapiens] |
| ACDV_MOUSE | Acyl-CoA dehydrogenase, very-long-chain specific, mitochondrial precursor (EC 1.3.99.-) (VLCAD) (MVLCAD). [Mus musculus] |
| ADH1_RABIT | Alcohol dehydrogenase alpha chain (EC 1.1.1.1) (ADH). [Oryctolagus cuniculus] |
| ADH6_HUMAN | Alcohol dehydrogenase 6 (EC 1.1.1.1). [Homo sapiens] |
| ADHA_PERMA | Alcohol dehydrogenase A chain (EC 1.1.1.1). [Peromyscus manicul |
| ADHX_RAT | Alcohol dehydrogenase class III (EC 1.1.1.1) (Alcohol dehydrogenase 2) (Glutathione-dependent formaldehyde dehydrogenase) (EC 1.2.1.1) (FDH) (FALDH) (Alcohol dehydrogenase-B2). [Rattus norvegicus] |
| ADH_MACMU | Alcohol dehydrogenase alpha chain (EC 1.1.1.1) (ADH). [Macaca mulatta] |
| AKBA_HUMAN | Aldo-keto reductase family 1 member B10 (EC 1.1.1.-) (Aldose reductase-like) (ARL-1) (Small intestine reductase) (SI reductase) (Aldose reductase-related protein) (ARP) (hARP). [Homo sapiens] |
| AKC1_HUMAN | Aldo-keto reductase family 1 member C1 (EC 1.1.1.-) (Trans-1,2- dihydrobenzene-1,2-diol dehydrogenase) (EC 1.3.1.20) (High-affinity hepatic bile acid-binding protein) (HBAB) (Chlordecone reductase homolog HAKRC) (Dihydrodiol dehydrogenase 2) (DD2) (20 alp |
| AKD1_RAT | 3-oxo-5-beta-steroid 4-dehydrogenase (EC 1.3.99.6) (Delta(4)-3- ketosteroid 5-beta-reductase) (Aldo-keto reductase family 1 member D1). [Rattus norvegicus] |
| AR71_RAT | Aflatoxin B1 aldehyde reductase (EC 1.-.-.-) (AFB1-AR). [Rattus norvegicus] |
| AR72_HUMAN | Aflatoxin B1 aldehyde reductase 1 (EC 1.-.-.-) (AFB1-AR 1) (Aldoketoreductase 7). [Homo sapiens] |
| BIEA_HUMAN | Biliverdin reductase A precursor (EC 1.3.1.24) (Biliverdin-IX alpha- reductase). [Homo sapiens] |
| C26A_HUMAN | Cytochrome P450 26A2 (EC 1.14.-.-) (P450RAI-2) (Retinoic-acid metabolizing cytochrome). [Homo sapiens] |
| C343_HUMAN | Cytochrome P450 3A43 (EC 1.14.14.1). [Homo sapiens] |
| CAO1_HUMAN | Acyl-coenzyme A oxidase 1, peroxisomal (EC 1.3.3.6) (Palmitoyl-CoA oxidase) (AOX). [Homo sapiens] |
| CAO1_RAT | Acyl-coenzyme A oxidase 1, peroxisomal (EC 1.3.3.6) (Palmitoyl-CoA oxidase) (AOX). [Rattus norvegicus] |
| COXB_HUMAN | Cytochrome c oxidase polypeptide Vb, mitochondrial precursor (EC 1.9.3.1). [Homo sapiens] |
| COXB_MOUSE | Cytochrome c oxidase polypeptide Vb, mitochondrial precursor (EC 1.9.3.1). [Mus musculus] |
| COXD_RAT | Cytochrome c oxidase polypeptide VIa-heart, mitochondrial precursor (EC 1.9.3.1) (COXVIAH) (Fragment). [Rattus norvegicus] |
| COXE_RAT | Cytochrome c oxidase polypeptide VIa-liver, mltochondrial precursor (EC 1.9.3.1). [Rattus norvegicus] |
| COXI_MOUSE | Cytochrome c oxidase polypeptide VIc-2 (EC 1.9.3.1). [Mus musculus] |
| CP42_RAT | Cytochrome P450 4A2 precursor (EC 1.14.15.3) (CYPIVA2) (Lauric acid omega-hydroxylase) (P450-LA-omega 2) (P450 K-5) (P-450 K-2). [Rattus norvegicus] |
| CP4Y_HUMAN | Cytochrome P450 4A11 precursor (EC 1.14.15.3) (CYPIVA11) (Fatty acid omega-hydroxylase) (P-450 HK omega) (Lauric add omega-hydroxylase) (CYP4AII) (P450-HL-omega). [Homo sapiens] |
| CPC6_RAT | Cytochrome P450 2C6 (EC 1.14.14.1) (CYPIIC6) (P450 PB1) (PTF2). [Rattus norvegicus] |
| CTP1_HUMAN | C-terminal binding protein 1 (CtBP1). [Homo sapiens] |
| CX41_HUMAN | Cytochrome c oxidase subunit IV isoform 1, mitochondrial precursor (EC 1.9.3.1) (COX IV-1) (Cytochrome c oxidase polypeptide IV). [Homo sapiens] |
| D3HI_RAT | 3-hydroxyisobutyrate dehydrogenase, mitochondrial precursor (EC 1.1.1.31) (HIBADH). [Rattus norvegicus] |
| D7A1_HUMAN | Aldehyde dehydrogenase family 7 member A1 (EC 1.2.1.3) (Antiquitin 1). [Homo sapiens] |
| D7A1_RAT | Aldehyde dehydrogenase family 7 member A1 (EC 1.2.1.3) (Antiquitin 1) (Fragment). [Rattus norvegicus] |
| DECR_HUMAN | 2,4-dienoyl-CoA reductase, mitochondrial precursor (EC 1.3.1.34) (2,4- dienoyl-CoA reductase [NADPH]) (4-enoyl-CoA reductase [NADPH]). [Homo sapiens] |
| DH3I_MOUSE | 3-hydroxyisobutyrate dehydrogenase, mitochondrial precursor (EC 1.1.1.31) (HIBADH). [Mus musculus] |
| DHA1_MOUSE | Aldehyde dehydrogenase 1A1 (EC 1.2.1.3) (Aldehyde dehydrogenase, cytosolic) (ALDH class 1) (ALHDII) (ALDH-E1). [Mus musculus] |

-continued

| | |
|---|---|
| DHA5_HUMAN | Aldehyde dehydrogenase X, mitochondrial precursor (EC 1.2.1.3) (ALDH class 2). [*Homo sapiens*] |
| DHA6_HUMAN | Aldehyde dehydrogenase 6 (EC 1.2.1.5). [*Homo sapiens*] |
| DHA7_HUMAN | Aldehyde dehydrogenase 7 (EC 1.2.1.5). [*Homo sapiens*] |
| DHAG_HUMAN | Aldehyde dehydrogenase, E3 isozyme (EC 1.2.1.3) (Gamma- aminobutyraldehyde dehydrogenase) (EC 1.2.1.19) (R-aminobutyraldehyde dehydrogenase). [*Homo sapiens*] |
| DHAM_HUMAN | Aldehyde dehydrogenase, mitochondrial precursor (EC 1.2.1.3) (ALDH class 2) (ALDHI) (ALDH-E2). [*Homo sapiens*] |
| DHAM_MOUSE | Aldehyde dehydrogenase, mitochondrial precursor (EC 1.2.1.3) (ALDH class 2) (AHD-M1) (ALDHI) (ALDH-E2). [*Mus musculus*] |
| DHB2_HUMAN | Estradiol 17 beta-dehydrogenase 2 (EC 1.1.1.62) (17-beta-HSD 2) (Microsomal 17-beta-hydroxysteroid dehydrogenase) (20 alpha- hydroxysteroid dehydrogenase) (20-alpha-HSD) (E2DH). [*Homo sapiens*] |
| DHB3_HUMAN | Estradiol 17 beta-dehydrogenase 3 (EC 1.1.1.62) (17-beta-HSD 3) (Testicular 17-beta-hydroxysteroid dehydrogenase). [*Homo sapiens*] |
| DHB3_RAT | Estradiol 17 beta-dehydrogenase 3 (EC 1.1.1.62) (17-beta-HSD 3) (Testicular 17-beta-hydroxysteroid dehydrogenase). [*Rattus norvegicus*] |
| DHB4_HUMAN | Peroxisomal multifunctional enzyme type 2 (MFE-2) (D-bifunctional protein) (DBP) (17-beta-hydroxysteroid dehydrogenase 4) (17-beta-HSD 4) [Includes: D-3-hydroxyacyl-CoA dehydratase (EC 4.2.1.-); 3- hydroxyacyl-CoA dehydrogenase (EC 1.1.1.35)]. [*Homo sapie* |
| DHE3_BOVIN | Glutamate dehydrogenase (EC 1.4.1.3) (GDH). [*Bos taurus*] |
| DHE3_HUMAN | Glutamate dehydrogenase 1, mitochondrial precursor (EC 1.4.1.3) (GDH). [*Homo sapiens*] |
| DHE3_MOUSE | Glutamate dehydrogenase, mitochondrial precursor (EC 1.4.1.3) (GDH). [*Mus musculus*] |
| DHE3_RAT | Glutamate dehydrogenase, mitochondrial precursor (EC 1.4.1.3) (GD |
| DHI1_HUMAN | Corticosteroid 11-beta-dehydrogenase, isozyme 1 (EC 1.1.1.146) (11-DH) (11-beta-hydroxysteroid dehydrogenase 1) (11-beta-HSD1). [*Homo sapiens*] |
| DHI1_MOUSE | Corticosteroid 11-beta-dehydrogenase, isozyme 1 (EC 1.1.1.146) (11-DH) (11-beta-hydroxysteroid dehydrogenase 1) (11-beta-HSD1) (11beta- HSD1A). [*Mus musculus*] |
| DHS2_HUMAN | Dehydrogenase/reductase SDR family member 2 (EC 1.1.-.-) (HEP27 protein) (Protein D). [*Homo sapiens*] |
| DHSA_HUMAN | Succinate dehydrogenase [ubiquinone] flavoprotein subunit, mitochondrial precursor (EC 1.3.5.1) (Fp) (Flavoprotein subunit of complex II). [*Homo sapiens*] |
| DHSO_HUMAN | Sorbitol dehydrogenase (EC 1.1.1.14) (L-iditol 2-dehydrogenase). [*Homo sapiens*] |
| DHSO_MOUSE | Sorbitol dehydrogenase (EC 1.1.1.14) (L-iditol 2-dehydrogenase) (Fragment). [*Mus musculus*] |
| DHSO_RAT | Sorbitol dehydrogenase (EC 1.1.1.14) (L-iditol 2-dehydrogenase). [*Rattus norvegicus*] |
| DIDH_RAT | 3-alpha-hydroxysteroid dehydrogenase (EC 1.1.1.50) (3-alpha-HSD) (Hydroxyprostaglandin dehydrogenase). [*Rattus norvegicus*] |
| DLDH_HUMAN | Dihydrolipoamide dehydrogenase, mitochondrial precursor (EC 1.8.1.4) (Glycine cleavage system L protein). [*Homo sapiens*] |
| DLDH_MOUSE | Dihydrolipoamide dehydrogenase, mitochondrial precursor (EC 1.8.1.4). [*Mus musculus*] |
| DPYD_BOVIN | Dihydropyrimidine dehydrogenase [NADP+] (EC 1.3.1.2) (DPD) (DHPDHase) (Dihydrouracil dehydrogenase) (Dihydrothymine dehydrogenase). [*Bos taurus*] |
| DPYD_HUMAN | Dihydropyrimidine dehydrogenase [NADP+] precursor (EC 1.3.1.2) (DPD) (DHPDHase) (Dihydrouracil dehydrogenase) (Dihydrothymine dehydrogenase). [*Homo sapiens*] |
| ECHA_HUMAN | Trifunctional enzyme alpha subunit, mitochondrial precursor (TP-alpha) (78 kDa gastrin-binding protein) [Includes: Long-chain enoyl-CoA hydratase (EC 4.2.1.17); Long chain 3-hydroxyacyl-CoA dehydrogenase (EC 1.1.1.35)]. [*Homo sapiens*] |
| ECHA_PIG | Trifunctional enzyme alpha subunit, mitochondrial precursor (TP-alpha) (78 kDa gastrin-binding protein) [Includes: Long-chain enoyl-CoA hydratase (EC 4.2.1.17); Long chain 3-hydroxyacyl-CoA dehydrogenase (EC 1.1.1.35)]. [*Sus scrofa*] |
| ECHA_RAT | Trifunctional enzyme alpha subunit, mitochondrial precursor (TP-alpha) [Includes: Long-chain enoyl-CoA hydratase (EC 4.2.1.17); Long chain 3-hydroxyacyl-CoA dehydrogenase (EC 1.1.1.35)]. [*Rattus norvegicus*] |
| ECHB_HUMAN | Trifunctional enzyme beta subunit, mitochondrial precursor (TP-beta) [Includes: 3-ketoacyl-CoA thiolase (EC 2.3.1.16) (Acetyl-CoA acyltransferase) (Beta-ketothiolase)]. [*Homo sapiens*] |
| ECHP_CAVPO | Peroxisomal bifunctional enzyme (PBE) (PBFE) [Includes: Enoyl-C |
| ECHP_MOUSE | Peroxisomal bifunctional enzyme (PBE) (PBFE) [Includes: Enoyl-C |
| ER29_HUMAN | Endoplasmic reticulum protein ERp29 precursor (ERp31) (ERp28). [*Homo sapiens*] |
| ERG1_HUMAN | Squalene monooxygenase (EC 1.14.99.7) (Squalene epoxidase) (SE). [*Homo sapiens*] |
| FAS_HUMAN | Fatty acid synthase (EC 2.3.1.85) [Includes: EC 2.3.1.38; EC 2.3.1.39; EC 2.3.1.41; EC 1.1.1.100; EC 4.2.1.61; EC 1.3.1.10; EC 3.1.2.14]. [*Homo sapiens*] |
| FAS_RAT | Fatty acid synthase (EC 2.3.1.85) [Includes: EC 2.3.1.38; EC 2.3.1.39; EC 2.3.1.41; EC 1.1.1.100; EC 4.2.1.61; EC 1.3.1.10; EC 3.1.2.14]. [*Rattus norvegicus*] |
| FCL_HUMAN | GDP-L-fucose synthetase (EC 1.1.1.271) (FX protein) (Red cell NADP(H)- binding protein) (GDP-4-keto-6-deoxy-D-mannose-3,5-epimerase-4- reductase). [*Homo sapiens*] |
| FCL_MOUSE | GDP-L-fucose synthetase (EC 1.1.1.271) (FX protein) (Red cell NADP(H)- binding protein) (GDP-4-keto-6-deoxy-D-mannose-3,5-eplmerase-4- reductase) (Transplantation antigen P35B) (Tum-P35B antigen). [*Mus musculus*] |
| FMO1_RAT | Dimethylaniline monooxygenase [N-oxide forming] 1 (EC 1.14.13.8) (Hepatic flavin-containing monooxygenase 1) (FMO 1) (Dimethylaniline oxidase 1). [*Rattus norvegicus*] |
| FOX2_NEUCR | Peroxisomal hydratase-dehydrogenase-epimer |
| FTDH_HUMAN | 10-formyltetrahydrofolate dehydrogenase (EC 1.5.1.6) (10-FTHFDH). [*Homo sapiens*] |
| FTDH_MOUSE | 10-formyltetrahydrofolate dehydrogenase (EC 1.5.1.6) (10-FTHFDH). [*Mus musculus*] |
| FTDH_RAT | 10-formyltetrahydrofolate dehydrogenase (EC 1.5.1.6) (10-FTHFDH) (FBP-CI). [*Rattus norvegicus*] |
| G3P1_HUMAN | Glyceraldehyde 3-phosphate dehydrogenase, muscle (EC 1.2.1.12) (GAPDH). [*Homo sapiens*] |
| G3P1_JACOR | Glyceraldehyde 3-phosphate dehydrogenase, muscle (EC 1.2.1.12) |
| G3P_BOVIN | Glyceraldehyde 3-phosphate dehydrogenase (EC 1.2.1.12) (GAPDH) (Fragment). [*Bos taurus*] |
| G3P_MESAU | Glyceraldehyde 3-phosphate dehydrogenase (EC 1.2.1.12) (GAPDH) ( |
| G3P_RAT | Glyceraldehyde 3-phosphate dehydrogenase (EC 1.2.1.12) (GAPDH) (38 kDa BFA-dependent ADP-ribosylation substrate) (BARS-38). [*Rattus norvegicus*] |
| G6PD_HUMAN | Glucose-6-phosphate 1-dehydrogenase (EC 1.1.1.49) (G6PD). [*Homo sapiens*] |

-continued

| | |
|---|---|
| GLS1_ARATH | Ferredoxin-dependent glutamate synthase 1 |
| GST3_HUMAN | Microsomal glutathione S-transferase 3 (EC 2.5.1.18) (Microsomal GST- 3) (Microsomal GST-III). [*Homo sapiens*] |
| GTK1_RAT | Glutathione S-transferase, mitochondrial (GS |
| HCD2_HUMAN | 3-hydroxyacyl-CoA dehydrogenase type II (EC 1.1.1.35) (Type II HADH) (Endoplasmic reticulum-associated amyloid beta-peptide binding protein) (Short-chain type dehydrogenase/reductase XH98G2). [*Homo sapiens*] |
| HCD2_RAT | 3-hydroxyacyl-CoA dehydrogenase type II (EC 1.1.1.35) (Type II HADH) (Endoplasmic reticulum-associated amyloid beta-peptide binding protein). [*Rattus norvegicus*] |
| HCDH_HUMAN | Short chain 3-hydroxyacyl-CoA dehydrogenase, mitochondrial precursor (EC 1.1.1.35) (HCDH) (Medium and short chain L-3-hydroxyacyl-coenzyme A dehydrogenase). [*Homo sapiens*] |
| HCDH_MOUSE | Short chain 3-hydroxyacyl-CoA dehydrogenase, mitochondrial precursor (EC 1.1.1.35) (HCDH) (Medium and short chain L-3-hydroxyacyl-coenzyme A dehydrogenase). [*Mus musculus*] |
| HCDH_RAT | Short chain 3-hydroxyacyl-CoA dehydrogenase, mitochondrial precursor (EC 1.1.1.35) (HCDH) (Medium and short chain L-3-hydroxyacyl-coenzyme A dehydrogenase). [*Rattus norvegicus*] |
| HEM6_HUMAN | Coproporphyrinogen III oxidase, mitochondrial precursor (EC 1.3.3.3) (Coproporphyrinogenase) (Coprogen oxidase) (COX). [*Homo sapiens*] |
| HMDH_HUMAN | 3-hydroxy-3-methylglutaryl-coenzyme A reductase (EC 1.1.1.34) (HMG-CoA reductase). [*Homo sapiens*] |
| HO1_HUMAN | Heme oxygenase 1 (EC 1.14.99.3) (HO-1). [*Homo sapiens*] |
| HO2_HUMAN | Heme oxygenase 2 (EC 1.14.99.3) (HO-2). [*Homo sapiens*] |
| HPPD_MOUSE | 4-hydroxyphenylpyruvate dioxygenase (EC 1.13.11.27) (4HPPD) (HPD) (HPPDase) (F protein) (F Alloantigen). [*Mus musculus*] |
| HPPD_RAT | 4-hydroxyphenylpyruvate dioxygenase (EC 1.13.11.27) (4HPPD) (HPD) (HPPDase) (F protein) (F alloantigen) (Fragment). [*Rattus norvegicus*] |
| IDH1_KLULA | Isocitrate dehydrogenase [NAD] subunit 1, |
| IDHA_HUMAN | Isocitrate dehydrogenase [NAD] subunit alpha, mitochondrial precursor (EC 1.1.1.41) (Isocitric dehydrogenase) (NAD+-specific ICDH). [*Homo sapiens*] |
| IDHC_HUMAN | Isocitrate dehydrogenase [NADP] cytoplasmic (EC 1.1.1.42) (Oxalosuccinate decarboxylase) (IDH) (NADP+-specific ICDH) (IDP). [*Homo sapiens*] |
| IDHC_MICME | Isocitrate dehydrogenase [NADP] cytoplasmic (EC 1.1.1.42) (Oxal |
| IDHC_RAT | Isocitrate dehydrogenase [NADP] cytoplasmic (EC 1.1.1.42) (Oxalosuccinate decarboxylase) (IDH) (NADP+-specific ICDH) (IDP). [*Rattus norvegicus*] |
| IDHC_TOBAC | ISOCITRATE DEHYDROGENASE [NADP] (OXALOSUCC |
| IDHP_BOVIN | Isocitrate dehydrogenase [NADP], mitochondrial precursor (EC 1.1.1.42) (Oxalosuccinate decarboxylase) (IDH) (NADP+-specific ICDH) (IDP) (ICD-M). [*Bos taurus*] |
| IDHP_HUMAN | Isocitrate dehydrogenase [NADP], mitochondrial precursor (EC 1.1.1.42) (Oxalosuccinate decarboxylase) (IDH) (NADP+-specific ICDH) (IDP) (ICD-M). [*Homo sapiens*] |
| IDHP_MOUSE | Isocitrate dehydrogenase [NADP], mitochondrial precursor (EC 1.1.1.42) (Oxalosuccinate decarboxylase) (IDH) (NADP+-specific ICDH) (IDP) (ICD-M). [*Mus musculus*] |
| IDH_COREF | Isocitrate dehydrogenase [NADP] (Oxalosucc |
| IMD1_HUMAN | Inosine-5'-monophosphate dehydrogenase 1 (EC 1.1.1.205) (IMP dehydrogenase 1) (IMPDH-I) (IMPD 1). [*Homo sapiens*] |
| IMD1_MOUSE | Inosine-5'-monophosphate dehydrogenase 1 (EC 1.1.1.205) (IMP dehydrogenase 1) (IMPDH-I) (IMPD 1). [*Mus musculus*] |
| IMD2_HUMAN | Inosine-5'-monophosphate dehydrogenase 2 (EC 1.1.1.205) (IMP dehydrogenase 2) (IMPDH-II) (IMPD 2). [*Homo sapiens*] |
| IMD2_MESAU | Inosine-5'-monophosphate dehydrogenase 2 (EC 1.1.1.205) (IMP de |
| IMD2_MOUSE | Inosine-5'-monophosphate dehydrogenase 2 (EC 1.1.1.205) (IMP dehydrogenase 2) (IMPDH-II) (IMPD 2). [*Mus musculus*] |
| IVD_HUMAN | Isovaleryl-CoA dehydrogenase, mitochondrial precursor (EC 1.3.99.10) (IVD). [*Homo sapiens*] |
| LA_HUMAN | Lupus La protein (Sjogren syndrome type B antigen) (SS-B) (La ribonucleoprotein) (La autoantigen). [*Homo sapiens*] |
| LDHA_RAT | L-lactate dehydrogenase A chain (EC 1.1.1.27) (LDH-A) (LDH muscle subunit) (LDH-M). [*Rattus norvegicus*] |
| LEU3_CANGA | 3-isopropylmalate dehydrogenase (Beta-IPM |
| LOX5_MESAU | Arachidonate 5-lipoxygenase (EC 1.13.11.34) (5-lipoxygenase) (5 |
| LOX5_MOUSE | Arachidonate 5-lipoxygenase (EC 1.13.11.34) (5-lipoxygenase) (5-LO). [*Mus musculus*] |
| LOX5_RAT | Arachidonate 5-lipoxygenase (EC 1.13.11.34) (5-lipoxygenase) (5-LO). [*Rattus norvegicus*] |
| LOXP_HUMAN | Arachidonate 12-lipoxygenase, 12S-type (EC 1.13.11.31) (12-LOX) (Platelet-type lipoxygenase 12). [*Homo sapiens*] |
| LXE3_HUMAN | Epidermis-type lipoxygenase 3 (EC 1.13.11.-) (e-LOX-3). [*Homo sapiens*] |
| M2GD_RAT | Dimethylglycine dehydrogenase, mitochondrial precursor (EC 1.5.99.2) (ME2GLYDH). [*Rattus norvegicus*] |
| MAOM_HUMAN | NAD-dependent malic enzyme, mitochondrial precursor (EC 1.1.1.3 |
| MDHC_PIG | Malate dehydrogenase, cytoplasmic (EC 1.1.1.37). [*Sus scrofa*] |
| MDHM_HUMAN | Malate dehydrogenase, mitochondrial precursor (EC 1.1.1.37). [*Homo sapiens*] |
| MDHM_MOUSE | Malate dehydrogenase, mitochondrial precursor (EC 1.1.1.37). [*Mus musculus*] |
| MDHM_RAT | Malate dehydrogenase, mitochondrial precursor (EC 1.1.1.37). [*Rattus norvegicus*] |
| MMSA_HUMAN | Methylmalonate-semialdehyde dehydrogenase [acylating], mitochondrial precursor (EC 1.2.1.27) (MMSDH). [*Homo sapiens*] |
| MMSA_RAT | Methylmalonate-semialdehyde dehydrogenase [acylating], mitochondrial precursor (EC 1.2.1.27) (MMSDH). [*Rattus norvegicus*] |
| MTDH_ARATH | Probable mannitol dehydrogenase (NAD-depen |
| NAPA_ALCEU | PERIPLASMIC NITRATE REDUCTASE PRECURSOR |
| NIA_USTMA | Nitrate reductase [NADPH] (NR) |
| NOS1_HUMAN | Nitric-oxide synthase, brain (EC 1.14.13.39) (NOS, type I) (Neuronal NOS) (N-NOS) (nNOS) (Constitutive NOS) (NC-NOS) (bNOS). [*Homo sapiens*] |
| NS2A_HUMAN | Nitric oxide synthase, inducible (EC 1.14.13.39) (NOS, type II) (Inducible NOS) (INOS) (Hepatocyte NOS) (HEP-NOS). [*Homo sapiens*] |
| NSDL_HUMAN | NAD(P)-dependent steroid dehydrogenase (EC 1.1.1.-) (H105e3 protein). [*Homo sapiens*] |

-continued

| | |
|---|---|
| ODBA_HUMAN | 2-oxoisovalerate dehydrogenase alpha subunit, mitochondrial precursor (EC 1.2.4.4) (Branched-chain alpha-keto acid dehydrogenase E1 component alpha chain) (BCKDH E1-alpha). [*Homo sapiens*] |
| ODO1_HUMAN | 2-oxoglutarate dehydrogenase E1 component, mitochondrial precursor (EC 1.2.4.2) (Alpha-ketoglutarate dehydrogenase). [*Homo sapiens*] |
| OXLA_CROAD | L-amino acid oxidase precursor (LAO) (LAAO |
| PAHX_RAT | Phytanoyl-CoA dioxygenase, peroxisomal precursor (EC 1.14.11.18) (Phytanoyl-CoA alpha-hydroxylase) (PhyH) (Phytanic acid oxidase). [*Rattus norvegicus*] |
| PCD8_HUMAN | Programmed cell death protein 8, mitochondrial precursor (EC 1. |
| PCD8_MOUSE | Programmed cell death protein 8, mitochondrial precursor (EC 1.-.-.-) (Apoptosis-inducing factor). [*Mus musculus*] |
| PDA3_HUMAN | Protein disulfide isomerase A3 precursor (EC 5.3.4.1) (Disulfide isomerase ER-60) (ERp60) (58 kDa microsomal protein) (p58) (ERp57) (58 kDa glucose regulated protein). [*Homo sapiens*] |
| PDA3_MOUSE | Protein disulfide isomerase A3 precursor (EC 5.3.4.1) (Disulfide isomerase ER-60) (ERp60) (58 kDa microsomal protein) (p58) (ERp57). [*Mus musculus*] |
| PDA3_RAT | Protein disulfide isomerase A3 precursor (EC 5.3.4.1) (Disulfide isomerase ER-60) (ERp60) (58 kDa microsomal protein) (p58) (ERp57) (HIP-70) (Q-2). [*Rattus norvegicus*] |
| PDA4_HUMAN | Protein disulfide isomerase A4 precursor (EC 5.3.4.1) (Protein ERp-72) (ERp72). [*Homo sapiens*] |
| PDA5_HUMAN | Protein disulfide isomerase A5 precursor (EC 5.3.4.1) (Protein disulfide isomerase-related protein). [*Homo sapiens*] |
| PDA6_HUMAN | Protein disulfide isomerase A6 precursor (EC 5.3.4.1) (Protein disulfide isomerase P5). [*Homo sapiens*] |
| PDA6_RAT | Protein disulfide isomerase A6 precursor (EC 5.3.4.1) (Protein disulfide isomerase PS) (Calcium-binding protein 1) (CaBP1) (Fragment). [*Rattus norvegicus*] |
| PDI_BOVIN | Protein disulfide isomerase precursor (PDI) (EC 5.3.4.1) (Prolyl 4- hydroxylase beta subunit) (Cellular thyroid hormone binding protein) (P55). [*Bos taurus*] |
| PDI_HUMAN | Protein disulfide isomerase precursor (PDI) (EC 5.3.4.1) (Prolyl 4- hydroxylase beta subunit) (Cellular thyroid hormone binding protein) (P55). [*Homo sapiens*] |
| PDI_MOUSE | Protein disulfide isomerase precursor (PDI) (EC 5.3.4.1) (Prolyl 4- hydroxylase beta subunit) (Cellular thyroid hormone binding protein) (P55) (ERP59). [*Mus musculus*] |
| PDI_RAT | Protein disulfide isomerase precursor (PDI) (EC 5.3.4.1) (Prolyl 4- hydroxylase beta subunit) (Cellular thyroid hormone binding protein) (Thyroxine deiodinase) (EC 3.8.1.4) (Iodothyronine 5'-monodeiodinase) (5'-MD). [*Rattus norvegicus*] |
| PDX1_HUMAN | Peroxiredoxin 1 (EC 1.11.1.-) (Thioredoxin peroxidase 2) (Thioredoxin- dependent peroxide reductase 2) (Proliferation-associated protein PAG) (Natural killer cell enhancing factor A) (NKEF-A). [*Homo sapiens*] |
| PDX1_MOUSE | Peroxiredoxin 1 (EC 1.11.1.-) (Thioredoxin peroxidase 2) (Thioredoxin- dependent peroxide reductase 2) (Osteoblast specific factor 3) (OSF-3) (Macrophage 23 kDa stress protein). [*Mus musculus*] |
| PDX1_RAT | Peroxiredoxin 1 (EC 1.11.1.-) (Thioredoxin peroxidase 2) (Thioredoxin- dependent peroxide reductase 2) (Heme-binding 23 kDa protein) (HBP23). [*Rattus norvegicus*] |
| PDX2_HUMAN | Peroxiredoxin 2 (EC 1.11.1.-) (Thioredoxin peroxidase 1) (Thioredoxin- dependent peroxide reductase 1) (Thiol-specific antioxidant protein) (TSA) (PRP) (Natural killer cell enhancing factor B) (NKEF-B). [*Homo sapiens*] |
| PDX4_MOUSE | Peroxiredoxin 4 (EC 1.11.1.-) (Prx-IV) (Thioredoxin peroxidase AO372) (Thioredoxin-dependent peroxide reductase A0372) (Antioxidant enzyme AOE372). [*Mus musculus*] |
| PE2R_RAT | 20-alpha-hydroxysteroid dehydrogenase (EC 1.1.1.149) (20-alpha-HSD) (HSD1). [*Rattus norvegicus*] |
| PERL_HUMAN | Lactoperoxidase precursor (EC 1.11.1.7) (LPO) (Salivary peroxidase) (SPO). [*Homo sapiens*] |
| PERM_HUMAN | Myeloperoxidase precursor (EC 1.11.1.7) (MPO). [*Homo sapiens*] |
| PERT_HUMAN | Thyroid peroxidase precursor (EC 1.11.1.8) (TPO). [*Homo sapiens*] |
| PGH1_HUMAN | Prostaglandin G/H synthase 1 precursor (EC 1.14.99.1) (Cyclooxygenase -1) (COX-1) (Prostaglandin-endoperoxide synthase 1) (Prostaglandin H2 synthase 1) (PGH synthase 1) (PGHS-1) (PHS 1). [*Homo sapiens*] |
| PLO1_MOUSE | Procollagen-lysine,2-oxoglutarate 5-dioxygenase 1 precursor (EC |
| PLO2_HUMAN | Procollagen-lysine,2-oxoglutarate 5-dioxygenase 2 precursor (EC 1.14.11.4) (Lysyl hydroxylase 2) (LH2). [*Homo sapiens*] |
| PLO3_HUMAN | Procollagen-lysine,2-oxoglutarate 5-dioxygenase 3 precursor (EC 1.14.11.4) (Lysyl hydroxylase 3) (LH3). [*Homo sapiens*] |
| PROC_HUMAN | Pyrroline-5-carboxylate reductase (EC 1.5.1.2) (P5CR) (P5C reductase). [*Homo sapiens*] |
| PUT2_HUMAN | Delta-1-pyrroline-5-carboxylate dehydrogenase, mitochondrial precursor (EC 1.5.1.12) (P5C dehydrogenase). [*Homo sapiens*] |
| Q14400 | GLUD1 protein (Fragment). [*Homo sapiens*] |
| Q811C4 | Dihydrolipoamide dehydrogenase precursor (EC 1.8.1.4) (Fragment). [ |
| Q8K417 | Glyceraldehyde-3-phosphate dehydrogenase (EC 1.2.1.12) (GAPDH) (Fra |
| Q9N2D6 | Glyceraldehyde-3-phosphate dehydrogenase (EC 1.2.1.12) (GAPDH). [Ca |
| RIR1_HUMAN | Ribonucleoside-diphosphate reductase M1 chain (EC 1.17.4.1) (Ribonucleotide reductase large chain). [*Homo sapiens*] |
| ROH1_RAT | Retinol dehydrogenase type I (EC 1.1.1.105) (RODH I). [*Rattus norvegicus*] |
| SERA_HUMAN | D-3-phosphoglycerate dehydrogenase (EC 1.1.1.95) (3-PGDH). [*Homo sapiens*] |
| SSDH_HUMAN | Succinate semialdehyde dehydrogenase, mitochondrial precursor (EC 1.2.1.24) (NAD(+)-dependent succinic semialdehyde dehydrogenase). [*Homo sapiens*] |
| SSDH_RAT | Succinate semialdehyde dehydrogenase (EC 1.2.1.24) (NAD(+)-dependent succinic semialdehyde dehydrogenase). [*Rattus norvegicus*] |
| T23O_HUMAN | Tryptophan 2,3-dioxygenase (EC 1.13.11.11) (Tryptophan pyrrolase) (Tryptophanase) (Tryptophan oxygenase) (Tryptamin 2,3-dioxygenase) (TRPO). [*Homo sapiens*] |
| THIM_HUMAN | 3-ketoacyl-CoA thiolase, mitochondrial (EC 2.3.1.16) (Beta- ketothiolase) (Acetyl-CoA acyltransferase) (Mitochondrial 3-oxoacyl- CoA thiolase) (T1). [*Homo sapiens*] |
| TXNL_HUMAN | Thioredoxin-like protein (32 kDa thioredoxin-related protein). [*Homo sapiens*] |
| UCR2_HUMAN | Ubiquinol-cytochrome C reductase complex core protein 2, mitochondrial precursor (EC 1.10.2.2) (Complex III subunit II). [*Homo sapiens*] |
| UCR2_MOUSE | Ubiquinol-cytochrome C reductase complex core protein 2, mitochondrial precursor (EC 1.10.2.2) (Complex III subunit II). [*Mus musculus*] |
| UCRH_MOUSE | Ubiquinol-cytochrome C reductase complex 11 kDa protein, mitochondrial precursor (EC 1.10.2.2) |

-continued

| | |
|---|---|
| | (Mitochondrial hinge protein) (Cytochrome C1, nonheme 11 kDa protein) (Complex III subunit VIII). [*Mus musculus*] |
| UGDH_MOUSE | UDP-glucose 6-dehydrogenase (EC 1.1.1.22) (UDP-Glc dehydrogenase) (UDP-GlcDH) (UDPGDH). [*Mus musculus*] |

Kinase regulators

| | |
|---|---|
| 143S_HUMAN | 14-3-3 protein sigma (Stratifin) (Epithelial cell marker protein 1). [*Homo sapiens*] |
| 143T_HUMAN | 14-3-3 protein tau (14-3-3 protein theta) (14-3-3 protein T-cell) (HS1 protein). [*Homo sapiens*] |
| GLMG_HUMAN | Glia maturation factor gamma (GMF-gamma). [*Homo sapiens*] |

Other enzymes

| | |
|---|---|
| 4F2_HUMAN | 4F2 cell-surface antigen heavy chain (4F2hc) (Lymphocyte activation antigen 4F2 large subunit) (4F2 heavy chain antigen) (CD98 antigen). [*Homo sapiens*] |
| 5NTC_HUMAN | Cytosolic purine 5'-nucleotidase (EC 3.1.3.5) (5'-nucleotidase |
| 6PGL_HUMAN | 6-phosphogluconolactonase (EC 3.1.1.31) (6PGL). [*Homo sapiens*] |
| AATM_MOUSE | Aspartate aminotransferase, mitochondrial precursor (EC 2.6.1.1) (Transaminase A) (Glutamate oxaloacetate transaminase-2). [*Mus musculus*] |
| ACON_HUMAN | Aconitate hydratase, mitochondrial precursor (EC 4.2.1.3) (Citrate hydro-lyase) (Aconitase). [*Homo sapiens*] |
| ADA_HUMAN | Adenosine deaminase (EC 3.5.4.4) (Adenosine aminohydrolase). [*Homo sapiens*] |
| AGT2_RAT | Alanine--glyoxylate aminotransferase 2, mitochondrial precursor (EC 2.6.1.44) (AGT 2) (Beta-alanine-pyruvate aminotransferase) (Beta- ALAAT II). [*Rattus norvegicus*] |
| ALFA_RABIT | Fructose-bisphosphate aldolase A (EC 4.1.2.13) (Muscle-type aldolase). [*Oryctolagus cuniculus*] |
| ALFB_RABIT | Fructose-bisphosphate aldolase B (EC 4.1.2.13) (Liver-type aldolase). [*Oryctolagus cuniculus*] |
| ALFC_MOUSE | Fructose-bisphosphate aldolase C (EC 4.1.2.13) (Brain-type aldolase) (Fragment). [*Mus musculus*] |
| AMD2_HUMAN | AMP deaminase 2 (EC 3.5.4.6) (AMP deaminase isoform L). [*Homo s* |
| AMPB_RAT | Aminopeptidase B (EC 3.4.11.6) (Ap-B) (Arginyl aminopeptidase) (Arginine aminopeptidase) (Cytosol aminopeptidase IV). [*Rattus norvegicus*] |
| AMPE_HUMAN | Glutamyl aminopeptidase (EC 3.4.11.7) (EAP) (Aminopeptidase A) (APA) (Differentiation antigen gp160). [*Homo sapiens*] |
| AMPN_HUMAN | Aminopeptidase N (EC 3.4.11.2) (Microsomal aminopeptidase) (GP1 |
| AMYP_MOUSE | Alpha-amylase, pancreatic precursor (EC 3.2.1.1) (1,4-alpha-D-glucan glucanohydrolase). [*Mus musculus*] |
| ANM1_RAT | Protein arginine N-methyltransferase 1 (EC 2.1.1.-). [*Rattus norvegicus*] |
| ANM2_HUMAN | Protein arginine N-methyltransferase 2 (EC 2.1.1.-). [*Homo sapiens*] |
| ANM4_HUMAN | Protein arginine N-methyltransferase 4 (EC 2.1.1.-). [*Homo sapiens*] |
| ANX3_HUMAN | Annexin A3 (Annexin III) (Lipocortin III) (Placental anticoagulant protein III) (PAP-III) (35-alpha calcimedin) (Inositol 1,2-cyclic phosphate 2-phosphohydrolase). [*Homo sapiens*] |
| AP4A_MOUSE | Bis(5'-nucleosyl)-tetraphosphatase (Asymmetrical) (EC 3.6.1.17) (Diadenosine 5',5'''-P1,P4-tetraphosphate asymmetrical hydrolase) (Diadenosine tetraphosphatase) (AP4A hydrolase) (AP4AASE). [*Mus musculus*] |
| APT_MOUSE | Adenine phosphoribosyltransferase (EC 2.4.2.7) (APRT). [*Mus musculus*] |
| APT_RAT | Adenine phosphoribosyltransferase (EC 2.4.2.7) (APRT). [*Rattus norvegicus*] |
| ARDH_HUMAN | N-terminal acetyltransferase complex ARD1 subunit homolog (EC 2.3.1.-). [*Homo sapiens*] |
| ARGI_MOUSE | Arginase 1 (EC 3.5.3.1) (Liver-type arginase). [*Mus musculus*] |
| ARGI_RAT | Arginase 1 (EC 3.5.3.1) (Liver-type arginase). [*Rattus norvegicus*] |
| ARHY_HUMAN | ADP-ribosylarginine hydrolase (EC 3.2.2.19) (ADP-ribose-L-arginine cleaving enzyme). [*Homo sapiens*] |
| ARSB_HUMAN | Arylsulfatase B precursor (EC 3.1.6.12) (ASB) (N-acetylgalactosamine- 4-sulfatase) (G4S). [*Homo sapiens*] |
| ATE1_HUMAN | Arginyl-tRNA--protein transferase 1 (EC 2.3.2.8) (R-transferase 1) (Arginyltransferase 1) (Arginine-tRNA--protein transferase 1). [*Homo sapiens*] |
| ATPG_HUMAN | ATP synthase gamma chain, mitochondrial precursor (EC 3.6.3.14). [*Homo sapiens*] |
| ATPG_MOUSE | ATP synthase gamma chain, mitochondrial precursor (EC 3.6.3.14). [*Mus musculus*] |
| ATPO_HUMAN | ATP synthase oligomycin sensitivity conferral protein, mitochondrial precursor (EC 3.6.3.14) (OSCP). [*Homo sapiens*] |
| ATS4_HUMAN | ADAMTS-4 precursor (EC 3.4.24.82) (A disintegrin and metalloproteinase with thrombospondin motifs 4) (ADAM-TS 4) (ADAM-TS4) (Aggrecanase 1) (ADMP-1). [*Homo sapiens*] |
| ATS5_HUMAN | ADAMTS-5 precursor (EC 3.4.24.-) (A disintegrin and metalloproteinase with thrombospondin motifs 5) (ADAM-TS 5) (ADAM-TS5) (Aggrecanase-2) (ADMP-2) (ADAM-TS 11). [*Homo sapiens*] |
| B3G6_HUMAN | N-acetyllactosaminide beta-1,3-N-acetylglucosaminyltransferase (EC 2.4.1.149) (Poly-N-acetyllactosamine extension enzyme) (I-beta- 1,3-N-acetylglucosaminyltransferase) (IGnT) (UDP-GlcNAc:betaGal beta- 1,3-N-acetylglucosaminyltransferase 6). [*Homo sapiens*] |
| BACH_HUMAN | Cytosolic acyl coenzyme A thioester hydrolase (EC 3.1.2.2) (Long chain acyl-CoA thioester hydrolase) (CTE-II) (Brain acyl-CoA hydrolase). [*Homo sapiens*] |
| BAT5_HUMAN | Protein BAT5 (HLA-B-associated transcript 5) (NG26 protein) (G5 |
| BAT8_HUMAN | Histone-lysine N-methyltransferase, H3 lysine-9 specific 3 (EC 2.1.1.43) (Histone H3-K9 methyltransferase 3) (H3-K9-HMTase 3) (HLA-B associated transcript 8) (G9a) (NG36). [*Homo sapiens*] |
| BCA1_ARATH | Branched-chain amino acid aminotransferas |
| BHMT_HUMAN | Betaine--homocysteine S-methyltransferase (EC 2.1.1.5). [*Homo sapiens*] |
| BHMT_MOUSE | Betaine--homocysteine S-methyltransferase (EC 2.1.1.5). [*Mus musculus*] |
| BHMT_PIG | Betaine--homocysteine S-methyltransferase (EC 2.1.1.5) (Fragment). [*Sus scrofa*] |
| BHMT_RAT | Betaine--homocysteine S-methyltransferase (EC 2.1.1.5). [*Rattus norvegicus*] |
| BIR6_HUMAN | Baculoviral IAP repeat-containing protein 6 (Ubiquitin-conjugating BIR-domain enzyme apollon). [*Homo sapiens*] |
| BLMH_HUMAN | Bleomycin hydrolase (EC 3.4.22.40) (BLM hydrolase) (BMH) (BH). [*Homo sapiens*] |
| CACP_HUMAN | Carnitine O-acetyltransferase (EC 2.3.1.7) (Carnitine acetylase) (CAT). [*Homo sapiens*] |
| CACP_MOUSE | Carnitine O-acetyltransferase (EC 2.3.1.7) (Carnitine acetylase) (CAT). [*Mus musculus*] |
| CAH3_HUMAN | Carbonic anhydrase III (EC 4.2.1.1) (Carbonate dehydratase III) (CA- III). [*Homo sapiens*] |
| CAH4_MOUSE | Carbonic anhydrase IV precursor (EC 4.2.1.1) (Carbonate dehydratase IV) (CA-IV). [*Mus musculus*] |

| | |
|---|---|
| CAN1_HUMAN | Calpain 1, large [catalytic] subunit (EC 3.4.22.52) (Calcium-activated neutral proteinase) (CANP) (Mu-type) (muCANP) (Micromolar-calpain). [Homo sapiens] |
| CANS_HUMAN | Calcium-dependent protease, small subunit (Calpain regulatory subunit) (Calcium-activated neutral proteinase) (CANP). [Homo sapiens] |
| CATB_HUMAN | Cathepsin B precursor (EC 3.4.22.1) (Cathepsin B1) (APP secretase) (APPS). [Homo sapiens] |
| CATB_MOUSE | Cathepsin B precursor (EC 3.4.22.1) (Cathepsin B1). [Mus musculus] |
| CATD_HUMAN | Cathepsin D precursor (EC 3.4.23.5). [Homo sapiens] |
| CATG_HUMAN | Cathepsin G precursor (EC 3.4.21.20) (CG). [Homo sapiens] |
| CATH_HUMAN | Cathepsin H precursor (EC 3.4.22.16). [Homo sapiens] |
| CATH_RAT | Cathepsin H precursor (EC 3.4.22.16) (Cathepsin B3) (Cathepsin BA). [Rattus norvegicus] |
| CATZ_HUMAN | Cathepsin Z precursor (EC 3.4.22.-) (Cathepsin X) (Cathepsin P). [Homo sapiens] |
| CATZ_RAT | Cathepsin Z precursor (EC 3.4.22.-) (Cathepsin Y). [Rattus norvegicus] |
| CBP2_HUMAN | Collagen-binding protein 2 precursor (Colligin 2) (Rheumatoid arthritis related antigen RA-A47). [Homo sapiens] |
| CBP2_RAT | Carboxypeptidase A2 precursor (EC 3.4.17.15). [Rattus norvegicus] |
| CBPH_HUMAN | Carboxypeptidase H precursor (EC 3.4.17.10) (CPH) (Carboxypeptidase E) (CPE) (Enkephalin convertase) (Prohormone processing carboxypeptidase). [Homo sapiens] |
| CBP_HUMAN | CREB-binding protein (EC 2.3.1.48). [Homo sapiens] |
| CBS_RAT | Cystathionine beta-synthase (EC 4.2.1.22) (Serine sulfhydrase) (Beta-thionase) (Hemoprotein H-450). [Rattus norvegicus] |
| CETP_HUMAN | Cholesteryl ester transfer protein precursor (Lipid transfer protein I). [Homo sapiens] |
| CG16_HUMAN | Putative acyl-CoA thioester hydrolase CGI-16 (EC 3.1.2.-). [Homo sapiens] |
| CGL1_HUMAN | Cytosolic nonspecific dipeptidase (Glutamate carboxypeptidase-like protein 1). [Homo sapiens] |
| CISY_HUMAN | Citrate synthase, mitochondrial precursor (EC 2.3.3.1). [Homo sapiens] |
| CIXG_LEUMC | CitXG protein [Includes: Apo-citrate lyase |
| CLPP_HUMAN | Putative ATP-dependent Clp protease proteolytic subunit, mitochondrial precursor (EC 3.4.21.92) (Endopeptidase Clp). [Homo sapiens] |
| CN1A_HUMAN | Calcium/calmodulin-dependent 3',5'-cyclic nucleotide phosphodiesterase 1A (EC 3.1.4.17) (Cam-PDE 1A) (61 kDa Cam-PDE) (hCam-1). [Homo sapiens] |
| CN37_HUMAN | 2',3'-cyclic nucleotide 3'-phosphodiesterase (EC 3.1.4.37) (CNP) (CNPase). [Homo sapiens] |
| CN37_MOUSE | 2',3'-cyclic nucleotide 3'-phosphodiesterase (EC 3.1.4.37) (CNP) (CNPase). [Mus musculus] |
| CN3B_HUMAN | cGMP-inhibited 3',5'-cyclic phosphodiesterase B (EC 3.1.4.17) (Cyclic GMP inhibited phosphodiesterase B) (CGI-PDE B) (CGIPDE1) (CGIP1). [Homo sapiens] |
| CN4A_HUMAN | cAMP-specific 3',5'-cyclic phosphodiesterase 4A (EC 3.1.4.17) ( |
| CN4C_HUMAN | cAMP-specific 3',5'-cyclic phosphodiesterase 4C (EC 3.1.4.17) (DPDE1) (PDE21). [Homo sapiens] |
| CN7B_HUMAN | cAMP-specific 3',5'-cyclic phosphodiesterase 7B (EC 3.1.4.17). [Homo sapiens] |
| CN9A_HUMAN | High-affinity cGMP-specific 3',5'-cyclic phosphodiesterase 9A ( |
| CNRB_HUMAN | Rod cGMP-specific 3',5'-cyclic phosphodiesterase beta-subunit (EC 3.1.4.17) (GMP-PDE beta). [Homo sapiens] |
| COMT_HUMAN | Catechol O-methyltransferase, membrane-bound form (EC 2.1.1.6) (MB-COMT) [Contains: Catechol O-methyltransferase, soluble form (S-COMT)]. [Homo sapiens] |
| CPT1_HUMAN | Carnitine O-palmitoyltransferase I, mitochondrial liver isoform (EC 2.3.1.21) (CPT I) (CPTI-L). [Homo sapiens] |
| CPT2_HUMAN | Carnitine O-palmitoyltransferase II, mitochondrial precursor (EC 2.3.1.21) (CPT II). [Homo sapiens] |
| CPT2_MOUSE | Carnitine O-palmitoyltransferase II, mitochondrial precursor (EC 2.3.1.21) (CPT II). [Mus musculus] |
| CT13_HUMAN | Protein C20orf13. [Homo sapiens] |
| CYA8_HUMAN | Adenylate cyclase, type VIII (EC 4.6.1.1) (ATP pyrophosphate-lyase) (Ca(2+)/calmodulin activated adenylyl cyclase). [Homo sapiens] |
| CYA9_HUMAN | Adenylate cyclase, type IX (EC 4.6.1.1) (ATP pyrophosphate-lyase) (Adenylyl cyclase). [Homo sapiens] |
| D3D2_RAT | 3,2-trans-enoyl-CoA isomerase, mitochondrial precursor (EC 5.3.3.8) (Dodecenoyl-CoA delta-isomerase). [Rattus norvegicus] |
| DCE1_FELCA | Glutamate decarboxylase, 67 kDa isoform (EC 4.1.1.15) (GAD-67) |
| DCE2_HUMAN | Glutamate decarboxylase, 65 kDa isoform (EC 4.1.1.15) (GAD-65) (65 kDa glutamic acid decarboxylase). [Homo sapiens] |
| DCE2_MOUSE | Glutamate decarboxylase, 65 kDa isoform (EC 4.1.1.15) (GAD-65) (65 kDa glutamic acid decarboxylase). [Mus musculus] |
| DCTD_HUMAN | Deoxycytidylate deaminase (EC 3.5.4.12) (dCMP deaminase). [Homo sapiens] |
| DCUP_HUMAN | Uroporphyrinogen decarboxylase (EC 4.1.1.37) (URO-D) (UPD). [Homo sapiens] |
| DHYS_HUMAN | Deoxyhypusine synthase (EC 2.5.1.46) (DHS). [Homo sapiens] |
| DNM1_HUMAN | DNA (cytosine-5)-methyltransferase 1 (EC 2.1.1.37) (Dnmt1) (DNA methyltransferase HsaI) (DNA MTase HsaI) (MCMT) (M.HsaI). [Homo sapiens] |
| DPD4_HUMAN | DNA polymerase delta subunit 4 (DNA polymerase delta subunit p12). [Homo sapiens] |
| DPOM_HUMAN | DNA polymerase mu (EC 2.7.7.7) (Pol Mu). [Homo sapiens] |
| DPY1_RAT | Dihydropyrimidinase related protein-1 (DRP-1) (Collapsin response mediator protein 1) (CRMP-1). [Rattus norvegicus] |
| DPY2_HUMAN | Dihydropyrimidinase related protein-2 (DRP-2) (Collapsin response mediator protein 2) (CRMP-2) (N2A3). [Homo sapiens] |
| DPY2_MOUSE | Dihydropyrimidinase related protein-2 (DRP-2) (ULIP 2 protein). [Mus musculus] |
| DPY2_RAT | Dihydropyrimidinase related protein-2 (DRP-2) (Turned on after division, 64 kDa protein) (TOAD-64) (Collapsin response mediator protein 2) (CRMP-2). [Rattus norvegicus] |
| DRNG_HUMAN | Deoxyribonuclease gamma precursor (EC 3.1.21.-) (DNase gamma) (Deoxyribonuclease I-like 3) (DNase I homolog protein DHP2) (Liver and spleen DNase) (LS-DNase) (LSD). [Homo sapiens] |
| DSRA_HUMAN | Double-stranded RNA-specific adenosine deaminase (EC 3.5.4.-) (DRADA) (136 kDa double-stranded RNA binding protein) (P136) (K88DSRBP). [Homo sapiens] |
| DUT_HUMAN | Deoxyuridine 5'-triphosphate nucleotidohydrolase, mitochondrial precursor (EC 3.6.1.23) (dUTPase) (dUTP pyrophosphatase). [Homo sapiens] |
| DUT_RAT | Deoxyuridine 5'-triphosphate nucleotidohydrolase (EC 3.6.1.23) (dUTPase) (dUTP pyrophosphatase) (PPAR-interacting protein 4) (PIP4). [Rattus norvegicus] |
| E2BG_HUMAN | Translation initiation factor eIF-2B gamma subunit (eIF-2B GDP-GTP exchange factor). [Homo sapiens] |

| | -continued |
|---|---|
| ECE1_HUMAN | Endothelin-converting enzyme 1 (EC 3.4.24.71) (ECE-1). [*Homo sapiens*] |
| ECH1_HUMAN | Delta3,5-delta2,4-dienoyl-CoA Isomerase, mitochondrial precursor (EC 5.3.3.-). [*Homo sapiens*] |
| ECHM_HUMAN | Enoyl-CoA hydratase, mitochondrial precursor (EC 4.2.1.17) (Short chain enoyl-CoA hydratase) (SCEH) (Enoyl-CoA hydratase 1). [*Homo sapiens*] |
| ECHM_RAT | Enoyl-CoA hydratase, mitochondrial precursor (EC 4.2.1.17) (Short chain enoyl-CoA hydratase) (SCEH) (Enoyl-CoA hydratase 1). [*Rattus norvegicus*] |
| ECP1_MOUSE | Eosinophil cationic protein 1 precursor (EC 3.1.27.-) (ECP 1) (Ribonuclease 3-1) (RNase 3-1) (Eosinophil secondary granule ribonuclease-1) (EAR-1). [*Mus musculus*] |
| EL2_MOUSE | Elastase 2 precursor (EC 3.4.21.71). [*Mus musculus*] |
| ENOA_RAT | Alpha enolase (EC 4.2. 1.11) (2-phospho-D-glycerate hydro-lyase) (Non- neural enolase) (NNE) (Enolase 1). [*Rattus norvegicus*] |
| ENOB_HUMAN | Beta enolase (EC 4.2.1.11) (2-phospho-D-glycerate hydro-lyase) (Skeletal muscle enolase) (MSE) (Enolase 3). [*Homo sapiens*] |
| ENOL_HUMAN | Alpha enolase, lung specific (EC 4.2.1.11) (2-phospho-D-glycerate hydro-lyase) (Non-neural enolase) (NNE) (Phosphopyruvate hydratase) (HLE1). [*Homo sapiens*] |
| ENP5_HUMAN | Ectonucleoside triphosphate diphosphohydrolase 5 precursor (EC 3.6.1.6) (NTPDase5) (Nucleoside diphosphatase) (CD39 antigen-like 4) (ER-UDPase). [*Homo sapiens*] |
| ENP5_MOUSE | Ectonucleoside triphosphate diphosphohydrolase 5 precursor (EC 3.6.1.6) (NTPDase5) (Nucleoside diphosphatase) (CD39 antigen-like 4) (ER-UDPase). [*Mus musculus*] |
| EST1_HUMAN | Liver carboxylesterase precursor (EC 3.1.1.1) (Acyl coenzyme A:cholesterol acyltransferase) (ACAT) (Monocyte/macrophage serine esterase) (HMSE) (Serine esterase 1) (Brain carboxylesterase hBr1). [*Homo sapiens*] |
| ESTD_HUMAN | Esterase D (EC 3.1.1.1). [*Homo sapiens*] |
| EXL3_HUMAN | Exostosin-like 3 (EC 2.4.1.223) (Glucuronyl-galactosyl-proteoglycan 4- alpha-N-acetylglucosaminyltransferase) (Putative tumor suppressor protein EXTL3) (Multiple exostosis-like protein 3) (Hereditary multiple exostoses gene isolog) (EXT-related protein 1) |
| EXT2_HUMAN | Exostosin-2 (EC 2.4.1.224) (EC 2.4.1.225) (Glucuronosyl-N- acetylglucosaminyl-proteoglycan/N-acetylglucosaminyl-proteoglycan 4- alpha-N-acetylglucosaminyltransferase) (Putative tumor suppressor protein EXT2) (Multiple exostoses protein 2). [*Homo sapiens*] |
| F13A_HUMAN | Coagulation factor XIII A chain precursor (EC 2.3.2.13) (Protein- glutamine gamma-glutamyltransferase A chain) (Transglutaminase A chain). [*Homo sapiens*] |
| F16P_HUMAN | Fructose-1,6-bisphosphatase (EC 3.1.3.11) (D-fructose-1,6-bisphosphate 1-phosphohydrolase) (FBPase). [*Homo sapiens*] |
| F16P_RABIT | Fructose-1,6-bisphosphatase (EC 3.1.3.11) (D-fructose-1,6-bisphosphate 1-phosphohydrolase) (FBPase). [*Oryctolagus cuniculus*] |
| F16P_RAT | Fructose-1,6-bisphosphatase (EC 3.1.3.11) (D-fructose-1,6-bisphosphate 1-phosphohydrolase) (FBPase). [*Rattus norvegicus*] |
| F16Q_HUMAN | Fructose-1,6-bisphosphatase isozyme 2 (EC 3.1.3.11) (D-fructose-1,6- bisphosphate 1-phosphohydrolase) (FBPase). [*Homo sapiens*] |
| FAFX_HUMAN | Probable ubiquitin carboxyl-terminal hydrolase FAF-X (EC 3.1.2.15) (Ubiquitin thiolesterase FAF-X) (Ubiquitin-specific processing protease FAF-X) (Deubiquitinating enzyme FAF-X) (Fat facets protein related, X-linked) (Ubiquitin-specific protease 9, X chro |
| FBW2_HUMAN | F-box/WD-repeat protein 2. [*Homo sapiens*] |
| FEN1_HUMAN | Flap endonuclease-1 (EC 3.-.-.-) (Maturation factor 1) (MF1). [*Homo sapiens*] |
| FHIT_HUMAN | Bis(5'-adenosyl)-triphosphatase (EC 3.6.1.29) (Diadenosine 5',5'''- P1,P3-triphosphate hydrolase) (Dinucleosidetriphosphatase) (AP3A hydrolase) (AP3AASE) (Fragile histidine triad protein). [*Homo sapiens*] |
| FK10_MOUSE | FK506 binding protein 10 precursor (EC 5.2.1.8) (Peptidyl-prolyl cis- trans isomerase) (PPIase) (Rotamase) (65 kDa FK506-binding protein) (FKBP65) (Immunophilin FKBP65). [*Mus musculus*] |
| FKB2_HUMAN | FK506-binding protein 2 precursor (EC 5.2.1.8) (Peptidyl-prolyl cis- trans isomerase) (PPIase) (Rotamase) (13 kDa FKBP) (FKBP-13). [*Homo sapiens*] |
| FKB3_HUMAN | FK506-binding protein 3 (EC 5.2.1.8) (Peptidyl-prolyl cis-trans isomerase) (PPIase) (Rotamase) (25 kDa FKBP) (FKBP-25) (Rapamycin- selective 25 kDa Immunophilin). [*Homo sapiens*] |
| FKB5_HUMAN | FK506-binding protein 5 (EC 5.2.1.8) (Peptidyl-prolyl cis-trans isomerase) (PPIase) (Rotamase) (51 kDa FK506-binding protein) (FKBP- 51) (54 kDa progesterone receptor-associated immunophilin) (FKBP54) (P54) (FF1 antigen) (HSP90-binding immunophilin) (Andr |
| FPPS_HUMAN | Farnesyl pyrophosphate synthetase (FPP synthetase) (FPS) (Farnesyl diphosphate synthetase) [Includes: Dimethylallyltransferase (EC 2.5.1.1); Geranyltranstransferase (EC 2.5.1.10)]. [*Homo sapiens*] |
| FPPS_RAT | Farnesyl pyrophosphate synthetase (FPP synthetase) (FPS) (Farnesyl diphosphate synthetase) (Cholesterol-regulated 39 kDa protein) (CR 39) [Includes: Dimethylallyltransferase (EC 2.5.1.1); Geranyltranstransferase (EC 2.5.1.10)]. [*Rattus norvegicus*] |
| FUMH_HUMAN | Fumarate hydratase, mitochondrial precursor (EC 4.2.1.2) (Fumarase). [*Homo sapiens*] |
| FUMH_MOUSE | Fumarate hydratase, mitochondrial precursor (EC 4.2.1.2) (Fumarase) (EF-3). [*Mus musculus*] |
| G6NT_HUMAN | Beta-1,3-galactosyl-O-glycosyl-glycoprotein beta-1,6-N- acetylglucosaminyltransferase (EC 2.4.1.102) (Core 2 branching enzyme) (Core2-GlcNAc-transferase) (C2GNT) (Core 2 GNT). [*Homo sapiens*] |
| G6PI_HUMAN | Glucose-6-phosphate isomerase (EC 5.3.1.9) (GPI) (Phosphoglucose isomerase) (PGI) (Phosphohexose isomerase) (PHI) (Neuroleukin) (NLK) (Sperm antigen-36) (SA-36). [*Homo sapiens*] |
| GABT_HUMAN | 4-aminobutyrate aminotransferase, mitochondrial precursor (EC 2.6.1.19) (Gamma-amino-N-butyrate transaminase) (GABA transaminase) (GABA aminotransferase) (GABA-AT) (GABA-T). [*Homo sapiens*] |
| GALE_HUMAN | UDP-glucose 4-epimerase (EC 5.1.3.2) (Galactowaldenase) (UDP- galactose 4-epimerase). [*Homo sapiens*] |
| GAMT_HUMAN | Guanidinoacetate N-methyltransferase (EC 2.1.1.2). [*Homo sapiens*] |
| GATM_MOUSE | Glycine amidinotransferase, mitochondrial precursor (EC 2.1.4.1) (L- arginine:glycine amidinotransferase) (Transamidinase) (AT). [*Mus musculus*] |
| GCH1_HUMAN | GTP cyclohydrolase I (EC 3.5.4.16) (GTP-CH-I). [*Homo sapiens*] |
| GCST_HUMAN | Aminomethyltransferase, mitochondrial precursor (EC 2.1.2.10) (Glycine cleavage system T protein) (GCVT). [*Homo sapiens*] |

-continued

| | |
|---|---|
| GDE_HUMAN | Glycogen debranching enzyme (Glycogen debrancher) [Includes: 4-alpha- glucanotransferase (EC 2.4.1.25) (Oligo-1,4-1,4-glucantransferase); Amylo-alpha-1,6-glucosidase (EC 3.2.1.33) (Amylo-1,6-glucosidase) (Dextrin 6-alpha-D-glucosidase)]. [*Homo sapiens*] |
| GEPH_RAT | Gephyrin (Putative glycine receptor-tubulin linker protein). [*Rattus norvegicus*] |
| GL6S_HUMAN | N-acetylglucosamine-6-sulfatase precursor (EC 3.1.6.14) (G6S) (Glucosamine-6-sulfatase). [*Homo sapiens*] |
| GLO2_HUMAN | Hydroxyacylglutathione hydrolase (EC 3.1.2.6) (Glyoxalase II) (GLX II). [*Homo sapiens*] |
| GLO2_MOUSE | Hydroxyacylglutathione hydrolase (EC 3.1.2.6) (Glyoxalase II) (Glx II). [*Mus musculus*] |
| GLSK_HUMAN | Glutaminase, kidney isoform, mitochondrial precursor (EC 3.5.1.2) (GLS) (L-glutamine amidohydrolase) (K-glutaminase). [*Homo sapiens*] |
| GLSK_RAT | Glutaminase, kidney isoform, mitochondrial precursor (EC 3.5.1.2) (GLS) (L-glutamine amidohydrolase) (K-glutaminase). [*Rattus norvegicus*] |
| GLYM_HUMAN | Serine hydroxymethyltransferase, mitochondrial precursor (EC 2.1.2.1) (Serine methylase) (Glycine hydroxymethyltransferase) (SHMT). [*Homo sapiens*] |
| GMDS_HUMAN | GDP-mannose 4,6 dehydratase (EC 4.2.1.47) (GDP-D-mannose dehydratase) (GMD). [*Homo sapiens*] |
| GRAH_HUMAN | Granzyme H precursor (EC 3.4.21.-) (Cytotoxic T-lymphocyte proteinase) (Cathepsin G-like 2) (CTSGL2) (CCP-X) (Cytotoxic serine protease-C) (CSP-C). [*Homo sapiens*] |
| GRL2_RAT | Granzyme-like protein II precursor (EC 3.4.21.-). [*Rattus norvegicus*] |
| GST1_HUMAN | Microsomal glutathione S-transferase 1 (EC 2.5.1.18) (Microsomal GST- 1) (Microsomal GST-I). [*Homo sapiens*] |
| GTA1_MOUSE | Glutathione S-transferase Ya chain (EC 2.5.1.18) (GST class-alpha). [*Mus musculus*] |
| GTA1_RABIT | Glutathione S-transferase alpha I (EC 2.5.1.18) (GSTA1-1) (GST class- alpha). [*Oryctolagus cuniculus*] |
| GTA2_RAT | Glutathione S-transferase Ya-2 (EC 2.5.1.18) (Ligandin) (Chain 1) (GST class-alpha). [*Rattus norvegicus*] |
| GTA3_RAT | Glutathione S-transferase 8 (EC 2.5.1.18) (GST 8-8) (Chain 8) (GST class-alpha). [*Rattus norvegicus*] |
| GTC2_RAT | Glutathione S-transferase Yc-2 (EC 2.5.1.18) (Chain 2) (GST Yc2) |
| GTM2_RAT | Glutathione S-transferase YB2 (Chain 4) (GST |
| GTM6_MOUSE | Glutathione S-transferase Mu 6 (EC 2.5.1.18) (GST class-mu 6) (Glutathione-S-transferase class M5). [*Mus musculus*] |
| HDA1_HUMAN | Histone deacetylase 1 (HD1). [*Homo sapiens*] |
| HDA2_HUMAN | Histone deacetylase 2 (HD2). [*Homo sapiens*] |
| HEXB_HUMAN | Beta-hexosaminidase beta chain precursor (EC 3.2.1.52) (N-acetyl-beta- glucosaminidase) (Beta-N-acetylhexosaminidase) (Hexosaminidase B). [*Homo sapiens*] |
| HGFA_HUMAN | Hepatocyte growth factor activator precursor (EC 3.4.21.-) (HGF activator) (HGFA). [*Homo sapiens*] |
| HMCM_HUMAN | Hydroxymethylglutaryl-CoA synthase, mitochondrial precursor (EC 2.3.3.10) (HMG-CoA synthase) (3-hydroxy-3-methylglutaryl coenzyme A synthase). [*Homo sapiens*] |
| HMCM_MOUSE | Hydroxymethylglutaryl-CoA synthase, mitochondrial precursor (EC 2.3.3.10) (HMG-CoA synthase) (3-hydroxy-3-methylglutaryl coenzyme A synthase) (Fragment). [*Mus musculus*] |
| HMCM_RAT | Hydroxymethylglutaryl-CoA synthase, mitochondrial precursor (EC 2.3.3.10) (HMG-CoA synthase) (3-hydroxy-3-methylglutaryl coenzyme A synthase). [*Rattus norvegicus*] |
| HMCS_HUMAN | Hydroxymethylglutaryl-CoA synthase, cytoplasmic (EC 2.3.3.10) (HMG-CoA synthase) (3-hydroxy-3-methylglutaryl coenzyme A synthase). [*Homo sapiens*] |
| HMCS_RAT | Hydroxymethylglutaryl-CoA synthase, cytoplasmic (EC 2.3.3.10) (HMG-CoA synthase) (3-hydroxy-3-methylglutaryl coenzyme A synthase). [*Rattus norvegicus*] |
| HMGL_HUMAN | Hydroxymethylglutaryl-CoA lyase, mitochondrial precursor (EC 4.1.3.4) (HMG-CoA lyase) (HL) (3-hydroxy-3-methylglutarate-CoA lyase). [*Homo sapiens*] |
| HPRT_MUSSP | Hypoxanthine-guanine phosphoribosyltransferase (EC 2.4.2.8) (HGPRT) (HGPRTase) (HPRT A) (Fragment). [*Mus spretus*] |
| HPRT_RAT | Hypoxanthine-guanine phosphoribosyltransferase (EC 2.4.2.8) (HGPRT) (HGPRTase). [*Rattus norvegicus*] |
| HRA1_HUMAN | Serine protease HTRA1 precursor (EC 3.4.21.-) (L56). [*Homo sapiens*] |
| HUTH_RAT | Histidine ammonia-lyase (EC 4.3.1.3) (Histidase). [*Rattus norvegicus*] |
| HYEP_HUMAN | Epoxide hydrolase 1 (EC 3.3.2.3) (Microsomal epoxide hydrolase) (Epoxide hydratase). [*Homo sapiens*] |
| HYES_MOUSE | Soluble epoxide hydrolase (SEH) (EC 3.3.2.3) (Epoxide hydratase) (Cytosolic epoxide hydrolase) (CEH). [*Mus musculus*] |
| HYES_RAT | Soluble epoxide hydrolase (SEH) (EC 3.3.2.3) (Epoxide hydratase) (Cytosolic epoxide hydrolase) (CEH). [*Rattus norvegicus*] |
| I1BC_CANFA | Interleukin-1 beta convertase precursor (IL-1BC) (EC 3.4.22.36) (IL-1 beta converting enzyme) (ICE) (Interleukin-1 beta converting enzyme) (P45) (Caspase-1) (CASP-1). [*Canis familiaris*] |
| I1BC_RAT | Interleukin-1 beta convertase precursor (IL-1BC) (EC 3.4.22.36) (IL-1 beta converting enzyme) (ICE) (Interleukin-1 beta converting enzyme) (P45) (Caspase-1) (CASP-1). [*Rattus norvegicus*] |
| ICE6_HUMAN | Caspase-6 precursor (EC 3.4.22.-) (Apoptotic protease Mch-2). [*Homo sapiens*] |
| ICE9_HUMAN | Caspase-9 precursor (EC 3.4.22.-) (CASP-9) (ICE-like apoptotic protease 6) (ICE-LAP6) (Apoptotic protease Mch-6) (Apoptotic protease activating factor 3) (APAF-3). [*Homo sapiens*] |
| ICEA_HUMAN | Caspase-10 precursor (EC 3.4.22.-) (ICE-like apoptotic protease 4) (Apoptotic protease Mch-4) (FAS-associated death domain protein interleukin-1B-converting enzyme 2) (FLICE2). [*Homo sapiens*] |
| IPYR_HUMAN | Inorganic pyrophosphatase (EC 3.6.1.1) (Pyrophosphate phospho- hydrolase) (PPase). [*Homo sapiens*] |
| IRE1_HUMAN | Iron-responsive element binding protein 1 (IRE-BP 1) (Iron regulatory protein 1) (IRP1) (Ferritin repressor protein) (Aconitate hydratase) (EC 4.2.1.3) (Citrate hydro-lyase) (Aconitase). [*Homo sapiens*] |
| KYNU_HUMAN | Kynureninase (EC 3.7.1.3) (L-kynurenine hydrolase). [*Homo sapiens*] |
| LAGE_HUMAN | Glycosyltransferase-like protein LARGE (EC 2.4.-.-) (Acetylglucosamlnyltransferase-like protein). [*Homo sapiens*] |
| LCFA_HUMAN | Long-chain-fatty-acid--CoA ligase 1 (EC 6.2.1.3) (Long-chain acyl-CoA synthetase 1) (LACS 1) (Palmitoyl-CoA ligase). [*Homo sapiens*] |
| LCFB_MOUSE | Long-chain-fatty-acid--CoA ligase 2 (EC 6.2.1.3) (Long-chain acyl-CoA synthetase 2) (LACS 2). [*Mus musculus*] |
| LCFB_RAT | Long-chain-fatty-acid--CoA ligase, liver isozyme (EC 6.2.1.3) (Long-chain acyl-CoA synthetase 2) (LACS 2). [*Rattus norvegicus*] |
| LCFC_HUMAN | Long-chain-fatty-acid--CoA ligase 3 (EC 6.2.1.3) (Long-chain acyl-CoA synthetase 3) (LACS 3). [*Homo sapiens*] |

-continued

| | |
|---|---|
| LCFC_RAT | Long-chain-fatty-acid--CoA ligase 3 (EC 6.2.1.3) (Long-chain acyl-CoA synthetase 3) (LACS 3) (Brain acyl-CoA synthtase II). [*Rattus norvegicus*] |
| LCFE_HUMAN | Long-chain-fatty-acid--CoA ligase 5 (EC 6.2.1.3) (Long-chain acyl-CoA synthetase 5) (LACS 5). [*Homo sapiens*] |
| LCFE_RAT | Long-chain-fatty-acid--CoA ligase 5 (EC 6.2.1.3) (Long-chain acyl-CoA synthetase 5) (LACS 5). [*Rattus norvegicus*] |
| LCFF_HUMAN | Long-chain-fatty-acid--CoA ligase 6 (EC 6.2.1.3) (Long-chain acyl-CoA synthetase 6) (LACS 6). [*Homo sapiens*] |
| LEU2_BUCUM | 3-isopropylmalate dehydratase large subun |
| LIN1_HUMAN | LINE-1 reverse transcriptase homolog. [*Homo sapiens*] |
| LIPL_HUMAN | Lipoprotein lipase precursor (EC 3.1.1.34) (LPL). [*Homo sapiens*] |
| LPH_RAT | Lactase-phlorizin hydrolase precursor (Lactase-glycosylceramidase) [Includes: Lactase (EC 3.2.1.108); Phlorizin hydrolase (EC 3.2.1.62)]. [*Rattus norvegicus*] |
| LPPL_HUMAN | Eosinophil lysophospholipase (EC 3.1.1.5) (Charcot-Leyden crystal protein) (Lysolecithin acylhydrolase) (CLC) (Galactin-10). [*Homo sapiens*] |
| LYC_HUMAN | Lysozyme C precursor (EC 3.2.1.17) (1,4-beta-N-acetylmuramidase C). [*Homo sapiens*] |
| M2A1_MOUSE | Alpha-mannosidase II (EC 3.2.1.114) (Mannosyl-oligosaccharide 1,3-1,6-alpha-mannosidase) (MAN II) (Golgi alpha-mannosidase II) (Mannosidase alpha class 2A member 1) (AMAN II). [*Mus musculus*] |
| M2B1_HUMAN | Lysosomal alpha-mannosidase precursor (EC 3.2.1.24) (Mannosidase, alpha B) (Lysosomal acid alpha-mannosidase) (Laman) (Mannosidase alpha class 2B member 1). [*Homo sapiens*] |
| MAAI_MOUSE | Maleylacetoacetate isomerase (EC 5.2.1.2) (MAAI) (Glutathione S- transferase zeta 1) (EC 2.5.1.18) (GSTZ1-1). [*Mus musculus*] |
| MCT2_RAT | Mast cell protease II precursor (EC 3.4.21.-) (RMCP-II) (RMCP-2) (Group-specific protease). [*Rattus norvegicus*] |
| MM08_HUMAN | Neutrophil collagenase precursor (EC 3.4.24.34) (Matrix metalloproteinase-8) (MMP-8) (PMNL collagenase) (PMNL-CL). [*Homo sapiens*] |
| MPB1_HUMAN | C-myc promoter-binding protein (MPB-1) (MBP-1). [*Homo sapiens*] |
| MR11_RAT | Double-strand break repair protein MRE11A (MRE11 homolog 1). [*Rattus norvegicus*] |
| MS1P_HUMAN | Membrane-bound transcription factor site-1 protease precursor (EC 3.4.21.-) (Site-1 protease) (Subtilisin/kexin-isozyme-1) (SKI-1). [*Homo sapiens*] |
| MTR2_HUMAN | Myotubularin-related protein 2 (EC 3.1.3.-). [*Homo sapiens*] |
| MTR6_HUMAN | Myotubularin related protein 6 (EC 3.1.3.-). [*Homo sapiens*] |
| MUTA_HUMAN | Methylmalonyl-CoA mutase, mitochondrial precursor (EC 5.4.99.2) (MCM). [*Homo sapiens*] |
| NADC_MOUSE | Nicotinate-nucleotide pyrophosphorylase [carboxylating] (EC 2.4.2.19) (Quinolinate phosphoribosyltransferase [decarboxylating]) (QAPRTase) (QPRTase). [*Mus musculus*] |
| NAGA_HUMAN | Alpha-N-acetylgalactosaminidase precursor (EC 3.2.1.49) (Alpha- galactosidase B). [*Homo sapiens*] |
| NAR3_HUMAN | Ecto-ADP-ribosyltransferase 3 precursor (EC 2.4.2.31) (NAD(P)(+)-- arginine ADP-ribosyltransferase 3) (Mono(ADP-ribosyl)transferase 3). [*Homo sapiens*] |
| NEC2_HUMAN | Neuroendocrine convertase 2 precursor (EC 3.4.21.94) (NEC 2) (PC2) (Prohormone convertase 2) (Proprotein convertase 2) (KEX2-like endoprotease 2). [*Homo sapiens*] |
| NPL1_HUMAN | Nucleosome assembly protein 1-like 1 (NAP-1 related protein) (hNRP). [*Homo sapiens*] |
| NPP1_MOUSE | Ectonucleotide pyrophosphatase/phosphodiesterase 1 (E-NPP 1) (Phosphodiesterase I/nucleotide pyrophosphatase 1) (Plasma-cell membrane glycoprotein PC-1) (Ly-41) [Includes: Alkaline Phosphodiesterase I (EC 3.1.4.1); Nucleotide pyrophosphatase (EC 3.6.1.9) |
| NPP1_RAT | Ectonucleotide pyrophosphatase/phosphodiesterase 1 (E-NPP 1) (Phosphodiesterase I/nucleotide pyrophosphatase 1) (Plasma-cell membrane glycoprotein PC-1) [Includes: Alkaline phosphodiesterase I (EC 3.1.4.1); Nucleotide pyrophosphatase (EC 3.6.1.9) (NPPase) |
| NPP3_HUMAN | Ectonucleotide pyrophosphatase/phosphodiesterase 3 (E-NPP 3) (Phosphodiesterase I/nucleotide pyrophosphatase 3) (Phosphodiesterase I beta) (PD-Ibeta) (CD203c antigen) [Includes: Alkaline phosphodiesterase I (EC 3.1.4.1); Nucleotide pyrophosphatase (EC 3.6 |
| NPS1_HUMAN | NipSnap1 protein. [*Homo sapiens*] |
| NPS1_MOUSE | NipSnap1 protein. [*Mus musculus*] |
| NPS2_HUMAN | NipSnap2 protein (Glioblastoma amplified sequence). [*Homo sapiens*] |
| NUD5_HUMAN | ADP-sugar pyrophosphatase YSA1H (EC 3.6.1.-) (Nucleoside diphosphate- linked moiety X motif 5) (HSPC115). [*Homo sapiens*] |
| NUGL_HUMAN | Endonuclease G like 1 (EC 3.1.30.-) (Endo G like). [*Homo sapiens*] |
| OCRL_HUMAN | Inositol polyphosphate 5-phosphatase OCRL-1 (EC 3.1.3.36) (Lowe's oculocerebrorenal syndrome protein). [*Homo sapiens*] |
| ODB2_HUMAN | Lipoamide acyltransferase component of branched-chain alpha-keto acid dehydrogenase complex, mitochondrial precursor (EC 2.3.1.-) (E2) (Dihydrolipoamide branched chain transacylase) (BCKAD E2 subunit). [*Homo sapiens*] |
| ODB2_MOUSE | Lipoamide acyltransferase component of branched-chain alpha-keto acid dehydrogenase complex, mitochondrial precursor (EC 2.3.1.-) (E2) (Dihydrolipoamide branched chain transacylase) (BCKAD E2 subunit). [*Mus musculus*] |
| ODO2_HUMAN | Dihydrolipoamide succinyltransferase component of 2-oxoglutarate dehydrogenase complex, mitochondrial precursor (EC 2.3.1.61) (E2) (E2K). [*Homo sapiens*] |
| ODP2_HUMAN | Dihydrolipoamide acetyltransferase component of pyruvate dehydr |
| ODPX_HUMAN | Pyruvate dehydrogenase protein X component, mitochondrial precursor (Dihydrolipoamide dehydrogenase-binding protein of pyruvate dehydrogenase complex) (E3-binding protein) (E3BP) (proX). [*Homo sapiens*] |
| ORN_HUMAN | Oligoribonuclease, mitochondrial precursor (EC 3.1.-.-) (Small fragment nuclease) (CGI-114). [*Homo sapiens*] |
| OTC_HUMAN | Ornithine carbamoyltransferase, mitochondrial precursor (EC 2.1.3.3) (OTCase) (Ornithine transcarbamylase). [*Homo sapiens*] |
| OTC_PIG | Ornithine carbamoyltransferase, mitochondrial precursor (EC 2.1.3.3) (OTCase) (Ornithine transcarbamylase) (Fragment). [*Sus scrofa*] |
| OTC_RAT | Ornithine carbamoyltransferase, mitochondrial precursor (EC 2.1.3.3) (OTCase) (Ornithine transcarbamylase). [*Rattus norvegicus*] |

-continued

| | |
|---|---|
| P2CD_HUMAN | Protein phosphatase 2C delta isoform (EC 3.1.3.16) (PP2C-delta) (p53- induced protein phosphatase 1) (Protein phosphatase magnesium- dependent 1 delta). [*Homo sapiens*] |
| P2G4_HUMAN | Proliferation-associated protein 2G4 (Cell cycle protein p38-2G4 homolog) (hG4-1). [*Homo sapiens*] |
| P300_HUMAN | E1A-associated protein p300 (EC 2.3.1.48). [*Homo sapiens*] |
| PA1B_HUMAN | Platelet-activating factor acetylhydrolase IB beta subunit (EC 3.1.1.47) (PAF acetylhydrolase 30 kDa subunit) (PAF-AH 30 kDa subunit) (PAF-AH beta subunit) (PAFAH beta subunit). [*Homo sapiens*] |
| PA1G_HUMAN | Platelet-activating factor acetylhydrolase IB gamma subunit (EC 3.1.1.47) (PAF acetylhydrolase 29 kDa subunit) (PAF-AH 29 kDa subunit) (PAF-AH gamma subunit) (PAFAH gamma subunit). [*Homo sapiens*] |
| PA26_MOUSE | 85 kDa calcium-independent phosphotipase A2 (EC 3.1.1.4) (iPLA2) (CaI- PLA2) (Group VI phospholipase A2) (GVI PLA2). [*Mus musculus*] |
| PAI1_HUMAN | Plasminogen activator inhibitor-1 precursor (PAI-1) (Endothelial plasminogen activator inhibitor) (PAI). [*Homo sapiens*] |
| PAPA_HUMAN | Pappalysin-1 precursor (EC 3.4.24.79) (Pregnancy-associated plasma protein-A) (PAPP-A) (Insulin-like growth factor-dependent IGF binding protein-4 protease) (IGF-dependent IGFBP-4 protease) (IGFBP-4ase). [*Homo sapiens*] |
| PCCB_RAT | Propionyl-CoA carboxylase beta chain, mitochondrial precursor (EC 6.4.1.3) (PCCase beta subunit) (Propanoyl-CoA:carbon dioxide ligase beta subunit). [*Rattus norvegicus*] |
| PCNA_HUMAN | Proliferating cell nuclear antigen (PCNA) (Cyclin). [*Homo sapiens*] |
| PCNA_MOUSE | Proliferating cell nuclear antigen (PCNA) (Cyclin). [*Mus musculus*] |
| PCNA_RAT | Proliferating cell nuclear antigen (PCNA) (Cyclin). [*Rattus norvegicus*]. |
| PCY2_HUMAN | Ethanolamine-phosphate cytidylyltransferase (EC 2.7.7.14) (Phosphorylethanolamine transferase) (CTP:phosphoethanolamine cytidylyltransferase). [*Homo sapiens*] |
| PDI2_HUMAN | Protein-arginine deiminase type II (EC 3.5.3.15) (Peptidylarginine deiminase II) (PAD-H19). [*Homo sapiens*] |
| PEX_HUMAN | Phosphate regulating neutral endopeptidase (EC 3.4.24.-) (Metalloendopeptidase homolog PEX) (X-linked hypophosphatemia protein) (HYP) (Vitamin D-resistant hypophosphatemic rickets protein). [*Homo sapiens*] |
| PFTA_HUMAN | Protein farnesyltransferase alpha subunit (EC 2.5.1.-) (CAAX farnesyltransferase alpha subunit) (RAS proteins prenyltransferase alpha) (FTase-alpha). [*Homo sapiens*] |
| PGHD_CANFA | Prostaglandin-H2 D-isomerase precursor (EC 5.3.99.2) (Lipocalin-type prostaglandin-D synthase) (Glutathione-independent PGD synthetase) (Prostaglandin D2 synthase) (PGD2 synthase) (PGDS2) (PGDS). [*Canis familiaris*] |
| PGHD_MOUSE | Prostaglandin-H2 D-isomerase precursor (EC 5.3.99.2) (Lipocalin-type prostaglandin-D synthase) (Glutathione-independent PGD synthetase) (Prostaglandin-H2 D-isomerase) (PGD2 synthase) (PGDS2) (PGDS). [*Mus musculus*] |
| PGT1_HUMAN | Geranylgeranyl transferase type I beta subunit (EC 2.5.1.-) (Type I protein geranyl-geranyltransferase beta subunit) (GGTase-I-beta). [*Homo sapiens*] |
| PGT1_RAT | Geranylgeranyl transferase type I beta subunit (EC 2.5.1.-) (Type I protein geranyl-geranyltransferase beta subunit) (GGTase-I-beta). [*Rattus norvegicus*] |
| PGTA_HUMAN | RAB geranylgeranyltransferase alpha subunit (EC 2.5.1.-) (RAB geranyl- geranyltransferase alpha subunit) (RAB GG transferase alpha) (RAB GGTase alpha). [*Homo sapiens*] |
| PHS1_HUMAN | Glycogen phosphorylase, liver form (EC 2.4.1.1). [*Homo sapiens*] |
| PHS2_HUMAN | Glycogen phosphorylase, muscle form (EC 2.4.1.1) (Myophosphoryl |
| PHS3_HUMAN | Glycogen phosphorylase, brain form (EC 2.4.1.1). [*Homo sapiens*] |
| PIB1_HUMAN | 1-phosphatidylinositol-4,5-bisphosphate phosphodiesterase beta |
| PIB4_HUMAN | 1-phosphatidylinositol-4,5-bisphosphate phosphodiesterase beta 4 (EC 3.1.4.11) (Phosphoinositide phospholipase C) (PLC-beta-4) (Phospholipase C-beta-4). [*Homo sapiens*] |
| PIB4_RAT | 1-phosphatidylinositol-4,5-bisphosphate phosphodiesterase beta 4 (EC 3.1.4.11) (Phosphoinositide phospholipase C) (PLC-beta-4) (Phospholipase C-beta-4). [*Rattus norvegicus*] |
| PIG2_HUMAN | 1-phosphatidylinositol-4,5-bisphosphate phosphodiesterase gamma 2 (EC 3.1.4.11) (Phosphoinositide phospholipase C) (PLC-gamma-2) (Phospholipase C-gamma-2) (PLC-IV). [*Homo sapiens*] |
| PIN1_HUMAN | Peptidyl-prolyl cis-trans isomerase NIMA-interacting 1 (EC 5.2.1.8) (Rotamase Pin1) (PPIase Pin1). [*Homo sapiens*] |
| PIN4_HUMAN | Peptidyl-prolyl cis-trans isomerase NIMA-interacting 4 (EC 5.2.1.8) (Rotamase Pin4) (PPIase Pin4) (Parvulin 14) (Par14) (Peptidyl-prolyl cis/trans isomerase EPVH) (hPar14). [*Homo sapiens*] |
| PIN4_MOUSE | Peptidyl-prolyl cis-trans isomerase NIMA-interacting 4 (EC 5.2.1.8) (Rotamase Pin4) (PPIase Pin4). [*Mus musculus*] |
| PLD1_MOUSE | Phospholipase D1 (EC 3.1.4.4) (PLD 1) (Choline phosphatase 1) (Phosphatidylcholine-hydrolyzing phospholipase D1) (mPLD1). [*Mus musculus*] |
| PLSB_HUMAN | Glycerol-3-phosphate acyltransferase, mitochondrial precursor (EC 2.3.1.15) (GPAT). [*Homo sapiens*] |
| PLSB_RAT | Glycerol-3-phosphate acyltransferase, mitochondrial precursor (EC |
| PMG3_HUMAN | Putative phosphoglycerate mutase 3 (EC 5.4.2.1) (EC 5.4.2.4) (EC 3.1.3.13). [*Homo sapiens*] |
| PNPH_HUMAN | Purine nucleoside phosphorylase (EC 2.4.2.1) (Inosine phosphorylase) (PNP). [*Homo sapiens*] |
| PON3_HUMAN | Serum paraoxonase/arylesterase 3 (EC 3.1.1.2) (EC 3.1.8.1) (PON 3) (Serum aryldialkylphosphatase 3) (A-esterase 3) (Aromatic esterase 3). [*Homo sapiens*] |
| PP11_HUMAN | Placental protein 11 precursor (EC 3.4.21.-) (PP11). [*Homo sapiens*] |
| PPBN_HUMAN | Alkaline phosphatase, placental-like precursor (EC 3.1.3.1) (Nagao isozyme) (Germ-cell alkaline phosphatase) (PLAP-like) (ALP-1). [*Homo sapiens*] |
| PPO3_HUMAN | Poly [ADP-ribose] polymerase-3 (EC 2.4.2.30) (PARP-3) (NAD(+) A |
| PPOV_HUMAN | Vault poly(ADP-ribose) polymerase (EC 2.4.2.30) (VPARP) (193-kDa vault protein) (PARP-related/IalphaI-related H5/proline-rich) (PH5P). [*Homo sapiens*] |
| PPP6_HUMAN | Serine/threonine protein phosphatase 6 (EC 3.1.3.16) (PP6). [*Homo sapiens*] |
| PPT1_HUMAN | Palmitoyl-protein thioesterase 1 precursor (EC 3.1.2.22) (Palmitoyl- protein hydrolase 1). [*Homo sapiens*] |
| PS7L_HUMAN | Proteasome subunit alpha type 7-like (EC 3.4.25.1). [*Homo sapiens*] |
| PSA1_HUMAN | Proteasome subunit alpha type 1 (EC 3.4.25.1) (Proteasome component C2) (Macropain subunit C2) (Multicatalytic endopeptidase complex subunit C2) (Proteasome nu chain) (30 kDa prosomal protein) (PROS-30). [*Homo sapiens*] |

-continued

| | |
|---|---|
| PSA4__HUMAN | Proteasome subunit alpha type 4 (EC 3.4.25.1) (Proteasome component C9) (Macropain subunit C9) (Muiticatalytic endopeptidase complex subunit C9) (Proteasome subunit L). [*Homo sapiens*] |
| PSA6__HUMAN | Proteasome subunit alpha type 6 (EC 3.4.25.1) (Proteasome iota chain) (Macropain iota chain) (Multicatalytic endopeptidase complex iota chain) (27 kDa prosomal protein) (PROS-27) (p27K). [*Homo sapiens*] |
| PSA6__MOUSE | Proteasome subunit alpha type 6 (EC 3.4.25.1) (Proteasome iota chain) (Macropain iota chain) (Multicatalytic endopeptidase complex iota chain). [*Mus musculus*] |
| PSA7__HUMAN | Proteasome subunit alpha type 7 (EC 3.4.25.1) (Proteasome subunit RC6-1) (Proteasome subunit XAPC7). [*Homo sapiens*] |
| PSA__HUMAN | Puromycin-sensitive aminopeptidase (EC 3.4.11.-) (PSA). [*Homo sapiens*] |
| PSA__MOUSE | Puromycin-sensitive aminopeptidase (EC 3.4.11.-) (PSA). [*Mus mus* |
| PSB3__MOUSE | Proteasome subunit beta type 3 (EC 3.4.25.1) (Proteasome theta chain) (Proteasome chain 13) (Proteasome component C10-II). [*Mus musculus*] |
| PSBA__HUMAN | Proteasome subunit beta type 10 precursor (EC 3.4.25.1) (Proteasome MECl-1) (Macropain subunit MECI-1) (Multicatalytic endopeptidase complex subunit MECI-1). [*Homo sapiens*] |
| PSBA__MOUSE | Proteasome subunit beta type 10 precursor (EC 3.4.25.1) (Proteasome MECI-1) (Macropain subunit MECI-1) (Multicatalytic endopeptidase complex subunit MECI-1). [*Mus musculus*] |
| PTE1__HUMAN | Peroxisomal acyl-coenzyme A thioester hydrolase 1 (EC 3.1.2.2) (Peroxisomal long-chain acyl-coA thioesterase 1) (HIV-Nef associated acyl coA thioesterase) (Thioesterase II) (hTE). [*Homo sapiens*] |
| PTNB__MOUSE | Protein-tyrosine phosphatase, non-receptor type 11 (EC 3.1.3.48) (Protein-tyrosine phosphatase SYP) [*Mus musculus*] |
| PTNE__HUMAN | Protein tyrosine phosphatase, non-receptor type 14 (EC 3.1.3.48) (Protein-tyrosine phosphatase pez). [*Homo sapiens*] |
| PUR1__HUMAN | Amidophosphoribosyltransferase precursor (EC 2.4.2.14) (Glutamine phosphoribosylpyrophosphate amidotransferase) (ATASE) (GPAT). [*Homo sapiens*] |
| PUR1__RAT | Amidophosphoribosyltransferase precursor (EC 2.4.2.14) (Glutamine phosphoribosylpyrophosphate amidotransferase) (ATASE) (GPAT). [*Rattus norvegicus*] |
| PUR2__HUMAN | Trifunctional purine biosynthetic protein adenosine-3 [Includes: Phosphoribosylamine-glycine ligase (EC 6.3.4.13) (GARS) (Glycinamide ribonucleotide synthetase) (Phosphoribosylglycinamide synthetase); Phosphoribosylformylglycinamidine cyclo-ligase (EC 6. |
| PUR6__HUMAN | Multifunctional protein ADE2 [Includes: Phosphoribosylaminoimidazole- succinocarboxamide synthase (EC 6.3.2.6) (SAICAR synthetase); Phosphoribosylaminoimidazole carboxylase (EC 4.1.1.21) (AIR carboxylase) (AIRC)]. [*Homo sapiens*] |
| PUR6__RAT | Multifunctional protein ADE2 [Includes: Phosphoribosylaminoimidazole- succinocarboxamide synthase (EC 6.3.2.6) (SAICAR synthetase); Phosphoribosylaminoimidazole carboxylase (EC 4.1.1.21) (AIR carboxylase) (AIRC)]. [*Rattus norvegicus*] |
| PUR9__HUMAN | Bifunctional purine biosynthesis protein PURH [Includes: Phosphoribosylaminoimidazolecarboxamide formyltransferase (EC 2.1.2.3) (AICAR transformylase); IMP cyclohydrolase (EC 3.5.4.10) (Inosinicase) (IMP synthetase) (ATIC)]. [*Homo sapiens*] |
| PUR9__MOUSE | Bifunctional purine biosynthesis protein PURH [Includes: Phosphoribosylaminoimidazolecarboxamide formyltransferase (EC 2.1.2.3) (AICAR transformylase); IMP cyclohydrolase (EC 3.5.4.10) (Inosinicase) (IMP synthetase) (ATIC)]. [*Mus musculus*] |
| PYRG__HUMAN | CTP synthase (EC 6.3.4.2) (UTP--ammonia ligase) (CTP synthetase). [*Homo sapiens*] |
| Q29476 | Phenol sulfotransferase (EC 2.8.2.1) (Aryl sulfotransferase) (Sulfo |
| Q8N7N8 | Hypothetical protein FLJ40785. [*Homo sapiens*] |
| Q96LX4 | Hypothetical protein FLJ33088. [*Homo sapiens*] |
| Q9DCY1 | Peptidylprolyl isomerase B (EC 5.2.1.8) (Peptidyl-prolyl cis-trans isomerase) (PPIase) (Rotamase). [*Mus musculus*] |
| Q9TTC6 | Cyclophilin 18 (EC 5.2.1.8) (Peptidyl-prolyl cis-trans isomerase) (PPIase) (Rotamase). [*Oryctolagus cuniculus*] |
| RAG1__HUMAN | V(D)J recombination activating protein 1 (RAG-1). [*Homo sapiens*] |
| RBP2__HUMAN | Ran-binding protein 2 (RanBP2) (Nuclear pore complex protein Nup358) (Nucleoporin Nup358) (358 kDa nucleoporin) (P270). [*Homo sapiens*] |
| RELN__HUMAN | Reelln precursor (EC 3.4.21.-). [*Homo sapiens*] |
| RENI__HUMAN | Renin precursor, renal (EC 3.4.23.15) (Angiotensinogenase). [*Homo sapiens*] |
| RIB1__HUMAN | Dolichyl-diphosphooligosaccharide--protein glycosyltransferase 67 kDa subunit precursor (EC 2.4.1.119) (Ribophorin I) (RPN-I). [*Homo sapiens*] |
| RIB2__HUMAN | Dolichyl-diphosphooligosaccharide--protein glycosyltransferase 63 kDa subunit precursor (EC 2.4.1.119) (Ribophorin II) (RPN-II) (RIBIIR). [*Homo sapiens*] |
| RISC__HUMAN | Retinoid-inducible serine carboxypeptidase precursor (EC 3.4.16.-) (Serine carboxypeptidase 1) (MSTP034). [*Homo sapiens*] |
| RNBP__HUMAN | N-acylglucosamine 2-epimerase (EC 5.1.3.8) (GlcNAc 2-epimerase) (N-acetyl-D-glucosamine 2-epimerase) (Renin-binding protein) (RNBP). [*Homo sapiens*] |
| RNBP__RAT | N-acylglucosamine 2-epimerase (EC 5.1.3.8) (GlcNAc 2-epimerase) (N-acetyl-D-glucosamine 2-epimerase) (Renin-binding protein) (RNBP). [*Rattus norvegicus*] |
| RNP6__HUMAN | Ribonuclease 6 precursor (EC 3.1.27.-). [*Homo sapiens*] |
| RNP__MOUSE | Ribonuclease pancreatic precursor (EC 3.1.27.5) (RNase 1) (RNase A). [*Mus musculus*] |
| RNP__RATRT | Ribonuclease pancreatic precursor (EC 3.1.27.5) (RNase 1) (RNase A). [*Rattus rattus*] |
| RPA1__MOUSE | DNA-directed RNA polymerase I largest subunit (EC 2.7.7.6) (RNA polymerase I 194 kDa subunit) (RPA194). [*Mus musculus*] |
| RR42__HUMAN | Exosome complex exonuclease RRP42 (EC 3.1.13.-) (Ribosomal RNA processing protein 42) (p8). [*Homo sapiens*] |
| RR44__HUMAN | Exosome complex exonuclease RRP44 (EC 3.1.13.-) (Ribosomal RNA processing protein 44) (DIS3 protein homolog). [*Homo sapiens*] |
| SAH2__HUMAN | Putative adenosylhomocysteinase 2 (EC 3.3.1.1) (S-adenosyl-L- homocysteine hydrolase) (AdoHcyase). [*Homo sapiens*] |
| SAHH__HUMAN | Adenosylhomocysteinase (EC 3.3.1.1) (S-adenosyl-L-homocysteine hydrolase) (AdoHcyase). [*Homo sapiens*] |

-continued

| | |
|---|---|
| SCB2_HUMAN | Succinyl-CoA ligase [GDP-forming] beta-chain, mitochondrial precursor (EC 6.2.1.4) (Succinyl-CoA synthetase, betaG chain) (SCS-betaG) (GTP- specific succinyl-CoA synthetase beta subunit) (Fragment). [*Homo sapiens*] |
| SCOT_HUMAN | Succinyl-CoA:3-ketoacid-coenzyme A transferase, mitochondrial precursor (EC 2.8.3.5) (Succinyl CoA:3-oxoacid CoA-transferase). [*Homo sapiens*] |
| SDHL_RAT | L-serine dehydratase/L-threonine deaminase [Includes: L-serine dehydratase (EC 4.3.1.17) (L-serine deaminase) (SDH); L-threonine dehydratase (EC 4.3.1.19) (L-threonine deaminase) (TDH)]. [*Rattus norvegicus*] |
| SEN1_HUMAN | Sentrin-specific protease 1 (EC 3.4.22.-) (Sentrin/SUMO-specific protease SENP1). [*Homo sapiens*] |
| SEN6_HUMAN | Sentrin-specific protease 6 (EC 3.4.22.-) (Sentrin/SUMO-specific protease SENP6) (SUMO-1 specific protease 1) (Protease FKSG6). [*Homo sapiens*] |
| SEN7_HUMAN | Sentrin-specific protease 7 (EC 3.4.22.-) (Sentrin/SUMO-specific protease SENP7) (SUMO-1 specific protease 2). [*Homo sapiens*] |
| SERC_HUMAN | Phosphoserine aminotransferase (EC 2.6.1.52) (PSAT). [*Homo sapiens*] |
| SHH_HUMAN | Sonic hedgehog protein precursor (SHH) (HHG-1). [*Homo sapiens*] |
| SI4C_HUMAN | CMP-N-acetylneuraminate-beta-galactosamide-alpha-2,3-sialyltransferase (EC 2.4.99.-) (Beta-galactoside alpha-2,3-sialyltransferase) (Alpha 2,3-sialyltransferase IV) (Alpha 2,3-ST) (Gal-NAc6S) (STZ) (SIAT4-C) (ST3Gal III) (SAT-3) (ST-4). [*Homo sapiens*] |
| SIA1_HUMAN | CMP-N-acetylneuraminate-beta-galactosamide-alpha-2,6-sialyltransferase (EC 2.4.99.1) (Beta-galactoside alpha-2,6-sialyltransferase) (Alpha 2,6-ST) (Sialyltransferase 1) (ST6Gal I) (B-cell antigen CD75). [*Homo sapiens*] |
| SP25_HUMAN | Microsomal signal peptidase 25 kDa subunit (EC 3.4.-.-) (SPase 25 kDa subunit) (SPC25). [*Homo sapiens*] |
| SP25_MOUSE | Microsomal signal peptidase 25 kDa subunit (EC 3.4.-.-) (SPase 25 kDa subunit) (SPC25). [*Mus musculus*] |
| SPEE_HUMAN | Spermidine synthase (EC 2.5.1.16) (Putrescine aminopropyltransferase) (SPDSY). [*Homo sapiens*] |
| SRR_MOUSE | Serine racemase (EC 5.1.1.-). [*Mus musculus*] |
| STK1_RAT | Sulfotransferase K1 (EC 2.8.2.-) (rSULT1C2). [*Rattus norvegicus*] |
| STK2_RAT | Sulfotransferase K2 (EC 2.8.2.-) (rSULT1C2A). [*Rattus norvegicus*] |
| SUAC_RAT | N-hydroxyarylamine sulfotransferase (EC 2.8.2.-) (HAST-I). [*Rattus norvegicus*] |
| SUAR_RAT | Aryl sulfotransferase (EC 2.8.2.1) (Phenol sulfotransferase) (PST-1) (Sulfokinase) (Aryl sulfotransferase IV) (ASTIV) (Tyrosine-ester sulfotransferase) (Minoxidil sulfotransferase). [*Rattus norvegicus*] |
| SUDY_RAT | DOPA/tyrosine sulfotransferase (EC 2.8.1.-). [*Rattus norvegicus*] |
| SUH3_RAT | Alcohol sulfotransferase (EC 2.8.2.2) (Hydroxysteroid sulfotransferase) (ST) (ST-60). [*Rattus norvegicus*] |
| SUHS_RAT | Alcohol sulfotransferase (EC 2.8.2.2) (Hydroxysteroid sulfotransferase) (ST) (ST-20). [*Rattus norvegicus*] |
| SUO1_RAT | Estrogen sulfotransferase, isoform 1 (EC 2.8.2.4) (EST-1) (Sulfotransferase, estrogen-preferring) (Estrone sulfotransferase). [*Rattus norvegicus*] |
| SUP1_HUMAN | Phenol-sulfating phenol sulfotransferase 1 (EC 2.8.2.1) (P-PST) (Thermostable phenol Sulfotransferase) (Ts-PST) (HAST1/HAST2) (ST1A3). [*Homo sapiens*] |
| SUPM_HUMAN | Monoamine-sulfating phenol sulfotransferase (EC 2.8.2.1) (Sulfotransferase, monoamine-preferring) (M-PST) (Thermolabile phenol sulfotransferase) (TL-PST) (Placental estrogen sulfotransferase) (Catecholamine-sulfating phenol sulfotransferase) (HAST3). [Hom |
| SUPP_BOVIN | Phenol-sulfating phenol sulfotransferase (EC 2.8.2.1) (P-PST). [*Bos taurus*] |
| SYJ1_BOVIN | Synaptojanin 1 (EC 3.1.3.36) (Synaptic inositol-1,4,5-trisphosphate 5- phosphatase 1) (p150) (Fragment). [*Bos taurus*] |
| TAL1_HUMAN | Transaldolase (EC 2.2.1.2). [*Homo sapiens*] |
| THEA_HUMAN | Brown fat inducible thioesterase (EC 3.1.2.-) (BFIT) (Adipose associated thioesterase). [*Homo sapiens*] |
| THIK_HUMAN | 3-ketoacyl-CoA thiolase, peroxisomal precursor (EC 2.3.1.16) (Beta- ketothiolase) (Acetyl-CoA acyltransferase) (Peroxisomal 3-oxoacyl- CoA thiolase). [*Homo sapiens*] |
| THIL_HUMAN | Acetyl-CoA acetyltransferase, mitochondrial precursor (EC 2.3.1.9) (Acetoacetyl-CoA thiolase) (T2). [*Homo sapiens*] |
| THIL_RAT | Acetyl-CoA acetyltransferase, mitochondrial precursor (EC 2.3.1.9) (Acetoacetyl-CoA thiolase). [*Rattus norvegicus*] |
| THIM_RAT | 3-ketoacyl-CoA thiolase, mitochondrial (EC 2.3.1.16) (Beta- ketothiolase) (Acetyl-CoA acyltransferase) (Mitochondrial 3-oxoacyl- CoA thiolase). [*Rattus norvegicus*] |
| THRB_HUMAN | Prothrombin precursor (EC 3.4.21.5) (Coagulation factor II). [*Homo sapiens*] |
| THTR_RAT | Thiosulfate sulfurtransferase (EC 2.8.1.1) (Rhodanese) (Fragment). [*Rattus norvegicus*] |
| TI60_HUMAN | 60 kDa Tat interactive protein (Tip60) (HIV-1 Tat Interactive protein) (cPLA(2) interacting protein). [*Homo sapiens*] |
| TKT2_HUMAN | Transketolase-like 1 (EC 2.2.1.1) (Transketolase 2) (TK 2) (Tra |
| TKT_HUMAN | Transketolase (EC 2.2.1.1) (TK). [*Homo sapiens*] |
| TKT_RAT | Transketolase (EC 2.2.1.1) (TK). [*Rattus norvegicus*] |
| TP3B_HUMAN | DNA topoisomerase III beta-1 (EC 5.99.1.2). [*Homo sapiens*] |
| TPP1_RAT | Tripeptidyl-peptidase I precursor (EC 3.4.14.9) (TPP-I) (Tripeptidyl aminopeptidase) (Lysosomal pepstatin insensitive protease) (LPIC). [*Rattus norvegicus*] |
| TRFL_HUMAN | Lactotransferrin precursor (Lactoferrin) [Contains: Lactoferroxin A; Lactoferroxin B; Lactoferroxin C]. [*Homo sapiens*] |
| TRPC_ARATH | Indole-3-glycerol phosphate synthase, chlo |
| TRUA_HUMAN | tRNA pseudouridine synthase A (EC 4.2.1.70) (Pseudouridylate synthase I) (Pseudouridine synthase I) (Uracil hydrolyase). [*Homo sapiens*] |
| TRY2_MOUSE | Trypsin II, anionic precursor (EC 3.4.21.4) (Pretrypsinogen II). [*Mus musculus*] |
| TRY3_RAT | Trypsin III, cationic precursor (EC 3.4.21.4) (Pretrypsinogen III). [*Rattus norvegicus*] |
| UBA1_HUMAN | Ubiquitin-activating enzyme E1 (A1S9 protein). [*Homo sapiens*] |
| UBA1_MOUSE | Ubiquitin-activating enzyme E1 1. [*Mus musculus*] |
| UBC7_HUMAN | Ubiquitin-conjugating enzyme E2-18 kDa UbcH7 (EC 6.3.2.19) (Ubiquitin- protein ligase) (Ubiquitin carrier protein) (UbcM4) (E2-F1) (L-UBC). [*Homo sapiens*] |
| UBCI_HUMAN | Ubiquitin-like protein SUMO-1 conjugating enzyme (EC 6.3.2.19) (SUMO- 1-protein ligase) (Ubiquitin carrier protein) (Ubiquitin-conjugating enzyme UbcE2A) (P18). [*Homo sapiens*] |

-continued

| | |
|---|---|
| UBCN_HUMAN | Ubiquitin-conjugating enzyme E2 N (EC 6.3.2.19) (Ubiquitin-protein ligase N) (Ubiquitin carrier protein N) (Ubc13) (Bendless-like ubiquitin conjugating enzyme). [*Homo sapiens*] |
| UBL1_HUMAN | Ubiquitin carboxyl-terminal hydrolase isozyme L1 (EC 3.4.19.12) (UCH- L1) (Ubiquitin thiolesterase L1) (Neuron cytoplasmic protein 9.5) (PGP 9.5) (PGP9.5). [*Homo sapiens*] |
| UBP5_HUMAN | Ubiquitin carboxyl-terminal hydrolase 5 (EC 3.1.2.15) (Ubiquitin thiolesterase 5) (Ubiquitin-specific processing protease 5) (Deubiquitinating enzyme 5) (Isopeptidase T). [*Homo sapiens*] |
| UBP7_HUMAN | Ubiquitin carboxyl-terminal hydrolase 7 (EC 3.1.2.15) (Ubiquitin thiolesterase 7) (Ubiquitin-specific processing protease 7) (Deubiquitinating enzyme 7) (Herpesvirus associated ubiquitin-specific protease). [*Homo sapiens*] |
| UD13_RAT | UDP-glucuronosyltransferase 1-3 precursor, microsomal (EC 2.4.1.17) (UDPGT) (UGT1*3) (UGT1-03) (UGT1.3) (UGT1A3) (B3). [*Rattus norvegicus*] |
| UDB4_HUMAN | UDP-glucuronosyltransferase 2B4 precursor, microsomal (EC 2.4.1.17) (UDPGT) (Hyodeoxycholic acid) (HLUG25) (UDPGTH-1). [*Homo sapiens*] |
| UDB6_RAT | UDP-glucuronosyltransferase 2B6 precursor, microsomal (EC 2.4.1.17) (UDPGT) (17-beta-hydroxysteroid specific) (UDPGTR-5). [*Rattus norvegicus*] |
| UDBC_RAT | UDP-glucuronosyltransferase 2B12 precursor, microsomal (EC 2.4.1.17) (UDPGT). [*Rattus norvegicus*] |
| UGG2_HUMAN | UDP-glucose:glycoprotein glucosyltransferase 2 precursor (EC 2.4.1.-) (UDP--Glc:glycoprotein glucosyltransferase 2) (UGT 2) (HUGT2). [*Homo sapiens*] |
| VAG1_HUMAN | Vacuolar ATP synthase subunit G 1 (EC 3.6.3.14) (V-ATPase G subunit 1) (Vacuolar proton pump G subunit 1) (V-ATPase 13 kDa subunit 1) (Vacuolar ATP synthase subunit M16). [*Homo sapiens*] |
| VLCS_HUMAN | Very-long-chain acyl-CoA synthetase (EC 6.2.1.-) (Very-long-chain- fatty-acid-CoA ligase). [*Homo sapiens*] |
| VLCS_MOUSE | Very-long-chain acyl-CoA synthetase (EC 6.2.1.-) (Very-long-chain- fatty-acid-CoA ligase). [*Mus musculus*] |
| VLCS_RAT | Very-long-chain acyl-CoA synthetase (EC 6.2.1.-) (Very-long-chain- fatty-acid-CoA ligase). [*Rattus norvegicus*] |
| VNN1_HUMAN | Pantetheinase precursor (EC 3.5.1.-) (Pantetheine hydrolase) (Vascular non-inflammatory molecule 1) (Vanin 1) (Tiff66). [*Homo sapiens*] |
| VNN2_HUMAN | Vascular non-inflammatory molecule 2 precursor (Vanin 2) (Glycosylphosphatidyl inositol-anchored protein GPI-80) (FOAP-4 protein). [*Homo sapiens*] |
| Y153_HUMAN | Hypothetical protein KIAA0153. [*Homo sapiens*] |
| Y173_HUMAN | Hypothetical protein KIAA0173. [*Homo sapiens*] |
| Y934_HUMAN | Hypothetical protein KIAA0934. [*Homo sapiens*] |
| Structural molecules | |
| AAC1_HUMAN | Alpha-actinin 1 (Alpha-actinin cytoskeletal isoform) (Non-muscle alpha-actinin 1) (F-actin cross linking protein). [*Homo sapiens*] |
| AAC3_HUMAN | Alpha-actinin 3 (Alpha actinin skeletal muscle isoform 3) (F-actin cross linking protein). [*Homo sapiens*] |
| AAC4_HUMAN | Alpha-actinin 4 (Non-muscle alpha-actinin 4) (F-actin cross linking protein). [*Homo sapiens*] |
| ACTA_HUMAN | Actin, aortic smooth muscle (Alpha-actin 2). [*Homo sapiens*] |
| ACTB_CRIGR | Actin, cytoplasmic 1 (Beta-actin). [*Cricetulus griseus*] |
| ACTB_HUMAN | Actin, cytoplasmic 1 (Beta-actin). [*Homo sapiens*] |
| ACTB_RABIT | Actin, cytoplasmic 1 (Beta-actin). [*Oryctolagus cuniculus*] |
| ACTC_HUMAN | Actin, alpha cardiac. [*Homo sapiens*] |
| ACTH_HUMAN | Actin, gamma-enteric smooth muscle (Alpha-actin 3). [*Homo sapiens*] |
| ACTS_HUMAN | Actin, alpha skeletal muscle (Alpha-actin 1). [*Homo sapiens*] |
| ANK2_HUMAN | Ankyrin 2 (Brain ankyrin) (Ankyrin B) (Ankyrin, nonerythroid). [*Homo sapiens*] |
| AR16_HUMAN | ARP2/3 complex 16 kDa subunit (P16-ARC) (Actin-related protein |
| AR1B_HUMAN | ARP2/3 complex 41 kDa subunit (P41-ARC) (Actin-related protein 2/3 complex subunit 1B). [*Homo sapiens*] |
| AR21_HUMAN | ARP2/3 complex 21 kDa subunit (P21-ARC) (Actin-related protein 2/3 complex subunit 3). [*Homo sapiens*] |
| AR34_HUMAN | ARP2/3 complex 34 kDa subunit (P34-ARC) (Actin-related protein 2/3 complex subunit 2). [*Homo sapiens*] |
| ARP2_HUMAN | Actin-like protein 2 (Actin-related protein 2). [*Homo sapiens*] |
| ARP3_HUMAN | Actin-like protein 3 (Actin-related protein 3) (Actin-2). [*Homo sapiens*] |
| B53A_HUMAN | 53 kDa BRG1-associated factor A (Actin-related protein Baf53a) (ArpNbeta). [*Homo sapiens*] |
| BPEA_HUMAN | Bullous pemphigoid antigen 1, isoforms 6/9/10 (Trabeculin-beta) (Bullous pemphigoid antigen) (BPA) (Hemidesmosomal plaque protein) (Dystonia musculorum protein). [*Homo sapiens*] |
| CA11_MOUSE | Collagen alpha 1(I) chain precursor. [*Mus musculus*] |
| CA13_HUMAN | Collagen alpha 1(III) chain precursor. [*Homo sapiens*] |
| CA14_HUMAN | Collagen alpha 1(IV) chain precursor. [*Homo sapiens*] |
| CA15_HUMAN | Collagen alpha 1(V) chain precursor. [*Homo sapiens*] |
| CA16_HUMAN | Collagen alpha 1(VI) chain precursor. [*Homo sapiens*] |
| CA18_MOUSE | Collagen alpha 1(VIII) chain precursor. [*Mus musculus*] |
| CA1A_HUMAN | Collagen alpha 1(X) chain precursor. [*Homo sapiens*] |
| CA1B_HUMAN | Collagen alpha 1(XI) chain precursor. [*Homo sapiens*] |
| CA1C_HUMAN | Collagen alpha 1(XII) chain precursor. [*Homo sapiens*] |
| CA1C_RAT | Collagen alpha 1(XII) chain (Fragment). [*Rattus norvegicus*] |
| CA1E_HUMAN | Collagen alpha 1(XV) chain precursor. [*Homo sapiens*] |
| CA1F_HUMAN | Collagen alpha 1(XVI) chain precursor. [*Homo sapiens*] |
| CA21_MOUSE | Collagen alpha 2(I) chain precursor. [*Mus musculus*] |
| CA24_HUMAN | Collagen alpha 2(IV) chain precursor. [*Homo sapiens*] |
| CA2B_HUMAN | Collagen alpha 2(XI) chain precursor. [*Homo sapiens*] |
| CA34_HUMAN | Collagen alpha 3(IV) chain precursor (Goodpasture antigen). [*Homo sapiens*] |
| CA36_HUMAN | Collagen alpha 3(VI) chain precursor. [*Homo sapiens*] |
| CCG4_HUMAN | Voltage-dependent calcium channel gamma-4 subunit (Neuronal voltage- gated calcium channel gamma-4 subunit). [*Homo sapiens*] |
| CLH1_HUMAN | Clathrin heavy chain 1 (CLH-17). [*Homo sapiens*] |

-continued

| | |
|---|---|
| CO1A_HUMAN | Coronin-like protein p57 (Coronin 1A). [*Homo sapiens*] |
| COMP_HUMAN | Cartilage oligomeric matrix protein precursor (COMP). [*Homo sapiens*] |
| CRAA_HUMAN | Alpha crystallin A chain. [*Homo sapiens*] |
| CTD1_HUMAN | Catenin delta-1 (p120 catenin) (p120(ctn)) (Cadherin-associated Src substrate) (CAS) (p120(cas)). [*Homo sapiens*] |
| CTN1_HUMAN | Alpha-1 catenin (Cadherin-associated protein) (Alpha E-catenin). [*Homo sapiens*] |
| DMD_CANFA | Dystrophin. [*Canis familiaris*] |
| DMD_HUMAN | Dystrophin. [*Homo sapiens*] |
| E4L2_HUMAN | Band 4.1-like protein 2 (Generally expressed protein 4.1) (4.1G). [*Homo sapiens*] |
| E4L2_MOUSE | Band 4.1-like protein 2 (Generally expressed protein 4.1) (4.1G). [*Mus musculus*] |
| FBN2_HUMAN | Fibrillin 2 precursor. [*Homo sapiens*] |
| FINC_HUMAN | Fibronectin precursor (FN) (Cold-insoluble globulin) (CIG). [*Homo sapiens*] |
| K1CJ_HUMAN | Keratin, type I cytoskeletal 10 (Cytokeratin 10) (K10) (CK 10). [*Homo sapiens*] |
| K1CS_HUMAN | Keratin, type I cytoskeletal 19 (Cytokeratin 19) (K19) (CK 19). [*Homo sapiens*] |
| K22E_HUMAN | Keratin, type II cytoskeletal 2 epidermal (Cytokeratin 2e) (K2e) (CK 2e). [*Homo sapiens*] |
| K22O_HUMAN | Keratin, type II cytoskeletal 2 oral (Cytokeratin 2P) (K2P) (CK 2P). [*Homo sapiens*] |
| K2C1_HUMAN | Keratin, type II cytoskeletal 1 (Cytokeratin 1) (K1) (CK 1) (67 kDa Cytokeratin) (Hair alpha protein). [*Homo sapiens*] |
| K2C5_HUMAN | Keratin, type II cytoskeletal 5 (Cytokeratin 5) (K5) (CK 5) (58 kDa Cytokeratin). [*Homo sapiens*] |
| K2C7_HUMAN | Keratin, type II cytoskeletal 7 (Cytokeratin 7) (K7) (CK 7) (Sarcolectin). [*Homo sapiens*] |
| K2C8_HUMAN | Keratin, type II cytoskeletal 8 (Cytokeratin 8) (K8) (CK 8). [*Homo sapiens*] |
| LAMA_HUMAN | Lamin A/C (70 kDa lamin). [*Homo sapiens*] |
| LMA1_HUMAN | Laminin alpha-1 chain precursor (Laminin A chain). [*Homo sapiens*] |
| LMA2_HUMAN | Laminin alpha-2 chain precursor (Laminin M chain) (Merosin heavy chain). [*Homo sapiens*] |
| LMA2_MOUSE | Laminin alpha-2 chain precursor (Laminin M chain) (Merosin heavy chain). [*Mus musculus*] |
| LMA3_HUMAN | Laminin alpha-3 chain precursor (Epilgrin 170 kDa subunit) (E170) (Nicein alpha subunit). [*Homo sapiens*] |
| LMA4_HUMAN | Laminin alpha-4 chain precursor. [*Homo sapiens*] |
| LMB1_HUMAN | Laminin beta-1 chain precursor (Laminin B1 chain). [*Homo sapiens*] |
| LMB2_HUMAN | Laminin beta-2 chain precursor (S-laminin) (Laminin B1s chain). [*Homo sapiens*] |
| LMB3_HUMAN | Laminin beta-3 chain precursor (Laminin 5 beta 3) (Laminin B1k |
| LMG1_HUMAN | Laminin gamma-1 chain precursor (Laminin B2 chain). [*Homo sapiens*] |
| LMG1_MOUSE | Laminin gamma-1 chain precursor (Laminin B2 chain). [*Mus musculus*] |
| MAT3_HUMAN | Matrin 3. [*Homo sapiens*] |
| MBP_HUMAN | Myelin basic protein (MBP) (Myelin A1 protein) (Myelin membrane encephalitogenic protein). [*Homo sapiens*] |
| MERL_HUMAN | Merlin (Moesin-ezrin-radixin-like protein) (Schwannomin) (Schwannomerlin) (Neurofibromin 2). [*Homo sapiens*] |
| MLEY_HUMAN | Myosin light chain 1, slow-twitch muscle A isoform (MLC1sa) (Alkali). [*Homo sapiens*] |
| MYM1_HUMAN | Myomesin 1 (190 kDa titin-associated protein) (190 kDa connectin- associated protein). [*Homo sapiens*] |
| MYPS_HUMAN | Myosin-binding protein C, slow-type (Slow MyBP-C) (C-protein, skeletal muscle slow-isoform). [*Homo sapiens*] |
| NEBL_HUMAN | Nebulette (Actin-binding Z-disk protein). [*Homo sapiens*] |
| NEBU_HUMAN | Nebulin. [*Homo sapiens*] |
| NHPX_HUMAN | NHP2-like protein 1 (High mobility group-like nuclear protein 2 homolog 1) ([U4/U6.U5] tri-snRNP 15.5 kDa protein) (OTK27). [*Homo sapiens*] |
| O18840 | Beta-actin. [*Canis familiaris*] |
| PKP3_HUMAN | Plakophilin 3. [*Homo sapiens*] |
| PLE1_HUMAN | Plectin 1 (PLTN) (PCN) (Hemidesmosomal protein 1) (HD1). [*Homo sapiens*] |
| PLSI_HUMAN | I-plastin (Intestine-specific plastin). [*Homo sapiens*] |
| PRLP_HUMAN | Prolargin precursor (Proline-arginine-rich end leucine-rich repeat protein). [*Homo sapiens*] |
| Q10465 | Elastic titin (Fragment). [*Homo sapiens*] |
| Q13707 | ACTA2 protein (Fragment). [*Homo sapiens*] |
| Q8SPX4 | Beta-actin (Fragment). [*Canis familiaris*] |
| Q95164 | Beta-actin (Fragment). [*Canis familiaris*] |
| R10A_HUMAN | 60S ribosomal protein L10a (CSA-19). [*Homo sapiens*] |
| R18A_HUMAN | 28S ribosomal protein S18a, mitochondrial precursor (MRP-S18-a) (Mrps18a) (MRP-S18-3). [*Homo sapiens*] |
| R261_HUMAN | 60S ribosomal protein L26-like 1. [*Homo sapiens*] |
| R27A_HUMAN | 40S ribosomal protein S27a. [*Homo sapiens*] |
| R35A_HUMAN | 60S ribosomal protein L35a. [*Homo sapiens*] |
| RADI_HUMAN | Radixin. [*Homo sapiens*] |
| RL11_MOUSE | 60S ribosomal protein L11. [*Mus musculus*] |
| RL12_HUMAN | 60S ribosomal protein L12. [*Homo sapiens*] |
| RL12_MOUSE | 60S ribosomal protein L12. [*Mus musculus*] |
| RL12_RAT | 60S ribosomal protein L12. [*Rattus norvegicus*] |
| RL13_RAT | 60S ribosomal protein L13. [*Rattus norvegicus*] |
| RL17_HUMAN | 60S ribosomal protein L17 (L23). [*Homo sapiens*] |
| RL19_HUMAN | 60S ribosomal protein L19. [*Homo sapiens*] |
| RL1X_HUMAN | 60S ribosomal protein L18a. [*Homo sapiens*] |
| RL23_HUMAN | 60S ribosomal protein L23 (L17). [*Homo sapiens*] |
| RL24_HUMAN | 60S ribosomal protein L24 (L30). [*Homo sapiens*] |
| RL2A_RAT | 60S ribosomal protein L27a. [*Rattus norvegicus*] |
| RL2B_HUMAN | 60S ribosomal protein L23a. [*Homo sapiens*] |
| RL31_HUMAN | 60S ribosomal protein L31. [*Homo sapiens*] |
| RL4_HUMAN | 60S ribosomal protein L4 (L1). [*Homo sapiens*] |
| RL4_RAT | 60S ribosomal protein L4 (L1). [*Rattus norvegicus*] |
| RL5_HUMAN | 60S ribosomal protein L5. [*Homo sapiens*] |
| RL7_HUMAN | 60S ribosomal protein L7. [*Homo sapiens*] |

-continued

| | |
|---|---|
| RL7_MOUSE | 60S ribosomal protein L7. [*Mus musculus*] |
| RL8_HUMAN | 60S ribosomal protein L8. [*Homo sapiens*] |
| RL9_RAT | 60S ribosomal protein L9. [*Rattus norvegicus*] |
| RLA0_HUMAN | 60S acidic ribosomal protein P0 (L10E). [*Homo sapiens*] |
| RLA1_HUMAN | 60S acidic ribosomal protein P1. [*Homo sapiens*] |
| RLA2_HUMAN | 60S acidic ribosomal protein P2. [*Homo sapiens*] |
| RM13_HUMAN | 60S ribosomal protein L13, mitochondrial (L13mt). [*Homo sapiens*] |
| RM39_HUMAN | Mitochondrial 39s ribosomal protein L39 (L39mt) (MRP-L39) (MRP-L5) (PRED22 protein). [*Homo sapiens*] |
| RS10_HUMAN | 40S ribosomal protein S10. [*Homo sapiens*] |
| RS11_HUMAN | 40S ribosomal protein S11. [*Homo sapiens*] |
| RS12_HUMAN | 40S ribosomal protein S12. [*Homo sapiens*] |
| RS14_HUMAN | 40S ribosomal protein S14 (PRO2640). [*Homo sapiens*] |
| RS18_HUMAN | 40S ribosomal protein S18 (KE-3) (KE3). [*Homo sapiens*] |
| RS19_RAT | 40S ribosomal protein S19. [*Rattus norvegicus*] |
| RS21_HUMAN | 40S ribosomal protein S21. [*Homo sapiens*] |
| RS21_MOUSE | 40S ribosomal protein S21. [*Mus musculus*] |
| RS21_RAT | 40S ribosomal protein S21. [*Rattus norvegicus*] |
| RS23_HUMAN | 40S ribosomal protein S23. [*Homo sapiens*] |
| RS24_HUMAN | 40S ribosomal protein S24 (S19). [*Homo sapiens*] |
| RS25_HUMAN | 40S ribosomal protein S25. [*Homo sapiens*] |
| RS28_HUMAN | 40S ribosomal protein S28. [*Homo sapiens*] |
| RS2_HUMAN | 40S ribosomal protein S2 (S4) (LLREP3 protein). [*Homo sapiens*] |
| RS2_RAT | 40S ribosomal protein S2. [*Rattus norvegicus*] |
| RS30_HUMAN | 40S ribosomal protein S30. [*Homo sapiens*] |
| RS3_HUMAN | 40S ribosomal protein S3. [*Homo sapiens*] |
| RS3_MOUSE | 40S ribosomal protein S3. [*Mus musculus*] |
| RS5_HUMAN | 40S ribosomal protein S5. [*Homo sapiens*] |
| RS5_MOUSE | 40S ribosomal protein S5. [*Mus musculus*] |
| RS5_RAT | 40S ribosomal protein S5. [*Rattus norvegicus*] |
| RS6_HUMAN | 40S ribosomal protein S6 (Phosphoprotein NP33). [*Homo sapiens*] |
| RS7_HUMAN | 40S ribosomal protein S7 (S8). [*Homo sapiens*] |
| RSP4_BOVIN | 40S ribosomal protein P40 (C10 protein). [*Bos taurus*] |
| RSP4_MOUSE | 40S ribosomal protein SA (P40) (34/67 kDa laminin receptor). [*Mus musculus*] |
| RSP4_RAT | 40S ribosomal protein SA (P40) (34/67 kDa laminin receptor). [*Rattus norvegicus*] |
| SPCB_HUMAN | Spectrin beta chain, erythrocyte (Beta-I spectrin). [*Homo sapiens*] |
| SPCN_HUMAN | Spectrin alpha chain, brain (Spectrin, non-erythroid alpha chain) (Alpha-II spectrin) (Fodrin alpha chain). [*Homo sapiens*] |
| SPCO_HUMAN | Spectrin beta chain, brain 1 (Spectrin, non-erythroid beta chain 1) (Beta-II spectrin) (Fodrin beta chain). [*Homo sapiens*] |
| SZ07_HUMAN | Platelet basic protein precursor (PBP) (Small inducible cytokine B7) (CXCL7) [Contains: Connective-tissue activating peptide III (CTAP- III); Low-affinity platelet factor IV (LA-PF4); Beta-thromboglobulin (Beta-TG); Neutrophil-activating peptide 2 (NAP-2) |
| TLN1_HUMAN | Talin 1. [*Homo sapiens*] |
| TLN2_HUMAN | Talin 2. [*Homo sapiens*] |
| TPM1_HUMAN | Tropomyosin 1 alpha chain (Alpha-tropomyosin). [*Homo sapiens*] |
| TPM2_HUMAN | Tropomyosin beta chain (Tropomyosin 2) (Beta-tropomyosin). [*Homo sapiens*] |
| TPM4_HUMAN | Tropomyosin alpha 4 chain (Tropomyosin 4) (TM30p1). [*Homo sapiens*] |
| TSP1_HUMAN | Thrombospondin 1 precursor. [*Homo sapiens*] |
| UTRO_HUMAN | Utrophin (Dystrophin-related protein 1) (DRP1) (DRP). [*Homo sapiens*] |
| VAPA_HUMAN | Vesicle-associated membrane protein-associated protein A (VAMP- associated protein A) (VAMP-A) (VAP-A) (33 kDa Vamp-associated protein) (VAP-33). [*Homo sapiens*] |
| VAPA_MOUSE | Vesicle-associated membrane protein-associated protein A (VAMP- associated protein A) (VAMP-A) (VAP-A) (33 kDa Vamp-associated protein) (VAP-33). [*Mus musculus*] |
| VAPB_HUMAN | Vesicle-associated membrane protein-associated protein B/C (VAMP- associated protein B/C) (VAMP-B/VAMP-C) (VAP-B/VAP-C). [*Homo sapiens*] |
| VILL_HUMAN | Villin-like protein. [*Homo sapiens*] |
| VINC_HUMAN | Vinculin (Metavinculin). |
| Y256_HUMAN | Hypothetical protein KIAA0256 (Fragment). [*Homo sapiens*] |

The invention illustratively described herein may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other documents.

The inventions illustratively described herein may suitably be practiced in the absence of any element or elements, limitation or limitations, not specifically disclosed herein. Thus, for example, the terms "comprising", "including,"

containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

Other embodiments are set forth within the following claims.

We claim:

1. A tagged acyl phosphate or phosphonate probe having the formula:

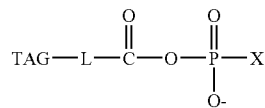

wherein
X is an affinity moiety for directing the binding of said TAPP to one or more target proteins linked to the phosphate through an oxygen or carbon;
TAG is a detectable label;
L is an optionally present alkyl or heteroalkyl group of 1-40 backbone atoms selected from the group consisting of —N(R)—, —O—, —S— or —C(R)(R)—, wherein said alkyl or heteroalkyl group optionally includes a carbocyclic or heterocyclic group;
each R is independently H or —C$_{1-6}$ alkyl straight or branched chain, or optionally form an optionally substituted fused carbocyclic or heterocyclic ring structure; and
the carbonyl adjacent to L is bound to a carbon to form an acyl group;
or a pharmaceutically acceptable salt or complex thereof.

2. The tagged acyl phosphate probe of claim 1, wherein X is selected from the group consisting of a nucleotide, nucleotide analogue, optionally substituted naphthyl group, small molecule, steroid, peptide hormone, enzyme cofactor, vitamin, enzyme substrate, lipid, prostaglandin, or receptor ligand.

3. A tagged acyl phosphate or phosphonate probe according to claim 2 wherein X is a nucleotide, such that said probe has the formula:

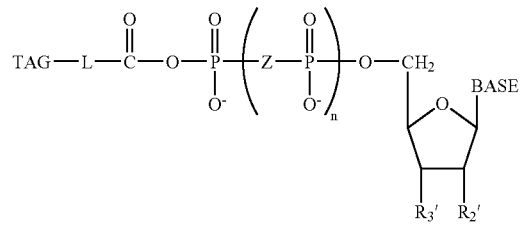

wherein
BASE is a 5- or 6-membered unsaturated heterocyclic ring comprising from 1 to 3 ring nitrogens, wherein the 5- or 6-membered unsaturated heterocyclic ring is covalently attached through a ring nitrogen to the 1' position of the ribose or deoxy-ribose, wherein the 5- or 6-membered unsaturated heterocyclic ring optionally comprises a 6-membered unsaturated carbocyclic or heterocyclic ring fused thereto, said fused ring comprising from 1 to 2 ring nitrogens, and wherein each carbon position in the BASE may be optionally substituted by a substituent independently selected from the group consisting of —H, —F, —Br, —Cl, —SCH$_3$, —C(O)N(R)(R), —CN, —NO$_2$, —N(R)(R), =O, acetoxy, —C(R)(R)(R), —OCH$_3$, —OCH$_2$CH$_3$, methylene dioxy, trihalomethyl, trihalomethoxy. or —(CH$_2$)$_m$OH;
R$_{2'}$ and R$_{3'}$ are independently selected from the group consisting of —H, —OH, —F, —Br, —Cl, —SCH$_3$, —C(O)N(R)(R), —CN, —NO$_2$, —N(R)(R), acetoxy, —C(R)(R)(R), —OCH$_3$, —OCH$_2$CH$_3$, methylene dioxy, trihalomethyl, trihalomethoxy, —(CH$_2$)$_m$OH, or —(CH$_2$)$_m$-phenyl where phenyl is optionally substituted with —F, —Br, —Cl, —SCH$_3$, —C(O)N(R)(R), —CN, —NO$_2$, —N(R)(R), acetoxy, —C(R)(R)(R), —OCH$_3$, —OCH$_2$CH$_3$, methylene dioxy, trihalomethyl, trihalomethoxy, —(CH$_2$)$_m$OH;
n is 0-2;
m is 0 to 6;
TAG is a detectable label;
each Z is independently O, S, NH, or methylene;
L is an optionally present alkyl or heteroalkyl group of 1-40 backbone atoms selected from the group consisting of —N(R)—, —O—, —S— or —C(R)(R)13 , wherein said alkyl or heteroalkyl group optionally includes a carbocyclic or heterocyclic group; and
each R is independently H or —C$_{1-6}$ alkyl straight or branched chain, or optionally form an optionally substituted fused carbocyclic or heterocyclic ring structure.

4. A tagged acyl-nucleotide probe according to claim 3, wherein BASE is a purine.

5. A tagged acyl-nucleotide probe according to claim 3, wherein BASE is a pyrimidine.

6. A tagged acyl-nucleotide probe according to claim 3, wherein BASE is selected from the group consisting of adenine, thymine, uracil, guanine, cytosine, inosine, 5-bromouracil, 5-fluorouracil, 2-aminopurine, N$^6$-cyclohexyl adenine, 8-azaguanine, and 5-fluorocytosine.

7. A tagged acyl-nucleotide probe according to claim 6, wherein BASE is selected from the group consisting of adenine, thymine, uracil, guanine, and cytosine.

8. A tagged acyl-nucleotide probe according to claim 3, wherein R$_{2'}$ and R$_{3'}$ are independently H or OH.

9. A tagged acyl-nucleotide probe according to claim 3, wherein R$_{2'}$ and R$_{3'}$ are each OH.

10. A tagged acyl-nucleotide probe according to claim 3, wherein L has the structure:

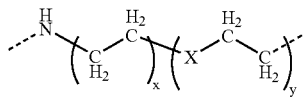

wherein
x and y are independently in the range of 0 to 4, and
X is O or $CH_2$.

11. A tagged acyl-nucleotide probe according to claim 3, wherein L has the structure:

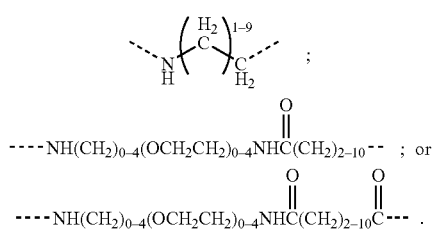

12. A tagged acyl-nucleotide probe according to claim 10, wherein L has the structure —$NH(CH_2)_2(OCH_2CH_2)_{1-4}$—.

13. A tagged acyl-nucleotide probe according to claim 3, wherein L comprises a triazole moiety.

14. A tagged acyl nucleotide probe according to claim 3, wherein L comprises the following moiety:

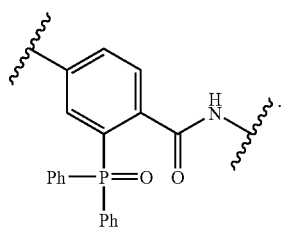

15. A tagged acyl-nucleotide probe according to claim 3, wherein the TAG is selected from the group consisting of:

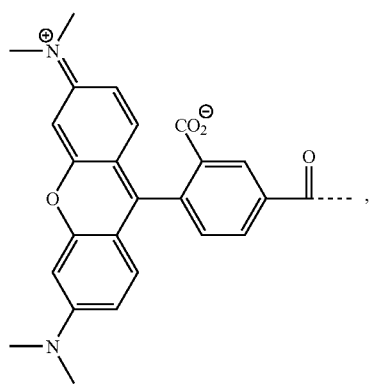

-continued

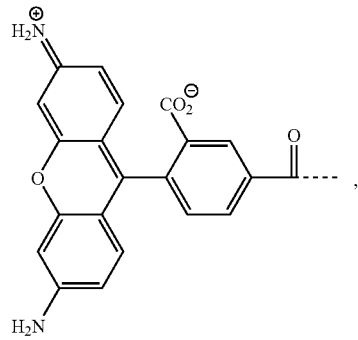

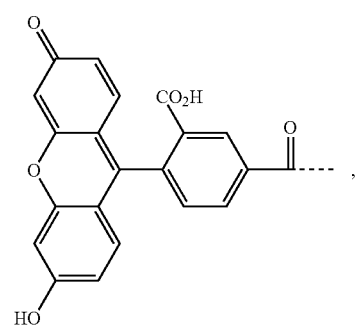

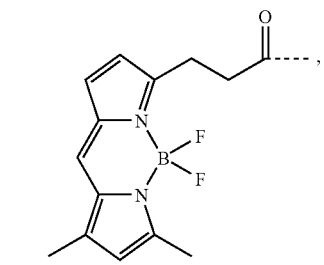

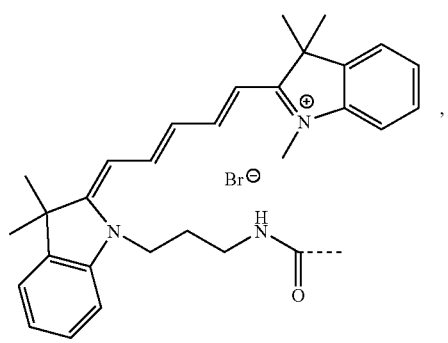

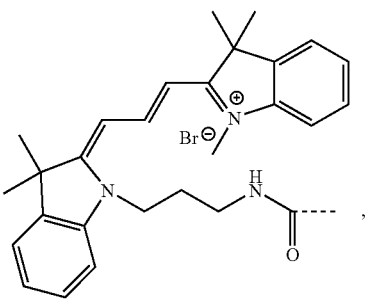

-continued

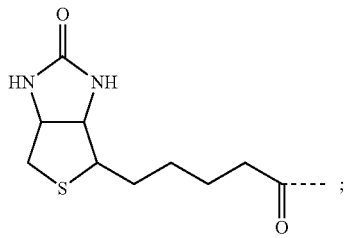

and dethiobiotin; wherein 5-substituted carboxyrhodamine or 5-substituted carboxyfluorescein maybe replaced with 6-carboxyrhodamine or 6-carboxyfluorescein, or with a mixture of 5- and 6-substituted carboxyrhodamine or carboxyfluorescein.

16. A tagged acyl phosphate or phosphonate probe according to claim 2 wherein X is a nucleotide, such that said probe has the structure:

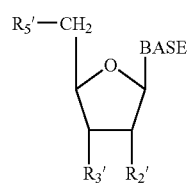

wherein

BASE is a 5 or 6-membered unsaturated heterocyclic ring comprising from 1 to 3 ring nitrogens, wherein the 5- or 6-membered unsaturated heterocyclic ring is covalently attached through a ring nitrogen to the 1' position of the ribose or deoxy-ribose, wherein the 5- or 6-membered unsaturated heterocyclic ring optionally comprises a 6-membered unsaturated carbocyclic or heterocyclic ring fused thereto, said fused ring comprising from 1 to 2 ring nitrogens, and wherein each carbon position in the BASE may be optionally substituted by a substituent independently selected from the group consisting of —H, —F, —Br, —Cl, —SCH$_3$, —C(O)N(R)(R), —CN, —NO$_2$, —N(R)(R), =O, acetoxy, —C(R)(R)(R), —OCH$_3$, —OCH$_2$CH$_3$, methylene dioxy, trihalomethyl, trihalomethoxy, or —(CH$_2$)$_m$OH;

one of $R_{2'}$ and $R_{3'}$ and $R_{5'}$ has the following structure;

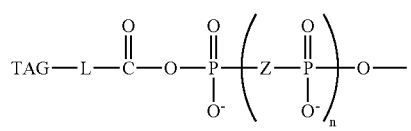

and the other two of $R_{2'}$ and $R_{3'}$ and $R_{5'}$ are independently selected from the group consisting of —H, —OH, —F, —Br, —Cl, —SCH$_3$, —C(O)N(R)(R), —CN, —NO$_2$, —N(R)(R), acetoxy, —C(R)(R)(R), —OCH$_3$, —OCH$_2$CH$_3$, methylene dioxy, trihalomethyl, trihalomethoxy, —(CH$_2$)$_m$H, or —(CH$_2$)$_m$-phenyl where phenyl is optionally substituted with —F, —Br, —Cl, —SCH$_3$, —C(O)N(R)(R), —CN, —NO$_2$, —N(R)(R), acetoxy, —C(R)(R)(R), —OCH$_3$, —OCH$_2$CH$_3$, methylene dioxy, trihalomethyl, trihalomethoxy, —(CH$_2$)$_m$OH;

n is 0-2;

m is 0 to 6;

TAG is a detectable label, each Z is independently O, S, NH, or methylene;

L is an optionally present alkyl or heteroalkyl group of 1-40 backbone atoms selected from the group consisting of —N(R)—, —O—, —S— or —C(R)(R)—, wherein said alkyl or heteroalkyl group optionally includes a carbocyclic or heterocyclic group; and each R is independently H or —C$_{1-6}$ alkyl straight or branched chain, or optionally form an optionally substituted fused carbocyclic or heterocyclic ring structure.

17. A tagged acyl-nucleotide probe having the structure:

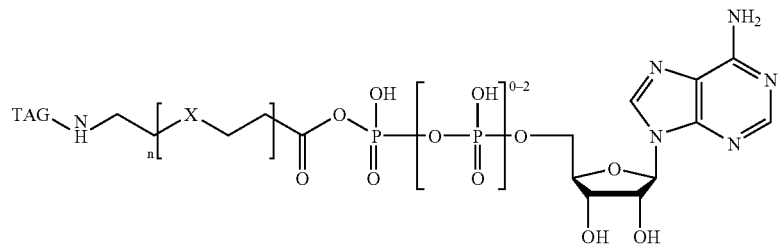

wherein n is 1-4;

X is O or CH$_2$; and

TAG is a detectable label;

or a pharmaceutically acceptable salt or complex thereof.

18. A tagged acyl-nucleotide probe having the structure:

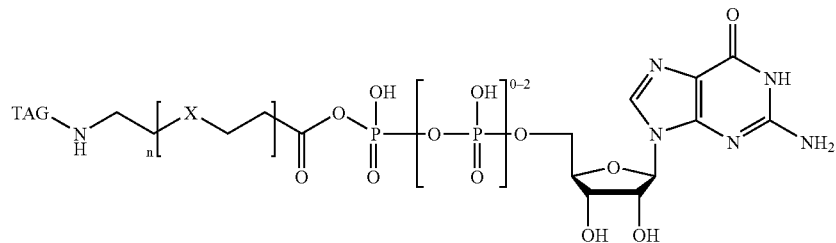

wherein
n is 1-4;
X is O or CH$_2$; and
TAG is a detectable label;
or a pharmaceutically acceptable salt or complex thereof.

19. A tagged acyl-nucleotide probe having the structure:

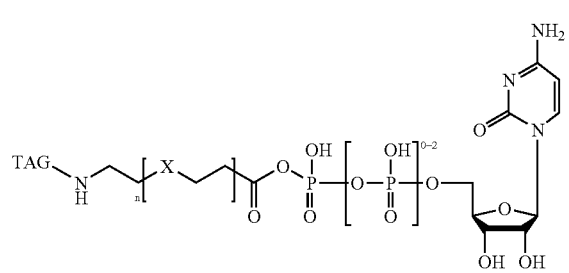

wherein
n is 1-4;
X is O or CH$_2$; and
TAG is a detectable label;
or a pharmaceutically acceptable salt or complex thereof.

20. A tagged acyl-nucleotide probe having the structure:

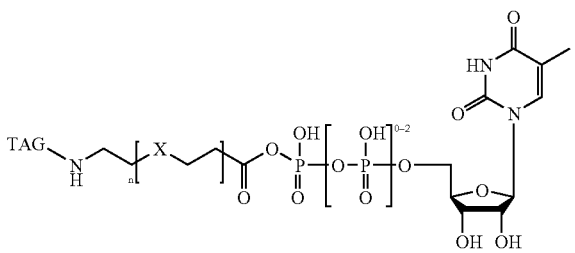

wherein
n is 1-4;
X is O or CH$_2$; and
TAG is a detectable label;
or a pharmaceutically acceptable salt or complex thereof.

21. A tagged acyl-nucleotide probe having the structure:

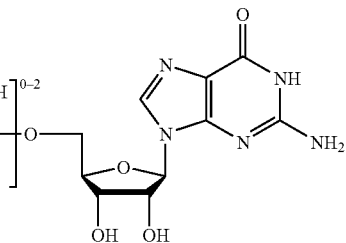

wherein
n is 1-4;
X is O or CH$_2$; and
TAG is a detectable label;
or a pharmaceutically acceptable salt or complex thereof.

22. A tagged acyl-nucleotide probe having the structure:

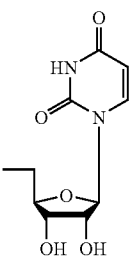

wherein TAG is biotin or dethiobiotin;
or a pharmaceutically acceptable salt or complex thereof.

23. A tagged acyl-nucleotide probe having the structure:

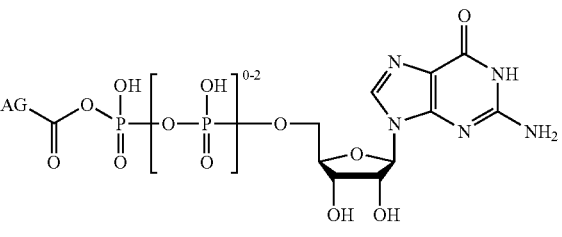

wherein TAG is biotin or dethiobiotin;
or a pharmaceutically acceptable salt or complex thereof.

24. A tagged acyl-nucleotide probe having the structure:

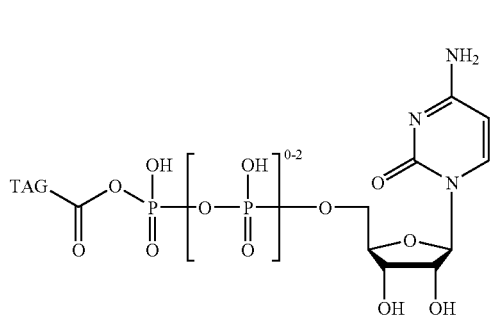

wherein TAG is biotin or dethiobiotin;
or a pharmaceutically acceptable salt or complex thereof.

25. A tagged acyl-nucleotide probe having the structure:

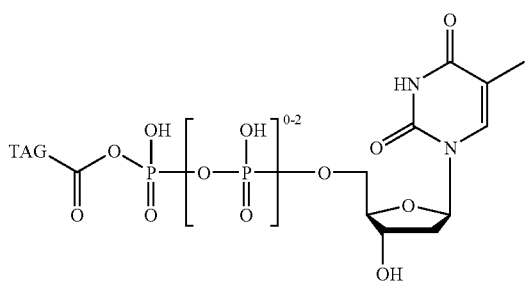

wherein TAG is biotin or dethiobiotin;
or a pharmaceutically acceptable salt or complex thereof.

26. A tagged acyl-nucleotide probe having the structure:

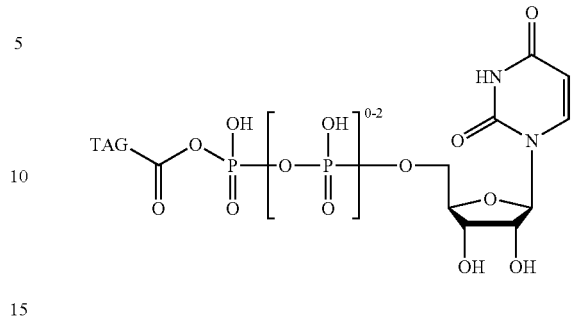

wherein TAG is biotin or dethiobiotin;
or a pharmaceutically acceptable salt or complex thereof.

27. A method for determining the enzyme profile of one or more target proteins in a complex protein mixture, employing one or more probes comprising a nucleotide covalently bound through the terminal phosphate of a 5' mono- di- or tri-phosphate to an acyl group, which is further covalently bound to a TAG via a linker moiety "L", wherein said acyl group forms an adduct with said target protein(s) when said probe is bound to said target protein(s), said method comprising:
  combining in a reaction medium said probe(s) and said complex protein mixture under conditions of reaction of said probe(s) with said nucleotide binding protein(s), whereby a conjugate of said probe(s) and said target protein(s) is formed; and
  determining said enzyme profile by generating a signal from one or more conjugates formed thereby;
wherein said probe(s) are selected from the nucleotide binding protein-directed probes of one of claims 3, 21, 1, 2 or 22-26.

28. A method according to claim 27, wherein said probe binds to a plurality of target proteins.

* * * * *